US006800445B2

(12) United States Patent
Palmer et al.

(10) Patent No.: US 6,800,445 B2
(45) Date of Patent: Oct. 5, 2004

(54) SYSTEMS FOR SENSITIVE DETECTION OF G-PROTEIN COUPLED RECEPTOR AND ORPHAN RECEPTOR FUNCTION USING REPORTER ENZYME MUTANT COMPLEMENTATION

(75) Inventors: Michelle A. J. Palmer, Arlington, MA (US); Melissa Gee, Bedford, MA (US); Bonnie Tillotson, Belmont, MA (US); Xiao-jia Chang, Lincoln, MA (US)

(73) Assignee: Applera Corporation, Bedford, MA (US)

( * ) Notice: Subject to any disclaimer, the term of this patent is extended or adjusted under 35 U.S.C. 154(b) by 0 days.

(21) Appl. No.: 09/759,152

(22) Filed: Jan. 16, 2001

(65) Prior Publication Data

US 2002/0028433 A1 Mar. 7, 2002

Related U.S. Application Data

(63) Continuation-in-part of application No. 09/654,499, filed on Sep. 1, 2000.
(60) Provisional application No. 60/180,669, filed on Feb. 7, 2000.

(51) Int. Cl.[7] .................. G01N 33/567; C12N 15/62
(52) U.S. Cl. .................. 435/7.1; 435/7.1; 435/7.21; 435/69.7; 436/501; 536/23.4
(58) Field of Search .................. 435/7.1, 7.2, 7.21, 435/69.7; 436/501; 536/23.4

(56) References Cited

U.S. PATENT DOCUMENTS

| 4,931,569 | A | 6/1990 | Edwards et al. |
| 4,978,614 | A | 12/1990 | Bronstein |
| 5,145,772 | A | 9/1992 | Voyta et al. |
| 5,326,882 | A | 7/1994 | Bronstein et al. |
| 5,538,847 | A | 7/1996 | Bronstein et al. |
| 5,851,771 | A | 12/1998 | Bronstein et al. |
| 5,891,646 | A | 4/1999 | Barak et al. |
| 6,110,693 | A | 8/2000 | Barak et al. |
| 6,342,345 | B1 | 1/2002 | Blau et al. |

FOREIGN PATENT DOCUMENTS

| WO | 00/35724 | 6/2000 |
| WO | PCT/US00/24043 | 12/2000 |

OTHER PUBLICATIONS

Stephane Angers, et al., "Detection of $\beta_2$–adrenergic receptor dimerization in living cells using bioluminescence resonance energy transfer (BRET)", Proc. Natl. Acad. Sci. USA, 97(7):3684–3689 (2000).
Gurevich, et al., "Arrestin Interactions with G Protein–coupled Receptors. Direct Binding Studies of Wild Type and Mutant Arrestins with Rhodopsin, $\beta_2$–Adrenergic, and m2 Muscarinic Cholinergic Receptors", J. Biol. Chem., 270 (2):720–731 (1995).
Gurevich, et al., "Mechanism of Phosphorylation–Recognition by Visual Arrestin and the Transition of Arrestin into a High Affinity Binding State", Mol. Pharmacol., 51:161–169 (1997).
Rossi et al., "Monitoring Protein–Protein Interactions in Intact Eukaryotic Cells by $\beta$–galactosidase Complementation", Proc. Natl. Acad. Sci., 94:8405–8410 (1997).
Barak et al., "A $\beta$–Arrestin/Green Fluorescent Protein Biosensor for Detecting G Protein–coupled Receptor Activation", the Journal of Biological Chemistry, 272 (44):27497–27500 (1997).
Ferguson, et al., "G–protein–coupled receptor regulation: role of G–protein–coupled receptor kinases and arrestins", Can. J. Physiol Pharmacol., 74:1095–1110 (1996).
Pitcher et al., "G–protein–coupled receptor kinases", Annu. Rev. Biochem., 67:653–692(1998).
Lefkowitz, et al., "Adenylate cyclase–coupled beta–adrenergic receptors: structure and mechanisms of activation and desensitization", Annul. Rev. Biochem., 52:159–186 (1983).
Germino, et al., "Screening for in vivo protein–protein interactions", Proc. Natl. Acad. Sci., 90:933–937 (1993).
Phizicky, et al., "Protein–protein interactions: methods for detection and analysis", Microbiol. Rev., 59(1):94–123 (1995).
Offermanns, et al., "$G\alpha_{15}$ and $G\alpha_{16}$ couple a wide variety of receptors to phospholipase C", J. Biol. Chem., 270(25):15175–15180 (1995).
AbdAlla, et al., "$AT_1$–receptor heterodimers show enhanced G–protein activation and altered receptor sequestration", Nature, 407:94–98 (2000).

(List continued on next page.)

Primary Examiner—John Ulm
(74) Attorney, Agent, or Firm—Piper Rudnick LLP; Steven B. Kelber

(57) ABSTRACT

Methods for detecting G-protein coupled receptor (GPCR) activity; methods for assaying GPCR activity; and methods for screening for GPCR ligands, G-protein-coupled receptor kinase (GRK) activity, and compounds that interact with components of the GPCR regulatory process are described. Included are methods for expanding ICAST technologies for assaying GPCR activity with applications for ligand fishing, and agonist or antagonist screening. These methods include: engineering seronine/threonine phosphorylation sites into known or orphan GPCR open reading frames in order to increase the affinity of arrestin for the activated form of the GPCR or to increase the reside time of arrestin on the activated GPCR; engineering mutant arrestin proteins that bind to activated GPCRs in the absence of G-protein coupled receptor kinases which may be limiting; and engineering mutant super arrestin proteins that have an increased affinity for activated GPCRs with or without phosphorylation. These methods are intended to increase the robustness of the GPCR/ICAST technology in situations in which G-protein coupled receptor kinases are absent or limiting, or in which the GPCR is not efficiently down-regulated or is rapidly resensitized (thus having a labile interaction with arrestin). Included are also more specific methods for using ICAST complementary enzyme fragments to monitor GPCR homo- and hetero-dimerization with applications for drug lead discovery and ligand and function discovery for orphan GPCRs.

22 Claims, 83 Drawing Sheets

OTHER PUBLICATIONS

Bockaert, et al., "Molecular tinkering of G protein–coupled receptors: an evolutionary success", The EMBO Journal, 18(7):1723–1729 (1999).

Jordan, et al., "G–protein–coupled receptor heterodimerization modulates receptor function", Nature, 399:697–700 (1999).

Ng, et al., "Dopamine D2 receptor dimers and receptor–blocking peptides", Bioch. Biophys. Res. Commun., 227:200–204 (1996).

Hebert, et al., "A peptide derived from a $\beta_2$–adrenergic receptor transmembrane domain inhibits both receptor dimerization and activation", J. Biol. Chem. 271(27):16384–16392 (1996).

Krupnick, et al., "The role of receptor kinases and arrestins in G protein–coupled receptor regulation", Ann. Rev. Pharmacol. Toxicol., 38:289–319 (1998).

Hamm, "The many faces of G–protein signaling", J. Biol. Chem., 273(2):669–672 (1998).

Oakley, et al., "Association of β–arrestin with G protein–coupled receptors during clathrin–mediated endocytosis dictates the profile of receptor resensitization", J. Biol. Chem., 274(45):32248–32257 (1999).

Zhang, et al., "Cellular trafficking of G protein–coupled receptor/β–arrestin endocytic complexes", J. Biol. Chem., 274(16):10999–11006 (1999).

Kovoor, et al., "Targeted construction of phosphorylation–independent β–arrestin mutants with constitutive activity in cells", J. Biol. Chem., 274(11):6831–6834 (1999).

pICAST ALC

```
  1  CTGCAGCCTG AATATGGGCC AAACAGGATA TCTGTGGTAA GCAGTTCCTG
     GACGTCGGAC TTATACCCGG TTTGTCCTAT AGACACCATT CGTCAAGGAC

51  CCCCGGCTCA GGGCCAAGAA CAGATGGAAC AGCTGAATAT GGGCCAAACA
     GGGGCCGAGT CCCGGTTCTT GTCTACCTTG TCGACTTATA CCCGGTTTGT

101  GGATATCTGT GGTAAGCAGT TCCTGCCCCG GCTCAGGGCC AAGAACAGAT
     CCTATAGACA CCATTCGTCA AGGACGGGGC CGAGTCCCGG TTCTTGTCTA

151  GGTCCCCAGA TGCGGTCCAG CCCTCAGCAG TTTCTAGAGA ACCATCAGAT
     CCAGGGGTCT ACGCCAGGTC GGGAGTCGTC AAAGATCTCT TGGTAGTCTA

201  GTTTCCAGGG TGCCCCAAGG ACCTGAAATG ACCCTGTGCC TTATTTGAAC
     CAAAGGTCCC ACGGGGTTCC TGGACTTTAC TGGGACACGG AATAAACTTG

251  TAACCAATCA GTTCGCTTCT CGCTTCTGTT CGCGCGCTTC TGCTCCCCGA
     ATTGGTTAGT CAAGCGAAGA GCGAAGACAA GCGCGCGAAG ACGAGGGGCT

301  GCTCAATAAA AGAGCCCACA ACCCCTCACT CGGGGCGCCA GTCCTCCGAT
     CGAGTTATTT TCTCGGGTGT TGGGGAGTGA GCCCCGCGGT CAGGAGGCTA

351  TGACTGAGTC GCCCGGGTAC CCGTGTATCC AATAAACCCT CTTGCAGTTG
     ACTGACTCAG CGGGCCCATG GGCACATAGG TTATTTGGGA GAACGTCAAC

401  CATCCGACTT GTGGTCTCGC TGTTCCTTGG GAGGGTCTCC TCTGAGTGAT
     GTAGGCTGAA CACCAGAGCG ACAAGGAACC CTCCCAGAGG AGACTCACTA

451  TGACTACCCG TCAGCGGGGG TCTTTCATTT GGGGGCTCGT CCGGGATCGG
     ACTGATGGGC AGTCGCCCCC AGAAAGTAAA CCCCCGAGCA GGCCCTAGCC

501  GAGACCCCTG CCCAGGGACC ACCGACCCAC CACCGGGAGG CAAGCTGGCC
     CTCTGGGGAC GGGTCCCTGG TGGCTGGGTG GTGGCCCTCC GTTCGACCGG

551  AGCAACTTAT CTGTGTCTGT CCGATTGTCT AGTGTCTATG ACTGATTTTA
     TCGTTGAATA GACACAGACA GGCTAACAGA TCACAGATAC TGACTAAAAT

601  TGCGCCTGCG TCGGTACTAG TTAGCTAACT AGCTCTGTAT CTGGCGGACC
     ACGCGGACGC AGCCATGATC AATCGATTGA TCGAGACATA GACCGCCTGG
```

FIG. 10B pICAST ALC

```
 651   CGTGGTGGAA CTGACGAGTT CTGAACACCC GGCCGCAACC CTGGGAGACG
       GCACCACCTT GACTGCTCAA GACTTGTGGG CCGGCGTTGG GACCCTCTGC

701   TCCCAGGGAC TTTGGGGGCC GTTTTTGTGG CCCGACCTGA GGAAGGGAGT
       AGGGTCCCTG AAACCCCCGG CAAAAACACC GGGCTGGACT CCTTCCCTCA

751   CGATGTGGAA TCCGACCCCG TCAGGATATG TGGTTCTGGT AGGAGACGAG
       GCTACACCTT AGGCTGGGGC AGTCCTATAC ACCAAGACCA TCCTCTGCTC

801   AACCTAAAAC AGTTCCCGCC TCCGTCTGAA TTTTTGCTTT CGGTTTGGAA
       TTGGATTTTG TCAAGGGCGG AGGCAGACTT AAAAACGAAA GCCAAACCTT

851   CCGAAGCCGC GCGTCTTGTC TGCTGCAGCA TCGTTCTGTG TTGTCTCTGT
       GGCTTCGGCG CGCAGAACAG ACGACGTCGT AGCAAGACAC AACAGAGACA

901   CTGACTGTGT TTCTGTATTT GTCTGAAAAT TAGGGCCAGA CTGTTACCAC
       GACTGACACA AAGACATAAA CAGACTTTTA ATCCCGGTCT GACAATGGTG

951   TCCCTTAAGT TTGACCTTAG GTAACTGGAA AGATGTCGAG CGGCTCGCTC
       AGGGAATTCA AACTGGAATC CATTGACCTT TCTACAGCTC GCCGAGCGAG

1001   ACAACCAGTC GGTAGATGTC AAGAAGAGAC GTTGGGTTAC CTTCTGCTCT
       TGTTGGTCAG CCATCTACAG TTCTTCTCTG CAACCCAATG GAAGACGAGA

1051   GCAGAATGGC CAACCTTTAA CGTCGGATGG CCGCGAGACG GCACCTTTAA
       CGTCTTACCG GTTGGAAATT GCAGCCTACC GGCGCTCTGC CGTGGAAATT

1101   CCGAGACCTC ATCACCCAGG TTAAGATCAA GGTCTTTTCA CCTGGCCCGC
       GGCTCTGGAG TAGTGGGTCC AATTCTAGTT CCAGAAAAGT GGACCGGGCG

1151   ATGGACACCC AGACCAGGTC CCCTACATCG TGACCTGGGA AGCCTTGGCT
       TACCTGTGGG TCTGGTCCAG GGGATGTAGC ACTGGACCCT TCGGAACCGA

1201   TTTGACCCCC CTCCCTGGGT CAAGCCCTTT GTACACCCTA AGCCTCCGCC
       AAACTGGGGG GAGGGACCCA GTTCGGGAAA CATGTGGGAT TCGGAGGCGG

1251   TCCTCTTCCT CCATCCGCCC CGTCTCTCCC CCTTGAACCT CCTCGTTCGA
       AGGAGAAGGA GGTAGGCGGG GCAGAGAGGG GGAACTTGGA GGAGCAAGCT
```

FIG.10C pICAST ALC

```
1301  CCCCGCCTCG ATCCTCCCTT TATCCAGCCC TCACTCCTTC TCTAGGCGCC
      GGGGCGGAGC TAGGAGGGAA ATAGGTCGGG AGTGAGGAAG AGATCCGCGG

351  GGCCGCTCTA GCCCATTAAT ACGACTCACT ATAGGGCGAT TCGAATCAGG
      CCGGCGAGAT CGGGTAATTA TGCTGAGTGA TATCCCGCTA AGCTTAGTCC

1401  CCTTGGCGCG CCGGATCCTT AATTAAGCGC AATTGGGAGG TGGCGGTAGC
      GGAACCGCGC GGCCTAGGAA TTAATTCGCG TTAACCCTCC ACCGCCATCG
```

```
+2            M  G  V  I  T  D  S  L  A  V  V  A  R  T  D
           ]------------------------------------------------
1451  CTCGAGATGG GCGTGATTAC GGATTCACTG GCCGTCGTGG CCCGCACCGA
      GAGCTCTACC CGCACTAATG CCTAAGTGAC CGGCAGCACC GGGCGTGGCT
```

```
+2       R  P  S  Q  Q  L  R  S  L  N  G  E  W  R  F  A
      -------------------------------------------------------
1501  TCGCCCTTCC CAACAGTTAC GCAGCCTGAA TGGCGAATGG CGCTTTGCCT
      AGCGGGAAGG GTTGTCAATG CGTCGGACTT ACCGCTTACC GCGAAACGGA
```

```
+2       W  F  P  A  P  E  A  V  P  E  S  W  L  E  C  D  L
      ----------------------------------------------------------
1551  GGTTTCCGGC ACCAGAAGCG GTGCCGGAAA GCTGGCTGGA GTGCGATCTT
      CCAAAGGCCG TGGTCTTCGC CACGGCCTTT CGACCGACCT CACGCTAGAA
```

```
+2       P  E  A  D  T  V  V  V  P  S  N  W  Q  M  H  G  Y
      ----------------------------------------------------------
1601  CCTGAGGCCG ATACTGTCGT CGTCCCCTCA AACTGGCAGA TGCACGGTTA
      GGACTCCGGC TATGACAGCA GCAGGGGAGT TTGACCGTCT ACGTGCCAAT
```

```
+2       D  A  P  I  Y  T  N  V  T  Y  P  I  T  V  N  P
      ------------------------------------------------------
1651  CGATGCGCCC ATCTACACCA ACGTGACCTA TCCCATTACG GTCAATCCGC
      GCTACGCGGG TAGATGTGGT TGCACTGGAT AGGGTAATGC CAGTTAGGCG
```

```
+2       P  F  V  P  T  E  N  P  T  G  C  Y  S  L  T  F  N
      ----------------------------------------------------------
1701  CGTTTGTTCC CACGGAGAAT CCGACGGGTT GTTACTCGCT CACATTTAAT
      GCAAACAAGG GTGCCTCTTA GGCTGCCCAA CAATGAGCGA GTGTAAATTA
```

FIG. 10D pICAST ALC

```
+2       V  D  E  S  W  L  Q  E  G  Q  T  R  I  I  F  D  G
         ---------------------------------------------------
1751   GTTGATGAAA GCTGGCTACA GGAAGGCCAG ACGCGAATTA TTTTTGATGG
       CAACTACTTT CGACCGATGT CCTTCCGGTC TGCGCTTAAT AAAAACTACC

+2        V  N  S  A  F  H  L  W  C  N  G  R  W  V  G  Y
         ---------------------------------------------------
1801   CGTTAACTCG GCGTTTCATC TGTGGTGCAA CGGGCGCTGG GTCGGTTACG
       GCAATTGAGC CGCAAAGTAG ACACCACGTT GCCCGCGACC CAGCCAATGC

+2        G  Q  D  S  R  L  P  S  E  F  D  L  S  A  F  L  R
         ---------------------------------------------------
1851   GCCAGGACAG TCGTTTGCCG TCTGAATTTG ACCTGAGCGC ATTTTTACGC
       CGGTCCTGTC AGCAAACGGC AGACTTAAAC TGGACTCGCG TAAAAATGCG

+2        A  G  E  N  R  L  A  V  M  V  L  R  W  S  D  G  S
         ---------------------------------------------------
1901   GCCGGAGAAA ACCGCCTCGC GGTGATGGTG CTGCGCTGGA GTGACGGCAG
       CGGCCTCTTT TGGCGGAGCG CCACTACCAC GACGCGACCT CACTGCCGTC

+2        Y  L  E  D  Q  D  M  W  R  M  S  G  I  F  R  D
         ---------------------------------------------------
1951   TTATCTGGAA GATCAGGATA TGTGGCGGAT GAGCGGCATT TTCCGTGACG
       AATAGACCTT CTAGTCCTAT ACACCGCCTA CTCGCCGTAA AAGGCACTGC

+2        V  S  L  L  H  K  P  T  T  Q  I  S  D  F  H  V  A
         ---------------------------------------------------
2001   TCTCGTTGCT GCATAAACCG ACTACACAAA TCAGCGATTT CCATGTTGCC
       AGAGCAACGA CGTATTTGGC TGATGTGTTT AGTCGCTAAA GGTACAACGG

+2        T  R  F  N  D  D  F  S  R  A  V  L  E  A  E  V  Q
         ---------------------------------------------------
2051   ACTCGCTTTA ATGATGATTT CAGCCGCGCT GTACTGGAGG CTGAAGTTCA
       TGAGCGAAAT TACTACTAAA GTCGGCGCGA CATGACCTCC GACTTCAAGT
```

FIG. 10E pICAST ALC

```
+2       M  C  G  E  L  R  D  Y  L  R  V  T  V  S  L  W
         ---------------------------------------------------------
2101    GATGTGCGGC GAGTTGCGTG ACTACCTACG GGTAACAGTT TCTTTATGGC
        CTACACGCCG CTCAACGCAC TGATGGATGC CCATTGTCAA AGAAATACCG

+2        Q  G  E  T  Q  V  A  S  G  T  A  P  F  G  G  E  I
         ---------------------------------------------------------
2151    AGGGTGAAAC GCAGGTCGCC AGCGGCACCG CGCCTTTCGG CGGTGAAATT
        TCCCACTTTG CGTCCAGCGG TCGCCGTGGC GCGGAAAGCC GCCACTTTAA

+2         I  D  E  R  G  G  Y  A  D  R  V  T  L  R  L  N  V
         ---------------------------------------------------------
2201    ATCGATGAGC GTGGTGGTTA TGCCGATCGC GTCACACTAC GTCTGAACGT
        TAGCTACTCG CACCACCAAT ACGGCTAGCG CAGTGTGATG CAGACTTGCA

+2        E  N  P  K  L  W  S  A  E  I  P  N  L  Y  R  A
         ---------------------------------------------------------
2251    CGAAAACCCG AAACTGTGGA GCGCCGAAAT CCCGAATCTC TATCGTGCGG
        GCTTTTGGGC TTTGACACCT CGCGGCTTTA GGGCTTAGAG ATAGCACGCC

+2        V  V  E  L  H  T  A  D  G  T  L  I  E  A  E  A  C
         ---------------------------------------------------------
2301    TGGTTGAACT GCACACCGCC GACGGCACGC TGATTGAAGC AGAAGCCTGC
        ACCAACTTGA CGTGTGGCGG CTGCCGTGCG ACTAACTTCG TCTTCGGACG

+2        D  V  G  F  R  E  V  R  I  E  N  G  L  L  L  N
         ---------------------------------------------------------
2351    GATGTCGGTT TCCGCGAGGT GCGGATTGAA AATGGTCTGC TGCTGCTGAA
        CTACAGCCAA AGGCGCTCCA CGCCTAACTT TTACCAGACG ACGACGACTT

+2       G  K  P  L  L  I  R  G  V  N  R  H  E  H  H  P
         ---------------------------------------------------------
2401    CGGCAAGCCG TTGCTGATTC GAGGCGTTAA CCGTCACGAG CATCATCCTC
        GCCGTTCGGC AACGACTAAG CTCCGCAATT GGCAGTGCTC GTAGTAGGAG
```

FIG. 10F pICAST ALC

```
+2      L  H  G  Q  V  M  D  E  Q  T  M  V  Q  D  I  L  L
        ---------------------------------------------------
2451    TGCATGGTCA GGTCATGGAT GAGCAGACGA TGGTGCAGGA TATCCTGCTG
        ACGTACCAGT CCAGTACCTA CTCGTCTGCT ACCACGTCCT ATAGGACGAC

+2         M  K  Q  N  N  F  N  A  V  R  C  S  H  Y  P  N  H
        ---------------------------------------------------
2501    ATGAAGCAGA ACAACTTTAA CGCCGTGCGC TGTTCGCATT ATCCGAACCA
        TACTTCGTCT TGTTGAAATT GCGGCACGCG ACAAGCGTAA TAGGCTTGGT

+2         P  L  W  Y  T  L  C  D  R  Y  G  L  Y  V  V  D
        ---------------------------------------------------
2551    TCCGCTGTGG TACACGCTGT GCGACCGCTA CGGCCTGTAT GTGGTGGATG
        AGGCGACACC ATGTGCGACA CGCTGGCGAT GCCGGACATA CACCACCTAC

+2         E  A  N  I  E  T  H  G  M  V  P  M  N  R  L  T  D
        ---------------------------------------------------
2601    AAGCCAATAT TGAAACCCAC GGCATGGTGC CAATGAATCG TCTGACCGAT
        TTCGGTTATA ACTTTGGGTG CCGTACCACG GTTACTTAGC AGACTGGCTA

+2         D  P  R  W  L  P  A  M  S  E  R  V  T  R  M  V  Q
        ---------------------------------------------------
2651    GATCCGCGCT GGCTACCGGC GATGAGCGAA CGCGTAACGC GAATGGTGCA
        CTAGGCGCGA CCGATGGCCG CTACTCGCTT GCGCATTGCG CTTACCACGT

+2         R  D  R  N  H  P  S  V  I  I  W  S  L  G  N  E
        ---------------------------------------------------
2701    GCGCGATCGT AATCACCCGA GTGTGATCAT CTGGTCGCTG GGGAATGAAT
        CGCGCTAGCA TTAGTGGGCT CACACTAGTA GACCAGCGAC CCCTTACTTA

+2         S  G  H  G  A  N  H  D  A  L  Y  R  W  I  K  S  V
        ---------------------------------------------------
2751    CAGGCCACGG CGCTAATCAC GACGCGCTGT ATCGCTGGAT CAAATCTGTC
        GTCCGGTGCC GCGATTAGTG CTGCGCGACA TAGCGACCTA GTTTAGACAG
```

FIG. 10G pICAST ALC

```
 +2        D  P  S   R  P  V  Q   Y  E  G   G  G  A  D   T  T  A
           ................................................................
2801      GATCCTTCCC GCCCGGTGCA GTATGAAGGC GGCGGAGCCG ACACCACGGC
          CTAGGAAGGG CGGGCCACGT CATACTTCCG CCGCCTCGGC TGTGGTGCCG

+2         T  D  I   I  C  P  M   Y  A  R   V  D  E   D  Q  P
           ................................................................
2851      CACCGATATT ATTTGCCCGA TGTACGCGCG CGTGGATGAA GACCAGCCCT
          GTGGCTATAA TAAACGGGCT ACATGCGCGC GCACCTACTT CTGGTCGGGA

+2        F  P  A  V   P  K  W   S  I  K  K   W  L  S   L  P  G
           ................................................................
2901      TCCCGGCTGT GCCGAAATGG TCCATCAAAA AATGGCTTTC GCTACCTGGA
          AGGGCCGACA CGGCTTTACC AGGTAGTTTT TTACCGAAAG CGATGGACCT

+2         E  T  R  P   L  I  L   C  E  Y   A  H  A  M   G  N  S
           ................................................................
2951      GAGACGCGCC CGCTGATCCT TTGCGAATAC GCCCACGCGA TGGGTAACAG
          CTCTGCGCGG GCGACTAGGA AACGCTTATG CGGGTGCGCT ACCCATTGTC

+2         L  G  G   F  A  K  Y   W  Q  A   F  R  Q   Y  P  R
           ................................................................
3001      TCTTGGCGGT TTCGCTAAAT ACTGGCAGGC GTTTCGTCAG TATCCCCGTT
          AGAACCGCCA AAGCGATTTA TGACCGTCCG CAAAGCAGTC ATAGGGGCAA

+2         L  Q  G  G   F  V  W   D  W  V  D   Q  S  L   I  K  Y
           ................................................................
3051      TACAGGGCGG CTTCGTCTGG GACTGGGTGG ATCAGTCGCT GATTAAATAT
          ATGTCCCGCC GAAGCAGACC CTGACCCACC TAGTCAGCGA CTAATTTATA

+2         D  E  N   G  N  P  W   S  A  Y   G  G  D   F  G  D  T
           ................................................................
3101      GATGAAAACG GCAACCCGTG GTCGGCTTAC GGCGGTGATT TTGGCGATAC
          CTACTTTTGC CGTTGGGCAC CAGCCGAATG CCGCCACTAA AACCGCTATG
```

FIG. 10H pICAST ALC

+2     P  N  D   R  Q  F   C   M  N  G   L  V  F   A  D  R

```
3151   GCCGAACGAT CGCCAGTTCT GTATGAACGG TCTGGTCTTT GCCGACCGCA
       CGGCTTGCTA GCGGTCAAGA CATACTTGCC AGACCAGAAA CGGCTGGCGT
```

+2     T  P  H  P   A  L   T   E  A  K   H   Q  Q   F  F  Q

```
3201   CGCCGCATCC AGCGCTGACG GAAGCAAAAC ACCAGCAGCA GTTTTTCCAG
       GCGGCGTAGG TCGCGACTGC CTTCGTTTTG TGGTCGTCGT CAAAAAGGTC
```

+2     F   R   L   S   G  Q   T    I   E   V    T   S  E   Y   L   F   R

```
3251   TTCCGTTTAT CCGGGCAAAC CATCGAAGTG ACCAGCGAAT ACCTGTTCCG
       AAGGCAAATA GGCCCGTTTG GTAGCTTCAC TGGTCGCTTA TGGACAAGGC
```

+2      H   S  D   N  E  L  L   H  W  M   V  A  L   D  G  K

```
3301   TCATAGCGAT AACGAGCTCC TGCACTGGAT GGTGGCGCTG GATGGTAAGC
       AGTATCGCTA TTGCTCGAGG ACGTGACCTA CCACCGCGAC CTACCATTCG
```

+2     P   L  A  S   G  E  V   P  L  D   V   A  P  Q    G  K  Q

```
3351   CGCTGGCAAG CGGTGAAGTG CCTCTGGATG TCGCTCCACA AGGTAAACAG
       GCGACCGTTC GCCACTTCAC GGAGACCTAC AGCGAGGTGT TCCATTTGTC
```

+2     L   I   E  L   P  E  L   P  Q  P   E  S  A  G   Q  L  W

```
3401   TTGATTGAAC TGCCTGAACT ACCGCAGCCG GAGAGCGCCG GCAACTCTG
       AACTAACTTG ACGGACTTGA TGGCGTCGGC CTCTCGCGGC CGTTGAGAC
```

+2     L   T  V   R  V  V   Q   P  N  A   T  A  W   S  E  A

```
3451   GCTCACAGTA CGCGTAGTGC AACCGAACGC GACCGCATGG TCAGAAGCCG
       CGAGTGTCAT GCGCATCACG TTGGCTTGCG CTGGCGTACC AGTCTTCGGC
```

FIG. 101 pICAST ALC

```
+2      G  H  I  S  A  W  Q   Q  W  R  L   A  E  N  L  S  V
        ..................................................
3501    GGCACATCAG CGCCTGGCAG CAGTGGCGTC TGGCGGAAAA CCTCAGTGTG
        CCGTGTAGTC GCGGACCGTC GTCACCGCAG ACCGCCTTTT GGAGTCACAC

+2       T  L  P  A   A  S  H   A  I  P   H  L  T  T   S  E  M
         ................................................
3551    ACGCTCCCCG CCGCGTCCCA CGCCATCCCG CATCTGACCA CCAGCGAAAT
        TGCGAGGGGC GGCGCAGGGT GCGGTAGGGC GTAGACTGGT GGTCGCTTTA

+2        D  F  C   I  E  L  G   N  K  R   W  Q  F   N  R  Q
          ..............................................
3601    GGATTTTTGC ATCGAGCTGG GTAATAAGCG TTGGCAATTT AACCGCCAGT
        CCTAAAAACG TAGCTCGACC CATTATTCGC AACCGTTAAA TTGGCGGTCA

+2       S  G  F  L   S  Q  M  W   I  G  D   K  K  Q  L   L  T
         ................................................
3651    CAGGCTTTCT TTCACAGATG TGGATTGGCG ATAAAAAACA ACTGCTGACG
        GTCCGAAAGA AAGTGTCTAC ACCTAACCGC TATTTTTTGT TGACGACTGC

+2       P  L  R  D   Q  F  T   R  A  P   L  D  N  D   I  G  V
         ................................................
3701    CCGCTGCGCG ATCAGTTCAC CCGTGCACCG CTGGATAACG ACATTGGCGT
        GGCGACGCGC TAGTCAAGTG GGCACGTGGC GACCTATTGC TGTAACCGCA

+2        S  E  A   T  R  I  D   P  N  A   W  V  E  R   W  K
          ..............................................
3751    AAGTGAAGCG ACCCGCATTG ACCCTAACGC CTGGGTCGAA CGCTGGAAGG
        TTCACTTCGC TGGGCGTAAC TGGGATTGCG GACCCAGCTT GCGACCTTCC

+2       A  A  G  H   Y  Q  A   E  A  A  L   L  Q  C   T  A  D
         ................................................
3801    CGGCGGGCCA TTACCAGGCC GAAGCAGCGT TGTTGCAGTG CACGGCAGAT
        GCCGCCCGGT AATGGTCCGG CTTCGTCGCA ACAACGTCAC GTGCCGTCTA
```

FIG. 10J pICAST ALC

```
+2       T  L  A  D  A  V  L  I  T  T  A  H  A  W  Q  H  Q
         ----------------------------------------------------
3851    ACACTTGCTG ATGCGGTGCT GATTACGACC GCTCACGCGT GGCAGCATCA
        TGTGAACGAC TACGCCACGA CTAATGCTGG CGAGTGCGCA CCGTCGTAGT

+2         G  K  T  L  F  I  S  R  K  T  Y  R  I  D  G  S
         ----------------------------------------------------
3901    GGGGAAAACC TTATTTATCA GCCGGAAAAC CTACCGGATT GATGGTAGTG
        CCCCTTTTGG AATAAATAGT CGGCCTTTTG GATGGCCTAA CTACCATCAC

+2        G  Q  M  A  I  T  V  D  V  E  V  A  S  D  T  P  H
         ----------------------------------------------------
3951    GTCAAATGGC GATTACCGTT GATGTTGAAG TGGCGAGCGA TACACCGCAT
        CAGTTTACCG CTAATGGCAA CTACAACTTC ACCGCTCGCT ATGTGGCGTA

+2        P  A  R  I  G  L  N  C  Q  L  A  Q  V  A  E  R  V
         ----------------------------------------------------
4001    CCGGCGCGGA TTGGCCTGAA CTGCCAGCTG GCGCAGGTAG CAGAGCGGGT
        GGCCGCGCCT AACCGGACTT GACGGTCGAC CGCGTCCATC GTCTCGCCCA

+2         N  W  L  G  L  G  P  Q  E  N  Y  P  D  R  L  T
         ----------------------------------------------------
4051    AAACTGGCTC GGATTAGGGC CGCAAGAAAA CTATCCCGAC CGCCTTACTG
        TTTGACCGAG CCTAATCCCG GCGTTCTTTT GATAGGGCTG GCGGAATGAC

+2        A  A  C  F  D  R  W  D  L  P  L  S  D  M  Y  T  P
         ----------------------------------------------------
4101    CCGCCTGTTT TGACCGCTGG GATCTGCCAT TGTCAGACAT GTATACCCCG
        GGCGGACAAA ACTGGCGACC CTAGACGGTA ACAGTCTGTA CATATGGGGC

+2        T  V  F  P  S  E  N  G  L  R  C  G  T  R  E  L  N
         ----------------------------------------------------
4151    TACGTCTTCC CGAGCGAAAA CGGTCTGCGC TGCGGGACGC GCGAATTGAA
        ATGCAGAAGG GCTCGCTTTT GCCAGACGCG ACGCCCTGCG CGCTTAACTT
```

FIG.10K pICAST ALC

```
+2      Y   G   P   H   Q   W   R   G   D   F   Q   F   N   I   S   R
        ----------------------------------------------------------------
4201    TTATGGCCCA CACCAGTGGC GCGGCGACTT CCAGTTCAAC ATCAGCCGCT
        AATACCGGGT GTGGTCACCG CGCCGCTGAA GGTCAAGTTG TAGTCGGCGA

+2      Y   S   Q   Q   Q   L   M   E   T   S   H   R   H   L   L   H   A
        ----------------------------------------------------------------
4251    ACAGTCAACA GCAACTGATG GAAACCAGCC ATCGCCATCT GCTGCACGCG
        TGTCAGTTGT CGTTGACTAC CTTTGGTCGG TAGCGGTAGA CGACGTGCGC

+2      E   E   G   T   W   L   N   I   D   G   F   H   M   G   I   G   G
        ----------------------------------------------------------------
4301    GAAGAAGGCA CATGGCTGAA TATCGACGGT TTCCATATGG GGATTGGTGG
        CTTCTTCCGT GTACCGACTT ATAGCTGGCA AAGGTATACC CCTAACCACC

+2      D   D   S   W   S   P   S   V   S   A   E   F   Q   L   S   A
        ----------------------------------------------------------------
4351    CGACGACTCC TGGAGCCCGT CAGTATCGGC GGAATTCCAG CTGAGCGCCG
        GCTGCTGAGG ACCTCGGGCA GTCATAGCCG CCTTAAGGTC GACTCGCGGC

+2      G   R   Y   H   Y   Q   L   V   W   C   Q   K   R   S   D   Y   K
        ----------------------------------------------------------------
4401    GTCGCTACCA TTACCAGTTG GTCTGGTGTC AAAAAAGATC TGACTATAAA
        CAGCGATGGT AATGGTCAAC CAGACCACAG TTTTTTCTAG ACTGATATTT

+2      D   E   D   L   D   H   H   H   H   H   R
        ---------------------------------------->
4451    GATGAGGACC TCGACCATCA TCATCATCAT CACCGGTAAT AATAGGTAGA
        CTACTCCTGG AGCTGGTAGT AGTAGTAGTA GTGGCCATTA TTATCCATCT

4501    TAAGTGACTG ATTAGATGCA TTGATCCCTC GACCAATTCC GGTTATTTTC
        ATTCACTGAC TAATCTACGT AACTAGGGAG CTGGTTAAGG CCAATAAAAG

4551    CACCATATTG CCGTCTTTTG GCAATGTGAG GGCCCGGAAA CCTGGCCCTG
        GTGGTATAAC GGCAGAAAAC CGTTACACTC CCGGGCCTTT GGACCGGGAC
```

FIG. 10L pICAST ALC

```
4601   TCTTCTTGAC GAGCATTCCT AGGGGTCTTT CCCCTCTCGC CAAAGGAATG
       AGAAGAACTG CTCGTAAGGA TCCCCAGAAA GGGGAGAGCG GTTTCCTTAC

4651   CAAGGTCTGT TGAATGTCGT GAAGGAAGCA GTTCCTCTGG AAGCTTCTTG
       GTTCCAGACA ACTTACAGCA CTTCCTTCGT CAAGGAGACC TTCGAAGAAC

4701   AAGACAAACA ACGTCTGTAG CGACCCTTTG CAGGCAGCGG AACCCCCCAC
       TTCTGTTTGT TGCAGACATC GCTGGGAAAC GTCCGTCGCC TTGGGGGGTG

4751   CTGGCGACAG GTGCCTCTGC GGCCAAAAGC CACGTGTATA AGATACACCT
       GACCGCTGTC CACGGAGACG CCGGTTTTCG GTGCACATAT TCTATGTGGA

4801   GCAAAGGCGG CACAACCCCA GTGCCACGTT GTGAGTTGGA TAGTTGTGGA
       CGTTTCCGCC GTGTTGGGGT CACGGTGCAA CACTCAACCT ATCAACACCT

4851   AAGAGTCAAA TGGCTCTCCT CAAGCGTATT CAACAAGGGG CTGAAGGATG
       TTCTCAGTTT ACCGAGAGGA GTTCGCATAA GTTGTTCCCC GACTTCCTAC

4901   CCCAGAAGGT ACCCCATTGT ATGGGATCTG ATCTGGGGCC TCGGTGCACA
       GGGTCTTCCA TGGGGTAACA TACCCTAGAC TAGACCCCGG AGCCACGTGT

4951   TGCTTTACAT GTGTTTAGTC GAGGTTAAAA AACGTCTAGG CCCCCCGAAC
       ACGAAATGTA CACAAATCAG CTCCAATTTT TTGCAGATCC GGGGGGCTTG

5001   CACGGGGACG TGGTTTTCCT TTGAAAAACA CGATGATAAT ACCATGATTG
       GTGCCCCTGC ACCAAAAGGA AACTTTTTGT GCTACTATTA TGGTACTAAC

5051   AACAAGATGG ATTGCACGCA GGTTCTCCGG CCGCTTGGGT GGAGAGGCTA
       TTGTTCTACC TAACGTGCGT CCAAGAGGCC GGCGAACCCA CCTCTCCGAT

5101   TTCGGCTATG ACTGGGCACA ACAGACAATC GGCTGCTCTG ATGCCGCCGT
       AAGCCGATAC TGACCCGTGT TGTCTGTTAG CCGACGAGAC TACGGCGGCA

5151   GTTCCGGCTG TCAGCGCAGG GGCGCCCGGT TCTTTTTGTC AAGACCGACC
       CAAGGCCGAC AGTCGCGTCC CCGCGGGCCA AGAAAAACAG TTCTGGCTGG
```

FIG. 10M pICAST ALC

```
5201   TGTCCGGTGC CCTGAATGAA CTGCAGGACG AGGCAGCGCG GCTATCGTGG
       ACAGGCCACG GGACTTACTT GACGTCCTGC TCCGTCGCGC CGATAGCACC

5251   CTGGCCACGA CGGGCGTTCC TTGCGCAGCT GTGCTCGACG TTGTCACTGA
       GACCGGTGCT GCCCGCAAGG AACGCGTCGA CACGAGCTGC AACAGTGACT

5301   AGCGGGAAGG GACTGGCTGC TATTGGGCGA AGTGCCGGGG CAGGATCTCC
       TCGCCCTTCC CTGACCGACG ATAACCCGCT TCACGGCCCC GTCCTAGAGG

5351   TGTCATCTCA CCTTGCTCCT GCCGAGAAAG TATCCATCAT GGCTGATGCA
       ACAGTAGAGT GGAACGAGGA CGGCTCTTTC ATAGGTAGTA CCGACTACGT

5401   ATGCGGCGGC TGCATACGCT TGATCCGGCT ACCTGCCCAT TCGACCACCA
       TACGCCGCCG ACGTATGCGA ACTAGGCCGA TGGACGGGTA AGCTGGTGGT

5451   AGCGAAACAT CGCATCGAGC GAGCACGTAC TCGGATGGAA GCCGGTCTTG
       TCGCTTTGTA GCGTAGCTCG CTCGTGCATG AGCCTACCTT CGGCCAGAAC

5501   TCGATCAGGA TGATCTGGAC GAAGAGCATC AGGGGCTCGC GCCAGCCGAA
       AGCTAGTCCT ACTAGACCTG CTTCTCGTAG TCCCCGAGCG CGGTCGGCTT

5551   CTGTTCGCCA GGCTCAAGGC GCGCATGCCC GACGGCGAGG ATCTCGTCGT
       GACAAGCGGT CCGAGTTCCG CGCGTACGGG CTGCCGCTCC TAGAGCAGCA

5601   GACCCATGGC GATGCCTGCT TGCCGAATAT CATGGTGGAA AATGGCCGCT
       CTGGGTACCG CTACGGACGA ACGGCTTATA GTACCACCTT TTACCGGCGA

5651   TTTCTGGATT CATCGACTGT GGCCGGCTGG GTGTGGCGGA CCGCTATCAG
       AAAGACCTAA GTAGCTGACA CCGGCCGACC CACACCGCCT GGCGATAGTC

5701   GACATAGCGT TGGCTACCCG TGATATTGCT GAAGAGCTTG GCGGCGAATG
       CTGTATCGCA ACCGATGGGC ACTATAACGA CTTCTCGAAC CGCCGCTTAC

5751   GGCTGACCGC TTCCTCGTGC TTTACGGTAT CGCCGCTCCC GATTCGCAGC
       CCGACTGGCG AAGGAGCACG AAATGCCATA GCGGCGAGGG CTAAGCGTCG
```

FIG.10N pICAST ALC

```
5801    GCATCGCCTT CTATCGCCTT CTTGACGAGT TCTTCTGAGC GGGACTCTGG
        CGTAGCGGAA GATAGCGGAA GAACTGCTCA AGAAGACTCG CCCTGAGACC

5851    GGTTCGCATC GATAAAATAA AAGATTTTAT TTAGTCTCCA GAAAAAGGGG
        CCAAGCGTAG CTATTTTATT TTCTAAAATA AATCAGAGGT CTTTTTCCCC

5901    GGAATGAAAG ACCCCACCTG TAGGTTTGGC AAGCTAGCTT AAGTAACGCC
        CCTTACTTTC TGGGGTGGAC ATCCAAACCG TTCGATCGAA TTCATTGCGG

5951    ATTTTGCAAG GCATGGAAAA ATACATAACT GAGAATAGAG AAGTTCAGAT
        TAAAACGTTC CGTACCTTTT TATGTATTGA CTCTTATCTC TTCAAGTCTA

6001    CAAGGTCAGG AACAGATGGA ACAGCTGAAT ATGGGCCAAA CAGGATATCT
        GTTCCAGTCC TTGTCTACCT TGTCGACTTA TACCCGGTTT GTCCTATAGA

6051    GTGGTAAGCA GTTCCTGCCC CGGCTCAGGG CCAAGAACAG ATGGAACAGC
        CACCATTCGT CAAGGACGGG GCCGAGTCCC GGTTCTTGTC TACCTTGTCG

6101    TGAATATGGG CCAAACAGGA TATCTGTGGT AAGCAGTTCC TGCCCCGGCT
        ACTTATACCC GGTTTGTCCT ATAGACACCA TTCGTCAAGG ACGGGGCCGA

6151    CAGGGCCAAG AACAGATGGT CCCCAGATGC GGTCCAGCCC TCAGCAGTTT
        GTCCCGGTTC TTGTCTACCA GGGGTCTACG CCAGGTCGGG AGTCGTCAAA

6201    CTAGAGAACC ATCAGATGTT TCCAGGGTGC CCCAAGGACC TGAAATGACC
        GATCTCTTGG TAGTCTACAA AGGTCCCACG GGGTTCCTGG ACTTTACTGG

6251    CTGTGCCTTA TTTGAACTAA CCAATCAGTT CGCTTCTCGC TTCTGTTCGC
        GACACGGAAT AAACTTGATT GGTTAGTCAA GCGAAGAGCG AAGACAAGCG

6301    GCGCTTCTGC TCCCCGAGCT CAATAAAAGA GCCCACAACC CCTCACTCGG
        CGCGAAGACG AGGGGCTCGA GTTATTTTCT CGGGTGTTGG GGAGTGAGCC

6351    GGCGCCAGTC CTCCGATTGA CTGAGTCGCC CGGGTACCCG TGTATCCAAT
        CCGCGGTCAG GAGGCTAACT GACTCAGCGG GCCCATGGGC ACATAGGTTA
```

FIG.100 pICAST ALC

```
6401  AAACCCTCTT GCAGTTGCAT CCGACTTGTG GTCTCGCTGT TCCTTGGGAG
      TTTGGGAGAA CGTCAACGTA GGCTGAACAC CAGAGCGACA AGGAACCCTC

6451  GGTCTCCTCT GAGTGATTGA CTACCCGTCA GCGGGGGTCT TTCATTCATG
      CCAGAGGAGA CTCACTAACT GATGGGCAGT CGCCCCCAGA AAGTAAGTAC

6501  CAGCATGTAT CAAAATTAAT TGGTTTTTTT TTCTTAAGTA TTTACATTAA
      GTCGTACATA GTTTTAATTA AACCAAAAAA AAGAATTCAT AAATGTAATT

6551  ATGGCCATAG TTGCATTAAT GAATCGGCCA ACGCGCGGGG AGAGGCGGTT
      TACCGGTATC AACGTAATTA CTTAGCCGGT TGCGCGCCCC TCTCCGCCAA

6601  TGCGTATTGG CGCTCTTCCG CTTCCTCGCT CACTGACTCG CTGCGCTCGG
      ACGCATAACC GCGAGAAGGC GAAGGAGCGA GTGACTGAGC GACGCGAGCC

6651  TCGTTCGGCT GCGGCGAGCG GTATCAGCTC ACTCAAAGGC GGTAATACGG
      AGCAAGCCGA CGCCGCTCGC CATAGTCGAG TGAGTTTCCG CCATTATGCC
```

FIG.10P pICAST ALN

```
CTGCAGCCTG AATATGGGCC AAACAGGATA TCTGTGGTAA GCAGTTCCTG CCCCGGCTCA      60
GACGTCGGAC TTATACCCGG TTTGTCCTAT AGACACCATT CGTCAAGGAC GGGGCCGAGT      60

GGGCCAAGAA CAGATGGAAC AGCTGAATAT GGGCCAAACA GGATATCTGT GGTAAGCAGT     120
CCCGGTTCTT GTCTACCTTG TCGACTTATA CCCGGTTTGT CCTATAGACA CCATTCGTCA     120

TCCTGCCCCG GCTCAGGGCC AAGAACAGAT GGTCCCCAGA TGCGGTCCAG CCCTCAGCAG     180
AGGACGGGGC CGAGTCCCGG TTCTTGTCTA CCAGGGGTCT ACGCCAGGTC GGGAGTCGTC     180

TTTCTAGAGA ACCATCAGAT GTTTCCAGGG TGCCCCAAGG ACCTGAAATG ACCCTGTGCC     240
AAAGATCTCT TGGTAGTCTA CAAAGGTCCC ACGGGGTTCC TGGACTTTAC TGGGACACGG     240

TTATTTGAAC TAACCAATCA GTTCGCTTCT CGCTTCTGTT CGCGCGCTTC TGCTCCCCGA     300
AATAAACTTG ATTGGTTAGT CAAGCGAAGA GCGAAGACAA GCGCGCGAAG ACGAGGGGCT     300

GCTCAATAAA AGAGCCCACA ACCCGTCACT CGGGGCGCCA GTCCTCCGAT TGACTGAGTC     360
CGAGTTATTT TCTCGGGTGT TGGGGAGTGA GCCCCGCGGT CAGGAGGCTA ACTGACTCAG     360

GCCCGGGTAC CCGTGTATCC AATAAACCCT CTTGCAGTTG CATCCGACTT GTGGTCTCGC     420
CGGGCCCATG GGCACATAGG TTATTTGGGA GAACGTCAAC GTAGGCTGAA CACCAGAGCG     420

TGTTCCTTGG GAGGGTCTCC TCTGAGTGAT TGACTACCCG TCAGCGGGGG TCTTTCATTT     480
ACAAGGAACC CTCCCAGAGG AGACTCACTA ACTGATGGGC AGTCGCCCCC AGAAAGTAAA     480

GGGGGCTCGT CCGGGATCGG GAGACCCCTG CCCAGGGACC ACCGACCCAC CACCGGGAGG     540
CCCCCGAGCA GGCCCTAGCC CTCTGGGGAC GGGTCCCTGG TGGCTGGGTG GTGGCCCTCC     540

CAAGCTGGCC AGCAACTTAT CTGTGTCTGT CCGATTGTCT AGTGTCTATG ACTGATTTTA     600
GTTCGACCGG TCGTTGAATA GACACAGACA GGCTAACAGA TCACAGATAC TGACTAAAAT     600

TGCGCCTGCG TCGGTACTAG TTAGCTAACT AGCTCTGTAT CTGGCGGACC CGTGGTGGAA     660
ACGCGGACGC AGCCATGATC AATCGATTGA TCGAGACATA GACCGCCTGG GCACCACCTT     660

CTGACGAGTT CTGAACACCC GGCCGCAACC CTGGGAGACG TCCCAGGGAC TTTGGGGGCC     720
GACTGCTCAA GACTTGTGGG CCGGCGTTGG GACCCTCTGC AGGGTCCCTG AAACCCCCGG     720

GTTTTTGTGG CCCGACCTGA GGAAGGGAGT CGATGTGGAA TCCGACCCCG TCAGGATATG     780
CAAAAACACC GGGCTGGACT CCTTCCCTCA GCTACACCTT AGGCTGGGGC AGTCCTATAC     780
```

FIG. 11B pICAST ALN

```
TGGTTCTGGT AGGAGACGAG AACCTAAAAC AGTTCCCGCC TCCGTCTGAA TTTTTGCTTT    840
ACCAAGACCA TCCTCTGCTC TTGGATTTTG TCAAGGGCGG AGGCAGACTT AAAAACGAAA    840

CGGTTTGGAA CCGAAGCCGC GCGTCTTGTC TGCTGCAGCA TCGTTCTGTG TTGTCTCTGT    900
GCCAAACCTT GGCTTCGGCG CGCAGAACAG ACGACGTCGT AGCAAGACAC AACAGAGACA    900

CTGACTGTGT TTCTGTATTT GTCTGAAAAT TAGGGCCAGA CTGTTACCAC TCCCTTAAGT    960
GACTGACACA AAGACATAAA CAGACTTTTA ATCCCGGTCT GACAATGGTG AGGGAATTCA    960

TTGACCTTAG GTAACTGGAA AGATGTCGAG CGGCTCGCTC ACAACCAGTC GGTAGATGTC   1020
AACTGGAATC CATTGACCTT TCTACAGCTC GCCGAGCGAG TGTTGGTCAG CCATCTACAG   1020

AAGAAGAGAC GTTGGGTTAC CTTCTGCTCT GCAGAATGGC CAACCTTTAA CGTCGGATGG   1080
TTCTTCTCTG CAACCCAATG GAAGACGAGA CGTCTTACCG GTTGGAAATT GCAGCCTACC   1080

CCGCGAGACG GCACCTTTAA CCGAGACCTC ATCACCCAGG TTAAGATCAA GGTCTTTTCA   1140
GGCGCTCTGC CGTGGAAATT GGCTCTGGAG TAGTGGGTCC AATTCTAGTT CCAGAAAAGT   1140

CCTGGCCCGC ATGGACACCC AGACCAGGTC CCCTACATCG TGACCTGGGA AGCCTTGGCT   1200
GGACCGGGCG TACCTGTGGG TCTGGTCCAG GGGATGTAGC ACTGGACCCT TCGGAACCGA   1200

TTTGACCCCC CTCCCTGGGT CAAGCCCTTT GTACACCCTA AGCCTCCGCC TCCTCTTCCT   1260
AAACTGGGGG GAGGGACCCA GTTCGGGAAA CATGTGGGAT TCGGAGGCGG AGGAGAAGGA   1260

CCATCCGCCC CGTCTCTCCC CCTTGAACCT CCTCGTTCGA CCCCGCCTCG ATCCTCCCTT   1320
GGTAGGCGGG GCAGAGAGGG GGAACTTGGA GGAGCAAGCT GGGGCGGAGC TAGGAGGGAA   1320

TATCCAGCCC TCACTCCTTC TCTAGGCGCC GGCCGCTCTA GCCCATTAAT ACGACTCACT   1380
ATAGGTCGGG AGTGAGGAAG AGATCCGCGG CCGGCGAGAT CGGGTAATTA TGCTGAGTGA   1380

ATAGGGCGAT TCGAACACCA TGCACCATCA TCATCATCAC GTCGACTATA AAGATGAGGA   1440
TATCCCGCTA AGCTTGTGGT ACGTGGTAGT AGTAGTAGTG CAGCTGATAT TTCTACTCCT   1440

CCTCGAGATG GGCGTGATTA CGGATTCACT GGCCGTCGTG GCCCGCACCG ATCGCCCTTC   1500
GGAGCTCTAC CCGCACTAAT GCCTAAGTGA CCGGCAGCAC CGGGCGTGGC TAGCGGGAAG   1500

CCAACAGTTA CGCAGCCTGA ATGGCGAATG GCGCTTTGCC TGGTTTCCGG CACCAGAAGC   1560
GGTTGTCAAT GCGTCGGACT TACCGCTTAC CGCGAAACGG ACCAAAGGCC GTGGTCTTCG   1560
```

FIG.11C pICAST ALN

```
GGTGCCGGAA AGCTGGCTGG AGTGCGATCT TCCTGAGGCC GATACTGTCG TCGTCCCCTC   1620
CCACGGCCTT TCGACCGACC TCACGCTAGA AGGACTCCGG CTATGACAGC AGCAGGGGAG   1620

AAACTGGCAG ATGCACGGTT ACGATGCGCC CATCTACACC AACGTGACCT ATCCCATTAC   1680
TTTGACCGTC TACGTGCCAA TGCTACGCGG GTAGATGTGG TTGCACTGGA TAGGGTAATG   1680

GGTCAATCCG CCGTTTGTTC CCACGGAGAA TCCGACGGGT TGTTACTCGC TCACATTTAA   1740
CCAGTTAGGC GGCAAACAAG GGTGCCTCTT AGGCTGCCCA ACAATGAGCG AGTGTAAATT   1740

TGTTGATGAA AGCTGGCTAC AGGAAGGCCA GACGCGAATT ATTTTTGATG GCGTTAACTC   1800
ACAACTACTT TCGACCGATG TCCTTCCGGT CTGCGCTTAA TAAAAACTAC CGCAATTGAG   1800

GGCGTTTCAT CTGTGGTGCA ACGGGCGCTG GGTCGGTTAC GGCCAGGACA GTCGTTTGCC   1860
CCGCAAAGTA GACACCACGT TGCCCGCGAC CCAGCCAATG CCGGTCCTGT CAGCAAACGG   1860

GTCTGAATTT GACCTGAGCG CATTTTTACG CGCCGGAGAA AACCGCCTCG CGGTGATGGT   1920
CAGACTTAAA CTGGACTCGC GTAAAAATGC GCGGCCTCTT TTGGCGGAGC GCCACTACCA   1920

GCTGGGCTGG AGTGACGGCA GTTATCTGGA AGATCAGGAT ATGTGGCGGA TGAGCGGCAT   1980
CGACGCGACC TCACTGCCGT CAATAGACCT TCTAGTCCTA TACACCGCCT ACTCGCCGTA   1980

TTTCCGTGAC GTCTCGTTGC TGCATAAACC GACTACACAA ATCAGCGATT TCCATGTTGC   2040
AAAGGCACTG CAGAGCAACG ACGTATTTGG CTGATGTGTT TAGTCGCTAA AGGTACAACG   2040

CACTCGCTTT AATGATGATT RCAGCCGCGC TGTACTGGAG GCTGAAGTTC AGATGTGCGG   2100
GTGAGCGAAA TTACTACTAA AGTCGGCGCG ACATGACCTC CGACTTCAAG TCTACACGCC   2100

CGAGTTGCGT GACTACCTAC GGGTAACAGT TTCTTTATGG CAGGGTGAAA CGCAGGTCGC   2160
GCTCAACGCA CTGATGGATG CCCATTGTCA AAGAAATACC GTCCCACTTT GCGTCCAGCG   2160

CAGCGGCACC GCGCCTTTCG GCGGTGAAAT TATCGATGAG CGTGGTGGTT ATGCCGATCG   2220
GTCGCCGTGG CGCGGAAAGC CGCCACTTTA ATAGCTACTC GCACCACCAA TACGGCTAGC   2220

CGTCACACTA CGTCTGAACG TCGAAAACCC GAAACTGTGG AGCGCCGAAA TCCCGAATCT   2280
GCAGTGTGAT GCAGACTTGC AGCTTTTGGG CTTTGACACC TCGCGGCTTT AGGGCTTAGA   2280

CTATCGTGCG GTGGTTGAAC TGCACACCGC CGACGGCACG CTGATTGAAG CAGAAGCCTG   2340
GATAGCACGC CACCAACTTG ACGTGTGGCG GCTGCCGTGC GACTAACTTC GTCTTCGGAC   2340
```

FIG. 11D pICAST ALN

```
CGATGTCGGT TTCCGCGAGG TGCGGATTGA AAATGGTCTG CTGCTGCTGA ACGGCAAGCC  2400
GCTACAGCCA AAGGCGCTCC ACGCCTAACT TTTACCAGAC GACGACGACT TGCCGTTCGG  2400

GTTGCTGATT CGAGGCGTTA ACCGTCACGA GCATCATCCT CTGCATGGTC AGGTCATGGA  2460
CAACGACTAA GCTCCGCAAT TGGCAGTGCT CGTAGTAGGA GACGTACCAG TCCAGTACCT  2460

TGAGCAGACG ATGGTGCAGG ATATCCTGCT GATGAAGCAG AACAACTTTA ACGCCGTGCG  2520
ACTCGTCTGC TACCACGTCC TATAGGACGA CTACTTCGTC TTGTTGAAAT TGCGGCACGC  2520

CTGTTCGCAT TATCCGAACC ATCCGCTGTG GTACACGCTG TGCGACCGCT ACGGCCTGTA  2580
GACAAGCGTA ATAGGCTTGG TAGGCGACAC CATGTGCGAC ACGCTGGCGA TGCCGGACAT  2580

TGTGGTGGAT GAAGCCAATA TTGAAACCCA CGGCATGGTG CCAATGAATC GTCTGACCGA  2640
ACACCACCTA CTTCGGTTAT AACTTTGGGT GCCGTACCAC GGTTACTTAG CAGACTGGCT  2640

TGATCCGCGC TGGCTACCGG CGATGAGCGA ACGCGTAACG CGAATGGTGC AGCGCGATCG  2700
ACTAGGCGCG ACCGATGGCC GCTACTCGCT TGCGCATTGC GCTTACCACG TCGCGCTAGC  2700

TAATCACCCG AGTGTGATCA TCTGGTCGCT GGGGAATGAA TCAGGCCACG GCGCTAATCA  2760
ATTAGTGGGC TCACACTAGT AGACCAGCGA CCCCTTACTT AGTCCGGTGC CGCGATTAGT  2760

CGACGCGCTG TATCGCTGGA TCAAATCTGT CGATCCTTCC CGCCCGGTGC AGTATGAAGG  2820
GCTGCGCGAC ATAGCGACCT AGTTTAGACA GCTAGGAAGG GCGGGCCACG TCATACTTCC  2820

CGGCGGAGCC GACACCACGG CCACCGATAT TATTTGCCCG ATGTACGCGC GCGTGGATGA  2880
GCCGCCTCGG CTGTGGTGCC GGTGGCTATA ATAAACGGGC TACATGCGCG CGCACCTACT  2880

AGACCAGCCC TTCCCGGCTG TGCCGAAATG GTCCATCAAA AAATGGCTTT CGCTACCTGG  2940
TCTGGTCGGG AAGGGCCGAC ACGGCTTTAC CAGGTAGTTT TTTACCGAAA GCGATGGACC  2940

AGAGACGCGC CCGCTGATCC TTTGCGAATA CGCCCACGCG ATGGGTAACA GTCTTGGCGG  3000
TCTCTGCGCG GGCGACTAGG AAACGCTTAT GCGGGTGCGC TACCCATTGT CAGAACCGCC  3000

TTTCGCTAAA TACTGGCAGG CGTTTCGTCA GTATCCCCGT TTACAGGGCG GCTTCGTCTG  3060
AAAGCGATTT ATGACCGTCC GCAAAGCAGT CATAGGGGCA AATGTCCCGC CGAAGCAGAC  3060

GGACTGGGTG GATCAGTCGC TGATTAAATA TGATGAAAAC GGCAACCCGT GGTCGGCTTA  3120
CCTGACCCAC CTAGTCAGCG ACTAATTTAT ACTACTTTTG CCGTTGGGCA CCAGCCGAAT  3120
```

FIG.11E pICAST ALN

```
CGGCGGTGAT TTTGGCGATA CGCCGAACGA TCGCCAGTTC TGTATGAACG GTCTGGTCTT  3180
GCCGCCACTA AAACCGCTAT GCGGCTTGCT AGCGGTCAAG ACATACTTGC CAGACCAGAA  3180

TGCCGACCGC ACGCCGCATC CAGCGCTGAC GGAAGCAAAA CACCAGCAGC AGTTTTTCCA  3240
ACGGCTGGCG TGCGGCGTAG GTCGCGACTG CCTTCGTTTT GTGGTCGTCG TCAAAAAGGT  3240

GTTCCGTTTA TCCGGGCAAA CCATCGAAGT GACCAGCGAA TACCTGTTCC GTCATAGCGA  3300
CAAGGCAAAT AGGCCCGTTT GGTAGCTTCA CTGGTCGCTT ATGGACAAGG CAGTATCGCT  3300

TAACGAGCTC CTGCACTGGA TGGTGGCGCT GGATGGTAAG CCGCTGGCAA GCGGTGAAGT  3360
ATTGCTCGAG GACGTGACCT ACCACCGCGA CCTACCATTC GGCGACCGTT CGCCACTTCA  3360

GCCTCTGGAT GTCGCTCCAC AAGGTAAACA GTTGATTGAA CTGCCTGAAC TACCGCAGCC  3420
CGGAGACCTA CAGCGAGGTG TTCCATTTGT CAACTAACTT GACGGACTTG ATGGCGTCGG  3420

GGAGAGCGCC GGGCAACTCT GGCTCACAGT ACGCGTAGTG CAACCGAACG CGACCGCATG  3480
CCTCTCGCGG CCCGTTGAGA CCGAGTGTCA TGCGCATCAC GTTGGCTTGC GCTGGCGTAC  3480

GTCAGAAGCC GGGCACATCA GCGCCTGGCA GCAGTGGCGT CTGGCGGAAA ACCTCAGTGT  3540
CAGTCTTCGG CCCGTGTAGT CGCGGACCGT CGTCACCGCA GACCGCCTTT TGGAGTCACA  3540

GACGCTCCCC GCCGCGTCCC ACGCCATCCC GCATCTGACC ACCAGCGAAA TGGATTTTTG  3600
CTGCGAGGGG CGGCGCAGGG TGCGGTAGGG CGTAGACTGG TGGTCGCTTT ACCTAAAAAC  3600

CATCGAGCTG GGTAATAAGC GTTGGCAATT TAACCGCCAG TCAGGCTTTC TTTCACAGAT  3660
GTAGCTCGAC CCATTATTCG CAACCGTTAA ATTGGCGGTC AGTCCGAAAG AAAGTGTCTA  3660

GTGGATTGGC GATAAAAAAC AACTGCTGAC GCCGCTGCGC GATCAGTTCA CCCGTGCACC  3720
CACCTAACCG CTATTTTTTG TTGACGACTG CGGCGACGCG CTAGTCAAGT GGGCACGTGG  3720

GCTGGATAAC GACATTGGCG TAAGTGAAGC GACCCGCATT GACCCTAACG CCTGGGTCGA  3780
CGACCTATTG CTGTAACCGC ATTCACTTCG CTGGGCGTAA CTGGGATTGC GGACCCAGCT  3780

ACGCTGGAAG GCGGCGGGCC ATTACCAGGC CGAAGCAGCG TTGTTGCAGT GCACGGCAGA  3840
TGCGACCTTC CGCCGCCCGG TAATGGTCCG GCTTCGTCGC AACAACGTCA CGTGCCGTCT  3840

TACACTTGCT GATGCGGTGC TGATTACGAC CGCTCACGCG TGGCAGCATC AGGGGAAAAC  3900
ATGTGAACGA CTACGCCACG ACTAATGCTG GCGAGTGCGC ACCGTCGTAG TCCCCTTTTG  3900
```

FIG.11F pICAST ALN

```
CTTATTTATC AGCCGGAAAA CCTACCGGAT TGATGGTAGT GGTCAAATGG CGATTACCGT  3960
GAATAAATAG TCGGCCTTTT GGATGGCCTA ACTACCATCA CCAGTTTACC GCTAATGGCA  3960

TGATGTTGAA GTGGCGAGCG ATACACCGCA TCCGGCGCGG ATTGGCCTGA ACTGCCAGCT  4020
ACTACAACTT CACCGCTCGC TATGTGGCGT AGGCCGCGCC TAACCGGACT TGACGGTCGA  4020

GGCGCAGGTA GCAGAGCGGG TAAACTGGCT CGGATTAGGG CCGCAAGAAA ACTATCCCGA  4080
CCGCGTCCAT CGTCTCGCCC ATTTGACCGA GCCTAATCCC GGCGTTCTTT TGATAGGGCT  4080

CCGCCTTACT GCCGCCTGTT TTGACCGCTG GATCTGCCA TTGTCAGACA TGTATACCCC  4140
GGCGGAATGA CGGCGGACAA AACTGGCGAC CCTAGACGGT AACAGTCTGT ACATATGGGG  4140

GTACGTCTTC CCGAGCGAAA ACGGTCTGCG CTGCGGGACG CGCGAATTGA ATTATGGCCC  4200
CATGCAGAAG GGCTCGCTTT TGCCAGACGC GACGCCCTGC GCGCTTAACT TAATACCGGG  4200

ACACCAGTGG CGCGGCGACT TCCAGTTCAA CATCAGCCGC TACAGTCAAC AGCAACTGAT  4260
TGTGGTCACC GCGCCGCTGA AGGTCAAGTT GTAGTCGGCG ATGTCAGTTG TCGTTGACTA  4260

GGAAACCAGC CATCGCCATC TGCTGCACGC GGAAGAAGGC ACATGGCTGA ATATCGACGG  4320
CCTTTGGTCG GTAGCGGTAG ACGACGTGCG CCTTCTTCCG TGTACCGACT TATAGCTGCC  4320

TTTCCATATG GGGATTGGTG GCGACGACTC CTGGAGCCCG TCAGTATCGG CGGAATTCCA  4380
AAAGGTATAC CCCTAACCAC CGCTGCTGAG GACCTCGGGC AGTCATAGCC GCCTTAAGGT  4380

GCTGAGCGCC GGTCGCTACC ATTACCAGTT GGTCTGGTGT CAAAAAAGAT CTGGAGGTGG  4440
CGACTCGCGG CCAGCGATGG TAATGGTCAA CCAGACCACA GTTTTTTCTA GACCTCCACC  4440

TGGCAGCAGG CCTTGGCGCG CCGGATCCTT AATTAACAAT TGACCGGTAA TAATAGGTAG  4500
ACCGTCGTCC GGAACCGCGC GGCCTAGGAA TTAATTGTTA ACTGGCCATT ATTATCCATC  4500

ATAAGTGACT GATTAGATGC ATTGATCCCT CGACCAATTC CGGTTATTTT CCACCATATT  4560
TATTCACTGA CTAATCTACG TAACTAGGGA GCTGGTTAAG GCCAATAAAA GGTGGTATAA  4560

GCCGTCTTTT GGCAATGTGA GGGCCCGGAA ACCTGGCCCT GTCTTCTTGA CGAGCATTCC  4620
CGGCAGAAAA CCGTTACACT CCCGGGCCTT TGGACCGGGA CAGAAGAACT GCTCGTAAGG  4620

TAGGGGTCTT TCCCCTCTCG CCAAAGGAAT GCAAGGTCTG TTGAATGTCG TGAAGGAAGC  4680
ATCCCCAGAA AGGGGAGAGC GGTTTCCTTA CGTTCCAGAC AACTTACAGC ACTTCCTTCG  4680
```

FIG.11G pICAST ALN

```
AGTTCCTCTG GAAGCTTCTT GAAGACAAAC AACGTCTGTA GCGACCCTTT GCAGGCAGCG    4740
TCAAGGAGAC CTTCGAAGAA CTTCTGTTTG TTGCAGACAT CGCTGGGAAA CGTCCGTCGC    4740

GAACCCCCCA CCTGGCGACA GGTGCCTCTG CGGCCAAAAG CCACGTGTAT AAGATACACC    4800
CTTGGGGGGT GGACCGCTGT CCACGGAGAC GCCGGTTTTC GGTGCACATA TTCTATGTGG    4800

TGCAAAGGCG GCACAACCCC AGTGCCACGT TGTGAGTTGG ATAGTTGTGG AAAGAGTCAA    4860
ACGTTTCCGC CGTGTTGGGG TCACGGTGCA ACACTCAACC TATCAACACC TTTCTCAGTT    4860

ATGGCTCTCC TCAAGCGTAT TCAACAAGGG GCTGAAGGAT GCCCAGAAGG TACCCCATTG    4920
TACCGAGAGG AGTTCGCATA AGTTGTTCCC CGACTTCCTA CGGGTCTTCC ATGGGGTAAC    4920

TATGGGATCT GATCTGGGGC CTCGGTGCAC ATGCTTTACA TGTGTTTAGT CGAGGTTAAA    4980
ATACCCTAGA CTAGACCCCG GAGCCACGTG TACGAAATGT ACACAAATCA GCTCCAATTT    4980

AAACGTCTAG GCCCCCCGAA CCACGGGGAC GTGGTTTTCC TTTGAAAAAC ACGATGATAA    5040
TTTGCAGATC CGGGGGGCTT GGTGCCCCTG CACCAAAAGG AAACTTTTTG TGCTACTATT    5040

TACCATGATT GAACAAGATG GATTGCACGC AGGTTCTCCG GCCGCTTGGG TGGAGAGGCT    5100
ATGGTACTAA CTTGTTCTAC CTAACGTGCG TCCAAGAGGC CGGCGAACCC ACCTCTCCGA    5100

ATTCGGCTAT GACTGGGCAC AACAGACAAT CGGCTGCTCT GATGCCGCCG TGTTCCGGCT    5160
TAAGCCGATA CTGACCCGTG TTGTCTGTTA GCCGACGAGA CTACGGCGGC ACAAGGCCGA    5160

GTCAGCGCAG GGGCGCCCGG TTCTTTTTGT CAAGACCGAC CTGTCCGGTG CCCTGAATGA    5220
CAGTCGCGTC CCCGCGGGCC AAGAAAAACA GTTCTGGCTG GACAGGCCAC GGGACTTACT    5220

ACTGCAGGAC GAGGCAGCGC GGCTATCGTG GCTGGCCACG ACGGGCGTTC CTTGCGCAGC    5280
TGACGTCCTG CTCCGTCGCG CCGATAGCAC CGACCGGTGC TGCCCGCAAG GAACGCGTCG    5280

TGTGCTCGAC GTTGTCACTG AAGCGGGAAG GGACTGGCTG CTATTGGGCG AAGTGCCGGG    5340
ACACGAGCTG CAACAGTGAC TTCGCCCTTC CCTGACCGAC GATAACCCGC TTCACGGCCC    5340

GCAGGATCTC CTGTCATCTC ACCTTGCTCC TGCCGAGAAA GTATCCATCA TGGCTGATGC    5400
CGTCCTAGAG GACAGTAGAG TGGAACGAGG ACGGCTCTTT CATAGGTAGT ACCGACTACG    5400

AATGCGGCGG CTGCATACGC TTGATCCGGC TACCTGCCCA TTCGACCACC AAGCGAAACA    5460
TTACGCCGCC GACGTATGCG AACTAGGCCG ATGGACGGGT AAGCTGGTGG TTCGCTTTGT    5460
```

FIG. 11H pICAST ALN

```
TCGCATCGAG CGAGCACGTA CTCGGATGGA AGCCGGTCTT GTCGATCAGG ATGATCTGGA   5520
AGCGTAGCTC GCTCGTGCAT GAGCCTACCT TCGGCCAGAA CAGCTAGTCC TACTAGACCT   5520

CGAAGAGCAT CAGGGGCTCG CGCCAGCCGA ACTGTTCGCC AGGCTCAAGG CGCGCATGCC   5580
GCTTCTCGTA GTCCCCGAGC GCGGTCGGCT TGACAAGCGG TCCGAGTTCC GCGCGTACGG   5580

CGACGGCGAG GATCTCGTCG TGACCCATGG CGATGCCTGC TTGCCGAATA TCATGGTGGA   5640
GCTGCCGCTC CTAGAGCAGC ACTGGGTACC GCTACGGACG AACGGCTTAT AGTACCACCT   5640

AAATGGCCGC TTTTCTGGAT TCATCGACTG TGGCCGGCTG GGTGTGGCGG ACCGCTATCA   5700
TTTACCGGCG AAAAGACCTA AGTAGCTGAC ACCGGCCGAC CCACACCGCC TGGCGATAGT   5700

GGACATAGCG TTGGCTACCC GTGATATTGC TGAAGAGCTT GGCGGCGAAT GGGCTGACCG   5760
CCTGTATCGC AACCGATGGG CACTATAACG ACTTCTCGAA CCGCCGCTTA CCCGACTGGC   5760

CTTCCTCGTG CTTTACGGTA TCGCCGCTCC CGATTCGCAG CGCATCGCCT TCTATCGCCT   5820
GAAGGAGCAC GAAATGCCAT AGCGGCGAGG GCTAAGCGTC GCGTAGCGGA AGATAGCGGA   5820

TCTTGACGAG TTCTTCTGAG CGGGACTCTG GGGTTCGCAT CGATAAAATA AAAGATTTTA   5880
AGAACTGCTC AAGAAGACTC GCCCTGAGAC CCCAAGCGTA GCTATTTTAT TTTCTAAAAT   5880

TTTAGTCTCC AGAAAAAGGG GGGAATGAAA GACCCCACCT GTAGGTTTGG CAAGCTAGCT   5940
AAATCAGAGG TCTTTTTCCC CCCTTACTTT CTGGGGTGGA CATCCAAACC GTTCGATCGA   5940

TAAGTAACGC CATTTTGCAA GGCATGGAAA AATACATAAC TGAGAATAGA GAAGTTCAGA   6000
ATTCATTGCG GTAAAACGTT CCGTACCTTT TTATGTATTG ACTCTTATCT CTTCAAGTCT   6000

TCAAGGTCAG GAACAGATGG AACAGCTGAA TATGGGCCAA ACAGGATATC TGTGGTAAGC   6060
AGTTCCAGTC CTTGTCTACC TTGTCGACTT ATACCCGGTT TGTCCTATAG ACACCATTCG   6060

AGTTCCTGCC CCGGCTCAGG GCCAAGAACA GATGGAACAG CTGAATATGG GCCAAACAGG   6120
TCAAGGACGG GGCCGAGTCC CGGTTCTTGT CTACCTTGTC GACTTATACC CGGTTTGTCC   6120

ATATCTGTGG TAAGCAGTTC CTGCCCCGGC TCAGGGCCAA GAACAGATGG TCCCCAGATG   6180
TATAGACACC ATTCGTCAAG GACGGGGCCG AGTCCCGGTT CTTGTCTACC AGGGGTCTAC   6180

CGGTCCAGCC CTCAGCAGTT TCTAGAGAAC CATCAGATGT TTCCAGGGTG CCCCAAGGAC   6240
GCCAGGTCGG GAGTCGTCAA AGATCTCTTG GTAGTCTACA AAGGTCCCAC GGGGTTCCTG   6240
```

FIG. 11I pICAST ALN

```
CTGAAATGAC CCTGTGCCTT ATTTGAACTA ACCAATCAGT TCGCTTCTCG CTTCTGTTCG  6300
GACTTTACTG GGACACGGAA TAAACTTGAT TGGTTAGTCA AGCGAAGAGC GAAGACAAGC  6300

CGCGCTTCTG CTCCCCGAGC TCAATAAAAG AGCCCACAAC CCCTCACTCG GGGCGCCAGT  6360
GCGCGAAGAC GAGGGGCTCG AGTTATTTTC TCGGGTGTTG GGGAGTGAGC CCCGCGGTCA  6360

CCTCCGATTG ACTGAGTCGC CCGGGTACCC GTGTATCCAA TAAACCCTCT TGCAGTTGCA  6420
GGAGGCTAAC TGACTCAGCG GGCCCATGGG CACATAGGTT ATTTGGGAGA ACGTCAACGT  6420

TCCGACTTGT GGTCTCGCTG TTCCTTGGGA GGGTCTCCTC TGAGTGATTG ACTACCCGTC  6480
AGGCTGAACA CCAGAGCGAC AAGGAACCCT CCCAGAGGAG ACTCACTAAC TGATGGGCAG  6480

AGCGGGGGTC TTTCATTCAT GCAGCATGTA TCAAAATTAA TTTGGTTTTT TTTCTTAAGT  6540
TCGCCCCCAG AAAGTAAGTA CGTCGTACAT AGTTTTAATT AAACCAAAAA AAAGAATTCA  6540

ATTTACATTA AATGGCCATA GTTGCATTAA TGAATCGGCC AACGCGCGGG GAGAGGCGGT  6600
TAAATGTAAT TTACCGGTAT CAACGTAATT ACTTAGCCGG TTGCGCGCCC CTCTCCGCCA  6600

AACGCATAAC CGCGAGAAGG CGAAGGAGCG AGTGACTGAG CGACGCGAGC CAGCAAGCCG  6660
TTGCGTATTG GCGCTCTTCC GCTTCCTCGC TCACTGACTC GCTGCGCTCG GTCGTTCGGC  6660

TGCGGCGAGC GGTATCAGCT CACTCAAAGG CGGTAATACG GTTATCCACA GAATCAGGGG  6720
ACGCCGCTCG CCATAGTCGA GTGAGTTTCC GCCATTATGC CAATAGGTGT CTTAGTCCCC  6720

ATAACGCAGG AAAGAACATG TGAGCAAAAG GCCAGCAAAA GGCCAGGAAC CGTAAAAAGG  6780
TATTGCGTCC TTTCTTGTAC ACTCGTTTTC CGGTCGTTTT CCGGTCCTTG GCATTTTTCC  6780

CCGCGTTGCT GGCGTTTTTC CATAGGCTCC GCCCCCCTGA CGAGCATCAC AAAAATCGAC  6840
GGCGCAACGA CCGCAAAAAG GTATCCGAGG CGGGGGGACT GCTCGTAGTG TTTTTAGCTG  6840

GCTCAAGTCA GAGGTGGCGA AACCCGACAG GACTATAAAG ATACCAGGCG TTTCCCCCTG  6900
CGAGTTCAGT CTCCACCGCT TTGGGCTGTC CTGATATTTC TATGGTCCGC AAAGGGGGAC  6900

GAAGCTCCCT CGTGCGCTCT CCTGTTCCGA CCCTGCCGCT TACCGGATAC CTGTCCGCCT  6960
CTTCGAGGGA GCACGCGAGA GGACAAGGCT GGGACGGCGA ATGGCCTATG GACAGGCGGA  6960

TTCTCCCTTC GGGAAGCGTG GCGCTTTCTC ATAGCTCACG CTGTAGGTAT CTCAGTTCGG  7020
AAGAGGGAAG CCCTTCGCAC CGCGAAAGAG TATCGAGTGC GACATCCATA GAGTCAAGCC  7020
```

FIG.11J pICAST ALN

```
TGTAGGTCGT TCGCTCCAAG CTGGGCTGTG TGCACGAACC CCCCGTTCAG CCCGACCGCT  7080
ACATCCAGCA AGCGAGGTTC GACCCGACAC ACGTGCTTGG GGGGCAAGTC GGGCTGGCGA  7080

GCGCCTTATC CGGTAACTAT CGTCTTGAGT CCAACCCGGT AAGACACGAC TTATCGCCAC  7140
CGCGGAATAG GCCATTGATA GCAGAACTCA GGTTGGGCCA TTCTGTGCTG AATAGCGGTG  7140

TGGCAGCAGC CACTGGTAAC AGGATTAGCA GAGCGAGGTA TGTAGGCGGT GCTACAGAGT  7200
ACCGTCGTCG GTGACCATTG TCCTAATCGT CTCGCTCCAT ACATCCGCCA CGATGTCTCA  7200

TCTTGAAGTG GTGGCCTAAC TACGGCTACA CTAGAAGAAC AGTATTTGGT ATCTGCGCTC  7260
AGAACTTCAC CACCGGATTG ATGCCGATGT GATCTTCTTG TCATAAACCA TAGACGCGAG  7260

TGCTGAAGCC AGTTACCTTC GGAAAAAGAG TTGGTAGCTC TTGATCCGGC AAACAAACCA  7320
ACGACTTCGG TCAATGGAAG CCTTTTTCTC AACCATCGAG AACTAGGCCG TTTGTTTGGT  7320

CCGCTGGTAG CGGTGGTTTT TTTGTTTGCA AGCAGCAGAT TACGCGCAGA AAAAAAGGAT  7380
GGCGACCATC GCCACCAAAA AAACAAACGT TCGTCGTCTA ATGCGCGTCT TTTTTTCCTA  7380

CTCAAGAAGA TCCTTTGATC TTTTCTACGG GGTCTGACGC TCAGTGGAAC GAAAACTCAC  7440
GAGTTCTTCT AGGAAACTAG AAAAGATGCC CCAGACTGCG AGTCACCTTG CTTTTGAGTG  7440

GTTAAGGGAT TTTGGTCATG AGATTATCAA AAAGGATCTT CACCTAGATC CTTTTGCGGC  7500
CAATTCCCTA AAACCAGTAC TCTAATAGTT TTTCCTAGAA GTGGATCTAG GAAAACGCCG  7500

CGCAAATCAA TCTAAAGTAT ATATGAGTAA ACTTGGTCTG ACAGTTACCA ATGCTTAATC  7560
GCGTTTAGTT AGATTTCATA TATACTCATT TGAACCAGAC TGTCAATGGT TACGAATTAG  7560

AGTGAGGCAC CTATCTCAGC GATCTGTCTA TTTCGTTCAT CCATAGTTGC CTGACTCCCC  7620
TCACTCCGTG GATAGAGTCG CTAGACAGAT AAAGCAAGTA GGTATCAACG GACTGAGGGG  7620

GTCGTGTAGA TAACTACGAT ACGGGAGGGC TTACCATCTG GCCCCAGTGC TGCAATGATA  7680
CAGCACATCT ATTGATGCTA TGCCCTCCCG AATGGTAGAC CGGGGTCACG ACGTTACTAT  7680

CCGCGAGACC CACGCTCACC GGCTCCAGAT TTATCAGCAA TAAACCAGCC AGCCGGAAGG  7740
GGCGCTCTGG GTGCGAGTGG CCGAGGTCTA AATAGTCGTT ATTTGGTCGG TCGGCCTTCC  7740

GCCGAGCGCA GAAGTGGTCC TGCAACTTTA TCCGCCTCCA TCCAGTCTAT TAATTGTTGC  7800
CGGCTCGCGT CTTCACCAGG ACGTTGAAAT AGGCGGAGGT AGGTCAGATA ATTAACAACG  7800
```

FIG.11K pICAST ALN

```
CGGGAAGCTA GAGTAAGTAG TTCGCCAGTT AATAGTTTGC GCAACGTTGT TGCCATTGCT    7860
GCCCTTCGAT CTCATTCATC AAGCGGTCAA TTATCAAACG CGTTGCAACA ACGGTAACGA    7860

ACAGGCATCG TGGTGTCACG CTCGTCGTTT GGTATGGCTT CATTCAGCTC CGGTTCCCAA    7920
TGTCCGTAGC ACCACAGTGC GAGCAGCAAA CCATACCGAA GTAAGTCGAG GCCAAGGGTT    7920

CGATCAAGGC GAGTTACATG ATCCCCCATG TTGTGCAAAA AAGCGGTTAG CTCCTTCGGT    7980
GCTAGTTCCG CTCAATGTAC TAGGGGGTAC AACACGTTTT TTCGCCAATC GAGGAAGCCA    7980

CCTCCGATCG TTGTCAGAAG TAAGTTGGCC GCAGTGTTAT CACTCATGGT TATGGCAGCA    8040
GGAGGCTAGC AACAGTCTTC ATTCAACCGG CGTCACAATA GTGAGTACCA ATACCGTCGT    8040

CTGCATAATT CTCTTACTGT CATGCCATCC GTAAGATGCT TTTCTGTGAC TGGTGAGTAC    8100
GACGTATTAA GAGAATGACA GTACGGTAGG CATTCTACGA AAAGACACTG ACCACTCATG    8100

TCAACCAAGT CATTCTGAGA ATAGTGTATG CGGCGACCGA GTTGCTCTTG CCCGGCGTCA    8160
AGTTGGTTCA GTAAGACTCT TATCACATAC GCCGCTGGCT CAACGAGAAC GGGCCGCAGT    8160

ATACGGGATA ATACCGCGCC ACATAGCAGA ACTTTAAAAG TGCTCATCAT TGGAAAACGT    8220
TATGCCCTAT TATGGCGCGG TGTATCGTCT TGAAATTTTC ACGAGTAGTA ACCTTTTGCA    8220

TCTTCGGGGC GAAAACTCTC AAGGATCTTA CCGCTGTTGA GATCCAGTTC GATGTAACCC    8280
AGAAGCCCCG CTTTTGAGAG TTCCTAGAAT GGCGACAACT CTAGGTCAAG CTACATTGGG    8280

ACTCGTGCAC CCAACTGATC TTCAGCATCT TTTACTTTCA CCAGCGTTTC TGGGTGAGCA    8340
TGAGCACGTG GGTTGACTAG AAGTCGTAGA AAATGAAAGT GGTCGCAAAG ACCCACTCGT    8340

AAAACAGGAA GGCAAAATGC CGCAAAAAAG GGAATAAGGG CGACACGGAA ATGTTGAATA    8400
TTTTGTCCTT CCGTTTTACG GCGTTTTTTC CCTTATTCCC GCTGTGCCTT TACAACTTAT    8400

CTCATACTCT TCCTTTTTCA ATATTATTGA AGCATTTATC AGGGTTATTG TCTCATGAGC    8460
GAGTATGAGA AGGAAAAAGT TATAATAACT TCGTAAATAG TCCCAATAAC AGAGTACTCG    8460

GGATACATAT TTGAATGTAT TTAGAAAAAT AAACAAATAG GGGTTCCGCG CACATTTC     8518
CCTATGTATA AACTTACATA AATCTTTTTA TTTGTTTATC CCCAAGGCGC GTGTAAAG     8518
```

FIG. 11L pICAST OMC

```
CTGCAGCCTG AATATGGGCC AAACAGGATA TCTGTGGTAA GCAGTTCCTG CCCCGGCTCA    60
GACGTCGGAC TTATACCCGG TTTGTCCTAT AGACACCATT CGTCAAGGAC GGGGCCGAGT    60

GGGCCAAGAA CAGATGGAAC AGCTGAATAT GGGCCAAACA GGATATCTGT GGTAAGCAGT   120
CCCGGTTCTT GTCTACCTTG TCGACTTATA CCCGGTTTGT CCTATAGACA CCATTCGTCA   120

TCCTGCCCCG GCTCAGGGCC AAGAACAGAT GGTCCCCAGA TGCGGTCCAG CCCTCAGCAG   180
AGGACGGGGC CGAGTCCCGG TTCTTGTCTA CCAGGGGTCT ACGCCAGGTC GGGAGTCGTC   180

TTTCTAGAGA ACCATCAGAT GTTTCCAGGG TGCCCCAAGG ACCTGAAATG ACCCTGTGCC   240
AAAGATCTCT TGGTAGTCTA CAAAGGTCCC ACGGGGTTCC TGGACTTTAC TGGGACACGG   240

TTATTTGAAC TAACCAATCA GTTCGCTTCT CGCTTCTGTT CGCGCGCTTC TGCTCCCCGA   300
AATAAACTTG ATTGGTTAGT CAAGCGAAGA GCGAAGACAA GCGCGCGAAG ACGAGGGGCT   300

GCTCAATAAA AGAGCCCACA ACCCCTCACT CGGGGCGCCA GTCCTCCGAT TGACTGAGTC   360
CGAGTTATTT TCTCGGGTGT TGGGGAGTGA GCCCCGCGGT CAGGAGGCTA ACTGACTCAG   360

GCCCGGGTAC CCGTGTATCC AATAAACCCT CTTGCAGTTG CATCCGACTT GTGGTCTCGC   420
CGGGCCCATG GGCACATAGG TTATTTGGGA GAACGTCAAC GTAGGCTGAA CACCAGAGCG   420

TGTTCCTTGG GAGGYTCTCC TCTGAGTGAT TGACTACCCG TCAGCGGGGG TCTTTCATTT   480
ACAAGGAACC CTCCCAGAGG AGACTCACTA ACTGATGGGC AGTCGCCCCC AGAAAGTAAA   480

GGGGGCTCGT CCGGGATCGG GAGACCCCTG CCCAGGGACC ACCGACCCAC CACCGGGAGG   540
CCCCCGAGCA GGCCCTAGCC CTCTGGGGAC GGGTCCCTGG TGGCTGGGTG GTGGCCCTCC   540

CAAGCTGGCC AGCAACTTAT CTGTGTCTGT CCGATTGTCT AGTGTCTATG ACTGATTTTA   600
GTTCGACCGG TCGTTGAATA GACACAGACA GGCTAACAGA TCACAGATAC TGACTAAAAT   600

TGCGCCTGCG TCGGTACTAG TTAGCTAACT AGCTCTGTAT CTGGCGGACC CGTGGTGGAA   660
ACGCGGACGC AGCCATGATC AATCGATTGA TCGAGACATA GACCGCCTGG GCACCACCTT   660

CTGACGAGTT CTGAACACCC GGCCGCAACC CTGGGAGACG TCCCAGGGAC TTTGGGGGCC   720
GACTGCTCAA GACTTGTGGG CCGGCGTTGG GACCCTCTGC AGGGTCCCTG AAACCCCCGG   720

GTTTTTGTGG CCCGACCTGA GGAAGGGAGT CGATGTGGAA TCCGACCCCG TCAGGATATG   780
CAAAAACACC GGGCTGGACT CCTTCCCTCA GCTACACCTT AGGCTGGGGC AGTCCTATAC   780
```

FIG. 12B pICAST OMC

```
TGGTTCTGGT AGGAGACGAG AACCTAAAAC AGTTCCCGCC TCCGTCTGAA TTTTTGCTTT    840
ACCAAGACCA TCCTCTGCTC TTGGATTTTG TCAAGGGCGG AGGCAGACTT AAAAACGAAA    840

CGGTTTGGAA CCGAAGCCGC GCGTCTTGTC TGCTGCAGCA TCGTTCTGTG TTGTCTCTGT    900
GCCAAACCTT GGCTTCGGCG CGCAGAACAG ACGACGTCGT AGCAAGACAC AACAGAGACA    900

CTGACTGTGT TTCTGTATTT GTCTGAAAAT TAGGGCCAGA CTGTTACCAC TCCCTTAAGT    960
GACTGACACA AAGACATAAA CAGACTTTTA ATCCCGGTCT GACAATGGTG AGGGAATTCA    960

TTGACCTTAG GTAACTGGAA AGATGTCGAG CGGCTCGCTC ACAACCAGTC GGTAGATGTC   1020
AACTGGAATC CATTGACCTT TCTACAGCTC GCCGAGCGAG TGTTGGTCAG CCATCTACAG   1020

AAGAAGAGAC GTTGGGTTAC CTTCTGCTCT GCAGAATGGC CAACCTTTAA CGTCGGATGG   1080
TTCTTCTCTG CAACCCAATG GAAGACGAGA CGTCTTACCG GTTGGAAATT GCAGCCTACC   1080

CCGCGAGACG GCACCTTTAA CCGAGACCTC ATCACCCAGG TTAAGATCAA GGTCTTTTCA   1140
GGCGCTCTGC CGTGGAAATT GGCTCTGGAG TAGTGGGTCC AATTCTAGTT CCAGAAAAGT   1140

CCTGGCCCGC ATGGACACCC AGACCAGGTC CCCTACATCG TGACCTGGGA AGCCTTGGCT   1200
GGACCGGGCG TACCTGTGGG TCTGGTCCAG GGGATGTAGC ACTGGACCCT TCGGAACCGA   1200

TTTGACCCCC CTCCCTGGGT CAAGCCCTTT GTACACCCTA AGCCTCCGCC TCCTCTTCCT   1260
AAACTGGGGG GAGGGACCCA GTTCGGGAAA CATGTGGGAT TCGGAGGCGG AGGAGAAGGA   1260

CCATCCGCCC CGTCTCTCCC CCTTGAACCT CCTCGTTCGA CCCCGCCTCG ATCCTCCCTT   1320
GGTAGGCGGG GCAGAGAGGG GGAACTTGGA GGAGCAAGCT GGGGCGGAGC TAGGAGGGAA   1320

TATCCAGCCC TCACTCCTTC TCTAGGCGCC GGCCGCTCTA GCCCATTAAT ACGACTCACT   1380
ATAGGTCGGG AGTGAGGAAG AGATCCGCGG CCGGCGAGAT CGGGTAATTA TGCTGAGTGA   1380

ATAGGGCGAT TCGAATCAGG CCTTGGCGCG CCGGATCCTT AATTAAGCGC AATTGGGAGG   1440
TATCCCGCTA AGCTTAGTCC GGAACCGCGC GGCCTAGGAA TTAATTCGCG TTAACCCTCC   1440

TGGCGGTAGC CTCGAGATGG GCGTGATTAC GGATTCACTG GCCGTCGTTT TACAACGTCG   1500
ACCGCCATCG GAGCTCTACC CGCACTAATG CCTAAGTGAC CGGCAGCAAA ATGTTGCAGC   1500

TGACTGGGAA AACCCTGGCG TTACCCAACT TAATCGCCTT GCAGCACATC CCCCTTTCGC   1560
ACTGACCCTT TTGGGACCGC AATGGGTTGA ATTAGCGGAA CGTCGTGTAG GGGGAAAGCG   1560
```

FIG.12C pICAST OMC

```
CAGCTGGCGT AATAGCGAAG AGGCCCGCAC CGATCGCCCT TCCCAACAGT TACGCAGCCT  1620
GTCGACCGCA TTATCGCTTC TCCGGGCGTG GCTAGCGGGA AGGGTTGTCA ATGCGTCGGA  1620

GAATGGCGAA TGGCGCTTTG CCTGGTTTCC GGCACCAGAA GCGGTGCCGG AAAGCTGGCT  1680
CTTACCGCTT ACCGCGAAAC GGACCAAAGG CCGTGGTCTT CGCCACGGCC TTTCGACCGA  1680

GGAGTGCGAT CTTCCTGAGG CCGATACTGT CGTCGTCCCC TCAAACTGGC AGATGCACGG  1740
CCTCACGCTA GAAGGACTCC GGCTATGACA GCAGCAGGGG AGTTTGACCG TCTACGTGCC  1740

TTACGATGCG CCCATCTACA CCAACGTGAC CTATCCCATT ACGGTCAATC CGCCGTTTGT  1800
AATGCTACGC GGGTAGATGT GGTTGCACTG GATAGGGTAA TGCCAGTTAG GCGGCAAACA  1800

TCCCACGGAG AATCCGACGG GTTGTTACTC GCTCACATTT AATGTTGATG AAAGCTGGCT  1860
AGGGTGCCTC TTAGGCTGCC CAACAATGAG CGAGTGTAAA TTACAACTAC TTTCGACCGA  1860

ACAGGAAGGC CAGACGCGAA TTATTTTTGA TGGCGTTAAC TCGGCGTTTC ATCTGTGGTG  1920
TGTCCTTCCG GTCTGCGCTT AATAAAAACT ACCGCAATTG AGCCGCAAAG TAGACACCAC  1920

CAACGGGCGC TGGGTCGGTT ACGGCCAGGA CAGTCGTTTG CCGTCTGAAT TTGACCTGAG  1980
GTTGCCCGCG ACCCAGCCAA TGCCGGTCCT GTCAGCAAAC GGCAGACTTA AACTGGACTC  1980

CGCATTTTTA CGCGCCGGAG AAAACCGCCT CGCGGTGATG GTGCTGCGCT GGAGTGACGG  2040
GCGTAAAAAT GCGCGGCCTC TTTTGGCGGA GCGCCACTAC CACGACGCGA CCTCACTGCC  2040

CAGTTATCTG GAAGATCAGG ATATGTGGCG GATGAGCGGC ATTTTCCGTG ACGTCTCGTT  2100
GTCAATAGAC CTTCTAGTCC TATACACCGC CTACTCGCCG TAAAAGGCAC TGCAGAGCAA  2100

GCTGCATAAA CCGACTACAC AAATCAGCGA TTTCCATGTT GCCACTCGCT TTAATGATGA  2160
CGACGTATTT GGCTGATGTG TTTAGTCGCT AAAGGTACAA CGGTGAGCGA AATTACTACT  2160

TTTCAGCCGC GCTGTACTGG AGGCTGAAGT TCAGATGTGC GGCGAGTTGC GTGACTACCT  2220
AAAGTCGGCG CGACATGACC TCCGACTTCA AGTCTACACG CCGCTCAACG CACTGATGGA  2220

ACGGGTAACA GTTTCTTTAT GGCAGGGTGA AACGCAGGTC GCCAGCGGCA CCGCGCCTTT  2280
TGCCCATTGT CAAAGAAATA CCGTCCCACT TTGCGTCCAG CGGTCGCCGT GGCGCGGAAA  2280

CGGCGGTGAA ATTATCGATG AGCGTGGTGG TTATGCCGAT CGCGTCACAC TACGTCTGAA  2340
GCCGCCACTT TAATAGCTAC TCGCACCACC AATACGGCTA GCGCAGTGTG ATGCAGACTT  2340
```

FIG. 12D pICAST OMC

```
CGTCGAAAAC CCGAAACTGT GGAGCGCCGA AATCCCGAAT CTCTATCGTG CGGTGGTTGA   2400
GCAGCTTTTG GGCTTTGACA CCTCGCGGCT TTAGGGCTTA GAGATAGCAC GCCACCAACT   2400

ACTGCACACC GCCGACGGCA CGCTGATTGA AGCAGAAGCC TGCGATGTCG GTTTCCGCGA   2460
TGACGTGTGG CGGCTGCCGT GCGACTAACT TCGTCTTCGG ACGCTACAGC CAAAGGCGCT   2460

GGTGCGGATT GAAAATGGTC TGCTGCTGCT GAACGGCAAG CCGTTGCTGA TTCGAGGCGT   2520
CCACGCCTAA CTTTTACCAG ACGACGACGA CTTGCCGTTC GGCAACGACT AAGCTCCGCA   2520

TAACCGTCAC GAGCATCATC CTCTGCATGG TCAGGTCATG GATGAGCAGA CGATGGTGCA   2580
ATTGGCAGTG CTCGTAGTAG GAGACGTACC AGTCCAGTAC CTACTCGTCT GCTACCACGT   2580

GGATATCCTG CTGATGAAGC AGAACAACTT TAACGCCGTG CGCTGTTCGC ATTATCCGAA   2640
CCTATAGGAC GACTACTTCG TCTTGTTGAA ATTGCGGCAC GCGACAAGCG TAATAGGCTT   2640

CCATCCGCTG TGGTACACGC TGTGCGACCG CTACGGCCTG TATGTGGTGG ATGAAGCCAA   2700
GGTAGGCGAC ACCATGTGCG ACACGCTGGC GATGCCGGAC ATACACCACC TACTTCGGTT   2700

TATTGAAACC CACGGCATGG TGCCAATGAA TCGTCTGACC GATGATCCGC GCTGGCTACC   2760
ATAACTTTGG GTGCCGTACC ACGGTTACTT AGCAGACTGG CTACTAGGCG CGACCGATGG   2760

GGCGATGAGC GAACGCGTAA CGCGAATGGT GCAGCGCGAT CGTAATCACC CGAGTGTGAT   2820
CCGCTACTCG CTTGCGCATT GCGCTTACCA CGTCGCGCTA GCATTAGTGG GCTCACACTA   2820

CATCTGGTCG CTGGGGAATG AATCAGGCCA CGGCGCTAAT CACGACGCGC TGTATCGCTG   2880
GTAGACCAGC GACCCCTTAC TTAGTCCGGT GCCGCGATTA GTGCTGCGCG ACATAGCGAC   2880

GATCAAATCT GTCGATCCTT CCCGCCCGGT GCAGTATGAA GGCGGCGGAG CCGACACCAC   2940
CTAGTTTAGA CAGCTAGGAA GGGCGGGCCA CGTCATACTT CCGCCGCCTC GGCTGTGGTG   2940

GGCCACCGAT ATTATTTGCC CGATGTACGC GCGCGTGGAT GAAGACCAGC CCTTCCCGGC   3000
CCGGTGGCTA TAATAAACGG GCTACATGCG CGCGCACCTA CTTCTGGTCG GGAAGGGCCG   3000

TGTGCCGAAA TGGTCCATCA AAAAATGGCT TTCGCTACCT GGAGAGACGC GCCCGCTGAT   3060
ACACGGCTTT ACCAGGTAGT TTTTTACCGA AAGCGATGGA CCTCTCTGCG CGGGCGACTA   3060

CCTTTGCGAA TACGCCCACG CGATGGGTAA CAGTCTTGGC GGTTTCGCTA AATACTGGCA   3120
GGAAACGCTT ATGCGGGTGC GCTACCCATT GTCAGAACCG CCAAAGCGAT TTATGACCGT   3120
```

FIG.12E pICAST OMC

```
GGCGTTTCGT CAGTATCCCC GTTTACAGGG CGGCTTCGTC TGGGACTGGG TGGATCAGTC    3180
CCGCAAAGCA GTCATAGGGG CAAATGTCCC GCCGAAGCAG ACCCTGACCC ACCTAGTCAG    3180

GCTGATTAAA TATGATGAAA ACGGCAACCC GTGGTCGGCT TACGGCGGTG ATTTTGGCGA    3240
CGACTAATTT ATACTACTTT TGCCGTTGGG CACCAGCCGA ATGCCGCCAC TAAAACCGCT    3240

TACGCCGAAC GATCGCCAGT TCTGTATGAA CGGTCTGGTC TTTGCCGACC GCACGCCGCA    3300
ATGCGGCTTG CTAGCGGTCA AGACATACTT GCCAGACCAG AAACGGCTGG CGTGCGGCGT    3300

TCCAGCGCTG ACGGAAGCAA ACACCAGCA GCAGTTTTTC CAGTTCCGTT TATCCGGGCA     3360
AGGTCGCGAC TGCCTTCGTT TTGTGGTCGT CGTCAAAAAG GTCAAGGCAA ATAGGCCCGT    3360

AACCATCGAA GTGACCAGCG AATACCTGTT CCGTCATAGC GATAACGAGC TCCTGCACTG    3420
TTGGTAGCTT CACTGGTCGC TTATGGACAA GGCAGTATCG CTATTGCTCG AGGACGTGAC    3420

GATGGTGGCG CTGGATGGTA AGCCGCTGGC AAGCGGTGAA GTGCCTCTGG ATGTCGCTCC    3480
CTACCACCGC GACCTACCAT TCGGCGACCG TTCGCCACTT CACGGAGACC TACAGCGAGG    3480

ACAAGGTAAA CAGTTGATTG AACTGCCTGA ACTACCGCAG CCGGAGAGCG CCGGGCAACT    3540
TGTTCCATTT GTCAACTAAC TTGACGGACT TGATGGCGTC GGCCTCTCGC GGCCCGTTGA    3540

CTGGCTCACA GTACGCGTAG TGCAACCGAA CGCGACCGCA TGGTCAGAAG CCGGGCACAT    3600
GACCGAGTGT CATGCGCATC ACGTTGGCTT GCGCTGGCGT ACCAGTCTTC GGCCCGTGTA    3600

CAGCGCCTGG CAGCAGTGGC GTCTGGCGGA AAACCTCAGT GTGACGCTCC CCGCCGCGTC    3660
GTCGCGGACC GTCGTCACCG CAGACCGCCT TTTGGAGTCA CACTGCGAGG GGCGGCGCAG    3660

CCACGCCATC CCGCATCTGA CCACCAGCGA AATGGATTTT TGCATCGAGC TGGGTAATAA    3720
GGTGCGGTAG GGCGTAGACT GGTGGTCGCT TTACCTAAAA ACGTAGCTCG ACCCATTATT    3720

GCGTTGGCAA TTTAACCGCC AGTCAGGCTT TCTTTCACAG ATGTGGATTG GCGATAAAAA    3780
CGCAACCGTT AAATTGGCGG TCAGTCCGAA AGAAAGTGTC TACACCTAAC CGCTATTTTT    3780

ACAACTGCTG ACGCCGCTGC GCGATCAGTT CACCCGTGTC GATAGATCTG AACAGAAACT    3840
TGTTGACGAC TGCGGCGACG CGCTAGTCAA GTGGGCACAG CTATCTAGAC TTGTCTTTGA    3840

CATTTCCGAA GAAGACCTAG TCGACCATCA TCATCATCAT CACCGGTAAT AATAGGTAGA    3900
GTAAAGGCTT CTTCTGGATC AGCTGGTAGT AGTAGTAGTA GTGGCCATTA TTATCCATCT    3900
```

FIG.12F pICAST OMC

```
TAAGTGACTG ATTAGATGCA TTTCGACTAG ATCCCTCGAC CAATTCCGGT TATTTTCCAC    3960
ATTCACTGAC TAATCTACGT AAAGCTGATC TAGGGAGCTG GTTAAGGCCA ATAAAAGGTG    3960

CATATTGCCG TCTTTTGGCA ATGTGAGGGC CCGGAAACCT GGCCCTGTCT TCTTGACGAG    4020
GTATAACGGC AGAAAACCGT TACACTCCCG GGCCTTTGGA CCGGGACAGA AGAACTGCTC    4020

CATTCCTAGG GGTCTTTCCC CTCTCGCCAA AGGAATGCAA GGTCTGTTGA ATGTCGTGAA    4080
GTAAGGATCC CCAGAAAGGG GAGAGCGGTT TCCTTACGTT CCAGACAACT TACAGCACTT    4080

GGAAGCAGTT CCTCTGGAAG CTTCTTGAAG ACAAACAACG TCTGTAGCGA CCCTTTGCAG    4140
CCTTCGTCAA GGAGACCTTC GAAGAACTTC TGTTTGTTGC AGACATCGCT GGGAAACGTC    4140

GCAGCGGAAC CCCCCACCTG GCGACAGGTG CCTCTGCGGC CAAAAGCCAC GTGTATAAGA    4200
CGTCGCCTTG GGGGGTGGAC CGCTGTCCAC GGAGACGCCG GTTTTCGGTG CACATATTCT    4200

TACACCTGCA AAGGCGGCAC AACCCCAGTG CCACGTTGTG AGTTGGATAG TTGTGGAAAG    4260
ATGTGGACGT TTCCGCCGTG TTGGGGTCAC GGTGCAACAC TCAACCTATC AACACCTTTC    4260

AGTCAAATGG CTCTCCTCAA GCGTATTCAA CAAGGGGCTG AAGGATGCCC AGAAGGTACC    4320
TCAGTTTACC GAGAGGAGTT CGCATAAGTT GTTCCCCGAC TTCCTACGGG TCTTCCATGG    4320

CCATTGTATG GGATCTGATC TGGGGCCTCG GTGCACATGC TTTACATGTG TTTAGTCGAG    4380
GGTAACATAC CCTAGACTAG ACCCCGGAGC CACGTGTACG AAATGTACAC AAATCAGCTC    4380

GTTAAAAAAC GTCTAGGCCC CCCGAACCAC GGGGACGTGG TTTTCCTTTG AAAAACACGA    4440
CAATTTTTTG CAGATCCGGG GGGCTTGGTG CCCCTGCACC AAAAGGAAAC TTTTTGTGCT    4440

TGATAATACC ATGAAAAAGC CTGAACTCAC CGCGACGTCT GTCGAGAAGT TTCTGATCGA    4500
ACTATTATGG TACTTTTTCG GACTTGAGTG GCGCTGCAGA CAGCTCTTCA AAGACTAGCT    4500

AAAGTTCGAC AGCGTCTCCG ACCTGATGCA GCTCTCGGAG GGCGAAGAAT CTCGTGCTTT    4560
TTTCAAGCTG TCGCAGAGGC TGGACTACGT CGAGAGCCTC CCGCTTCTTA GAGCACGAAA    4560

CAGCTTCGAT GTAGGAGGGC GTGGATATGT CCTGCGGGTA AATAGCTGCG CCGATGGTTT    4620
GTCGAAGCTA CATCCTCCCG CACCTATACA GGACGCCCAT TTATCGACGC GGCTACCAAA    4620

CTACAAAGAT CGTTATGTTT ATCGGCACTT TGCATCGGCC GCGCTCCCGA TTCCGGAAGT    4680
GATGTTTCTA GCAATACAAA TAGCCGTGAA ACGTAGCCGG CGCGAGGGCT AAGGCCTTCA    4680
```

FIG. 12G pICAST OMC

```
GCTTGACATT GGGGAATTTA GCGAGAGCCT GACCTATTGC ATCTCCCGCC GTGCACAGGG    4740
CGAACTGTAA CCCCTTAAAT CGCRCTCGGA CTGGATAACG TAGAGGGCGG CACGTGTCCC    4740

TGTCACGTTG CAAGACCTGC CTGAAACCGA ACTGCCCGCT GTTCTGCAGC CGGTCGCGGA    4800
ACAGTGCAAC GTTCTGGACG GACTTTGGCT TGACGGGCGA CAAGACGTCG GCCAGCGCCT    4800

GGCCATGGAT GCGATCGCTG CGGCCGATCT TAGCCAGACG AGCGGGTTCG GCCCATTCGG    4860
CCGGTACCTA CGCTAGCGAC GCCGGCTAGA ATCGGTCTGC TCGCCCAAGC CGGGTAAGCC    4860

ACCGCAAGGA ATCGGTCAAT ACACTACATG GCGTGATTTC ATATGCGCGA TTGCTGATCC    4920
TGGCGTTCCT TAGCCAGTTA TGTGATGTAC CGCACTAAAG TATACGCGCT AACGACTAGG    4920

CCATGTGTAT CACTGGCAAA CTGTGATGGA CGACACCGTC AGTGCGTCCG TCGCGCAGGC    4980
GGTACACATA GTGACCGTTT GACACTACCT GCTGTGGCAG TCACGCAGGC AGCGCGTCCG    4980

TCTCGATGAG CTGATGCTTT GGGCCGAGGA CTGCCCCGAA GTCCGGCACC TCGTGCACGC    5040
AGAGCTACTC GACTACGAAA CCCGGCTCCT GACGGGGCTT CAGGCCGTGG AGCACGTGCG    5040

GGATTTCGGC TCCAACAATG TCCTGACGGA CAATGGCCGC ATAACAGCGG TCATTGACTG    5100
CCTAAAGCCG AGGTTGTTAC AGGACTGCCT GTTACCGGCG TATTGTCGCC AGTAACTGAC    5100

GAGCGAGGCG ATGTTCGGGG ATTCCCAATA CGAGGTCGCC AACATCTTCT TCTGGAGGCC    5160
CTCGCTCCGC TACAAGCCCC TAAGGGTTAT GCTCCAGCGG TTGTAGAAGA AGACCTCCGG    5160

GTGGTTGGCT TGTATGGAGC AGCAGACGCG CTACTTCGAG CGGAGGCATC CGGAGCTTGC    5220
CACCAACCGA ACATACCTCG TCGTCTGCGC GATGAAGCTC GCCTCCGTAG GCCTCGAACG    5220

AGGATCGCCG CGGCTCCGGG CGTATATGCT CCGCATTGGT CTTGACCAAC TCTATCAGAG    5280
TCCTAGCGGC GCCGAGGCCC GCATATACGA GGCGTAACCA GAACTGCTTG AGATAGTCTC    5280

CTTGGTTGAC GGCAATTTCG ATGATGCAGC TTGGGCGCAG GGTCGATGCG ACGCAATCGT    5340
GAACCAACTG CCGTTAAAGC TACTACGTCG AACCCGCGTC CCAGCTACGC TGCGTTAGCA    5340

CCGATCCGGA GCCGGGACTG TCGGGCGTAC ACAAATCGCC CGCAGAAGCG CGGCCGTCTG    5400
GGCTAGGCCT CGGCCCTGAC AGCCCGCATG TGTTTAGCGG GCGTCTTCGC GCCGGCAGAC    5400

GACCGATGGC TGTGTAGAAG TACTCGCCGA TAGTGGAAAC CGACGCCCCA GCACTCGTCC    5460
CTGGCTACCG ACACATCTTC ATGAGCGGCT ATCACCTTTG GCTGCGGGGT CGTGAGCAGG    5460
```

FIG.12H pICAST CMC

```
GAGGGCAAAG GAATAGAGTA GATGCCGACC GGGATCTATC GATAAAATAA AAGATTTTAT    5520
CTCCCGTTTC CTTATCTCAT CTACGGCTGG CCCTAGATAG CTATTTTATT TTCTAAAATA    5520

TTAGTCTCCA GAAAAAGGGG GGAATGAAAG ACCCCACCTG TAGGTTTGGC AAGCTAGCTT    5580
AATCAGAGGT CTTTTTCCCC CCTTACTTTC TGGGGTGGAC ATCCAAACCG TTCGATCGAA    5580

AAGTAACGCC ATTTTGCAAG GCATGGAAAA ATACATAACT GAGAATAGAG AAGTTCAGAT    5640
TTCATTGCGG TAAAACGTTC CGTACCTTTT TATGTATTGA CTCTTATCTC TTCAAGTCTA    5640

CAAGGTCAGG AACAGATGGA ACAGCTGAAT ATGGGCCAAA CAGGATATCT GTGGTAAGCA    5700
GTTCCAGTCC TTGTCTACCT TGTCGACTTA TACCCGGTTT GTCCTATAGA CACCATTCGT    5700

GTTCCTGCCC CGGCTCAGGG CCAAGAACAG ATGGAACAGC TGAATATGGG CCAAACAGGA    5760
CAAGGACGGG GCCGAGTCCC GGTTCTTGTC TACCTTGTCG ACTTATACCC GGTTTGTCCT    5760

TATCTGTGGT AAGCAGTTCC TGCCCCGGCT CAGGGCCAAG AACAGATGGT CCCCAGATGC    5820
ATAGACACCA TTCGTCAAGG ACGGGGCCGA GTCCCGGTTC TTGTCTACCA GGGGTCTACG    5820

GGTCCAGCCC TCAGCAGTTT CTAGAGAACC ATCAGATGTT TCCAGGGTGC CCCAAGGACC    5880
CCAGGTCGGG AGTCGTCAAA GATCTCTTGG TAGTCTACAA AGGTCCCACG GGGTTCCTGG    5880

TGAAATGACC CTGTGCCTTA TTTGAACTAA CCAATCAGTT CGCTTCTCGC TTCTGTTCGC    5940
ACTTTACTGG GACACGGAAT AAACTTGATT GGTTAGTCAA GCGAAGAGCG AAGACAAGCG    5940

GCGCTTCTGC TCCCCGAGCT CAATAAAAGA GCCCACAACC CCTCACTCGG GGCGCCAGTC    6000
CGCGAAGACG AGGGGCTCGA GTTATTTTCT CGGGTGTTGG GGAGTGAGCC CCGCGGTCAG    6000

CTCCGATTGA CTGAGTCGCC CGGGTACCCG TGTATCCAAT AAACCCTCTT GCAGTTGCAT    6060
GAGGCTAACT GACTCAGCGG GCCCATGGGC ACATAGGTTA TTTGGGAGAA CGTCAACGTA    6060

CCGACTTGTG GTCTCGCTGT TCCTTGGGAG GGTCTCCTCT GAGTGATTGA CTACCCGTCA    6120
GGCTGAACAC CAGAGCGACA AGGAACCCTC CCAGAGGAGA CTCACTAACT GATGGGCAGT    6120

GCGGGGGTCT TTCATTCATG CAGCATGTAT CAAAATTAAT TTGGTTTTTT TTCTTAAGTA    6180
CGCCCCCAGA AAGTAAGTAC GTCGTACATA GTTTTAATTA AACCAAAAAA AAGAATTCAT    6180

TTTACATTAA ATGGCCATAG TTGCATTAAT GAATCGGCCA ACGCGCGGGG AGAGGCGGTT    6240
AAATGTAATT TACCGGTATC AACGTAATTA CTTAGCCGGT TGCGCGCCCC TCTCCGCCAA    6240
```

FIG. 121 pICAST OMC

```
TGCGTATTGG CGCTCTTCCG CTTCCTCGCT CACTGACTCG CTGCGCTCGG TCGTTCGGCT    6300
ACGCATAACC GCGAGAAGGC GAAGGAGCGA GTGACTGAGC GACGCGAGCC AGCAAGCCGA    6300

GCGGCGAGCG GTATCAGCTC ACTCAAAGGC GGTAATACGG TTATCCACAG AATCAGGGGA    6360
CGCCGCTCGC CATAGTCGAG TGAGTTTCCG CCATTATGCC AATAGGTGTC TTAGTCCCCT    6360

TAACGCAGGA AAGAACATGT GAGCAAAAGG CCAGCAAAAG GCCAGGAACC GTAAAAAGGC    6420
ATTGCGTCCT TTCTTGTACA CTCGTTTTCC GGTCGTTTTC CGGTCCTTGG CATTTTTCCG    6420

CGCGTTGCTG GCGTTTTTCC ATAGGCTCCG CCCCCCTGAC GAGCATCACA AAAATCGACG    6480
GCGCAACGAC CGCAAAAAGG TATCCGAGGC GGGGGGACTG CTCGTAGTGT TTTTAGCTGC    6480

CTCAAGTCAG AGGTGGCGAA ACCCGACAGG ACTATAAAGA TACCAGGCGT TTCCCCCTGG    6540
GAGTTCAGTC TCCACCGCTT TGGGCTGTCC TGATATTTCT ATGGTCCGCA AAGGGGGACC    6540

AAGCTCCCTC GTGCGCTCTC CTGTTCCGAC CCTGCCGCTT ACCGGATACC TGTCCGCCTT    6600
TTCGAGGGAG CACGCGAGAG GACAAGGCTG GGACGGCGAA TGGCCTATGG ACAGGCGGAA    6600

TCTCCCTTCG GGAAGCGTGG CGCTTTCTCA TAGCTCACGC TGTAGGTATC TCAGTTCGGT    6660
AGAGGGAAGC CCTTCGCACC GCGAAAGAGT ATCGAGTGCG ACATCCATAG AGTCAAGCCA    6660

GTAGGTCGTT CGCTCCAAGC TGGGCTGTGT GCACGAACCC CCCGTTCAGC CCGACCGCTG    6720
CATCCAGCAA GCGAGGTTCG ACCCGACACA CGTGCTTGGG GGGCAAGTCG GGCTGGCGAC    6720

CGCCTTATCC GGTAACTATC GTCTTGAGTC CAACCCGGTA AGACACGACT TATCGCCACT    6780
GCGGAATAGG CCATTGATAG CAGAACTCAG GTTGGGCCAT TCTGTGCTGA ATAGCGGTGA    6780

GGCAGCAGCC ACTGGTAACA GGATTAGCAG AGCGAGGTAT GTAGGCGGTG CTACAGAGTT    6840
CCGTCGTCGG TGACCATTGT CCTAATCGTC TCGCTCCATA CATCCGCCAC GATGTCTCAA    6840

CTTGAAGTGG TGGCCTAACT ACGGCTACAC TAGAAGAACA GTATTTGGTA TCTGCGCTCT    6900
GAACTTCACC ACCGGATTGA TGCCGATGTG ATCTTCTTGT CATAAACCAT AGACGCGAGA    6900

GCTGAAGCCA GTTACCTTCG GAAAAAGAGT TGGTAGCTCT TGATCCGGCA AACAAACCAC    6960
CGACTTCGGT CAATGGAAGC CTTTTTCTCA ACCATCGAGA ACTAGGCCGT TTGTTTGGTG    6960

CGCTGGTAGC GGTGGTTTTT TTGTTTGCAA GCAGCAGATT ACGCGCAGAA AAAAAGGATC    7020
GCGACCATCG CCACCAAAAA AACAAACGTT CGTCGTCTAA TGCGCGTCTT TTTTTCCTAG    7020
```

FIG.12J pICAST OMC

```
TCAAGAAGAT CCTTTGATCT TTTCTACGGG GTCTGACGCT CAGTGGAACG AAAACTCACG   7080
AGTTCTTCTA GGAAACTAGA AAAGATGCCC CAGACTGCGA GTCACCTTGC TTTTGAGTGC   7080

TTAAGGGATT TTGGTCATGA GATTATCAAA AAGGATCTTC ACCTAGATCC TTTTAAATTA   7140
AATTCCCTAA AACCAGTACT CTAATAGTTT TTCCTAGAAG TGGATCTAGG AAAATTTAAT   7140

AAAATGAAGT TTGCGGCCGC AAATCAATCT AAAGTATATA TGAGTAAACT TGGTCTGACA   7200
TTTTACTTCA AACGCCGGCG TTTAGTTAGA TTTCATATAT ACTCATTTGA ACCAGACTGT   7200

GTTACCAATG CTTAATCAGT GAGGCACCTA TCTCAGCGAT CTGTCTATTT CGTTCATCCA   7260
CAATGGTTAC GAATTAGTCA CTCCGTGGAT AGAGTCGCTA GACAGATAAA GCAAGTAGGT   7260

TAGTTGCCTG ACTCCCCGTC GTGTAGATAA CTACGATACG GGAGGGCTTA CCATCTGGCC   7320
ATCAACGGAC TGAGGGGCAG CACATCTATT GATGCTATGC CCTCCCGAAT GGTAGACCGG   7320

CCAGTGCTGC AATGATACCG CGAGACCCAC GCTCACCGGC TCCAGATTTA TCAGCAATAA   7380
GGTCACGACG TTACTATGGC GCTCTGGGTG CGAGTGGCCG AGGTCTAAAT AGTCGTTATT   7380

ACCAGCCAGC CGGAAGGGCC GAGCGCAGAA GTGGTCCTGC AACTTTATCC GCCTCCATCC   7440
TGGTCGGTCG GCCTTCCCGG CTCGCGTCTT CACCAGGACG TTGAAATAGG CGGAGGTAGG   7440

AGTCTATTAA TTGTTGCCGG GAAGCTAGAG TAAGTAGTTC GCCAGTTAAT AGTTTGCGCA   7500
TCAGATAATT AACAACGGCC CTTCGATCTC ATTCATCAAG CGGTCAATTA TCAAACGCGT   7500

ACGTTGTTGC CATTGCTACA GGCATCGTGG TGTCACGCTC GTCGTTTGGT ATGGCTTCAT   7560
TGCAACAACG GTAACGATGT CCGTAGCACC ACAGTGCGAG CAGCAAACCA TACCGAAGTA   7560

TCAGCTCCGG TTCCCAACGA TCAAGGCGAG TTACATGATC CCCCATGTTG TGCAAAAAAG   7620
AGTCGAGGCC AAGGGTTGCT AGTTCCGCTC AATGTACTAG GGGGTACAAC ACGTTTTTTC   7620

CGGTTAGCTC CTTCGGTCCT CCGATCGTTG TCAGAAGTAA GTTGGCCGCA GTGTTATCAC   7680
GCCAATCGAG GAAGCCAGGA GGCTAGCAAC AGTCTTCATT CAACCGGCGT CACAATAGTG   7680

TCATGGTTAT GGCAGCACTG CATAATTCTC TTACTGTCAT GCCATCCGTA AGATGCTTTT   7740
AGTACCAATA CCGTCGTGAC GTATTAAGAG AATGACAGTA CGGTAGGCAT TCTACGAAAA   7740

CTGTGACTGG TGAGTACTCA ACCAAGTCAT TCTGAGAATA GTGTATGCGG CGACCGAGTT   7800
GACACTGACC ACTCATGAGT TGGTTCAGTA AGACTCTTAT CACATACGCC GCTGGCTCAA   7800
```

FIG.12K pICAST OMC

```
GCTCTTGCCC GGCGTCAATA CGGGATAATA CCGCGCCACA TAGCAGAACT TTAAAAGTGC    7860
CGAGAACGGG CCGCAGTTAT GCCCTATTAT GGCGCGGTGT ATCGTCTTGA AATTTTCACG    7860

TCATCATTGG AAAACGTTCT TCGGGGCGAA AACTCTCAAG GATCTTACCG CTGTTGAGAT    7920
AGTAGTAACC TTTTGCAAGA AGCCCCGCTT TTGAGAGTTC CTAGAATGGC GACAACTCTA    7920

CCAGTTCGAT GTAACCCACT CGTGCACCCA ACTGATCTTC AGCATCTTTT ACTTTCACCA    7980
GGTCAAGCTA CATTGGGTGA GCACGTGGGT TGACTAGAAG TCGTAGAAAA TGAAAGTGGT    7980

GCGTTTCTGG GTGAGCAAAA ACAGGAAGGC AAAATGCCGC AAAAAAGGGA ATAAGGGCGA    8040
CGCAAAGACC CACTCGTTTT TGTCCTTCCG TTTTACGGCG TTTTTTCCCT TATTCCCGCT    8040

CACGGAAATG TTGAATACTC ATACTCTTCC TTTTTCAATA TTATTGAAGC ATTTATCAGG    8100
GTGCCTTTAC AACTTATGAG TATGAGAAGG AAAAAGTTAT AATAACTTCG TAAATAGTCC    8100

GTTATTGTCT CATGAGCGGA TACATATTTG AATGTATTTA GAAAAATAAA CAAATAGGGG    8160
CAATAACAGA GTACTCGCCT ATGTATAAAC TTACATAAAT CTTTTTATTT GTTTATCCCC    8160

TTCCGCGCAC ATTTC                                                    8175
AAGGCGCGTG TAAAG                                                    8175
```

FIG. 12L pICAST OMN

```
CTGCAGCCTG AATATGGGCC AAACAGGATA TCTGTGGTAA GCAGTTCCTG CCCCGGCTCA    60
GACGTCGGAC TTATACCCGG TTTGTCCTAT AGACACCATT CGTCAAGGAC GGGGCCGAGT    60

GGGCCAAGAA CAGATGGAAC AGCTGAATAT GGGCCAAACA GGATATCTGT GGTAAGCAGT   120
CCCGGTTCTT GTCTACCTTG TCGACTTATA CCCGGTTTGT CCTATAGACA CCATTCGTCA   120

TCCTGCCCCG GCTCAGGGCC AAGAACAGAT GGTCCCCAGA TGCGGTCCAG CCCTCAGCAG   180
AGGACGGGGC CGAGTCCCGG TTCTTGTCTA CCAGGGGTCT ACGCCAGGTC GGGAGTCGTC   180

TTTCTAGAGA ACCATCAGAT GTTTCCAGGG TGCCCCAAGG ACCTGAAATG ACCCTGTGCC   240
AAAGATCTCT TGGTAGTCTA CAAAGGTCCC ACGGGGTTCC TGGACTTTAC TGGGACACGG   240

TTATTTGAAC TAACCAATCA GTTCGCTTCT CGCTTCTGTT CGCGCGCTTC TGCTCCCCGA   300
AATAAACTTG ATTGGTTAGT CAAGCGAAGA GCGAAGACAA GCGCGCGAAG ACGAGGGGCT   300

GCTCAATAAA AGAGCCCACA ACCCCTCACT CGGGGCGCCA GTCCTCCGAT TGACTGAGTC   360
CGAGTTATTT TCTCGGGTGT TGGGGAGTGA GCCCCGCGGT CAGGAGGCTA ACTGACTCAG   360

GCCCGGGTAC CCGTGTATCC AATAAACCCT CTTGCAGTTG CATCCGACTT GTGGTCTCGC   420
CGGGCCCATG GGCACATAGG TTATTTGGGA GAACGTCAAC GTAGGCTGAA CACCAGAGCG   420

TGTTCCTTGG GAGGGTCTCC TCTGAGTGAT TGACTACCCG TCAGCGGGGG TCTTTCATTT   480
ACAAGGAACC CTCCCAGAGG AGACTCACTA ACTGATGGGC AGTCGCCCCC AGAAAGTAAA   480

GGGGGCTCGT CCGGGATCGG GAGACCCCTG CCCAGGGACC ACCGACCCAC CACCGGGAGG   540
CCCCCGAGCA GGCCCTAGCC CTCTGGGGAC GGGTCCCTGG TGGCTGGGTG GTGGCCCTCC   540

CAAGCTGGCC AGCAACTTAT CTGTGTCTGT CCGATTGTCT AGTGTCTATG ACTGATTTTA   600
GTTCGACCGG TCGTTGAATA GACACAGACA GGCTAACAGA TCACAGATAC TGACTAAAAT   600

TGCGCCTGCG TCGGTACTAG TTAGCTAACT AGCTCTGTAT CTGGCGGACC CGTGGTGGAA   660
ACGCGGACGC AGCCATGATC AATCGATTGA TCGAGACATA GACCGCCTGG GCACCACCTT   660

CTGACGAGTT CTGAACACCC GGCCGCAACC CTGGGAGACG TCCCAGGGAC TTTGGGGGCC   720
GACTGCTCAA GACTTGTGGG CCGGCGTTGG GACCCTCTGC AGGGTCCCTG AAACCCCCGG   720

GTTTTTGTGG CCCGACCTGA GGAAGGGAGT CGATGTGGAA TCCGACCCCG TCAGGATATG   780
CAAAAACACC GGGCTGGACT CCTTCCCTCA GCTACACCTT AGGCTGGGGC AGTCCTATAC   780
```

FIG.13B pICAST OMN

```
TGGTTCTGGT AGGAGACGAG AACCTAAAAC AGTTCCCGCC TCCGTCTGAA TTTTTGCTTT    840
ACCAAGACCA TCCTCTGCTC TTGGATTTTG TCAAGGGCGG AGGCAGACTT AAAAACGAAA    840

CGGTTTGGAA CCGAAGCCGC GCGTCTTGTC TGCTGCAGCA TCGTTCTGTG TTGTCTCTGT    900
GCCAAACCTT GGCTTCGGCG CGCAGAACAG ACGACGTCGT AGCAAGACAC AACAGAGACA    900

CTGACTGTGT TTCTGTATTT GTCTGAAAAT TAGGGCCAGA CTGTTACCAC TCCCTTAAGT    960
GACTGACACA AAGACATAAA CAGACTTTTA ATCCCGGTCT GACAATGGTG AGGGAATTCA    960

TTGACCTTAG GTAACTGGAA AGATGTCGAG CGGCTCGCTC ACAACCAGTC GGTAGATGTC   1020
AACTGGAATC CATTGACCTT TCTACAGCTC GCCGAGCGAG TGTTGGTCAG CCATCTACAG   1020

AAGAAGAGAC GTTGGGTTAC CTTCTGCTCT GCAGAATGGC CAACCTTTAA CGTCGGATGG   1080
TTCTTCTCTG CAACCCAATG GAAGACGAGA CGTCTTACCG GTTGGAAATT GCAGCCTACC   1080

CCGCGAGACG GCACCTTTAA CCGAGACCTC ATCACCCAGG TTAAGATCAA GGTCTTTTCA   1140
GGCGCTCTGC CGTGGAAATT GGCTCTGGAG TAGTGGGTCC AATTCTAGTT CCAGAAAAGT   1140

CCTGGCCCGC ATGGACACCC AGACCAGGTC CCCTACATCG TGACCTGGGA AGCCTTGGCT   1200
GGACCGGGCG TACCTGTGGG TCTGGTCCAG GGGATGTAGC ACTGGACCCT TCGGAACCGA   1200

TTTGACCCCC CTCCCTGGGT CAAGCCCTTT GTACACCCTA AGCCTCCGCC TCCTCTTCCT   1260
AAACTGGGGG GAGGGACCCA GTTCGGGAAA CATGTGGGAT TCGGAGGCGG AGGAGAAGGA   1260

CCATCCGCCC CGTCTCTCCC CCTTGAACCT CCTCGTTCGA CCCCGCCTCG ATCCTCCCTT   1320
GGTAGGCGGG GCAGAGAGGG GGAACTTGGA GGAGCAAGCT GGGGCGGAGC TAGGAGGGAA   1320

TATCCAGCCC TCACTCCTTC TCTAGGCGCC GGCCGCTCTA GCCCATTAAT ACGACTCACT   1380
ATAGGTCGGG AGTGAGGAAG AGATCCGCGG CCGGCGAGAT CGGGTAATTA TGCTGAGTGA   1380

ATAGGGCGAT TCGAACACCA TGCACCATCA TCATCATCAC GTCGACGAAC AGAAACTCAT   1440
TATCCCGCTA AGCTTGTGGT ACGTGGTAGT AGTAGTAGTG CAGCTGCTTG TCTTTGAGTA   1440

TTCCGAAGAA GACCTACTCG AGATGGGCGT GATTACGGAT TCACTGGCCG TCGTTTTACA   1500
AAGGCTTCTT CTGGATGAGC TCTACCCGCA CTAATGCCTA AGTGACCGGC AGCAAAATGT   1500

ACGTCGTGAC TGGGAAAACC CTGGCGTTAC CCAACTTAAT CGCCTTGCAG CACATCCCCC   1560
TGCAGCACTG ACCCTTTTGG GACCGCAATG GGTTGAATTA GCGGAACGTC GTGTAGGGGG   1560
```

FIG.13C pICAST OMN

```
TTTCGCCAGC TGGCGTAATA GCGAAGAGGC CCGCACCGAT CGCCCTTCCC AACAGTTACG   1620
AAAGCGGTCG ACCGCATTAT CGCTTCTCCG GGCGTGGCTA GCGGGAAGGG TTGTCAATGC   1620

CAGCCTGAAT GGCGAATGGC GCTTTGCCTG GTTTCCGGCA CCAGAAGCGG TGCCGGAAAG   1680
GTCGGACTTA CCGCTTACCG CGAAACGGAC CAAAGGCCGT GGTCTTCGCC ACGGCCTTTC   1680

CTGGCTGGAG TGCGATCTTC CTGAGGCCGA TACTGTCGTC GTCCCCTCAA ACTGGCAGAT   1740
GACCGACCTC ACGCTAGAAG GACTCCGGCT ATGACAGCAG CAGGGGAGTT TGACCGTCTA   1740

GCACGGTTAC GATGCGCCCA TCTACACCAA CGTGACCTAT CCCATTACGG TCAATCCGCC   1800
CGTGCCAATG CTACGCGGGT AGATGTGGTT GCACTGGATA GGGTAATGCC AGTTAGGCGG   1800

GTTTGTTCCC ACGGAGAATC CGACGGGTTG TTACTCGCTC ACATTTAATG TTGATGAAAG   1860
CAAACAAGGG TGCCTCTTAG GCTGCCCAAC AATGAGCGAG TGTAAATTAC AACTACTTTC   1860

CTGGCTACAG GAAGGCCAGA CGCGAATTAT TTTTGATGGC GTTAACTCGG CGTTTCATCT   1920
GACCGATGTC CTTCCGGTCT GCGCTTAATA AAAACTACCG CAATTGAGCC GCAAAGTAGA   1920

GTGGTGCAAC GGGCGCTGGG TCGGTTACGG CCAGGACAGT CGTTTGCCGT CTGAATTTGA   1980
CACCACGTTG CCCGCGACCC AGCCAATGCC GGTCCTGTCA GCAAACGGCA GACTTAAACT   1980

CCTGAGCGCA TTTTTACGCG CCGGAGAAAA CCGCCTCGCG GTGATGGTGC TGCGCTGGAG   2040
GGACTCGCGT AAAAATGCGC GGCCTCTTTT GGCGGAGCGC CACTACCACG ACGCGACCTC   2040

TGACGGCAGT TATCTGGAAG ATCAGGATAT GTGGCGGATG AGCGGCATTT TCCGTGACGT   2100
ACTGCCGTCA ATAGACCTTC TAGTCCTATA CACCGCCTAC TCGCCGTAAA AGGCACTGCA   2100

CTCGTTGCTG CATAAACCGA CTACACAAAT CAGCGATTTC CATGTTGCCA CTCGCTTTAA   2160
GAGCAACGAC GTATTTGGCT GATGTGTTTA GTCGCTAAAG GTACAACGGT GAGCGAAATT   2160

TGATGATTTC AGCCGCGCTG TACTGGAGGC TGAAGTTCAG ATGTGCGGCG AGTTGCGTGA   2220
ACTACTAAAG TCGGCGCGAC ATGACCTCCG ACTTCAAGTC TACACGCCGC TCAACGCACT   2220

CTACCTACGG GTAACAGTTT CTTTATGGCA GGGTGAAACG CAGGTCGCCA GCGGCACCGC   2280
GATGGATGCC CATTGTCAAA GAAATACCGT CCCACTTTGC GTCCAGCGGT CGCCGTGGCG   2280

GCCTTTCGGC GGTGAAATTA TCGATGAGCG TGGTGGTTAT GCCGATCGCG TCACACTACG   2340
CGGAAAGCCG CCACTTTAAT AGCTACTCGC ACCACCAATA CGGCTAGCGC AGTGTGATGC   2340
```

FIG. 13D pICAST OMN

```
TCTGAACGTC GAAAACCCGA AACTGTGGAG CGCCGAAATC CCGAATCTCT ATCGTGCGGT  2400
AGACTTGCAG CTTTTGGGCT TTGACACCTC GCGGCTTTAG GGCTTAGAGA TAGCACGCCA  2400

GGTTGAACTG CACACCGCCG ACGGCACGCT GATTGAAGCA GAAGCCTGCG ATGTCGGTTT  2460
CCAACTTGAC GTGTGGCGGC TGCCGTGCGA CTAACTTCGT CTTCGGACGC TACAGCCAAA  2460

CCGCGAGGTG CGGATTGAAA ATGGTCTGCT GCTGCTGAAC GGCAAGCCGT TGCTGATTCG  2520
GGCGCTCCAC GCCTAACTTT TACCAGACGA CGACGACTTG CCGTTCGGCA ACGACTAAGC  2520

AGGCGTTAAC CGTCACGAGC ATCATCCTCT GCATGGTCAG GTCATGGATG AGCAGACGAT  2580
TCCGCAATTG GCAGTGCTCG TAGTAGGAGA CGTACCAGTC CAGTACCTAC TCGTCTGCTA  2580

GGTGCAGGAT ATCCTGCTGA TGAAGCAGAA CAACTTTAAC GCCGTGCGCT GTTCGCATTA  2640
CCACGTCCTA TAGGACGACT ACTTCGTCTT GTTGAAATTG CGGCACGCGA CAAGCGTAAT  2640

TCCGAACCAT CCGCTGTGGT ACACGCTGTG CGACCGCTAC GGCCTGTATG TGGTGGATGA  2700
AGGCTTGGTA GGCGACACCA TGTGCGACAC GCTGGCGATG CCGGACATAC ACCACCTACT  2700

AGCCAATATT GAAACCCACG GCATGGTGCC AATGAATCGT CTGACCGATG ATCCGCGCTG  2760
TCGGTTATAA CTTTGGGTGC CGTACCACGG TTACTTAGCA GACTGGCTAC TAGGCGCGAC  2760

GCTACCGGCG ATGAGCGAAC GCGTAACGCG AATGGTGCAG CGCGATCGTA ATCACCCGAG  2820
CGATGGCCGC TACTCGCTTG CGCATTGCGC TTACCACGTC GCGCTAGCAT TAGTGGGCTC  2820

TGTGATCATC TGGTCGCTGG GGAATGAATC AGGCCACGGC GCTAATCACG ACGCGCTGTA  2880
ACACTAGTAG ACCAGCGACC CCTTACTTAG TCCGGTGCCG CGATTAGTGC TGCGCGACAT  2880

TCGCTGGATC AAATCTGTCG ATCCTTCCCG CCCGGTGCAG TATGAAGGCG GCGGAGCCGA  2940
AGCGACCTAG TTTAGACAGC TAGGAAGGGC GGGCCACGTC ATACTTCCGC CGCCTCGGCT  2940

CACCACGGCC ACCGATATTA TTTGCCCGAT GTACGCGCGC GTGGATGAAG ACCAGCCCTT  3000
GTGGTGCCGG TGGCTATAAT AAACGGGCTA CATGCGCGCG CACCTACTTC TGGTCGGGAA  3000

CCCGGCTGTG CCGAAATGGT CCATCAAAAA ATGGCTTTCG CTACCTGGAG AGACGCGCCC  3060
GGGCCGACAC GGCTTTACCA GGTAGTTTTT TACCGAAAGC GATGGACCTC TCTGCGCGGG  3060

GCTGATCCTT TGCGAATACG CCCACGCGAT GGGTAACAGT CTTGGCGGTT TCGCTAAATA  3120
CGACTAGGAA ACGCTTATGC GGGTGCGCTA CCCATTGTCA GAACCGCCAA AGCGATTTAT  3120
```

FIG.13E pICAST OMN

```
CTGGCAGGCG TTTCGTCAGT ATCCCCGTTT ACAGGGCGGC TTCGTCTGGG ACTGGGTGGA    3180
GACCGTCCGC AAAGCAGTCA TAGGGGCAAA TGTCCCGCCG AAGCAGACCC TGACCCACCT    3180

TCAGTCGCTG ATTAAATATG ATGAAAACGG CAACCCGTGG TCGGCTTACG GCGGTGATTT    3240
AGTCAGCGAC TAATTTATAC TACTTTTGCC GTTGGGCACC AGCCGAATGC CGCCACTAAA    3240

TGGCGATACG CCGAACGATC GCCAGTTCTG TATGAACGGT CTGGTCTTTG CCGACCGCAC    3300
ACCGCTATGC GGCTTGCTAG CGGTCAAGAC ATACTTGCCA GACCAGAAAC GGCTGGCGTG    3300

GCCGCATCCA GCGCTGACGG AAGCAAAACA CCAGCAGCAG TTTTTCCAGT TCCGTTTATC    3360
CGGCGTAGGT CGCGACTGCC TTCGTTTTGT GGTCGTCGTC AAAAAGGTCA AGGCAAATAG    3360

CGGGCAAACC ATCGAAGTGA CCAGCGAATA CCTGTTCCGT CATAGCGATA ACGAGCTCCT    3420
GCCCGTTTGG TAGCTTCACT GGTCGCTTAT GGACAAGGCA GTATCGCTAT TGCTCGAGGA    3420

GCACTGGATG GTGGCGCTGG ATGGTAAGCC GCTGGCAAGC GGTGAAGTGC CTCTGGATGT    3480
CGTGACCTAC CACCGCGACC TACCATTCGG CGACCGTTCG CCACTTCACG GAGACCTACA    3480

CGCTCCACAA GGTAAACAGT TGATTGAACT GCCTGAACTA CCGCAGCCGG AGAGCGCCGG    3540
GCGAGGTGTT CCATTTGTCA ACTAACTTGA CGGACTTGAT GGCGTCGGCC TCTCGCGGCC    3540

GCAACTCTGG CTCACAGTAC GCGTAGTGCA ACCGAACGCG ACCGCATGGT CAGAAGCCGG    3600
CGTTGAGACC GAGTGTCATG CGCATCACGT TGGCTTGCGC TGGCGTACCA GTCTTCGGCC    3600

GCACATCAGC GCCTGGCAGC AGTGGCGTCT GGCGGAAAAC CTCAGTGTGA CGCTCCCCGC    3660
CGTGTAGTCG CGGACCGTCG TCACCGCAGA CCGCCTTTTG GAGTCACACT GCGAGGGGCG    3660

CGCGTCCCAC GCCATCCCGC ATCTGACCAC CAGCGAAATG GATTTTTGCA TCGAGCTGGG    3720
GCGCAGGGTG CGGTAGGGCG TAGACTGGTG GTCGCTTTAC CTAAAAACGT AGCTCGACCC    3720

TAATAAGCGT TGGCAATTTA ACCGCCAGTC AGGCTTTCTT TCACAGATGT GGATTGGCGA    3780
ATTATTCGCA ACCGTTAAAT TGGCGGTCAG TCCGAAAGAA AGTGTCTACA CCTAACCGCT    3780

TAAAAAACAA CTGCTGACGC CGCTGCGCGA TCAGTTCACC CGTGTCGATA GATCTGGAGG    3840
ATTTTTTGTT GACGACTGCG GCGACGCGCT AGTCAAGTGG GCACAGCTAT CTAGACCTCC    3840

TGGTGGCAGC AGGCCTTGGC GCGCCGGATC CTTAATTAAC AATTGACCGG TAATAATAGG    3900
ACCACCGTCG TCCGGAACCG CGCGGCCTAG GAATTAATTG TTAACTGGCC ATTATTATCC    3900
```

FIG. 13F pICAST OMN

```
TAGATAAGTG ACTGATTAGA TGCATTTCGA CTAGATCCCT CGACCAATTC CGGTTATTTT    3960
ATCTATTCAC TGACTAATCT ACGTAAAGCT GATCTAGGGA GCTGGTTAAG GCCAATAAAA    3960

CCACCATATT GCCGTCTTTT GGCAATGTGA GGGCCCGGAA ACCTGGCCCT GTCTTCTTGA    4020
GGTGGTATAA CGGCAGAAAA CCGTTACACT CCCGGGCCTT TGGACCGGGA CAGAAGAACT    4020

CGAGCATTCC TAGGGGTCTT TCCCCTCTCG CCAAAGGAAT GCAAGGTCTG TTGAATGTCG    4080
GCTCGTAAGG ATCCCCAGAA AGGGGAGAGC GGTTTCCTTA CGTTCCAGAC AACTTACAGC    4080

TGAAGGAAGC AGTTCCTCTG GAAGCTTCTT GAAGACAAAC AACGTCTGTA GCGACCCTTT    4140
ACTTCCTTCG TCAAGGAGAC CTTCGAAGAA CTTCTGTTTG TTGCAGACAT CGCTGGGAAA    4140

GCAGGCAGCG GAACCCCCCA CCTGGCGACA GGTGCCTCTG CGGCCAAAAG CCACGTGTAT    4200
CGTCCGTCGC CTTGGGGGGT GGACCGCTGT CCACGGAGAC GCCGGTTTTC GGTGCACATA    4200

AAGATACACC TGCAAAGGCG GCACAACCCC AGTGCCACGT TGTGAGTTGG ATAGTTGTGG    4260
TTCTATGTGG ACGTTTCCGC CGTGTTGGGG TCACGGTGCA ACACTCAACC TATCAACACC    4260

AAAGAGTCAA ATGGCTCTCC TCAAGCGTAT TCAACAAGGG GCTGAAGGAT GCCCAGAAGG    4320
TTTCTCAGTT TACCGAGAGG AGTTCGCATA AGTTGTTCCC CGACTTCCTA CGGGTCTTCC    4320

TACCCCATTG TATGGGATCT GATCTGGGGC CTCGGTGCAC ATGCTTTACA TGTGTTTAGT    4380
ATGGGGTAAC ATACCCTAGA CTAGACCCCG GAGCCACGTG TACGAAATGT ACACAAATCA    4380

CGAGGTTAAA AAACGTCTAG GCCCCCCGAA CCACGGGGAC GTGGTTTTCC TTTGAAAAAC    4440
GCTCCAATTT TTTGCAGATC CGGGGGGCTT GGTGCCCCTG CACCAAAAGG AAACTTTTTG    4440

ACGATGATAA TACCATGAAA AAGCCTGAAC TCACCGCGAC GTCTGTCGAG AAGTTTCTGA    4500
TGCTACTATT ATGGTACTTT TTCGGACTTG AGTGGCGCTG CAGACAGCTC TTCAAAGACT    4500

TCGAAAAGTT CGACAGCGTC TCCGACCTGA TGCAGCTCTC GGAGGGCGAA GAATCTCGTG    4560
AGCTTTTCAA GCTGTCGCAG AGGCTGGACT ACGTCGAGAG CCTCCCGCTT CTTAGAGCAC    4560

CTTTCAGCTT CGATGTAGGA GGGCGTGGAT ATGTCCTGCG GGTAAATAGC TGCGCCGATG    4620
GAAAGTCGAA GCTACATCCT CCCGCACCTA TACAGGACGC CCATTTATCG ACGCGGCTAC    4620

GTTTCTACAA AGATCGTTAT GTTTATCGGC ACTTTGCATC GGCCGCGCTC CCGATTCCGG    4680
CAAAGATGTT TCTAGCAATA CAAATAGCCG TGAAACGTAG CCGGCGCGAG GGCTAAGGCC    4680
```

FIG. 13G pICAST OMN

```
AAGTGCTTGA CATTGGGGAA TTTAGCGAGA GCCTGACCTA TTGCATCTCC CGCCGTGCAC  4740
TTCACGAACT GTAACCCCTT AAATCGCTCT CGGACTGGAT AACGTAGAGG GCGGCACGTG  4740

AGGGTGTCAC GTTGCAAGAC CTGCCTGAAA CCGAACTGCC CGCTGTTCTG CAGCCGGTCG  4800
TCCCACAGTG CAACGTTCTG GACGGACTTT GGCTTGACGG GCGACAAGAC GTCGGCCAGC  4800

CGGAGGCCAT GGATGCGATC GCTGCGGCCG ATCTTAGCCA GACGAGCGGG TTCGGCCCAT  4860
GCCTCCGGTA CCTACGCTAG CGACGCCGGC TAGAATCGGT CTGCTCGCCC AAGCCGGGTA  4860

TCGGACCGCA AGGAATCGGT CAATACACTA CATGGCGTGA TTTCATATGC GCGATTGCTG  4920
AGCCTGGCGT TCCTTAGCCA GTTATGTGAT GTACCGCACT AAAGTATACG CGCTAACGAC  4920

ATCCCCATGT GTATCACTGG CAAACTGTGA TGGACGACAC CGTCAGTGCG TCCGTCGCGC  4980
TAGGGGTACA CATAGTGACC GTTTGACACT ACCTGCTGTG GCAGTCACGC AGGCAGCGCG  4980

AGGCTCTCGA TGAGCTGATG CTTTGGGCCG AGGACTGCCC CGAAGTCCGG CACCTCGTGC  5040
TCCGAGAGCT ACTCGACTAC GAAACCCGGC TCCTGACGGG GCTTCAGGCC GTGGAGCACG  5040

ACGCGGATTT CGGCTCCAAC AATGTCCTGA CGGACAATGG CCGCATAACA GCGGTCATTG  5100
TGCGCCTAAA GCCGAGGTTG TTACAGGACT GCCTGTTACC GGCGTATTGT CGCCAGTAAC  5100

ACTGGAGCGA GGCGATGTTC GGGGATTCCC AATACGAGGT CGCCAACATC TTCTTCTGGA  5160
TGACCTCGCT CCGCTACAAG CCCCTAAGGG TTATGCTCCA GCGGTTGTAG AAGAAGACCT  5160

GGCCGTGGTT GGCTTGTATG GAGCAGCAGA CGCGCTACTT CGAGCGGAGG CATCCGGAGC  5220
CCGGCACCAA CCGAACATAC CTCGTCGTCT GCGCGATGAA GCTCGCCTCC GTAGGCCTCG  5220

TTGCAGGATC GCCGCGGCTC CGGGCGTATA TGCTCCGCAT TGGTCTTGAC CAACTCTATC  5280
AACGTCCTAG CGGCGCCGAG GCCCGCATAT ACGAGGCGTA ACCAGAACTG GTTGAGATAG  5280

AGAGCTTGGT TGACGGCAAT TTCGATGATG CAGCTTGGGC GCAGGGTCGA TGCGACGCAA  5340
TCTCGAACCA ACTGCCGTTA AAGCTACTAC GTCGAACCCG CGTCCCAGCT ACGCTGCGTT  5340

TCGTCCGATC CGGAGCCGGG ACTGTCGGGC GTACACAAAT CGCCCGCAGA AGCGCGGCCG  5400
AGCAGGCTAG GCCTCGGCCC TGACAGCCCG CATGTGTTTA GCGGGCGTCT TCGCGCCGGC  5400

TCTGGACCGA TGGCTGTGTA GAAGTACTCG CCGATAGTGG AAACCGACGC CCCAGCACTC  5460
AGACCTGGCT ACCGACACAT CTTCATGAGC GGCTATCACC TTTGGCTGCG GGGTCGTGAG  5460
```

FIG. 13H pICAST OMN

```
GTCCGAGGGC AAAGGAATAG AGTAGATGCC GACCGGGATC TATCGATAAA ATAAAAGATT    5520
CAGGCTCCCG TTTCCTTATC TCATCTACGG CTGGCCCTAG ATAGCTATTT TATTTTCTAA    5520

TTATTTAGTC TCCAGAAAAA GGGGGGAATG AAGACCCCAA CCTGTAGGTT TGGCAAGCTA    5580
AATAAATCAG AGGTCTTTTT CCCCCCTTAC TTTCTGGGGT GGACATCCAA ACCGTTCGAT    5580

GCTTAAGTAA CGCCATTTTG CAAGGCATGG AAAAATACAT AACTGAGAAT AGAGAAGTTC    5640
CGAATTCATT GCGGTAAAAC GTTCCGTACC TTTTTATGTA TTGACTCTTA TCTCTTCAAG    5640

AGATCAAGGT CAGGAACAGA TGGAACAGCT GAATATGGGC CAAACAGGAT ATCTGTGGTA    5700
TCTAGTTCCA GTCCTTGTCT ACCTTGTCGA CTTATACCCG GTTTGTCCTA TAGACACCAT    5700

AGCAGTTCCT GCCCCGGCTC AGGGCCAAGA ACAGATGGAA CAGCTGAATA TGGGCCAAAC    5760
TCGTCAAGGA CGGGGCCGAG TCCCGGTTCT TGTCTACCTT GTCGACTTAT ACCCGGTTTG    5760

AGGATATCTG TGGTAAGCAG TTCCTGCCCC GGCTCAGGGC CAAGAACAGA TGGTCCCCAG    5820
TCCTATAGAC ACCATTCGTC AAGGACGGGG CCGAGTCCCG GTTCTTGTCT ACCAGGGGTC    5820

ATGCGGTCCA GCCCTCAGCA GTTTCTAGAG AACCATCAGA TGTTTCCAGG GTGCCCCAAG    5880
TACGCCAGGT CGGGAGTCGT CAAAGATCTC TTGGTAGTCT ACAAAGGTCC CACGGGGTTC    5880

GACCTGAAAT GACCCTGTGC CTTATTTGAA CTAACCAATC AGTTCGCTTC TCGCTTCTGT    5940
CTGGACTTTA CTGGGACACG GAATAAACTT GATTGGTTAG TCAAGCGAAG AGCGAAGACA    5940

TCGCGCGCTT CTGCTCCCCG AGCTCAATAA AAGAGCCCAC AACCCCTCAC TCGGGGCGCC    6000
AGCGCGCGAA GACGAGGGGC TCGAGTTATT TTCTCGGGTG TTGGGGAGTG AGCCCCGCGG    6000

AGTCCTCCGA TTGACTGAGT CGCCCGGGTA CCCGTGTATC CAATAAACCC TCTTGCAGTT    6060
TCAGGAGGCT AACTGACTCA GCGGGCCCAT GGGCACATAG GTTATTTGGG AGAACGTCAA    6060

GCATCCGACT TGTGGTCTCG CTGTTCCTTG GGAGGGTCTC CTCTGAGTGA TTGACTACCC    6120
CGTAGGCTGA ACACCAGAGC GACAAGGAAC CCTCCCAGAG GAGACTCACT AACTGATGGG    6120

GTCAGCGGGG GTCTTTCATT CATGCAGCAT GTATCAAAAT TAATTTGGTT TTTTTTCTTA    6180
CAGTCGCCCC CAGAAAGTAA GTACGTCGTA CATAGTTTTA ATTAAACCAA AAAAAAGAAT    6180

AGTATTTTACA TTAAATGGCC ATAGTTGCAT TAATGAATCG GCCAACGCGC GGGGAGAGGC    6240
TCATAAATGT AATTTACCGG TATCAACGTA ATTACTTAGC CGGTTGCGCG CCCCTCTCCG    6240
```

FIG.131 pICAST OMN

```
GGTTTGCGTA TTGGCGCTCT TCCGCTTCCT CGCTCACTGA CTCGCTGCGC TCGGTCGTTC    6300
CCAAACGCAT AACCGCGAGA AGGCGAAGGA GCGAGTGACT GAGCGACGCG AGCCAGCAAG    6300

GGCTGCGGCG AGCGGTATCA GCTCACTCAA AGGCGGTAAT ACGGTTATCC ACAGAATCAG    6360
CCGACGCCGC TCGCCATAGT CGAGTGAGTT TCCGCCATTA TGCCAATAGG TGTCTTAGTC    6360

GGGATAACGC AGGAAAGAAC ATGTGAGCAA AAGGCCAGCA AAAGGCCAGG AACCGTAAAA    6420
CCCTATTGCG TCCTTTCTTG TACACTCGTT TTCCGGTCGT TTTCCGGTCC TTGGCATTTT    6420

AGGCCGCGTT GCTGGCGTTT TTCCATAGGC TCCGCCCCCC TGACGAGCAT CACAAAAATC    6480
TCCGGCGCAA CGACCGCAAA AAGGTATCCG AGGCGGGGGG ACTGCTCGTA GTGTTTTTAG    6480

GACGCTCAAG TCAGAGGTGG CGAAACCCGA CAGGACTATA AAGATACCAG GCGTTTCCCC    6540
CTGCGAGTTC AGTCTCCACC GCTTTGGGCT GTCCTGATAT TTCTATGGTC CGCAAAGGGG    6540

CTGGAAGCTC CCTCGTGCGC TCTCCTGTTC CGACCCTGCC GCTTACCGGA TACCTGTCCG    6600
GACCTTCGAG GGAGCACGCG AGAGGACAAG GCTGGGACGG CGAATGGCCT ATGGACAGGC    6600

CCTTTCTCCC TTCGGGAAGC GTGGCGCTTT CTCATAGCTC ACGCTGTAGG TATCTCAGTT    6660
GGAAAGAGGG AAGCCCTTCG CACCGCGAAA GAGTATCGAG TGCGACATCC ATAGAGTCAA    6660

CGGTGTAGGT CGTTCGCTCC AAGCTGGGCT GTGTGCACGA ACCCCCCGTT CAGCCCGACC    6720
GCCACATCCA GCAAGCGAGG TTCGACCCGA CACACGTGCT TGGGGGGCAA GTCGGGCTGG    6720

GCTGCGCCTT ATCCGGTAAC TATCGTCTTG AGTCCAACCC GGTAAGACAC GACTTATCGC    6780
CGACGCGGAA TAGGCCATTG ATAGCAGAAC TCAGGTTGGG CCATTCTGTG CTGAATAGCG    6780

CACTGGCAGC AGCCACTGGT AACAGGATTA GCAGAGCGAG GTATGTAGGC GGTGCTACAG    6840
GTGACCGTCG TCGGTGACCA TTGTCCTAAT CGTCTCGCTC CATACATCCG CCACGATGTC    6840

AGTTCTTGAA GTGGTGGCCT AACTACGGCT ACACTAGAAG AACAGTATTT GGTATCTGCG    6900
TCAAGAACTT CACCACCGGA TTGATGCCGA TGTGATCTTC TTGTCATAAA CCATAGACGC    6900

CTCTGCTGAA GCCAGTTACC TTCGGAAAAA GAGTTGGTAG CTCTTGATCC GGCAAACAAA    6960
GAGACGACTT CGGTCAATGG AAGCCTTTTT CTCAACCATC GAGAACTAGG CCGTTTGTTT    6960

CCACCGCTGG TAGCGGTGGT TTTTTTGTTT GCAAGCAGCA GATTACGCGC AGAAAAAAAG    7020
GGTGGCGACC ATCGCCACCA AAAAAACAAA CGTTCGTCGT CTAATGCGCG TCTTTTTTTC    7020
```

FIG.13J pICAST OMN

```
GATCTCAAGA AGATCCTTTG ATCTTTTCTA CGGGGTCTGA CGCTCAGTGG AACGAAAACT    7080
CTAGAGTTCT TCTAGGAAAC TAGAAAAGAT GCCCCAGACT GCGAGTCACC TTGCTTTTGA    7080

CACGTTAAGG GATTTTGGTC ATGAGATTAT CAAAAAGGAT CTTCACCTAG ATCCTTTTGC    7140
GTGCAATTCC CTAAAACCAG TACTCTAATA GTTTTTCCTA GAAGTGGATC TAGGAAAACG    7140

GGCCGCAAAT CAATCTAAAG TATATATGAG TAAACTTGGT CTGACAGTTA CCAATGCTTA    7200
CCGGCGTTTA GTTAGATTTC ATATATACTC ATTTGAACCA GACTGTCAAT GGTTACGAAT    7200

ATCAGTGAGG CACCTATCTC AGCGATCTGT CTATTTCGTT CATCCATAGT TGCCTGACTC    7260
TAGTCACTCC GTGGATAGAG TCGCTAGACA GATAAAGCAA GTAGGTATCA ACGGACTGAG    7260

CCCGTCGTGT AGATAACTAC GATACGGGAG GGCTTACCAT CTGGCCCCAG TGCTGCAATG    7320
GGGCAGCACA TCTATTGATG CTATGCCCTC CCGAATGGTA GACCGGGGTC ACGACGTTAC    7320

ATACCGCGAG ACCCACGCTC ACCGGCTCCA GATTTATCAG CAATAAACCA GCCAGCCGGA    7380
TATGGCGCTC TGGGTGCGAG TGGCCGAGGT CTAAATAGTC GTTATTTGGT CGGTCGGCCT    7380

AGGGCCGAGC GCAGAAGTGG TCCTGCAACT TTATCCGCCT CCATCCAGTC TATTAATTGT    7440
TCCCGGCTCG CGTCTTCACC AGGACGTTGA AATAGGCGGA GGTAGGTCAG ATAATTAACA    7440

TGCCGGGAAG CTAGAGTAAG TAGTTCGCCA GTTAATAGTT TGCGCAACGT TGTTGCCATT    7500
ACGGCCCTTC GATCTCATTC ATCAAGCGGT CAATTATCAA ACGCGTTGCA ACAACGGTAA    7500

GCTACAGGCA TCGTGGTGTC ACGCTCGTCG TTTGGTATGG CTTCATTCAG CTCCGGTTCC    7560
CGATGTCCGT AGCACCACAG TGCGAGCAGC AAACCATACC GAAGTAAGTC GAGGCCAAGG    7560

CAACGATCAA GGCGAGTTAC ATGATCCCCC ATGTTGTGCA AAAAAGCGGT TAGCTCCTTC    7620
GTTGCTAGTT CCGCTCAATG TACTAGGGGG TACAACACGT TTTTTCGCCA ATCGAGGAAG    7620

GGTCCTCCGA TCGTTGTCAG AAGTAAGTTG GCCGCAGTGT TATCACTCAT GGTTATGGCA    7680
CCAGGAGGCT AGCAACAGTC TTCATTCAAC CGGCGTCACA ATAGTGAGTA CCAATACCGT    7680

GCACTGCATA ATTCTCTTAC TGTCATGCCA TCCGTAAGAT GCTTTTCTGT GACTGGTGAG    7740
CGTGACGTAT TAAGAGAATG ACAGTACGGT AGGCATTCTA CGAAAAGACA CTGACCACTC    7740

TACTCAACCA AGTCATTCTG AGAATAGTGT ATGCGGCGAC CGAGTTGCTC TTGCCCGGCG    7800
ATGAGTTGGT TCAGTAAGAC TCTTATCACA TACGCCGCTG GCTCAACGAG AACGGGCCGC    7800
```

FIG.13K pICAST OMN

```
TCAATACGGG ATAATACCGC GCCACATAGC AGAACTTTAA AAGTGCTCAT CATTGGAAAA    7860
AGTTATGCCC TATTATGGCG CGGTGTATCG TCTTGAAATT TTCACGAGTA GTAACCTTTT    7860

CGTTCTTCGG GGCGAAAACT CTCAAGGATC TTACCGCTGT TGAGATCCAG TTCGATGTAA    7920
GCAAGAAGCC CCGCTTTTGA GAGTTCCTAG AATGGCGACA ACTCTAGGTC AAGCTACATT    7920

CCCACTCGTG CACCCAACTG ATCTTCAGCA TCTTTTACTT TCACCAGCGT TTCTGGGTGA    7980
GGGTGAGCAC GTGGGTTGAC TAGAAGTCGT AGAAAATGAA AGTGGTCGCA AAGACCCACT    7980

GCAAAAACAG GAAGGCAAAA TGCCGCAAAA AAGGGAATAA GGGCGACACG GAAATGTTGA    8040
CGTTTTTGTC CTTCCGTTTT ACGGCGTTTT TTCCCTTATT CCCGCTGTGC CTTTACAACT    8040

ATACTCATAC TCTTCCTTTT TCAATATTAT TGAAGCATTT ATCAGGGTTA TTGTCTCATG    8100
TATGAGTATG AGAAGGAAAA AGTTATAATA ACTTCGTAAA TAGTCCCAAT AACAGAGTAC    8100

AGCGGATACA TATTTGAATG TATTTAGAAA AATAAACAAA TAGGGGTTCC GCGCACATTT    8160
TCGCCTATGT ATAAACTTAC ATAAATCTTT TTATTTGTTT ATCCCCAAGG CGCGTGTAAA    8160

Vector for Expression of a GPCR with inserted
Seronine/Threonine amino acid sequences as a fusion with β-gal Δα.

Vector for Expression of mutant (R170E) β-arrestin2 as a fusion with β-gal Δω.

GPCR dimerization measured by β-gal complementation

Ligand Fishing for Orphan Receptors by $\beta$-galactosidase mutant complementation in ICAST™ System

SYSTEMS FOR SENSITIVE DETECTION OF G-PROTEIN COUPLED RECEPTOR AND ORPHAN RECEPTOR FUNCTION USING REPORTER ENZYME MUTANT COMPLEMENTATION

This application is a continuation-in-part of U.S. application Ser. No. 09/654,499, filed Sep. 1, 2000, which claims the benefit from Provisional Application Ser. No. 60/180,669, filed Feb. 7, 2000. The entirety of U.S. application Ser. No. 09/654,499 and Provisional Application Ser. No. 60/180,669 are incorporated herein by reference.

BACKGROUND OF THE INVENTION

1. Field of the Invention

The present invention relates to methods of detecting G-protein-coupled receptor (GPCR) activity, and provides methods of assaying GPCR activity, methods for screening for GPCR ligands, agonists and/or antagonists, methods for screening natural and surrogate ligands for orphan GPCRs, and methods for screening compounds that interact with components of the GPCR regulatory process.

2. Background of the Technology

The actions of many extracellular signals are mediated by the interaction of G-protein-coupled receptors (GPCRs) and guanine nucleotide-binding regulatory proteins (G-proteins). G-protein-mediated signaling systems have been identified in many divergent organisms, such as mammals and yeast. The GPCRs represent a large super family of proteins which have divergent amino acid sequences, but share common structural features, in particular, the presence of seven transmembrane helical domains. GPCRs respond to, among other extracellular signals, neurotransmitters, hormones, odorants and light. Individual GPCR types activate a particular signal transduction pathway; at least ten different signal transduction pathways are known to be activated via GPCRs. For example, the beta 2-adrenergic receptor ($\beta$2AR) is a prototype mammalian GPCR. In response to agonist binding, $\beta$2AR receptors activate a G-protein (Gs) which in turn stimulates adenylate cyclase activity and results in increased cyclic adenosine monophosphate (cAMP) production in the cell.

The signaling pathway and final cellular response that result from GPCR stimulation depends on the specific class of G-protein with which the particular receptor is coupled (Hamm, "The Many Faces of G-Protein Signaling." J. Biol. Chem., 273:669–672 (1998)). For instance, coupling to the Gs class of G-proteins stimulates cAMP production and activation of the Protein Kinase A and C pathways, whereas coupling to the Gi class of G-proteins down regulates cAMP. Other second messenger systems such as calcium, phospholipase C, and phosphatidylinositol 3 may also be utilized. As a consequence, GPCR signaling events have predominantly been measured via quantification of these second messenger products.

The decrease of a response to a persistent stimulus is a widespread biological phenomenon. Signaling by diverse GPCRs is believed to be terminated by a uniform two-step mechanism. Activated receptor is first phosphorylated by a GPCR kinase (GRK). An arrestin protein binds to the activated and phosphorylated receptor, thus blocking G-protein interaction. This process is commonly referred to as desensitization, a general mechanism that has been demonstrated in a variety of functionally diverse GPCRs. Arrestin also plays a part in regulating GPCR internalization and resensitization, processes that are heterogenous among different GPCRs (Oakley, et al., J. Biol. Chem., 274:32248–32257 (1999)). The interaction between an arrestin and GPCR in processes of internalization and resensitization is dictated by the specific sequence motif in the carboxyl terminus of a given GPCR. Only a subset of GPCRs, which possess clusters of three serine or threonine residues at the carboxyl termini, were found to co-traffick with the arrestins into the endocytic vesicles after ligand stimulation. The number of receptor kinases and arrestins involved in desensitization of GPCRs is rather limited.

A common feature of GPCR physiology is desensitization and recycling of the receptor through the processes of receptor phosphorylation, endocytosis and dephosphorylation (Ferguson, et al., "G-protein-coupled receptor regulation: role of G-protein-coupled receptor kinases and arrestins." Can. J. Physiol. Pharmacol., 74:1095–1110 (1996)). Ligand-occupied GPCRs can be phosphorylated by two families of serine/threonine kinases, the G-protein-coupled receptor kinases (GRKs) and the second messenger-dependent protein kinases such as protein kinase A and protein kinase C. Phosphorylation by either class of kinases serves to down-regulate the receptor by uncoupling it from its corresponding G-protein. GRK-phosphorylation also serves to down-regulate the receptor by recruitment of a class of proteins known as the arrestins that bind the cytoplasmic domain of the receptor and promote clustering of the receptor into endocytic vescicles. Once the receptor is endocytosed, it will either be degraded in lysosomes or dephosphorylated and recycled back to the plasma membrane as a fully-functional receptor.

Binding of an arrestin protein to an activated receptor has been documented as a common phenomenon of a variety of GPCRs ranging from rhodopsin to $\beta$2AR to the neurotensin receptor (Barak, et al., "A $\beta$-arrestin/Green Fluorescent Fusion Protein Biosensor for Detecting G-Protein-Coupled Receptor Activation," J. Biol. Chem., 272:27497–500 (1997)). Consequently, monitoring arrestin interaction with a specific GPCR can be utilized as a generic tool for measuring GPCR activation. Similarly, a single G-protein and GRK also partner with a variety of receptors (Hamm, et al. (1998) and Pitcher et al., "G-Protein-Coupled Receptor Kinases," Annu. Rev. Biochem., 67:653–92 (1998)), such that these protein/protein interactions may also be monitored to determine receptor activity.

Many therapeutic drugs in use today target GPCRs, as they regulate vital physiological responses, including vasodilation, heart rate, bronchodilation, endocrine secretion and gut peristalsis. See, e.g., Lefkowitz et al., Annu. Rev. Biochem., 52:159 (1983). Some of these drugs mimic the ligand for this receptor. Other drugs act to antagonize the receptor in cases when disease arises from spontaneous activity of the receptor.

Efforts such as the Human Genome Project are identifying new GPCRs ("orphan" receptors) whose physiological roles and ligands are unknown. It is estimated that several thousand GPCRs exist in the human genome.

Various approaches have been used to monitor intracellular activity in response to a stimulant, e.g., enzyme-linked immunosorbent assay (ELISA); Fluorescense Imaging Plate Reader assay (FLIPR™, Molecular Devices Corp., Sunnyvale, Calif.); EVOscreen™, EVOTEC™, Evotec Biosystems Gmbh, Hamburg, Germany; and techniques developed by CELLOMICS™, Cellomics, Inc., Pittsburgh, Pa.

Germino et al., "Screening for in vivo protein-protein interactions." Proc. Natl. Acad. Sci., 90(3):933–937 (1993), discloses an in vivo approach for the isolation of proteins interacting with a protein of interest.

Phizicky et al., "Protein-protein interactions: methods for detection and analysis." Microbiol. Rev., 59(1): 94–123 (1995), discloses a review of biochemical, molecular biological and genetic methods used to study protein-protein interactions.

Offermanns et al., "G$\alpha_{15}$ and G$\alpha_{16}$ Couple a Wide Variety of Receptors to Phospholipase C." J. Biol. Chem., 270(25): 15175–15180 (1995), discloses that G$\alpha_{15}$ and G$\alpha_{16}$ can be activated by a wide variety of G-protein-coupled receptors. The selective coupling of an activated receptor to a distinct pattern of G-proteins is regarded as an important requirement to achieve accurate signal transduction. Id.

Barak et al., "A $\beta$-arrestin/Green Fluorescent Protein Biosensor for Detecting G Protein-coupled Receptor Activation." J. Biol. Chem., 272(44):27497–27500 (1997) and U.S. Pat. Nos. 5,891,646 and 6,110,693 disclose the use of a $\beta$-arrestin/green fluorescent fusion protein (GFP) for imaging protein translocation upon stimulation of GPCR with optical devices.

Each of the references described above has drawbacks. For example,

The prior art methodologies require over-expression of the proteins, which could cause artifact and tip the balance of cellular regulatory machineries.

The prior art visualization or imaging assays are low throughput and lack thorough quantification. Therefore, they are not suitable for high throughput pharmacological and kinetic assays.

In addition, many of the prior art assays require isolation of the GPCR rather than observation of the GPCR in a cell. There thus exists a need for improved methods for monitoring GPCR function.

SUMMARY OF THE INVENTION

The present invention provides modifications to the disclosure in U.S. application Ser. No. 09/654,499. In particular, the present invention is directed to modifications of the below aspects of the invention to further enhance assay sensitivity. The modifications include the use of genetically modified arrestins that exhibit enhanced binding to activated GPCR regardless of whether the GPCR is phosphorylated or non-phosphorylated; the use of a serine/threonine cluster strategy to facilitate screening assays for orphan receptors that do not possess this structural motif on their own; and the use of a combination of the above modifications to achieve even more enhanced detection.

A first aspect of the present invention is a method that monitors GPCR function proximally at the site of receptor activation, thus providing more information for drug discovery purposes due to fewer competing mechanisms. Activation of the GPCR is measured by a read-out for interaction of the receptor with a regulatory component such as arrestin, G-protein, GRK or other kinases, the binding of which to the receptor is dependent upon agonist occupation of the receptor. The present invention involves the detection of protein/protein interaction by complementation of mutant reporter enzymes.

Binding of arrestin to activated GPCR is a common process in the first step of desensitization that has been demonstrated for most, if not all, GPCRs studied so far. Measurement of GPCR interaction with arrestin via mutant enzyme complementation (i.e., ICAST) provides a more generic assay technology applicable for a wide variety of GPCRs and orphan receptors.

A further aspect of the present invention is a method of assessing GPCR pathway activity under test conditions by providing a test cell that expresses a GPCR, e.g., muscarinic, adrenergic, dopamine, angiotensin or endothelin, as a fusion protein to a mutant reporter enzyme and interacting a protein in the GPCR pathway, e.g., G-protein, arrestin or GRK, as a fusion protein with a complementing mutant reporter enzyme. When test cells are exposed to a known agonist to the target GPCR under test conditions, activation of the GPCR will be monitored by complementation of the reporter enzyme. Increased reporter enzyme activity reflects interaction of the GPCR with its interacting protein partner.

A further aspect of the present invention is a method of assessing GPCR pathway activity in the presence of a test arrestin, e.g., $\beta$-arrestin.

A further aspect of the present invention is a method of assessing GPCR pathway activity in the presence of a test G-protein.

A further aspect of the present invention is a method of assessing GPCR pathway activity upon exposure of the test cell to a test ligand.

A further aspect of the present invention is a method of assessing GPCR activity upon co-expression in the test cell of a second receptor. The second receptor could be the same GPCR or orphan receptor (i.e., homo-dimerization), a different GPCR or orphan receptor (i.e., hetero-dimerization) or could be a receptor of another type.

A further aspect of the present invention is a method for screening for a ligand or agonist to an orphan GPCR. The ligand or agonist could be contained in natural or synthetic libraries or mixtures or could be a physical stimulus. A test cell is provided that expresses the orphan GPCR as a fusion protein with a mutant reporter enzyme, e.g., a $\beta$-galactosidase mutant, and, for example, an arrestin or mutant form of arrestin as a fusion protein with a complementing mutant reporter enzyme, e.g., another $\beta$-galactosidase mutant. The interaction of the arrestin with the orphan GPCR upon receptor activation is measured by enzymatic activity of the complemented reporter enzyme. The test cell is exposed to a test compound, and an increase in reporter enzyme activity indicates the presence of a ligand or agonist.

A further aspect of the present invention is a method for screening a protein of interest, for example, an arrestin protein (or mutant form of the arrestin protein) for the ability to bind to a phosphorylated, or activated, GPCR. A test cell is provided that expresses a GPCR as a fusion protein with a mutant reporter enzyme, e.g., a $\beta$-galactosidase mutant, and contains arrestin (or a mutant form of arrestin) as a fusion protein with a complementing mutant reporter enzyme, e.g., another $\beta$-galactosidase mutant. The interaction of arrestin with the GPCR upon receptor activation is measured by enzymatic activity of the complemented reporter enzyme. The test cell is exposed to a known GPCR agonist and then reporter enzyme activity is detected. Increased reporter enzyme activity indicates that the $\beta$-arrestin molecule can bind to phosphorylated, or activated, GPCR in the test cell.

A further aspect of the present invention is a method to screen for an agonist to a specific GPCR. The agonist could be contained in natural or synthetic libraries or could be a physical stimulus. A test cell is provided that expresses a GPCR as a fusion protein with a mutant reporter enzyme, e.g., a $\beta$-galactosidase mutant, and, for example, an arrestin as a fusion protein with a complementing mutant reporter enzyme, e.g., another $\beta$-galactosidase mutant. The interaction of arrestin with the GPCR upon receptor activation is measured by enzymatic activity of the complemented reporter enzyme. The test cell is exposed to a test compound, and an increase in reporter enzyme activity indicates the presence of an agonist. The test cell may express a known GPCR or a variety of known GPCRs, or may express an unknown GPCR or a variety of unknown GPCRs. The GPCR may be, for example, an odorant GPCR or a βAR GPCR.

A further aspect of the present invention is a method for screening a test compound for GPCR antagonist activity. A test cell is provided that expresses a GPCR as a fusion protein with a mutant reporter enzyme, e.g., a β-galactosidase mutant, and, for example, an arrestin as a fusion protein with a complementing mutant reporter enzyme, e.g., another β-galactosidase mutant. The interaction of arrestin with the GPCR upon receptor activation is measured by enzymatic activity of the complemented reporter enzyme. The test cell is exposed to a test compound, and an increase in reporter enzyme activity indicates the presence of an agonist. The cell is exposed to a test compound and to a GPCR agonist, and reporter enzyme activity is detected. When exposure to the agonist occurs at the same time as or subsequent to exposure to the test compound, a decrease in reporter enzyme activity after exposure to the test compound indicates that the test compound has antagonist activity to the GPCR.

A further aspect of the present invention is a method of screening a sample solution for the presence of an agonist, antagonist or ligand to a GPCR. A test cell is provided that expresses GPCR as a fusion protein with a mutant reporter enzyme, e.g., a β-galactosidase mutant, and contains, for example, a β-arrestin as a fusion protein with a complementing reporter, e.g., another β-galactosidase mutant. The test cell is exposed to a sample solution, and reporter enzyme activity is assessed. Changed reporter enzyme activity after exposure to the sample solution indicates the sample solution contains an agonist, antagonist or ligand for a GPCR expressed in the cell.

A further aspect of the present invention is a method of screening a cell for the presence of a GPCR. According to this aspect, an arrestin fusion protein with a mutant reporter enzyme and a GPCR downstream signaling fusion protein with a mutant reporter enzyme are employed to detect GPCR action. A modification of this aspect of the invention can be employed to provide a method of screening a plurality of cells for those cells which contain a GPCR. According to this aspect, a plurality of cells containing a conjugate comprising a β-arrestin protein as a fusion protein with a reporter enzyme are provided; the plurality of cells are exposed to a GPCR agonist; and activity of reporter enzyme activity is detected. An increase in reporter enzymatic activity after exposure to the GPCR agonist indicates β-arrestin protein binding to a GPCR, thereby indicating that the cell contains a GPCR responsive to the GPCR agonist.

A further aspect of the invention is a method for mapping GPCR-mediated signaling pathways. For instance, the system could be utilized to monitor interaction of c-src with β-arrestin-1 upon GPCR activation. Additionally, the system could be used to monitor protein/protein interactions involved in cross-talk between GPCR signaling pathways and other pathways such as that of the receptor tyrosine kinases or Ras/Raf. According to this aspect, a test cell is provided that expresses a GPCR or other related protein with a mutant reporter enzyme, e.g., a β-galactosidase mutant, and contains a protein from another pathway as a fusion protein with a complementing mutant reporter enzyme, e.g., another β-galactosidase mutant. Increased reporter enzymatic activity indicates protein/protein interaction.

A further aspect of the invention is a method for monitoring homo- or hetero-dimerization of GPCRs upon agonist or antagonist stimulation. Increasing evidence indicates that GPCR dimerization is important for biological activity (AbdAlla, et al., "AT1-receptor heterodimers show enhanced G-protein activation and altered receptor sequestration." Nature, 407:94–98 (2000); Bockaert, et al., "Molecular tinkering of G protein-coupled receptors: an evolutionary success." EMBO J. 18:1723–29 (1999)). Jordan, et al., "G-protein-coupled receptor heterodimerization modulates receptor function." Nature, 399:697–700 (1999), demonstrated that two non-functional opioid receptors, κ and δ, heterodimerize to form a functional receptor. Gordon et al., "Dopamine D2 receptor dimers and receptor blocking peptides." Bioch. Biophys. Res. Commun. 227:200–204 (1996), showed different pharmacological properties associated with the monomeric and dimeric forms of Dopamine receptor D2. The D2 receptors exist either as monomers that are selective targets for spiperone or as dimer forms that are targets for nemonapride. Herbert, et al., "A peptide derived from a β2-adrenergic receptor transmembrane domain inhibits both receptor dimerization and activation." J.B.C. 271:16384–92 (1996), demonstrated that the agonist stimulation was found to stabilize the dimeric state of the receptor, whereas inverse agonists favored the monomeric form. Indeed, the same study showed that a peptide corresponding to the sixth transmembrane domain of the β2-adrenergic receptor inhibited both receptor dimerization and activation. Further, Angers et al., Detection of beta-2-adrenergic receptor dimerization in living cells using bioluminescence resonance energy transfer, Proc. Natl. Acad. Sci. USA, 97(7):3684–3689, discloses the use of β2-adrenergic receptor fusion proteins (i.e., β2-adrenergic receptor fused to luciferase and β2-adrenergic receptor fused to an enhanced red-shifted green fluorescent protein) to study β2-adrenergic receptor dimerization.

GPCR dimerization in the context of cellular physiology and pharmacology can be monitored in accordance with the invention. For example, β-galactosidase complementation can be measured in test cells that co-express GPCR fusion proteins of β-galactosidase mutant enzymes, e.g., $GPCR_1\Delta\alpha$ and $GPCR_2\Delta\omega$ (FIG. 27). According to this aspect, the interconversion between monomeric to dimeric forms of the GPCRs or orphan receptors can be measured by mutant reporter enzyme complementation. FIG. 27 illustrates a test cell co-expressing GPCR or an orphan receptor as a fusion protein with $\Delta\alpha$ form of β-galactosidase mutant (e.g., $GPCR_1\Delta\alpha$), and the same GPCR or orphan receptor as a fusion protein with $\Delta\omega$ form of β-galactosidase mutant (e.g. $GPCR_1\Delta\omega$). Formation of the GPCR homodimer is reflected by formation of an active enzyme, which can be measured by enzyme activity assays, such as the Gal-Screen™ assay. Similarly, hetero-dimerization between two distinct GPCRs, or two distinct orphan receptors, or between one known GPCR and one orphan receptor can be analyzed in test cells co-expressing two fusion proteins, e.g., $GPCR_1\Delta\alpha$ and $GPCR_2\Delta\omega$. The increased β-galactosidase activity indicates that the two receptors can form a heterodimer.

A further aspect of the invention is a method of monitoring the interconversion between the monomeric and dimeric form of GPCRs under the influence of agonist or antagonist treatment. The test receptor(s) can be between the same GPCR or orphan receptor (homodimer), or between two distinct GPCRs or orphan receptors (heterodimer). The increased β-galactosidase activity after treatment with a compound means that the compound binds to and/or stabilizes the dimeric form of the receptor. The decreased β-galactosidase activity after treatment with a compound means that the compound binds to and/or stabilizes the monomeric form of the receptor.

A further aspect of the invention is a method of screening a cell for the presence of a GPCR responsive to a GPCR agonist. A cell is provided that contains protein partners that interact downstream in the GPCR's pathway. The protein partners are expressed as fusion proteins to the mutant, complementing enzyme and are used to monitor activation of the GPCR. The cell is exposed to a GPCR agonist and then enzymatic activity of the reporter enzyme is detected. Increased reporter enzyme activity indicates that the cell contains a GPCR responsive to the agonist.

The present invention involves the use of a combination of proprietary technologies (including ICAST™, Intercistronic Complementation Analysis Screening Technology, Gal-Screen™, etc.) to monitor protein/protein interactions in GPCR signaling. As disclosed in U.S. application Ser. No. 09/654,499, the method of the invention in part involves using ICAST™, which in turn involves the use of two inactive β-galactosidase mutants, each of which is fused with one of two interacting target protein pairs, such as a GPCR and an arrestin. The formation of an active β-galactosidase complex is driven by interaction of the target proteins. In this system, β-galactosidase activity can be detected using, e.g., the Gal-Screen™ assay system, wherein direct cell lysis is combined with rapid ultrasensitive chemiluminescent detection of β-galactosidase reporter enzyme. This system uses, e.g., a Galacton-Star® chemiluminescent substrate for measurement in a luminometer as a read out of GPCR activity.

FIG. 23 is a schematic depicting the use of the complementation technology in the method of the present invention. FIG. 23 shows two inactive β-galactosidase mutants that become active when they are forced together by specific interactions between the fusion partners of an arrestin molecule and an activated GPCR or orphan receptor. This assay technology will be especially useful in high throughput screening assays for ligand fishing for orphan receptors, a process called de-orphaning. As illustrated in FIG. 28, a β-galactosidase fusion protein of an orphan receptor (e.g., GPCR$_{orphan}$Δα) is co-expressed in the test cell with a fusion protein of β-arrestin (e.g., β-ArrΔω). When the test cell is subjected to compounds, which could be natural or synthetic, the increased β-galactosidase activity means the compound is either a natural or surrogate ligand for this GPCR. The same assay system can be used to find drug leads for the new GPCRs. The increased β-galactosidase activity in the test cell after treatment indicates the agonist activity of the compound. The decreased β-galactosidase activity in the test cell indicates antagonist activity or inverse agonist activity of the compound. In addition, the method of the invention could be used to monitor GPCR-mediated signaling pathways via other downstream signaling components such as G-proteins, GRKs or the proto-oncogene c-Src.

The invention is achieved in part by using ICAST™ protein/protein interaction screening to map signaling pathways. This technology is applicable to a variety of known and unknown GPCRs with diverse functions. They include, but are not limited to, the following sub-families of GPCRs:

(a) receptors that bind to amine-like ligands-Acetylcholine muscarinic receptor (M1 to M5), alpha and beta Adrenoceptors, Dopamine receptors (D1, D2, D3 and D4), Histamine receptors (H1 and H2), Octopamine receptor and Serotonin receptors (5HT1, 5HT2, 5HT4, 5HT5, 5HT6, 5HT7);

(b) receptors that bind to a peptide ligand-Angiotensin receptor, Bombesin receptor, Bradykinin receptor, C—C chemokine receptors (CCR1 to CCR8, and CCR10), C-X-C type Chemokine receptors (CXC-R5), Cholecystokinin type A receptor, CCK type receptors, Endothelin receptor, Neurotesin receptor, FMLP-related receptors, Somatostatin receptors (type 1 to type 5) and Opioid receptors (type D, K, M, X);

(c) receptors that bind to hormone proteins-Follic stimulating hormone receptor, Thyrotrophin receptor and Lutropin-choriogonadotropic hormone receptor;

(d) receptors that bind to neurotransmitters-substance P receptor, Substance K receptor and neuropeptide Y receptor;

(e) Olfactory receptors-Olfactory type 1 to type 11, Gustatory and odorant receptors;

(f) Prostanoid receptors-Prostaglandin E2 (EP1 to EP4 subtypes), Prostacyclin and Thromboxane;

(g) receptors that bind to metabotropic substances-Metabotropic glutamate group I to group III receptors;

(h) receptors that respond to physical stimuli, such as light, or to chemical stimuli, such as taste and smell; and (i) orphan GPCRs-the natural ligand to the receptor is undefined.

Use of the ICAST™ technology in combination with the invention provides many benefits to the GPCR screening process, including the ability to monitor protein interactions in any sub-cellular compartment-membrane, cytosol and nucleus; the ability to achieve a more physiologically relevant model without requiring protein overexpression; and the ability to achieve a functional assay for receptor binding allowing high information content.

BRIEF DESCRIPTION OF THE DRAWINGS

FIG. 1. Cellular expression levels of β2 adrenergic receptor (β2AR) and β-arrestin-2 (βArr2) in C2 clones. Quantification of β-galactosidase (β-gal) fusion protein was performed using antibodies against β-gal and purified β-gal protein in a titration curve by a standardized ELISA assay.

FIG. 3. Interaction of activated receptor β2AR and arrestin can be measured by β-galactosidase complementation.

FIG. 4. Agonist dose response for interaction of β2AR and arrestin can be measured by β-galactosidase complementation.

FIG. 5. Antagonist mediated inhibition of receptor activity can be measured by β-galactosidase complementation in cells co-expressing β2AR-βgalΔα and βArr-βgalΔω.

FIG. 8. Variety of mammalian cell lines can be used to generate stable cells for monitoring GPCR and arrestin interactions.

FIG. 9. Beta-gal complementation can be used to monitor β2 adrenergic receptor homo-dimerization.

FIGS. 10B–10P. Nucleotide sequence for pICAST ALC (SEQ ID NO:01).

FIGS. 11B–11L. Nucleotide sequence for pICAST ALN (SEQ ID NO:02).

FIGS. 12B–12L. Nucleotide sequence for pICAST OMC (SEQ ID NO:03).

FIGS. 13B–13L. Nucleotide sequence for pICAST OMN (SEQ ID NO:04).

FIG. 23 shows two inactive mutant reporter enzymes that become active when the corresponding fusion partners, GPCR and β-arrestin interact.

DETAILED DESCRIPTION OF PREFERRED EMBODIMENTS

Figure 1A:
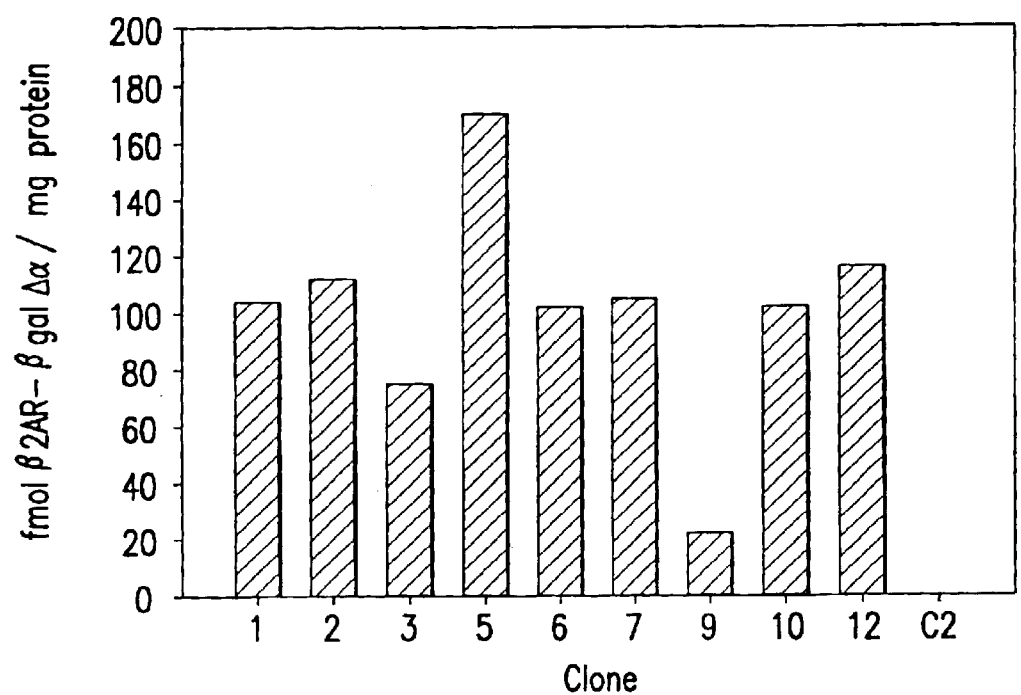
FIG. 1A shows expression levels of β2AR-βgalΔα clones (in expression vector pICAST ALC).
Figure 1B:
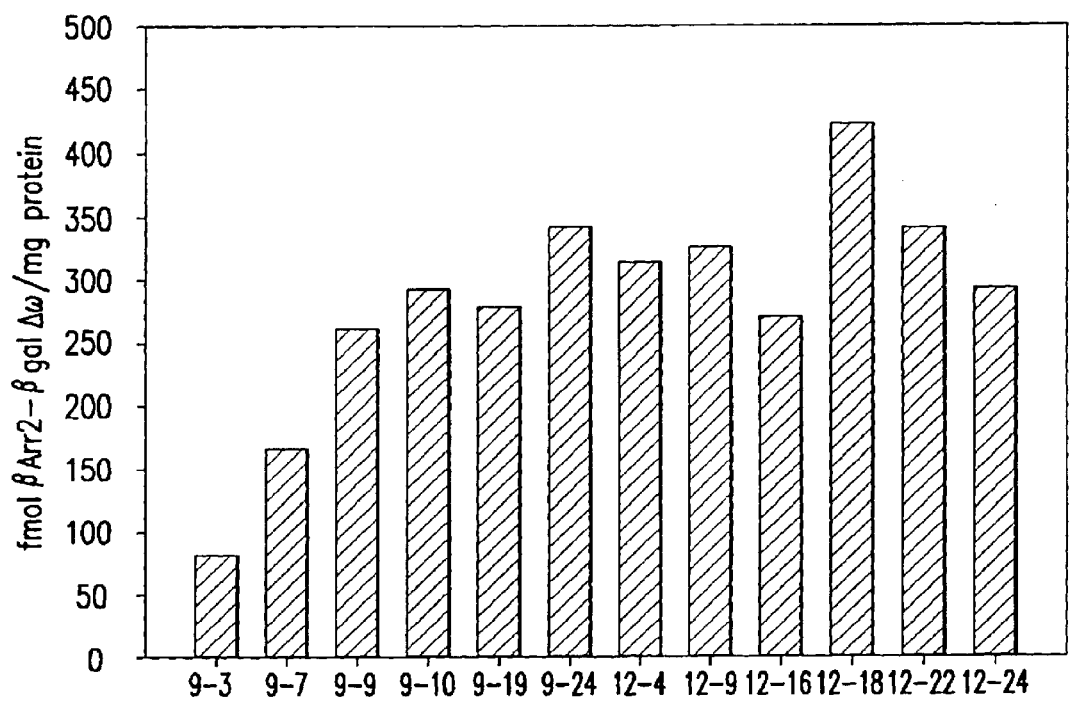
FIG. 1B shows expression levels of 3Arr2-βgalΔω in expression vector pICAST OMC4 for clones 9-3,-7,-9,-10,-19 and -24, or in expression vector pICAST OMN4 for clones 12-4,-9,-16,-18,-22 and -24.
Figure 2:
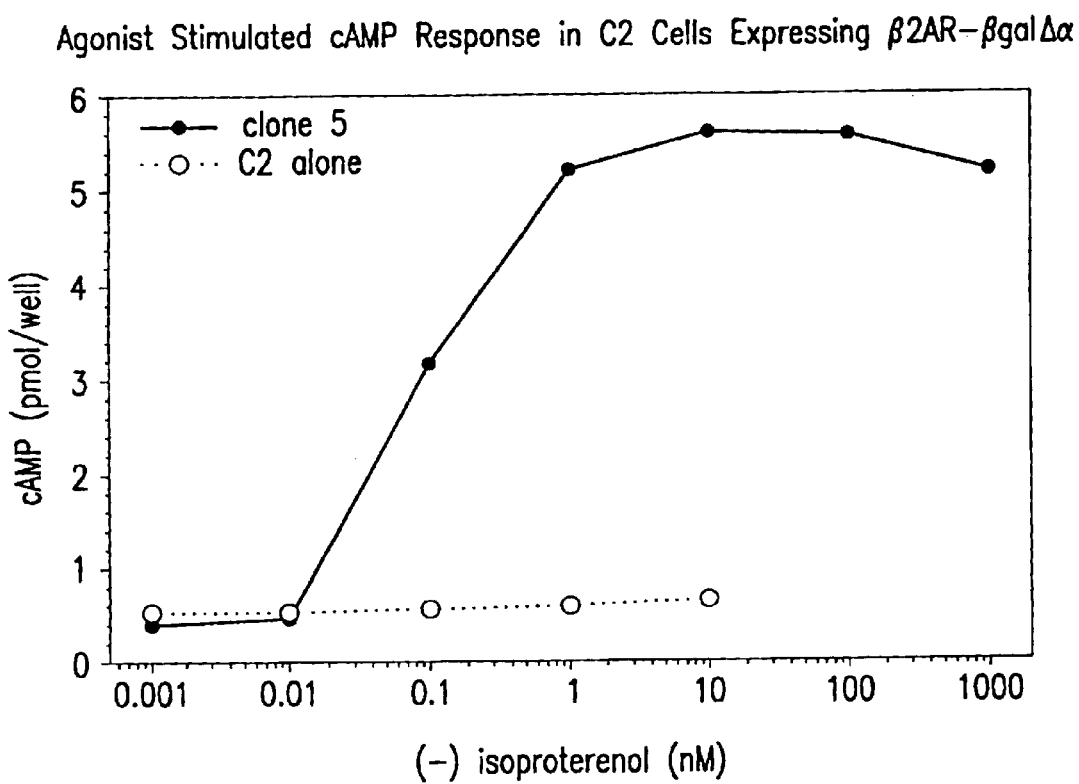
FIG. 2. Receptor β2AR activation was measured by agonist-stimulated cAMP production. C2 cells expressing pICAST ALC β2AR (clone 5) or parental cells were treated with increasing concentrations of (−)isoproterenol and 0.1 mM IBMX. The quantification of cAMP level was expressed as pmol/well.

The present invention provides a method to interrogate GPCR function and pathways. The G-protein-coupled superfamily continues to expand rapidly as new receptors are discovered through automated sequencing of cDNA libraries or genomic DNA. It is estimated that several thousand GPCRs may exist in the human genome. Only a portion have been cloned and even fewer have been associated with ligands. The means by which these, or newly discovered orphan receptors, will be associated with their cognate ligands and physiological functions represents a major challenge to biological and biomedical research. The identification of an orphan receptor generally requires an individualized assay and a guess as to its function. The present invention involves the interrogation of GPCR function by monitoring the activation of the receptor using activation dependent protein-protein interactions between the test GPCR or orphan receptor and a β-arrestin. The specific protein-protein interactions are measured using the mutant enzyme complementation technology disclosed herein. This assay system eliminates the prerequisite guessing because it can be performed with and without prior knowledge of other signaling events. It is sensitive, rapid and easily performed and is applicable to nearly all GPCRs because the majority of these receptors desensitize by a common mechanism.

The present invention provides a complete assay system for monitoring protein-protein interactions in GPCR pathways. The invention employs the complementation technology, ICAST™ (Intercistronic Complementation Analysis Screening Technology as disclosed in pending U.S. patent application Ser. No. 053,614, filed Apr. 1, 1998, the entire contents of which are incorporated herein by reference). The ICAST™ technology involves the use of two mutant forms of a reporter enzyme fused to proteins of interest. When the proteins of interest do not interact, the reporter enzyme remains inactive. When the proteins of interest do interact, the reporter enzyme mutants come together and form an active enzyme. According to an embodiment of the invention, the activity of β-galactosidase may be detected with the Gal-Screen™ assay system developed by Advanced Discovery Sciences™, which involves the use of Galacton-Star®, an ultrasensitive chemiluminescent substrate. The Gal-Screen™ assay system and the Galacton-Star® chemiluminescent substrate are disclosed in U.S. Pat. Nos. 5,851,771; 5,538,847; 5,326,882; 5,145,772; 4,978,614; and 4,931,569, the contents of which are incorporated herein by reference in their entirety. The invention provides an array of assays, including GPCR binding assays, that can be achieved directly within the cellular environment in a rapid, non-radioactive assay format. The methods of the invention are an advancement over the invention disclosed in U.S. Pat. Nos. 5,891,646 and 6,110,693 and the method disclosed in Angers et al., supra., which rely on microscopic imaging or spectrometry of GPCR components as fusion with Green-fluorescent-protein. The imaging technique disclosed in U.S. Pat. Nos. 5,891,646 and 6,110,693 and spectrometry-based technique in Angers et al. are limited by low-throughput and lack of thorough quantification.

The assay system of the invention combined with Advanced Discovery Sciences™ technologies provide highly sensitive cell-based methods for interrogating GPCR pathways which are amenable to high-throughput screening (HTS). Among some of the technologies developed by Advanced Discovery Sciences™ that may be used with the present invention are the Gal-Screen™ assay system (discussed above) and the cAMP-Screen™ immunoassay system. The cAMP-Screen™ immunoassay system provides ultrasensitive determination of cAMP levels in cell lysates. The cAMP-Screen™ assay utilizes the high-sensitivity chemiluminescent alkaline phosphatase (AP) substrate CSPD® (disodium 3-(4-methoxyspiro {1,2-dioxetane-3,2'-(5'-chloro) tricyclo 3.3.1.1.$^{3,7}$} decan-4-yl phenyl phosphate) with Sapphire-II™ luminescence enhancer.

Unlike yeast-based-two-hybrid assays used to monitor protein/protein interactions in high-throughput assays, the present invention (1) is applicable to a variety of cells including mammalian cells, plant cells, protozoa cells such as E. coli and cells of invertebrate origin such as yeast, slime mold (Dictyostelium) and insects; (2) detects interactions at the membrane at the site of the receptor target or in the cytosol at the site of downstream target proteins rather than a limited cellular localization, i.e., nucleus; and (3) does not rely on indirect read-outs such as transcriptional activation. The present invention thus provides assays with greater physiological relevance and fewer false positives.

The present inventors have developed modifications to the embodiment disclosed in U.S. patent application Ser. No. 053,614 described above in order to enhance the sensitivity of the inventive GPCR assay. According to an embodiment, the invention incorporates the use of serine/threonine clusters to enhance and prolong the interaction of GPCR with arrestin in order to make the detection more robust. The clusters can be utilized for orphan receptors or known GPCRs, which do not have this sequence motif. By adding this sequence to the C-terminal tail of the receptor, the activation of the receptor can be detected more readily by readouts of arrestin binding to GPCR, i.e., β-galactosidase complementation from fusion proteins of target proteins with β-galactosidase mutants.

According to another embodiment, the invention incorporates the use of arrestin point mutations to bypass the requirement of phosphorylation, by the action of specific GRK, on the C-terminal tail or intracellular loops of GPCR upon activation. The applications include i) wherein the cognate GRK for a particular GPCR or orphan receptor is unknown; and ii) wherein the specific GRK for the receptor of interest (or under test) may not be present or may have low activity in the host cell that is used for receptor activation assay.

According to another embodiment, the invention incorporates the use of a super arrestin to increase the binding efficiency of arrestin to an activated GPCR and to stabilize the GPCR/arrestin complex during GPCR desensitization. This application can be used to increase the robustness of ICAST/GPCR applications in cases where the GPCR is normally resensitized rapidly post desensitization.

Each of these methodologies is discussed below.

The invention will now be described in the following non-limiting examples.

EXAMPLE

Figure 23:
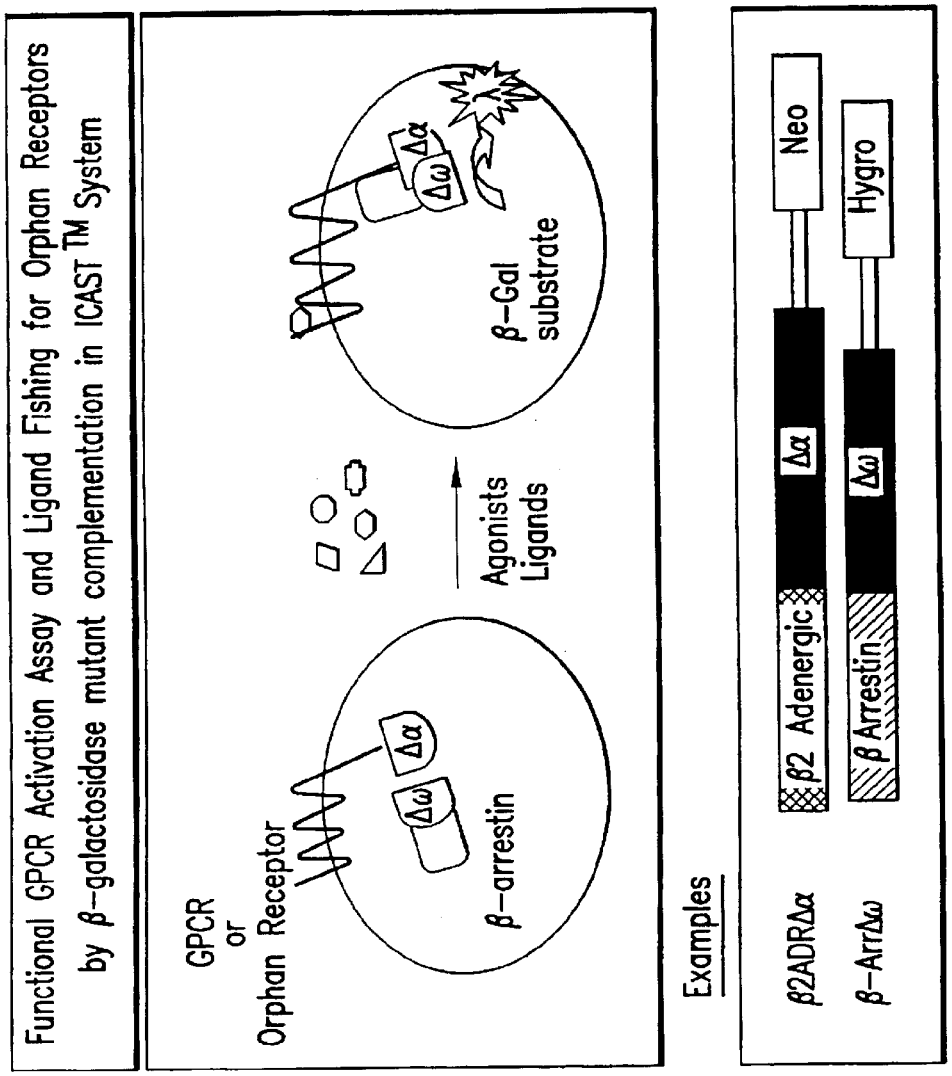
FIG. 23. A schematic depicting use of the complementation technology in the method of the invention.

According to an embodiment of the invention, GPCR activation is measured through monitoring the binding of arrestin to ligand-activated GPCR. In this assay system, a GPCR, e.g., β-adrenergic receptor (β2AR), and an arrestin, e.g., β-arrestin, are co-expressed in the same cell as fusion proteins with mutant forms of a reporter enzyme, e.g., β-galactosidase (β-gal). As illustrated in FIG. 23, the β2AR is expressed as a fusion protein with Δα form of β-gal mutant (β2ARΔα) and the β-arrestin as a fusion protein with the Δω form of β-gal mutant (β-ArrΔω). The two fusion proteins, which at first exist in a resting (or un-stimulated) cell in separate compartments, i.e., the membrane for GPCR and the cytosol for arrestin, cannot form an active β-galactosidase enzyme. When such a cell is treated with an agonist or a ligand, the ligand-occupied and activated receptor becomes a high affinity binding site for arrestin. The interaction between an activated GPCR, β2ARΔα, and arrestin, β-ArrΔω, drives the β-gal mutant complementation. The enzyme activity can be measured by using an enzyme substrate, which upon cleavage releases a product measurable by colorimetry, fluorescence, or chemiluminescence (e.g., the Gal-Screen™ assay system).

Experiment Protocol

Figure 3A:
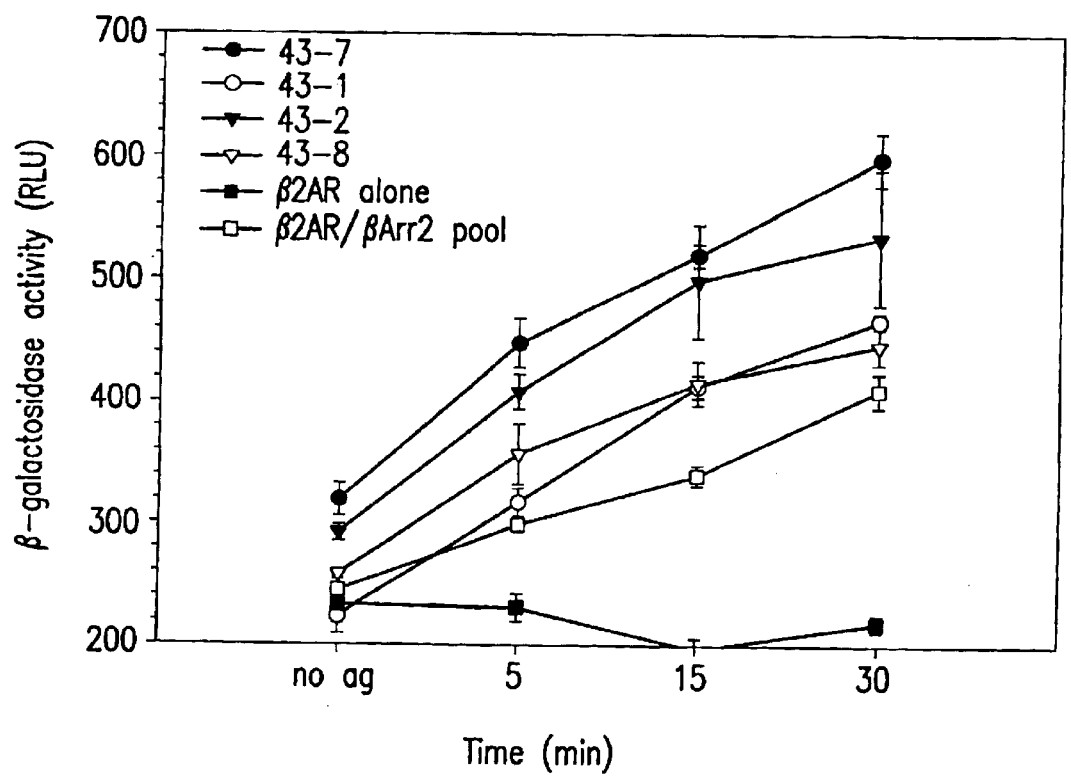
FIG. 3A shows a time course of β-galactosidase activity in response to agonist (−)isoproterenol stimulation in C2 expressing β2AR-βgalΔα (β2AR alone, in expression vector pICAST ALC), or a pool of doubly transduced C2 co-expressing β2AR-βgalΔα and βArr2-βgalΔω (in expression vectors pICAST ALC and pICAST OMC and clones isolated from the same pod (43-1, 43-2, 43-7 and 43-8)).
Figure 3B:
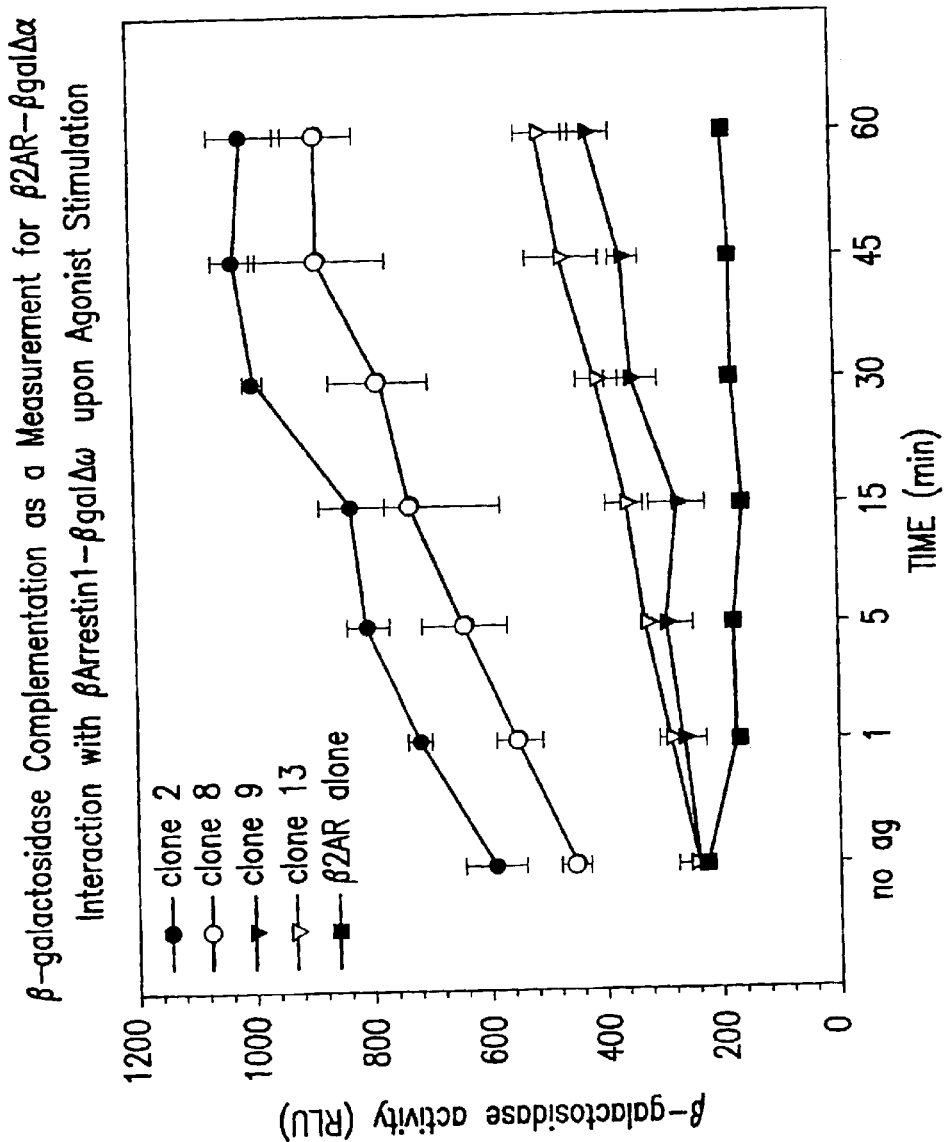
FIG. 3B shows a time course of β-galactosidase activity in response to agonist (−)isoproterenol stimulation in C2 cells expressing β2AR-βgalΔα alone (in expression vector pICAST ALC) and C2 clones co-expressing β2AR-βgalΔα and βArr1-βgalΔω (in expression vectors ICAST ALC and pICAST OMC).
Figure 4A:
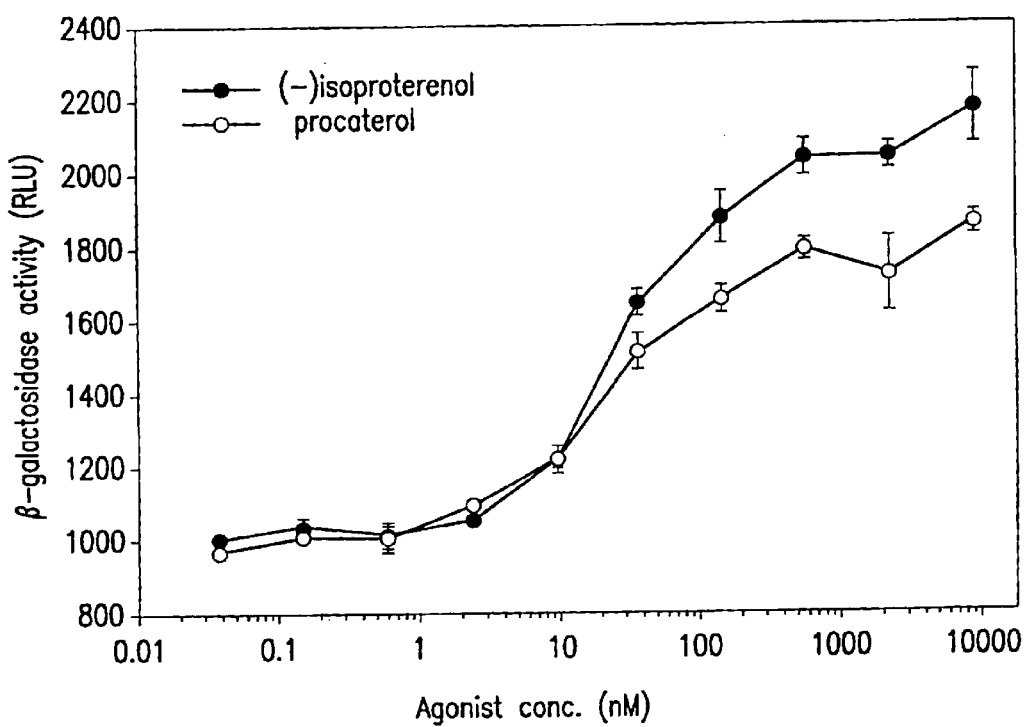
FIG. 4A shows a dose response to agonists (−)isoproterenol and procaterol in C2 cells co-expressing β2AR-βgalΔα and βArr2-βgalΔω fusion constructs.
Figure 4B:
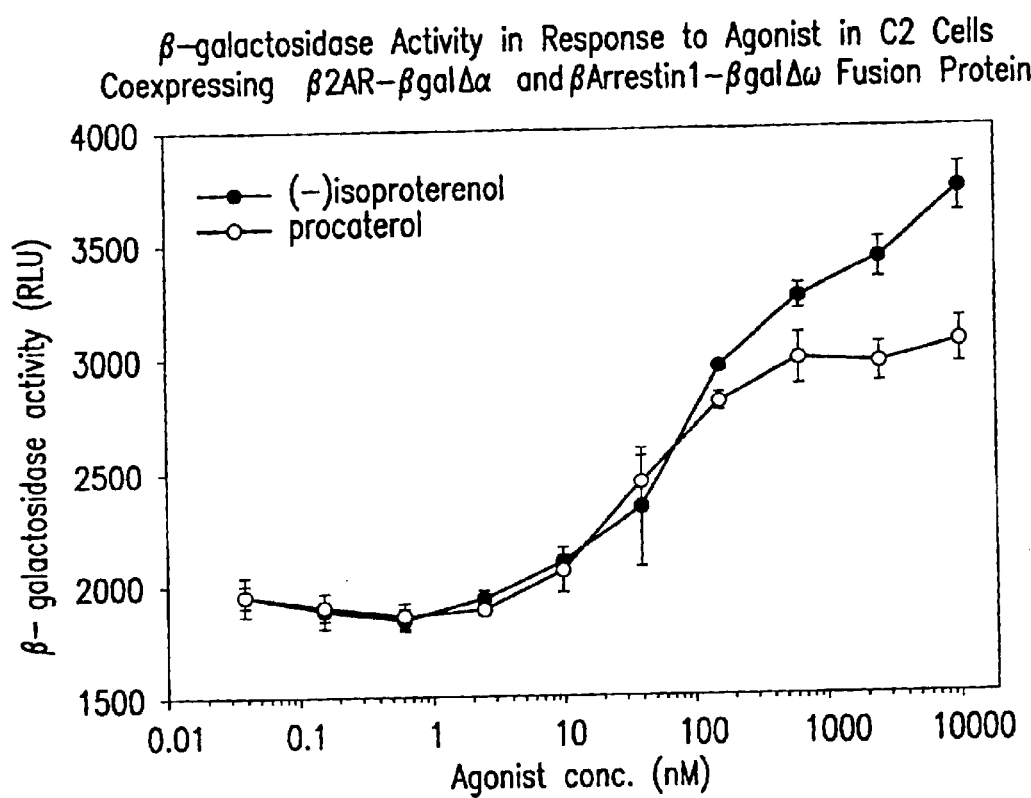
FIG. 4B shows a dose response to agonists (−)isoproterenol and procaterol in C2 cells co-expressing β2AR-βgalΔα and βArr1-βgalΔω fusion constructs.
Figure 5A:
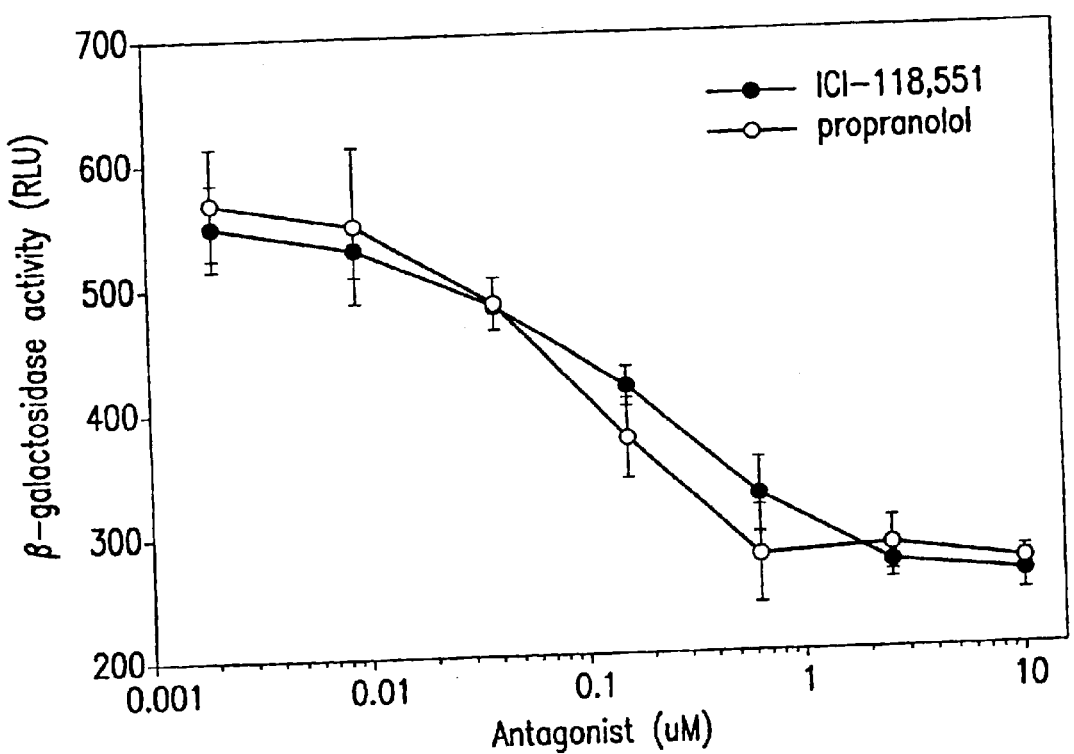
FIG. 5A shows specific inhibition with adrenergic antagonists ICI-118,551 and propranolol of β-galactosidase activity in C2 clones co-expressing β2AR-βgalΔα and βArr2-βgalΔω fusion constructs after incubation with agonist (−)isoproterenol.
Figure 5B:
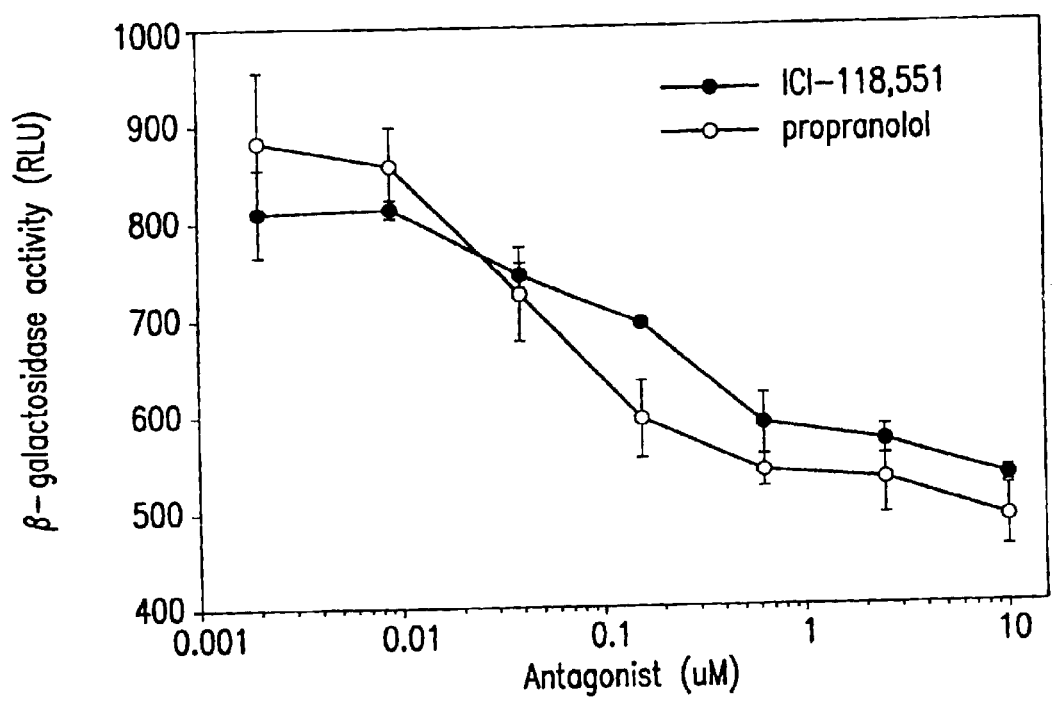
FIG. 5B shows specific inhibition of β-galactosidase activity with adrenergic antagonists ICI-118,551 and propranolol in C2 clones co-expressing β2AR-βgalΔα and βArr1-βgalΔω fusion constructs in the presence of agonist (−)isoproterenol.
Figure 6:
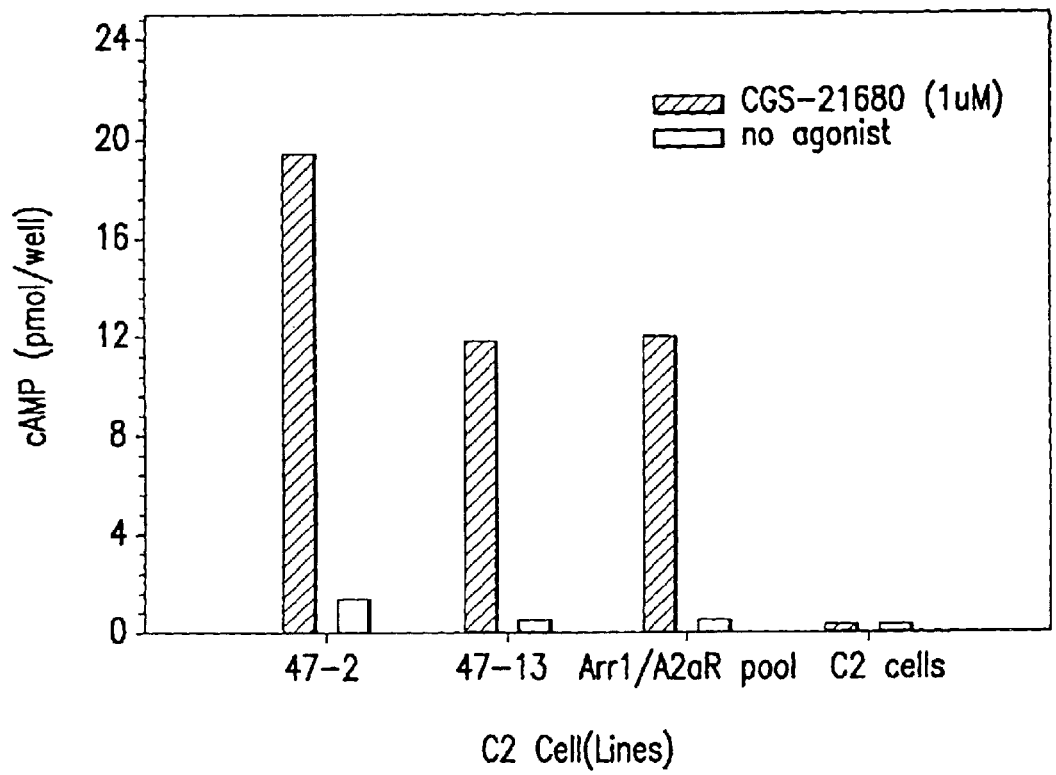
FIG. 6. C2 cells expressing adenosine receptor A2a show cAMP induction in response to agonist (CGS-21680) treatment. C2 parental cells and C2 cells co-expressing A2aR-βgalΔα and βArr1-βgalΔω as a pool or as selected clones (47-2 and 47-13) were measured for agonist-induced cAMP response (pmol/well).
Figure 7:
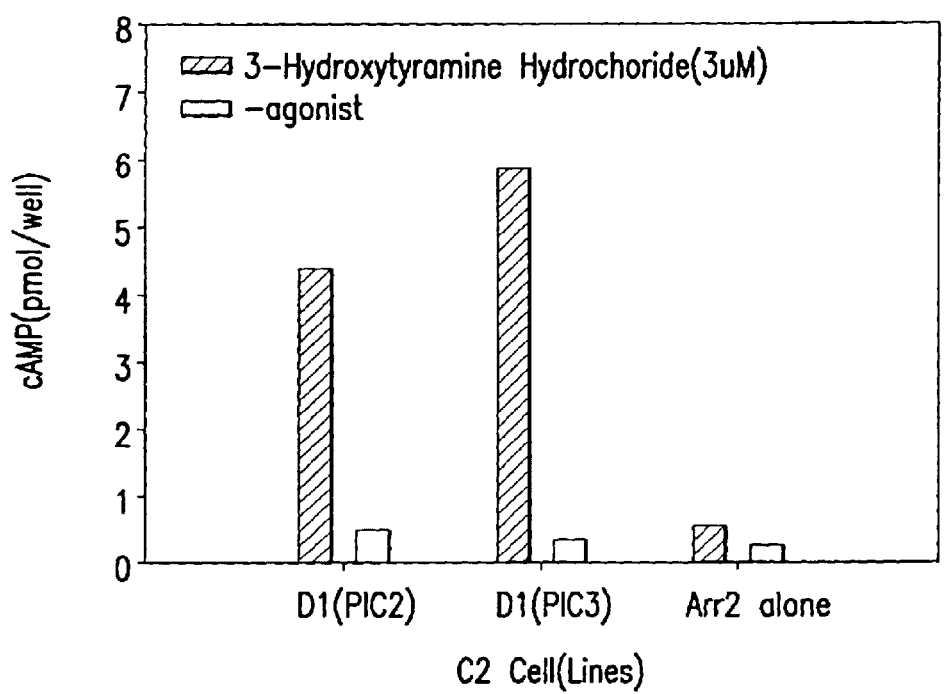
FIG. 7. Agonist stimulated cAMP response in C2 cells co-expressing Dopamine receptor D1 (D1-βgalΔα) and β-arrestin-2 (βArr2-βgalΔω). The clone expressing βArr2-βgalΔω (Arr2 alone) was used as a negative control in the assay. Cells expressing D1-βgalΔα in addition to βArr2-βgalΔω responded agonist treatment (3-hydroxytyramine hydrochloride at 3 μM). D1(PIC2) or D1(PIC3) designate D1 in expression vector pICAST ALC2 or pICAST ALC4, respectively.
Figure 8A:
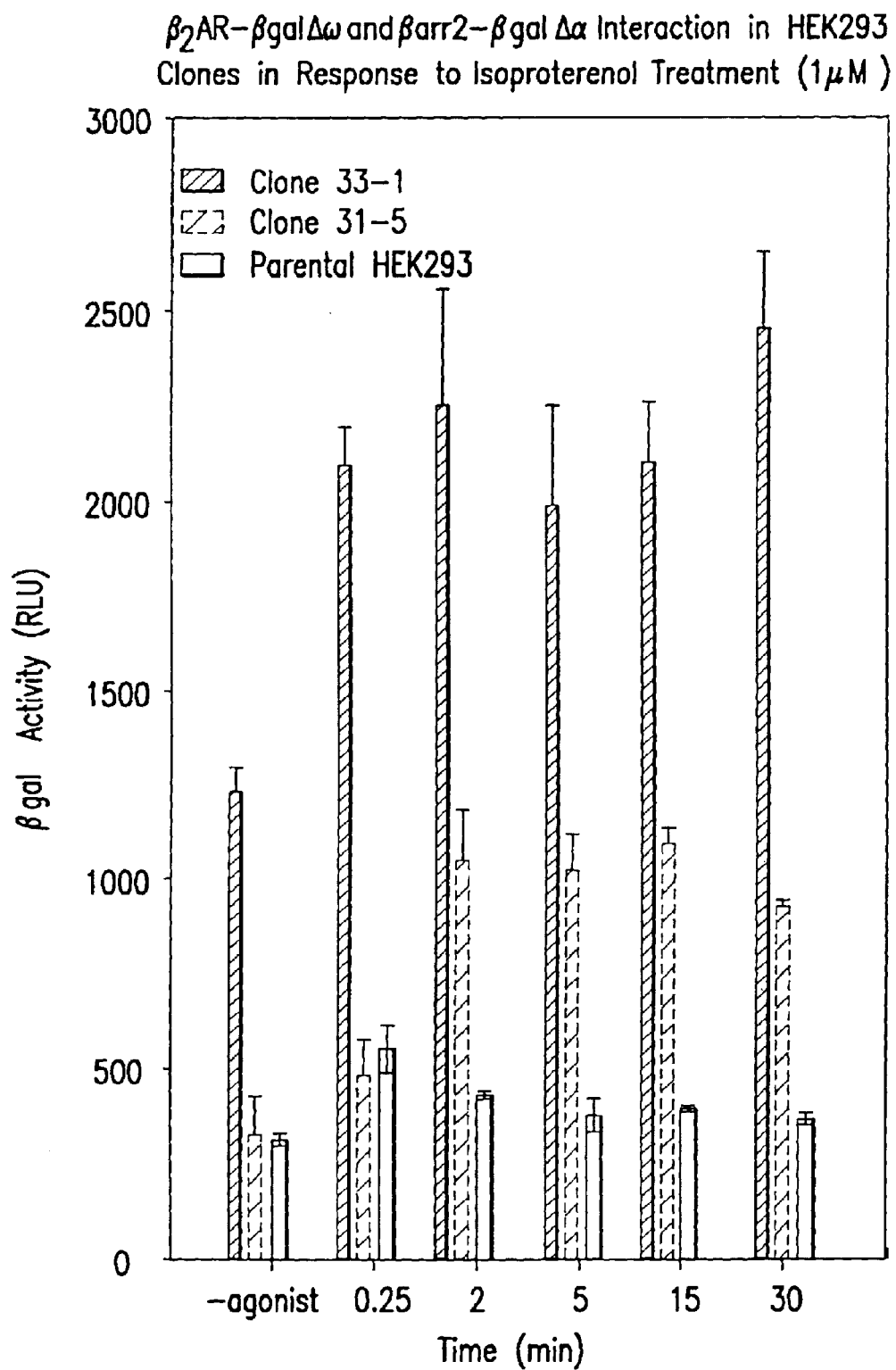
FIG. 8A, FIG. 8B and FIG. 8C show the examples of HEK 293, CHO and CHW cell lines co-expressing adrenergic receptor β2AR and arrestin fusion proteins of β-galactosidase mutants. The β-galactosidase activity was used to monitor agonist-induced interaction of β2AR and arrestin proteins.
Figure 8B:
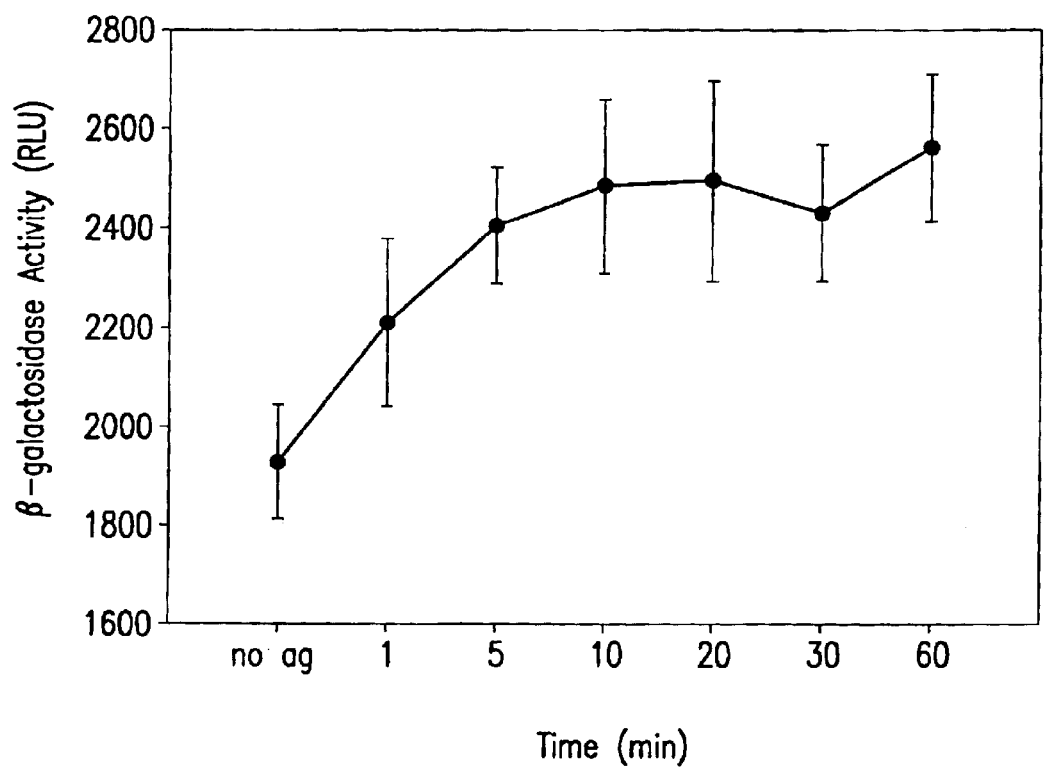
Figure 8C:
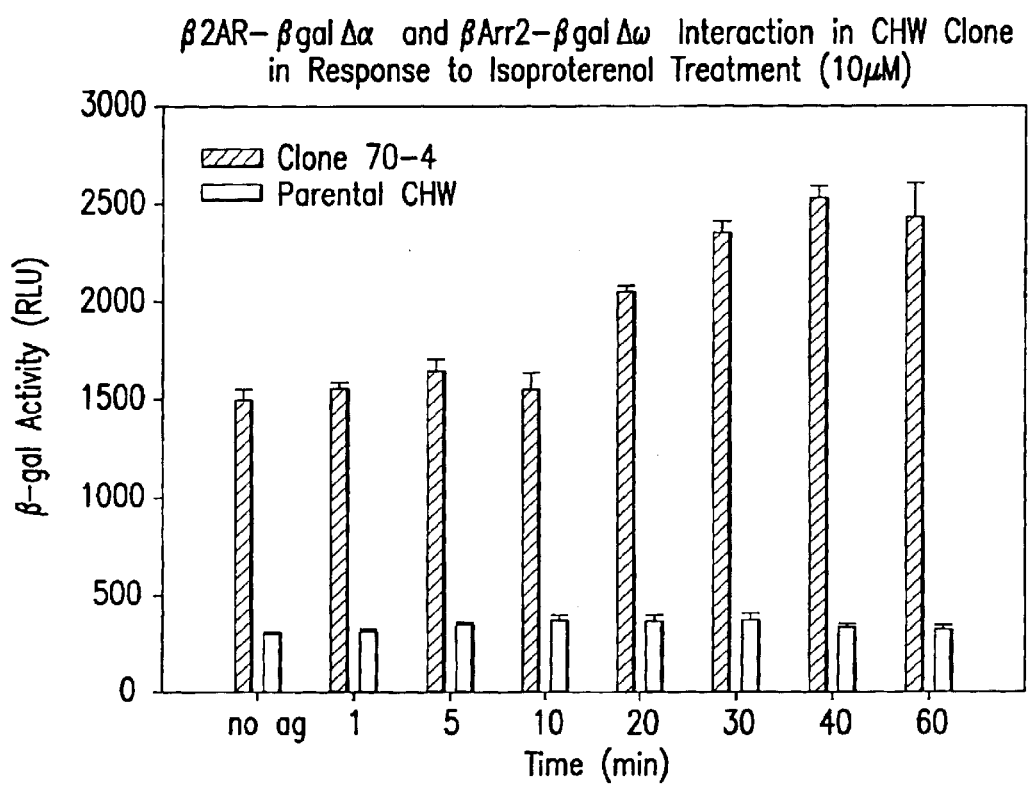
Figure 9A:
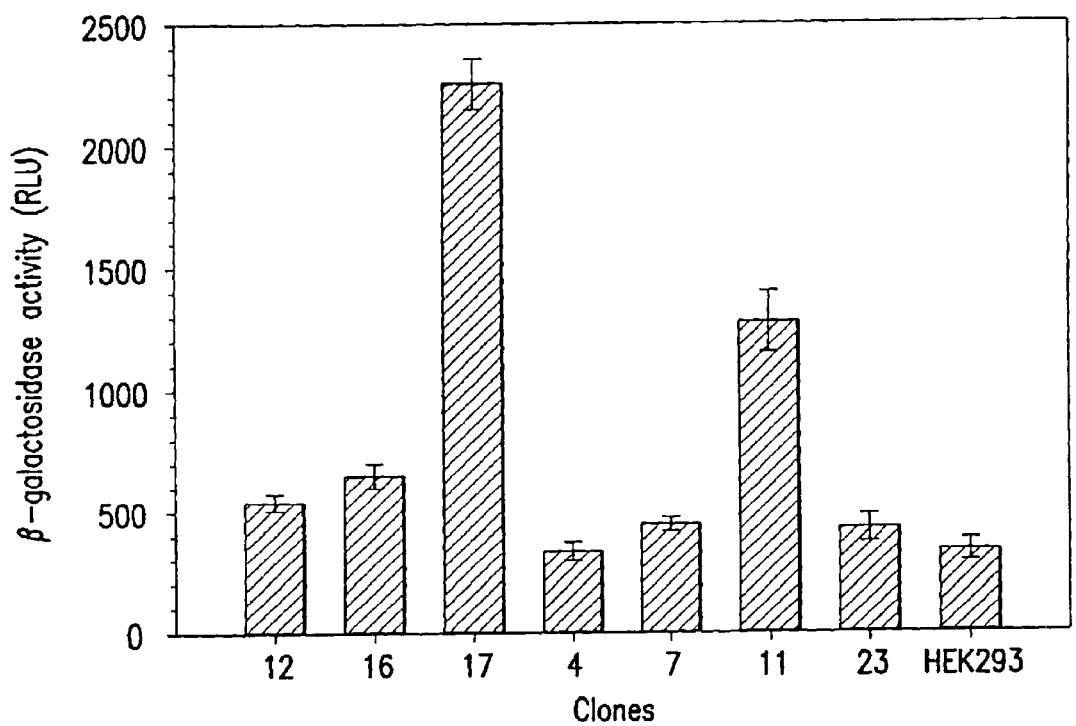
FIG. 9A shows β-galactosidase activity in HEK 293 clones co-expressing β2AR-βgalΔα and β2AR-βgalΔω.
Figure 9B:
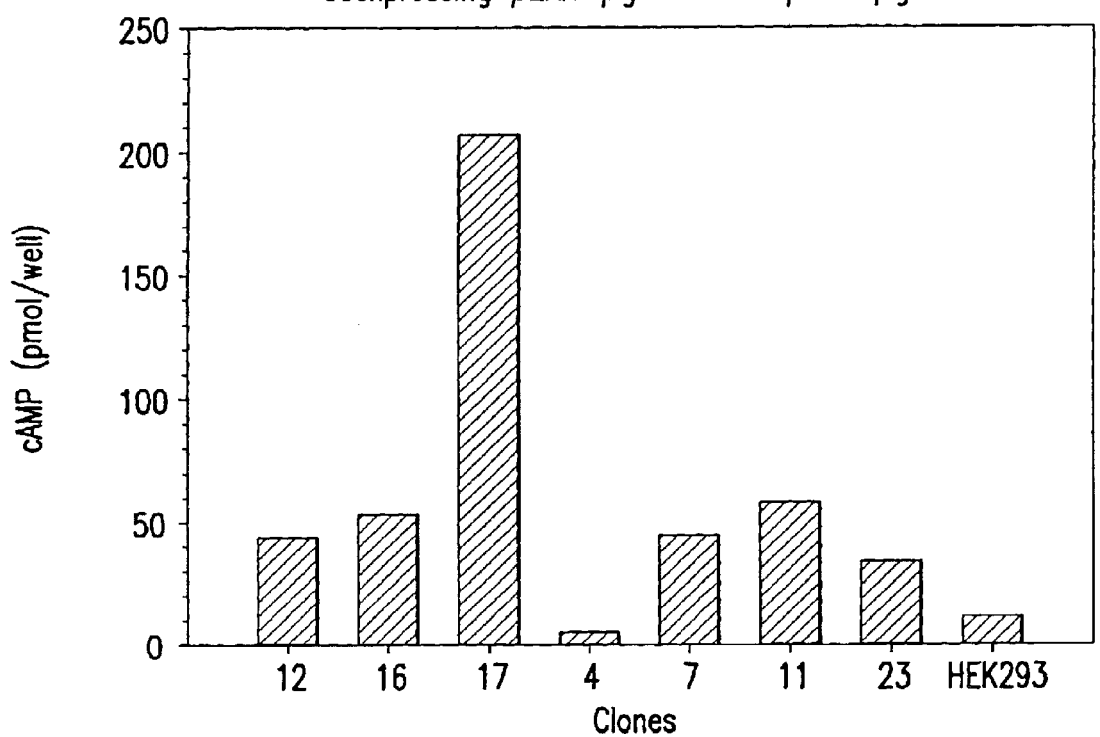
FIG. 9B shows a cAMP response to agonist (−)isoproterenol in HEK 293 clones co-expressing β2AR-βgalΔα and β2AR-βgalΔω. HEK293 parental cells were included in the assays as negative controls.
Figure 15:
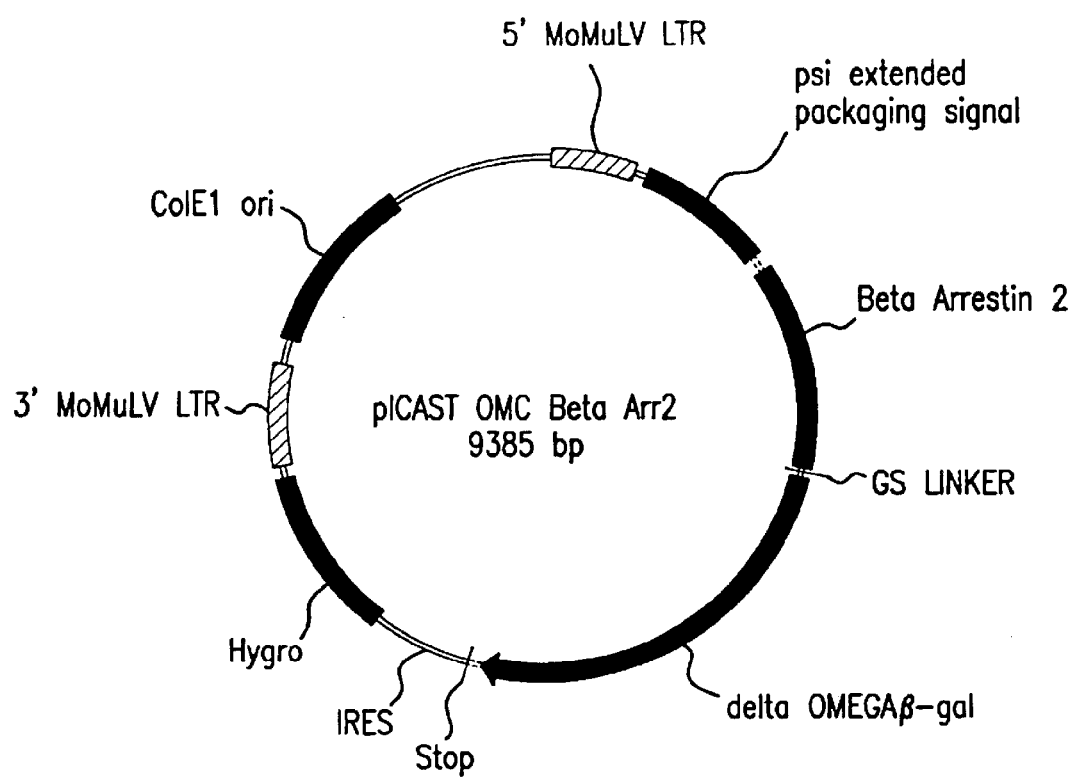
FIG. 15. pICAST OMC βArr2: Vector for expression of β-galΔω as a C-terminal fusion to β-arrestin-2. The coding sequence of human β-arrestin-2 (Genebank Accession Number: NM_004313) was cloned in frame to β-galΔω in a pICAST OMC vector.
Figure 16:
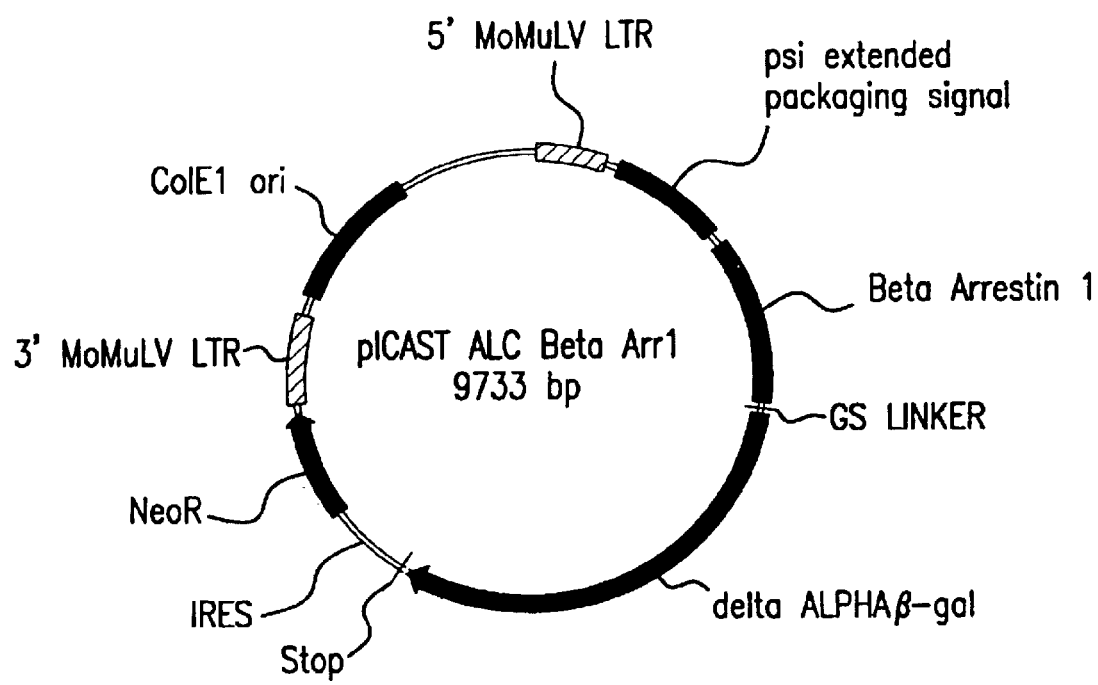
FIG. 16. pICAST ALC βArr1: Vector for expression of β-galΔα as a C-terminal fusion to β-arrestin-1. The coding sequence of human β-arrestin-1 (Genebank Accession Number: NM_004041) was cloned in frame to β-galΔα in a pICAST ALC vector.
Figure 17:
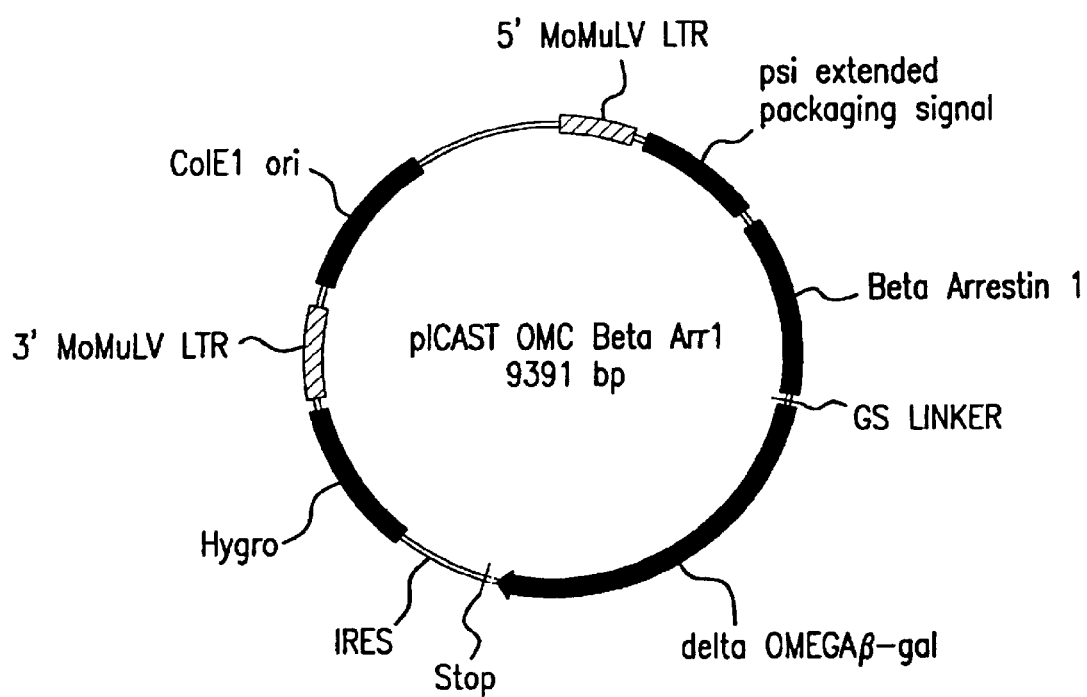
FIG. 17. pICAST OMC βArr1: Vector for expression of β-galΔω as a C-terminal fusion to β-arrestin-1. The coding sequence of human β-arrestin-1 (Genebank Accession Number: NM_004041) was cloned in frame to β-galΔω in a pICAST OMC vector.
Figure 18:
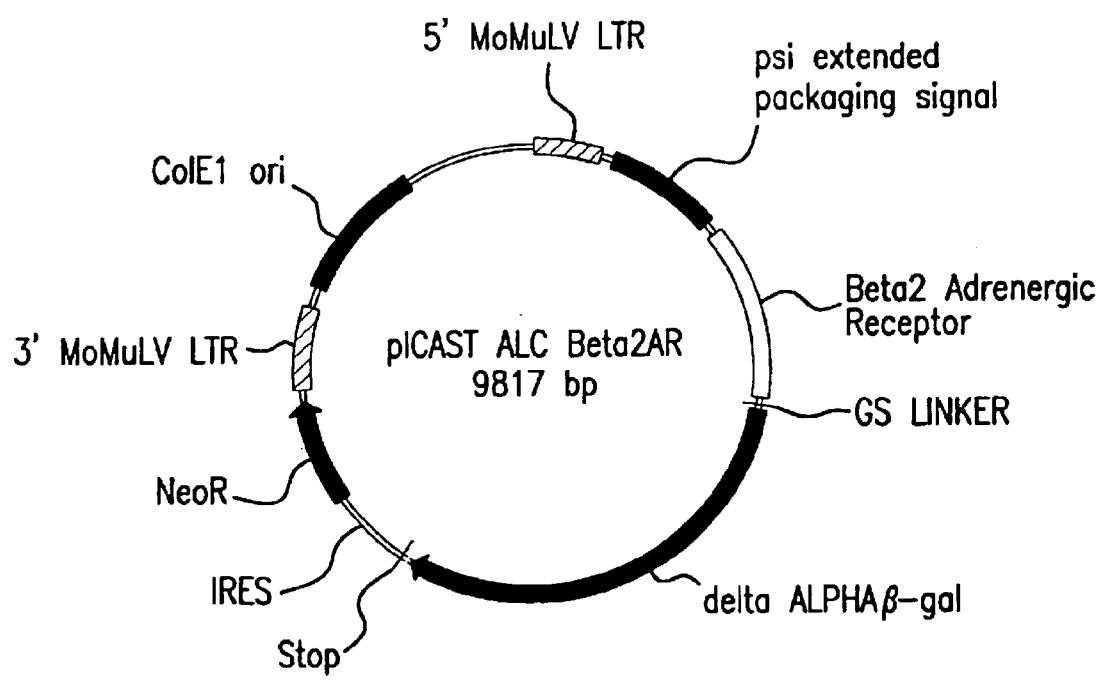
FIG. 18. pICAST ALC β2AR: Vector for expression of β-galΔ(α as a C-terminal fusion to β2 Adrenergic Receptor. The coding sequence of human β2 Adrenergic Receptor (Genebank Accession Number: NM_000024) was cloned in frame to β-galΔα in a pICAST ALC vector.
Figure 19:
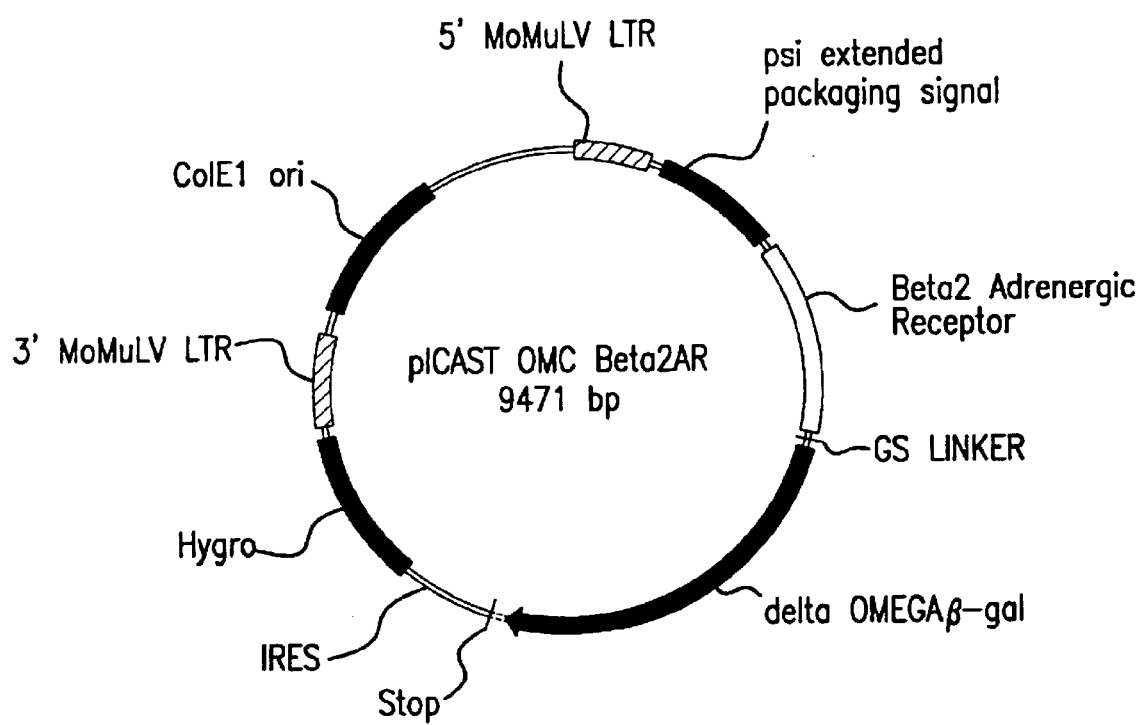
FIG. 19. pICAST OMC β2AR: Vector for expression of β-galΔω as a C-terminal fusion β2 Adrenergic Receptor. The coding sequence of human β2 Adrenergic Receptor (Genebank Accession Number: NM_000024) was cloned in frame to β-galΔω in a pICAST OMC vector.
Figure 20:
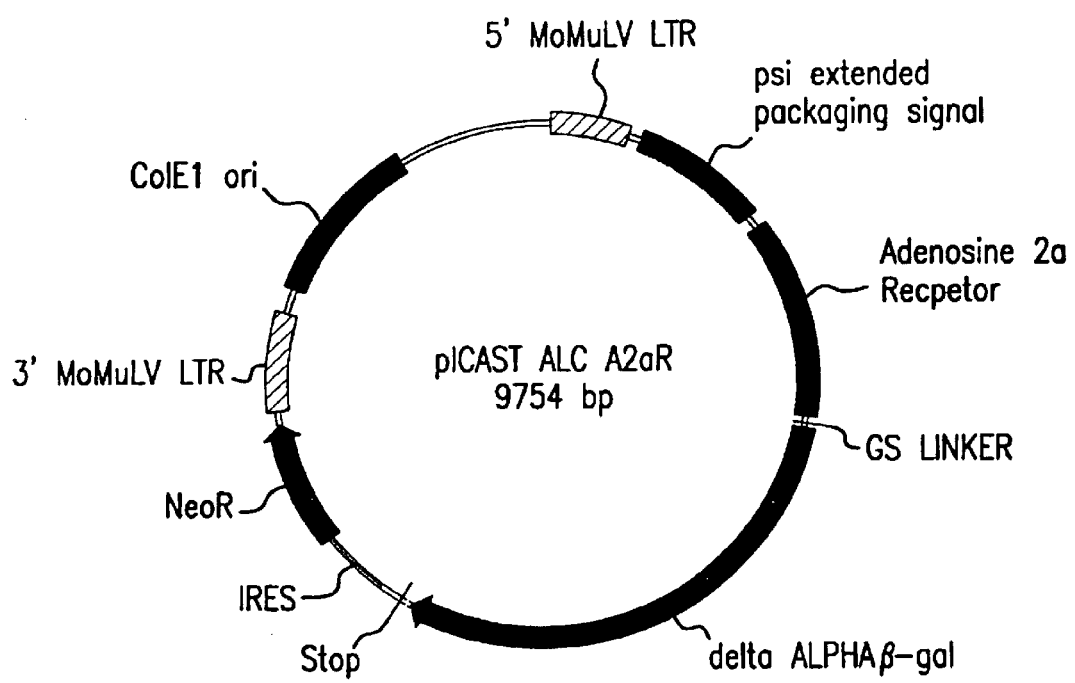
FIG. 20. pICAST ALC A2aR: Vector for expression of β-galΔα as a C-terminal fusion to Adenosine 2a Receptor. The coding sequence of human Adenosine 2a Receptor (Genebank Accession Number: NM_000675) was cloned in frame to β-galΔα in a pICAST ALC vector.
Figure 21:
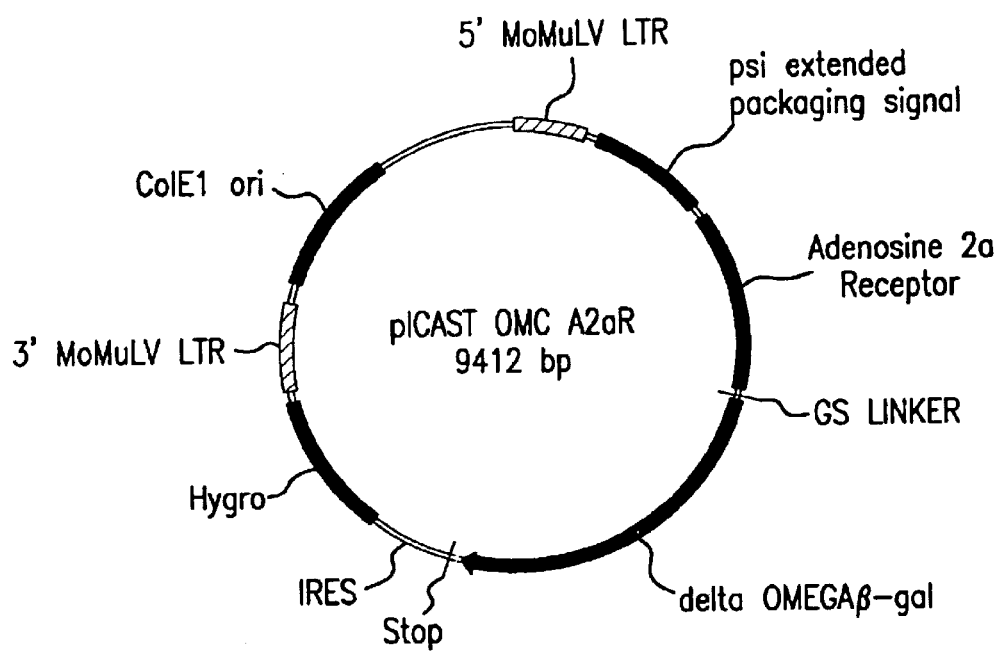
FIG. 21. pICAST OMC A2aR: Vector for expression of β-galΔω as a C-terminal fusion to Adenosine 2a Receptor. The coding sequence of human Adenosine 2a Receptor (Genebank Accession Number: NM_000675) was cloned in frame to β-galΔω in a pICAST OMC vector.
Figure 22:
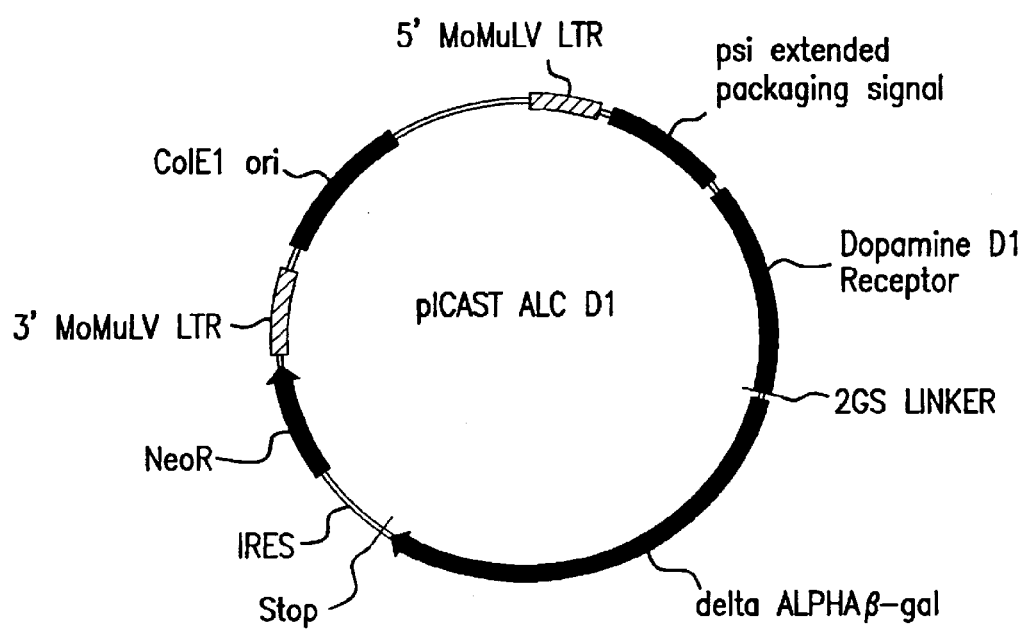
FIG. 22. pICAST ALC D1: Vector for expression of β-galΔα as a C-terminal fusion to Dopamine $D_1$ Receptor. The coding sequence of human Dopamine D1 Receptor (Genebank Accession Number: X58987) was cloned in frame to β-galΔα in a pICAST ALC vector.

1. In the first step, the expression vectors for β2ARΔα and βArr2Δω were engineered in selectable retroviral vectors pICAST ALC, as described in FIG. 18 and pICAST OMC, as described in FIG. 15.
2. In the second step, the two expression constructs were transduced into either C2C12 myoblast cells, or other mammalian cell lines, such as COS-7, CHO, A431, HEK 293, and CHW. Following selection with antibiotic drugs, stable clones expressing both fusion proteins at appropriate levels were selected.
3. In the last step, the cells expressing both β2ARΔα and βArr2Δω were tested for response by agonist/ligand stimulated β-galactosidase activity. Triplicate samples of cells were plated at 10,000 cells in 100 microliter volume into a well of 96-well culture plate. Cells were cultured for 24 hours before assay. For agonist assay (FIGS. 3 and 4), cells were treated with variable concentrations of agonist, for example, (−)isoproterenol, procaterol, dobutamine, terbutaline or L-L-phenylephrine for 60 min at 37° C. The induced β-galactosidase activity was measured by addition of Tropix Gal-Screen™ assay system substrate (Applied Biosystems) and luminescence measured in a Tropix TR717™ luminometer (Applied Biosystems). For antagonist assay (FIG. 5), cells were pre-incubated for 10 min in fresh medium without serum in the presence of ICI-118,551 or propranolol followed by addition of 10 micro molar (−)isoproterenol.

Serine/Threonine Cluster Strategy

Background

Based on structure-function relationship studies on β-arrestins, a large region within the amino-terminal half of β-arrestins (termed the activation-recognition domain) recognizes the agonist-activated state of GPCRs. This region of β-arrestin also contains a small positively charged domain (approximately 20 amino acids with net charge +7) called the phosphorylation-recognition domain, which appears to interact with the GRK-phosphorylated carboxyl termini of GPCRs.

GPCRs can be divided into two classes based on their affinities for β-arrestins. Oakley et al., "Association of β-Arrestin with G Protein-Coupled Receptors During Clathrin-Mediated Endocytosis Dictates the Profile of Receptor Resensitization." J. Biol. Chem., 274(45): 32248–32257 (1999). The molecular determinants underlying this classification appear to reside in specific serine or threonine residues located in the carboxyl-terminal tail of the receptor. The receptor class that contains serine/threonine clusters (defined as serine or threonine residues occupying three consecutive or three out of four positions) in the carboxyl-termini binds β-arrestin with high affinity upon activation and phosphorylation and remains bound with β-arrestin even after receptor internalization, whereas the receptor class that contains only scattered serine and threonine residues in the carboxy-terminal tail binds β-arrestins with less affinity and disassociates from the β-arrestin upon internalization. Several known GPCRs, such as vasopressin V2 receptor (Oakley, et al.), neurotensin receptor 1 and angiotensin II receptor type 1A (Zhang, et al.), "Cellular Trafficking of G Protein-Coupled Receptor/β-Arrestin Endocytic Complexes." J. Biol. Chem., 274(16): 10999–11006 (1999)), which possess one or more of such serine/threonine clusters in their carboxyl-termini, were shown to bind β-arrestins with high affinity.

EXAMPLE

Figure 24:
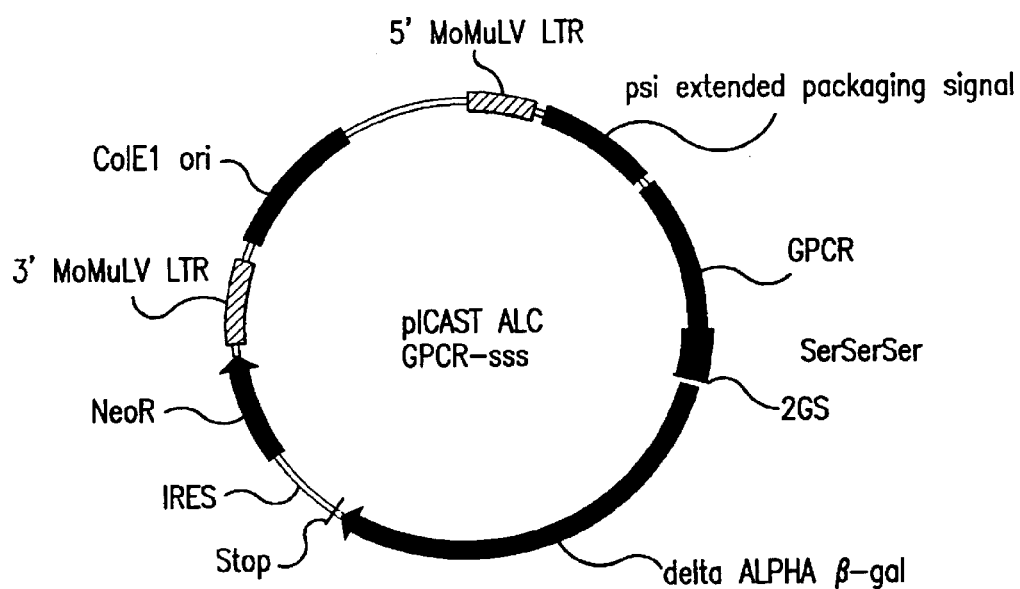
FIG. 24. Vector for expression of a GPCR with inserted seronine/threonine amino acid sequences as a fusion with β-galΔα. The open reading frame of a known or orphan GPCR is engineered to contain additional seronine/threonine sequences, such as SSS (seronine, seronine, seronine), within the C-terminal tail. The engineered GPCR is cloned in frame with β-galΔα in a pICAST ALC vector. The pICAST ALC vector contains the following features: MCS, multiple cloning site for cloning the target protein in frame with the β-galΔα; GS Linker, (GGGGS)n (SEQ ID NO:10); NeoR, neomycin resistance gene; IRES, internal ribosome entry site; ColE1ori, origin of replication for growth in *E. coli;* 5'MoMuLV LTR and 3'MoMuLV LTR, viral promotor and polyadenylation signals from the Moloney Murine leukemia virus.

According to an embodiment of the invention, a serine/threonine cluster strategy is used to facilitate screening assays for orphan receptors that do not possess this structural motif of their own. The orphan receptors are easily classified by sequence alignment. Orphan receptors lacking the serine/threonine clusters are each cloned into an expression vector that is modified to introduce one or more serine/threonine cluster(s) to the carboxyl-terminal tail of the receptor (FIG. 24). The serine/threonine clusters enhance the receptor activation dependent interaction between the activated and phosphorylated receptor (negative charges) and β-arrestin (positive charges in the phosphorylation-recognition domain) through strong ionic interactions, thus prolonging interaction between the receptor and arrestin. The modification of the orphan receptor tail thus makes detection of receptor activation more robust.

Experiment Protocol

Figure 10A:
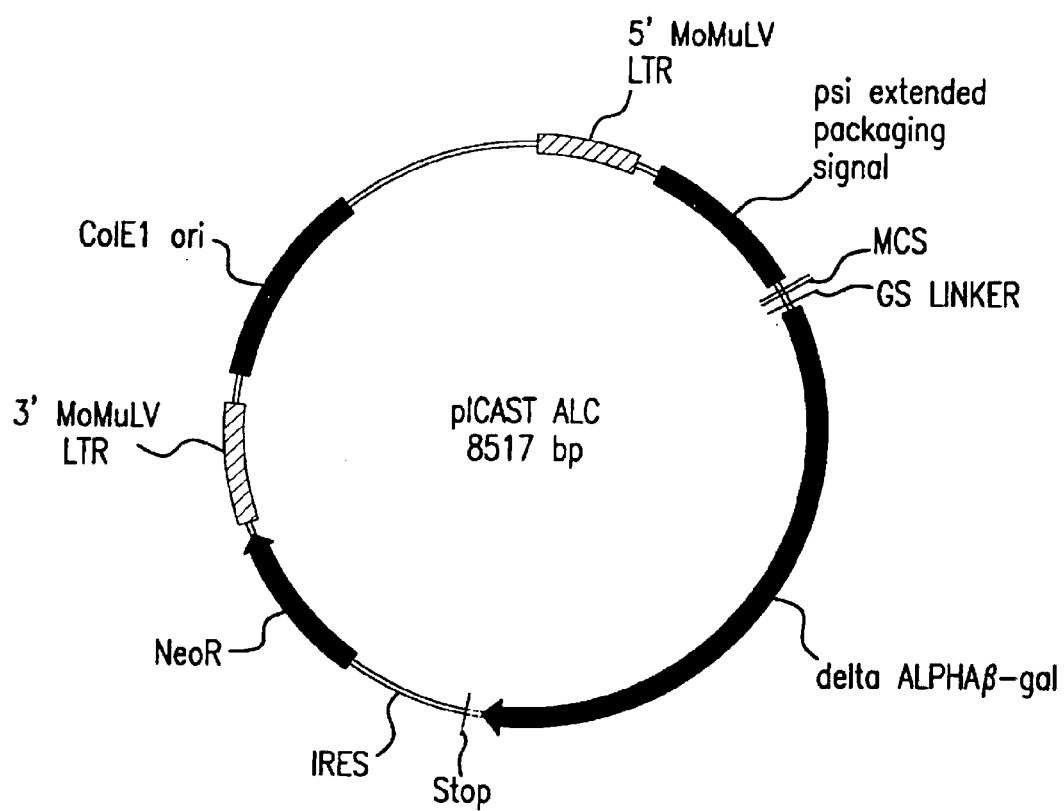
FIG. 10A. pICAST ALC: Vector for expression of β-galΔα as a C-terminal fusion to the target protein. This construct contains the following features: MCS, multiple cloning site for cloning the target protein in frame with the β-galΔα; GS Linker, (GGGGS)n (SEQ ID NO:10); NeoR, neomycin resistance gene; IRES, internal ribosome entry site; ColE1ori, origin of replication for growth in E. coli; 5'MoMuLV LTR and 3'MoMuLV LTR, viral promoter and polyadenylation signals from the Moloney Murine leukemia virus.
Figure 11A:
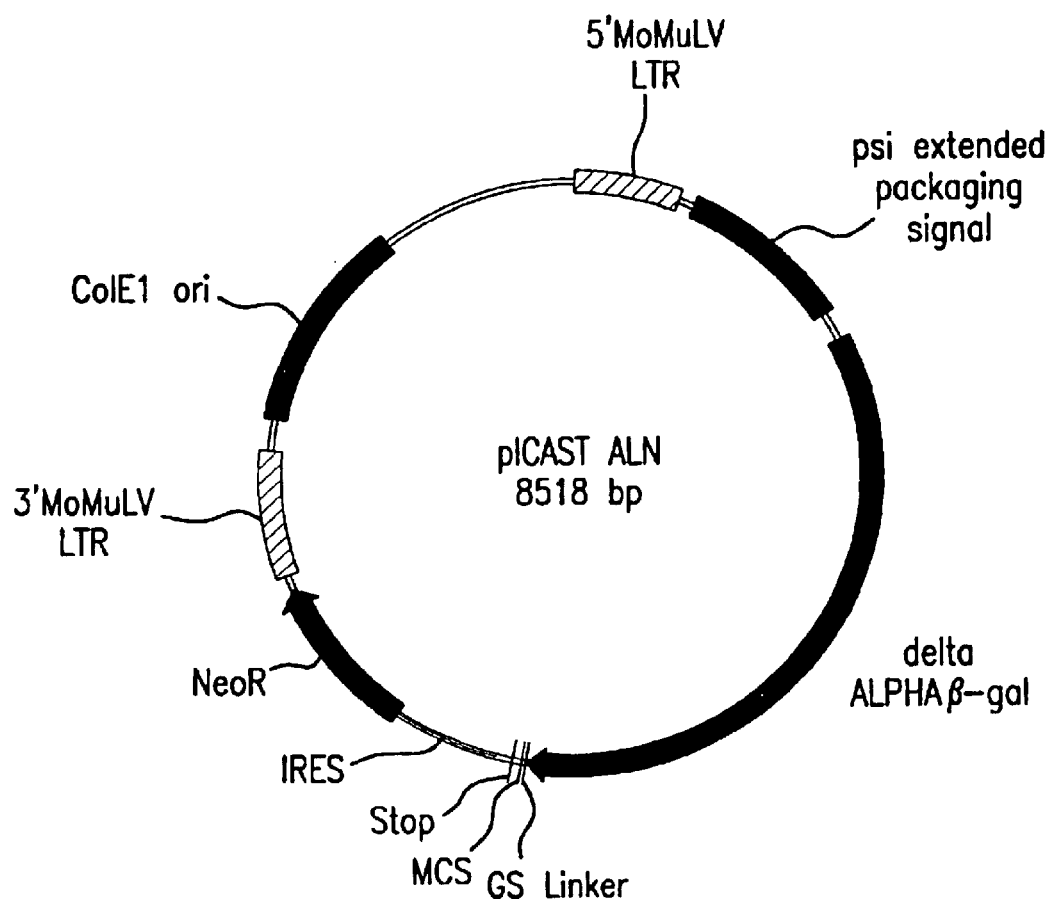
FIG. 11A. pICAST ALN: Vector for expression of β-galΔα as an N-terminal fusion to the target protein. This construct contains the following features: MCS, multiple cloning site for cloning the target protein in frame with the β-galΔα; GS Linker, (GGGGS)n (SEQ ID NO:10); NeoR, neomycin resistance gene; IRES, internal ribosome entry site; ColE1ori, origin of replication for growth in E. coli; 5'MoMuLV LTR and 3'MoMuLV LTR, viral promoter and polyadenylation signals from the Moloney Murine leukemia virus.
Figure 12A:
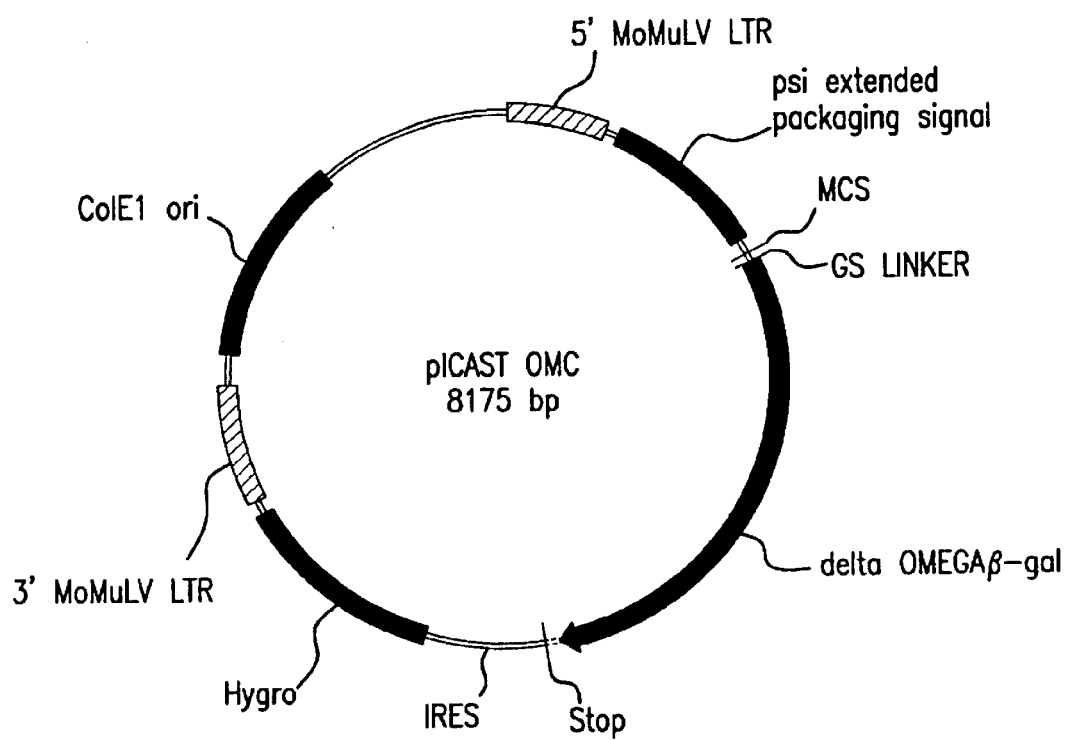
FIG. 12A. pICAST OMC: Vector for expression of β-galΔω as a C-terminal fusion to the target protein. This construct contains the following features: MCS, multiple cloning site for cloning the target protein in frame with the β-galΔω; GS Linker, (GGGGS)n (SEQ ID NO:10); Hygro, hygromycin resistance gene; IRES, internal ribosome entry site; ColE1ori, origin of replication for growth in E. coli; 5'MoMuLV LTR and 3'MoMuLV LTR, viral promoter and polyadenylation signals from the Moloney Murine leukemia virus.
Figure 13A:
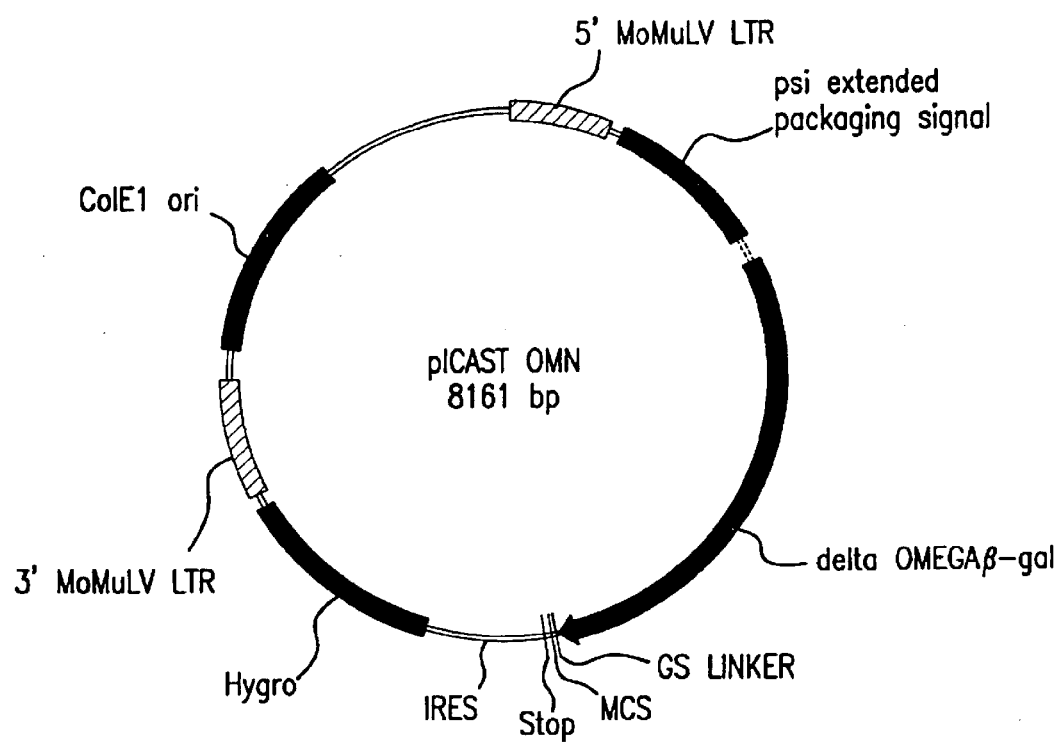
FIG. 13A. pICAST OMN: Vector for expression of β-galΔω as an N-terminal fusion to the target protein. This construct contains the following features: MCS, multiple cloning site for cloning the target protein in frame with the β-galΔω; GS Linker, (GGGGS)n (SEQ ID NO:10); Hygro, hygromycin resistance gene; IRES, internal ribosome entry site; ColE1ori, origin of replication for growth in E. coli; 5'MoMuLV LTR and 3'MoMuLV LTR, viral promoter and polyadenylation signals from the Moloney Murine leukemia virus.
Figure 14:
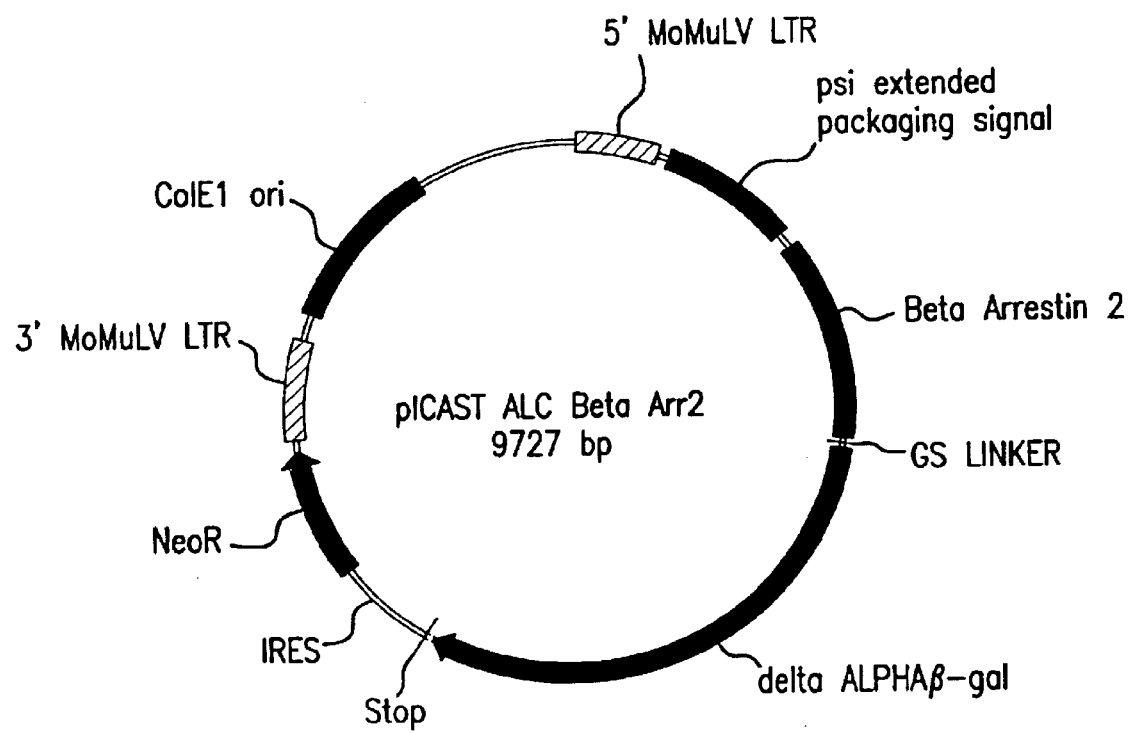
FIG. 14. pICAST ALC βArr2: Vector for expression of β-galΔα as a C-terminal fusion to β-arrestin-2. The coding sequence of human β-arrestin-2 (Genebank Accession Number: NM_004313) was cloned in frame to β-galΔα in a pICAST ALC vector.

1. In a first step, the open-reading-frame (ORF) of an orphan receptor, which lacks the serine/threonine clusters, is cloned into a modified expression vector such as pICAST ALC described in FIG. 10A. The modified pICAST ALC includes coding sequences for one or more sets of serine/threonine clusters (for example, SSS or SST) located downstream from the insert of the ORF of an orphan receptor (FIG. 24).

2. In a second step, chimeric orphan receptor, $ORF_{orphan}$ $R\text{-}(SSS)_n\text{-}\Delta\alpha$, is co-expressed in a mammalian cell with a β-arrestin chimera, such as βArr2Δω described in FIG. 15.

3. In a third step, the cell is treated with an agonist or a ligand and the activated receptor with phosphorylated serine cluster(s) binds the β-arrestin with high affinity producing strong signals in readouts of β-gal complementation.

Figure 28:
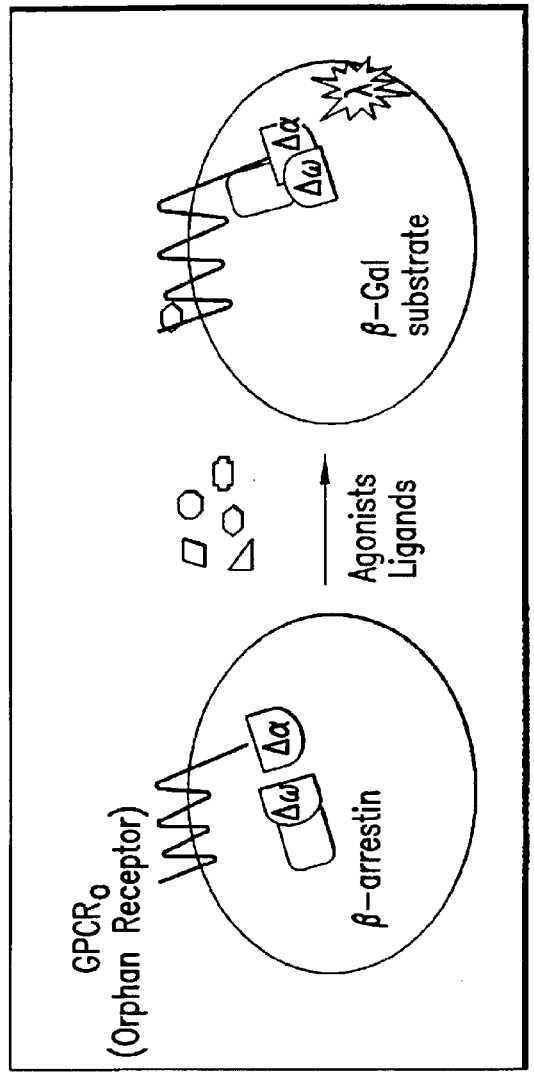
FIG. 28. Ligand fishing for orphan receptors by β-galactosidase mutant complementation in ICAST™ system. A schematic depicting the utilization of the invention for ligand fishing and agonist/antagonist screening for orphan GPCRs. As an example, a test cell expressing two β-gal fission proteins, GPCR$_{orphan}$-Δα and Arrestin-Δω, is subjected to treatments with samples from natural or synthetic compound libraries, or from tissue extracts, or from conditioned media of cultured cells. An increased β-gal activity after treatment indicates the activation of the orphan receptor by a ligand in the testing sample. The readout of increased β-gal activity reflects the interaction of an activated GPCR orphan receptor with a β-arrestin. Therefore, a cognate or a surrogate ligand for the testing receptor is identified.
Figure 28:
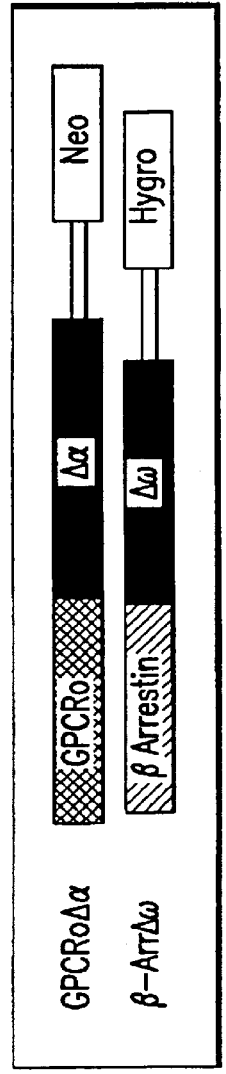

This assay, which provides a means for sensitive measurement of functional activation of the orphan receptors, can be used to screen for natural or surrogate ligands for orphan receptors, a process called de-orphaning or target discovery for new GPCRs (FIG. 28). Furthermore, this assay is also useful in screening for potential agonists and antagonists for lead discovery of GPCRs.

Enhanced Binding of Arrestin in the Presence and in the Absence of GPCR Phosphorylation Background Six different classes of G-protein coupled receptor kinases (GRKs) have been identified and each of these has been reported to be expressed as multiple splice variants. Krupnick et al., "The role of receptor kinases and arrestins in G protein-coupled receptor regulation." Ann. Rev. Pharmacol. Toxicol., 38:289–319 (1998). Although many cell lines express a variety of GRKs, the specific GRK required for phosphorylation of a given GPCR may not always be present in the cell line used for recombinant GPCR and arrestin expression. This is particularly an issue for applications using orphan receptors, in which case the cognate GRK will likely be unknown. In other cases, the cell line used for recombinant expression work may have the required GRK, but may express the GRK at low levels. In order to bypass such caveats, genetically modified arrestins that bind specifically to activated GPCRs, but without the requirement of GRK phosphorylation are employed.

Mutagenesis studies on arrestins demonstrate that point mutations in the phosphorylation-recognition domain, particularly mutations converting Arg175 (of visual arrestin) to an oppositely charged residue such as glutamate (R175E mutation), result in an arrestin which specifically binds to activated GPCRs, but does so without the requirement for phosphorylation.

Numerous observations have led to the hypothesis that arrestin exists in an inactive state that has a low affinity for GPCRs. Once a GPCR is both activated and phosphorylated, the phosphorylated region of the GPCR C-terminus interacts with the phosphorylation-recognition domain of arrestin causing the arrestin to change conformations allowing the activation-recognition region to be exposed for binding to the activated/phosphorylated receptor. Vishnivetskiy et al., "How does arrestin respond to the phosphorylated state of rhodopsin?" J. Biol. Chem., 274(17):11451–11454 (1999); Gurevich et al., "Arrestin interactions with G protein-coupled receptors. Direct binding studies of wild-type and mutant arrestins with rhodopsin, beta 2-adrenergic and m2 muscarinic cholinergic receptors." J. Biol. Chem., 270(2): 720–731, (1995); Gurevich et al., "Mechanism of phosphorylation-recognition by visual arrestin and the transition of arrestin into a high affinity binding site." Mol. Pharmacol., 51(1):161–169 (1997); Kovoor et al., "Targeted construction of phosphorylation-independent beta-arrestin mutants with constitutive activity in cells." J. Biol. Chem., 274(11):6831–6834 (1999). In summary, binding studies of single mutation, double mutation, deletion, and chimerical arrestins with inactive, inactive and phosphorylated, activated but not phosphorylated, or activated and phosphorylated visual or non-visual GPCRs all support this model.

EXAMPLE

Figure 25:
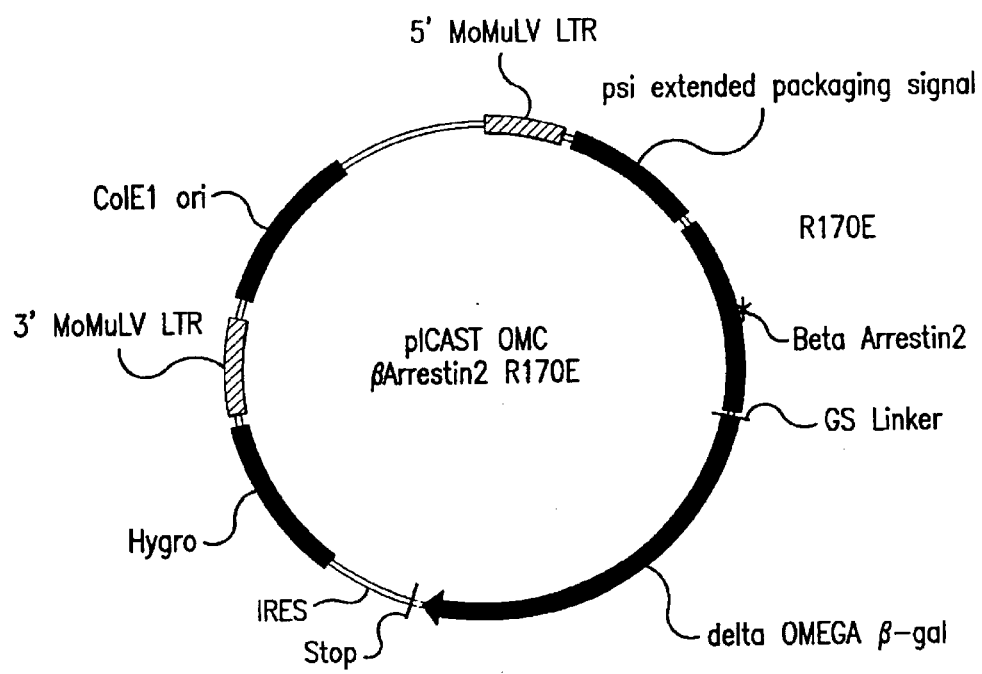
FIG. 25. Vector for expression of mutant (R170E) β-arrestin2 as a fusion with β-galΔω. The open reading frame of β-arrestin2 is engineered to contain a point mutation that converts arginine 170 to a glutamate. The mutant β-arrestin2 is cloned in frame with β-galΔω in a pICAST OMC vector. The pICAST OMC vector contains the following features: MCS, multiple cloning site for cloning the target protein in frame with the β-galΔα; GS Linker, (GGGGS)n (SEQ ID NO:10); Hygro, hygromycin resistance gene; IRES, internal ribosome entry site; ColE1 ori, origin of replication for growth in *E. coli;* 5'MoMuLV LTR and 3'MoMuLV LTR, viral promotor and polyadenylation signals from the Moloney Murine leukemia virus.
Figure 26:
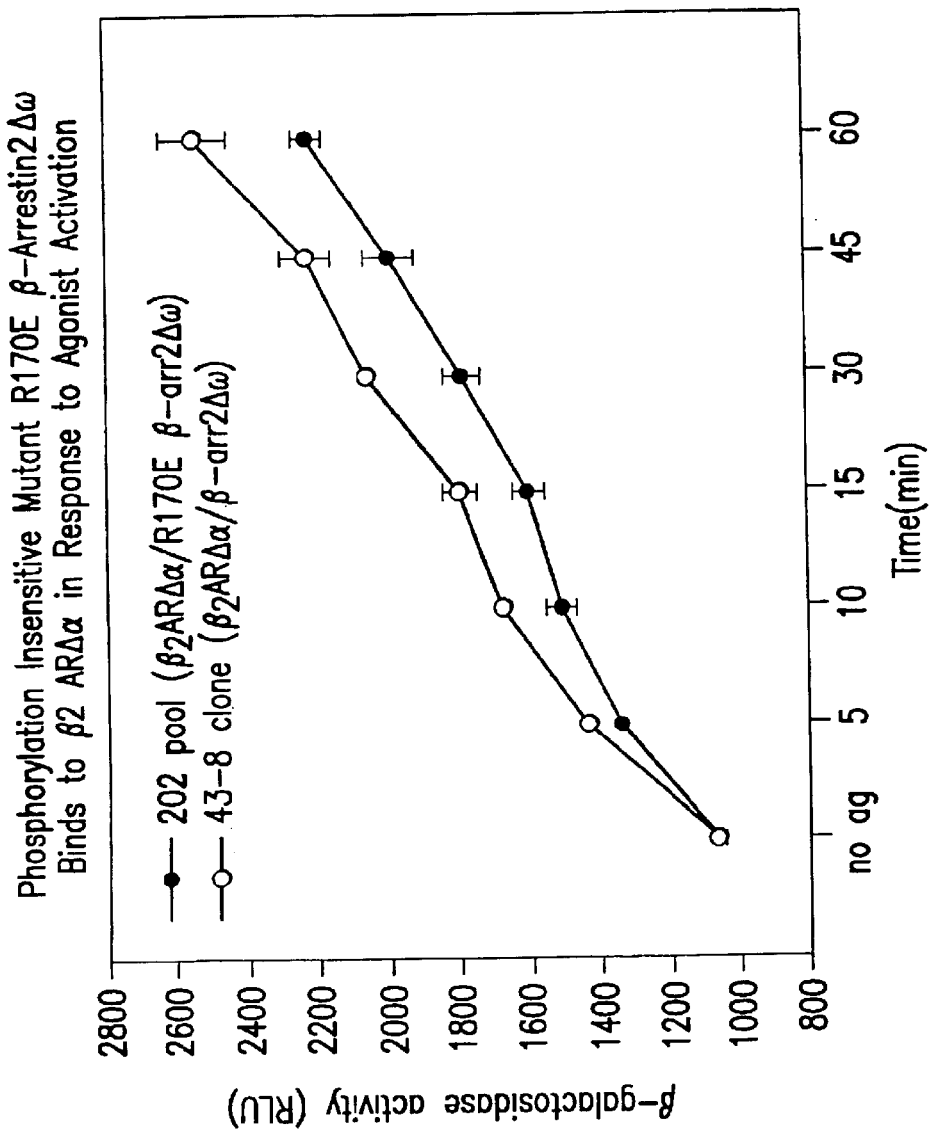
FIG. 26. Phosphorylation insensitive Mutant R170E β-Arrestin2Δω binds to β2ARΔα in Response to Agonist Activation. A parental β2ARΔα C2 cell line was tranduced with the Mutant R170E β-Arrestin2Δω construct. Clonal populations co-expressing the two constructions were plated at 10,000 cells/well in 96 well plates and treated with 10 μM (−)isoproterenol, 0.3 mM ascorbic acid for the indicated time period. β-galactosidase activity was measured by addition of Tropix Gal-Screen™ assay system substrate (Applied Biosystems) and luminescence was measured using a Tropix TR717™ luminometer (Applied Biosystems). Treatments were performed in triplicate. For comparison, a clonal cell line (43-8) co-expressing β2ARΔα and wild-type β-Arrestin2Δω was also plated at 10,000 cells/well and given the same agonist treatment regimen. Minutes of (−)isoproterenol treatment is shown on the X-axis and β-galactosidase activity indicated by relative light units (RLU) is shown on the Y-axis.
Figure 27:
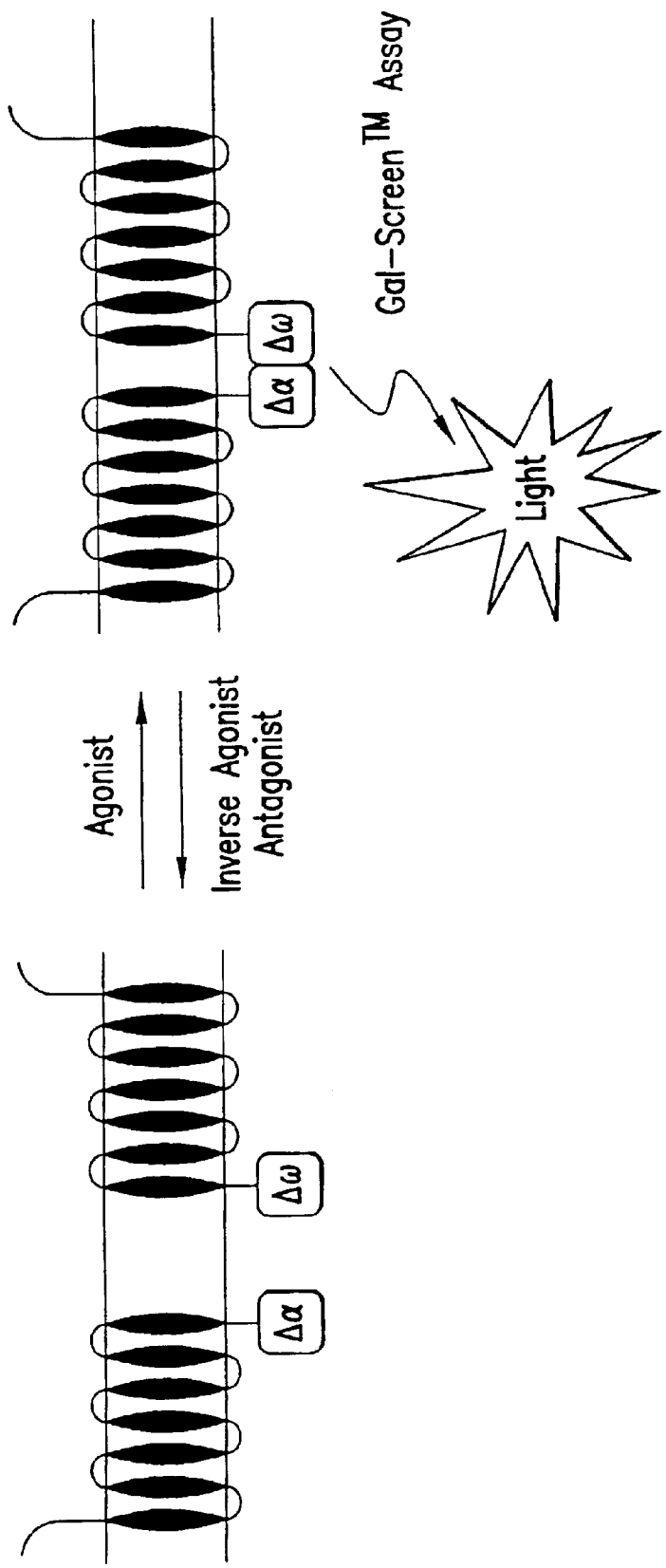
FIG. 27. GPCR dimerization measured by β-galactosidase complementation. A schematic depicting the utilization of the invention for monitoring GPCR homo- or hetero-dimerization. One GPCR is fused to one complement enzyme fragment, while the second GPCR is fused to the second complement enzyme fragment. Interaction of the two GPCRs is monitored by complementation of the enzyme fragments to produce an active enzyme complex (i.e., β-galactosidase activity). GPCR homo- or hetero-dimerization can be monitored in the absence or presence of ligand, agonists, inverse agonists or antagonists.

A phosphorylation insensitive mutant of arrestin fused to mutant reporter protein can be produced that will bind to activated GPCRs in a phosphorylation independent manner. As proof of concept, a point mutation for β-arrestin2, R170E β-arrestin2, has been produced and its interaction with β2AR has been analyzed in accordance with the invention.
Experimental Protocol:
1) In the first step, β-arrestin2 was mutated such that Arg170 was converted to Glu. This mutation is equivalent to the R175E mutation of visual arrestin. The mutant β-arrestin2 open reading frame was cloned in frame with Δω-β-galactosidase in the pICAST OMC expression vector to produce a modified expression vector R170E β-arrestin2 (FIG. 25).
2) In the second step, the R170E β-arrestin2 expression construct was transduced into a C2C12 myoblast cell line that had been engineered to express β2AR as a fusion to Δα-β-galactosidase as described in FIG. 18 of U.S. application Ser. No. 09/654,499. Following selection with antibiotic drugs, a population of clones expressing both fusion proteins was obtained.
3) In the last step, this population of cells expressing both R170E β-arrestin2Δω and β2AR Δα were tested for response by agonist/ligand stimulated β-galactosidase activity as demonstrated in FIG. 26. The C2C12 clone 43-8 co-expressing β2ARΔα and wild-type 1β-arrestin2Δω (FIG. 26) was used as reference control. Triplicate samples of cells were plated at 10,000 cells in 100 microliter volume into wells of a 96-well culture plate. Cells were cultured for 24 hours before assay. For agonist assay as in FIG. 26, cells were treated with 10 μm (−)isoproterenol stabilized with 0.3 mM ascorbic acid 37° C. for 0, 5, 10, 15, 30, 45 or 60 minutes. The induced β-galactosidase activity was measured by addition of Tropix Gal-Screen™ assay system substrate (Applied Biosystems) and luminescence measured in a Tropix TR717™ luminometer (Applied Biosystems). As shown in FIG. 26, the mutant arrestin interacts with β2AR in an agonist-dependent manner and was comparable with that of wild-type arrestin.
4) To expand the application of phosphorylation-insensitive arrestin, cell lines such as C2C12, CHO or HEK 293, are developed that express the R170E β-arrestin2Δω construction. These cell lines can be used to transduce orphan or known GPCRs as fusions with Δα-β-galactosidase in order to develop cell lines for agonist and antagonist screening and Development of Super Arrestins:

Background

Attenuation of GPCR signaling by the arrestin pathway serves to ensure that a cell or organism does not over-react to a stimulus. At the same time, the arrestin pathway often serves to recycle the GPCR such that it can be temporarily inactivated but then quickly resensitized to allow for sensitivity to new stimuli. The down-regulation process involves phosphorylation of the receptor, binding to arrestin and endocytosis. Following endocytosis of the desensitized receptor, the receptor is either degraded in lysosomes or resensitized and sent back to the membrane. Resensitization involves release of arrestin from the receptor, dephosphorylation and cycling back to the membrane. The actual route a GPCR follows upon activation depends on its biological function and the needs of the organism. Because of these diverse pathways that may be required of the down-regulation pathway, arrestin affinities for activated GPCRs vary from receptor to receptor. It would thus be very advantageous to engineer super arrestins that have a higher affinity and avidity for activated GPCRs than what nature has provided.

Although mutational, deletion and chimerical studies of arrestins have focused on understanding regulatory switches in the molecule that respond to GPCR phosphorylation states, several of these altered recombinant forms of arrestin have resulted in molecules with enhanced binding to activated, phosphorylated GPCRs. Conversion of Arg175 to histidine, tyrosine, phenylalanine or threonine results in significantly higher amounts of binding to phosphorylated, activated rhodopsin than wild-type arrestin or R175E arrestin, although these mutations result in less binding to activated, non-phosphorylated receptor. Gurevich et al. (1997). In addition, conversion of Valine 170 to alanine increased the constitutive affect of the R175E mutation, but also nearly doubled the amount of interaction of wild-type arrestin with activated, phosphorylated rhodopsin. Gurevich et al. (1997).

Truncation of β-arrestin1 at amino acid 382 has been reported to enhance binding of both R169E (equivalent to arrestin R175E) and wild-type β-arrestin1 to activated or activated and phosphorylated receptor, respectively. Kovoor et al. Chimerical arrestins in which functional regions of visual arrestin were swapped with those of β-arrestin1 have been reported to be altered in binding affinity to activated, phosphorylated GPCRs. Gurevich et al. (1995). Several of these chimeras, such as β-arrestin1 containing the visual arrestin extreme N-terminus, show increased specific binding to phosphorylated activated GPCRs compared to wild-type β-arrestin1 (Gurevich et al. (1995)). Modifications that enhance arrestin affinity for the activated GPCR such as described above, whether phosphorylated or non-phosphorylated, could also enhance signal to noise of β-galactosidase activity since the arrestin/GPCR complex is stabilized and/or more long-lived. The use of mutant arrestins with higher activated-GPCR affinity would improve the inventive technology for GPCR targets, without compromising receptor/ligand biology.

In addition, this "super arrestin" approach can be combined with the use of arrestin point mutations to provide a stronger signal to noise with or without GRK requirements.

EXAMPLE

An arrestin mutant fused to mutant reporter protein can be produced to enhance binding of the arrestin to an activated GPCR to enhance sensitivity of detection.

Experiment Protocol
1) In the first step, mutant β-arrestin2 constructions will be generated which include R170E/T/Y/or H, V165A, substitution of a.a. 1-43 with a.a. 1-47 of visual arrestin, or deletion of the C-terminal and combinations of these alterations. The mutant β-arrestin2 open reading frames will be cloned in frame with Δω-β-galactosidase in the pICAST OMC expression vector similar to cloning of the R170E β-arrestin2 mutation shown in FIG. 25.
2) In the second step, mutant expression constructs will be transduced into a C2C12 myoblast cell line that has been engineered to express β2AR as a fusion to Δα-β-galactosidase. Following selection with antibiotic drugs, a population of clones expressing both fusion proteins will be obtained. Wild type and R170E β-arrestin2 constructions will be transduced to generate control, reference clonal populations.
3) In the third step, populations of cells expressing both β-arrestin2Δω (mutant or wild type) and β2ARΔα will be tested for response by agonist/ligand stimulated β-galactosidase activity.

4) In the next step, mutant (super) β-arrestin2Δω constructions that show a significantly higher signal to noise ratio in the agonist assay compared with wild-type β-arrestin2Δω will be chosen. These constructions will be used to develop stable cell lines expressing the "super" β-arrestin2Δω that can be used for transducing in known or orphan GPCRs. Use of a super β-arrestin2Δω could increase the signal to noise of ICAST/GPCR applications allowing improved screening capabilities for lead and ligand discovery.

Super Arrestin is used to increase the binding efficiency of arrestin to an activated GPCR and to stabilize the GPCR/arrestin complex during GPCR desensitization. This application can be used to increase the robustness of ICAST/GPCR applications in cases where the GPCR is normally resensitized rapidly post desensitization.

The assays of this invention, and their application and preparation have been described both generically, and by specific example. The examples are not intended as limiting. Other substituent identities, characteristics and assays will occur to those of ordinary skill in the art, without the exercise of inventive faculty. Such modifications remain within the scope of the invention, unless excluded by the express recitation of the claims advanced below.

SEQUENCE LISTING

<160> NUMBER OF SEQ ID NOS: 10

<210> SEQ ID NO 1
<211> LENGTH: 6700
<212> TYPE: DNA
<213> ORGANISM: Unknown
<220> FEATURE:
<223> OTHER INFORMATION: pICAST ALC.
<220> FEATURE:
<221> NAME/KEY: CDS
<222> LOCATION: (1457)..(4486)

<400> SEQUENCE: 1

| | | | | | |
|---|---|---|---|---|---|
| ctgcagcctg | aatatgggcc | aaacaggata | tctgtggtaa | gcagttcctg | ccccggctca | 60 |
| gggccaagaa | cagatggaac | agctgaatat | gggccaaaca | ggatatctgt | ggtaagcagt | 120 |
| tcctgccccg | gctcagggcc | aagaacagat | ggtcccccaga | tgcggtccag | ccctcagcag | 180 |
| tttctagaga | accatcagat | gtttccaggg | tgccccaagg | acctgaaatg | accctgtgcc | 240 |
| ttatttgaac | taaccaatca | gttcgcttct | cgcttctgtt | cgcgcgcttc | tgctccccga | 300 |
| gctcaataaa | agagcccaca | accctcact | cggggcgcca | gtcctccgat | tgactgagtc | 360 |
| gcccgggtac | ccgtgtatcc | aataaaccct | cttgcagttg | catccgactt | gtggtctcgc | 420 |
| tgttccttgg | gagggtctcc | tctgagtgat | tgactacccg | tcagcggggg | tctttcattt | 480 |
| gggggctcgt | ccgggatcgg | gagaccctg | cccagggacc | accgacccac | caccgggagg | 540 |
| caagctggcc | agcaacttat | ctgtgtctgt | ccgattgtct | agtgtctatg | actgatttta | 600 |
| tgcgcctgcg | tcggtactag | ttagctaact | agctctgtat | ctggcggacc | cgtggtggaa | 660 |
| ctgacgagtt | ctgaacaccc | ggccgcaacc | ctgggagacg | tcccagggac | tttgggggcc | 720 |
| gtttttgtgg | cccgacctga | ggaagggagt | cgatgtggaa | tccgaccccg | tcaggatatg | 780 |
| tggttctggt | aggagacgag | aacctaaaac | agttcccgcc | tccgtctgaa | ttttttgcttt | 840 |
| cggtttggaa | ccgaagccgc | gcgtcttgtc | tgctgcagca | tcgttctgtg | ttgtctctgt | 900 |
| ccgactgtgt | ttctgtatt | gtctgaaaat | tagggccaga | ctgttaccac | tcccttaagt | 960 |
| ttgaccttag | gtaactggaa | agatgtcgag | cggctcgctc | acaaccagtc | ggtagatgtc | 1020 |
| aagaagagac | gttgggttac | cttctgctct | gcagaatggc | caacctttaa | cgtcggatgg | 1080 |
| ccgcgagacg | gcacctttaa | ccgagacctc | atcacccagg | ttaagatcaa | ggtcttttca | 1140 |
| cctggcccgc | atgacaccc | agaccaggtc | ccctacatcg | tgacctggga | agccttggct | 1200 |
| tttgaccccc | ctccctgggt | caagcccttt | gtacaccta | agcctccgcc | tcctcttcct | 1260 |
| ccatccgccc | cgtctctccc | ccttgaacct | cctcgttcga | ccccgcctcg | atcctccctt | 1320 |
| tatccagccc | tcactccttc | tctaggcgcc | ggccgctcta | gccattaat | acgactcact | 1380 |

-continued

```
ataggcgat tcgaatcagg ccttggcgcg ccggatcctt aattaagcgc aattgggagg    1440
tggcggtagc ctcgag atg ggc gtg att acg gat tca ctg gcc gtc gtg gcc   1492
              Met Gly Val Ile Thr Asp Ser Leu Ala Val Val Ala
                1               5                  10 cgc acc gat cgc cct tcc caa cag tta cgc agc ctg aat ggc gaa tgg     1540
Arg Thr Asp Arg Pro Ser Gln Gln Leu Arg Ser Leu Asn Gly Glu Trp
         15                  20                  25 cgc ttt gcc tgg ttt ccg gca cca gaa gcg gtg ccg gaa agc tgg ctg     1588
Arg Phe Ala Trp Phe Pro Ala Pro Glu Ala Val Pro Glu Ser Trp Leu
     30                  35                  40 gag tgc gat ctt cct gag gcc gat act gtc gtc gtc ccc tca aac tgg     1636
Glu Cys Asp Leu Pro Glu Ala Asp Thr Val Val Val Pro Ser Asn Trp
 45                  50                  55                  60 cag atg cac ggt tac gat gcg ccc atc tac acc aac gtg acc tat ccc     1684
Gln Met His Gly Tyr Asp Ala Pro Ile Tyr Thr Asn Val Thr Tyr Pro
                 65                  70                  75 att acg gtc aat ccg ccg ttt gtt ccc acg gag aat ccg acg ggt tgt     1732
Ile Thr Val Asn Pro Pro Phe Val Pro Thr Glu Asn Pro Thr Gly Cys
             80                  85                  90 tac tcg ctc aca ttt aat gtt gat gaa agc tgg cta cag gaa ggc cag     1780
Tyr Ser Leu Thr Phe Asn Val Asp Glu Ser Trp Leu Gln Glu Gly Gln
         95                  100                 105 acg cga att att ttt gat ggc gtt aac tcg gcg ttt cat ctg tgg tgc     1828
Thr Arg Ile Ile Phe Asp Gly Val Asn Ser Ala Phe His Leu Trp Cys
     110                 115                 120 aac ggg cgc tgg gtc ggt tac ggc cag gac agt cgt ttg ccg tct gaa     1876
Asn Gly Arg Trp Val Gly Tyr Gly Gln Asp Ser Arg Leu Pro Ser Glu
125                 130                 135                 140 ttt gac ctg agc gca ttt tta cgc gcc gga gaa aac cgc ctc gcg gtg     1924
Phe Asp Leu Ser Ala Phe Leu Arg Ala Gly Glu Asn Arg Leu Ala Val
                145                 150                 155 atg gtg ctg cgc tgg agt gac ggc agt tat ctg gaa gat cag gat atg     1972
Met Val Leu Arg Trp Ser Asp Gly Ser Tyr Leu Glu Asp Gln Asp Met
            160                 165                 170 tgg cgg atg agc ggc att ttc cgt gac gtc tcg ttg ctg cat aaa ccg     2020
Trp Arg Met Ser Gly Ile Phe Arg Asp Val Ser Leu Leu His Lys Pro
        175                 180                 185 act aca caa atc agc gat ttc cat gtt gcc act cgc ttt aat gat gat     2068
Thr Thr Gln Ile Ser Asp Phe His Val Ala Thr Arg Phe Asn Asp Asp
    190                 195                 200 ttc agc cgc gct gta ctg gag gct gaa gtt cag atg tgc ggc gag ttg     2116
Phe Ser Arg Ala Val Leu Glu Ala Glu Val Gln Met Cys Gly Glu Leu
205                 210                 215                 220 cgt gac tac cta cgg gta aca gtt tct tta tgg cag ggt gaa acg cag     2164
Arg Asp Tyr Leu Arg Val Thr Val Ser Leu Trp Gln Gly Glu Thr Gln
                225                 230                 235 gtc gcc agc ggc acc gcg cct ttc ggc ggt gaa att atc gat gag cgt     2212
Val Ala Ser Gly Thr Ala Pro Phe Gly Gly Glu Ile Ile Asp Glu Arg
            240                 245                 250 ggt ggt tat gcc gat cgc gtc aca cta cgt ctg aac gtc gaa aac ccg     2260
Gly Gly Tyr Ala Asp Arg Val Thr Leu Arg Leu Asn Val Glu Asn Pro
        255                 260                 265 aaa ctg tgg agc gcc gaa atc ccg aat ctc tat cgt gcg gtg gtt gaa     2308
Lys Leu Trp Ser Ala Glu Ile Pro Asn Leu Tyr Arg Ala Val Val Glu
    270                 275                 280 ctg cac acc gcc gac ggc acg ctg att gaa gca gaa gcc tgc gat gtc     2356
Leu His Thr Ala Asp Gly Thr Leu Ile Glu Ala Glu Ala Cys Asp Val
285                 290                 295                 300 ggt ttc cgc gag gtg cgg att gaa aat ggt ctg ctg ctg ctg aac ggc     2404
```

-continued

| | | |
|---|---|---|
| Gly Phe Arg Glu Val Arg Ile Glu Asn Gly Leu Leu Leu Leu Asn Gly<br>                        305                        310                        315 | | |
| aag ccg ttg ctg att cga ggc gtt aac cgt cac gag cat cat cct ctg<br>Lys Pro Leu Leu Ile Arg Gly Val Asn Arg His Glu His His Pro Leu<br>                320                        325                        330 | | 2452 |
| cat ggt cag gtc atg gat gag cag acg atg gtg cag gat atc ctg ctg<br>His Gly Gln Val Met Asp Glu Gln Thr Met Val Gln Asp Ile Leu Leu<br>      335                        340                        345 | | 2500 |
| atg aag cag aac aac ttt aac gcc gtg cgc tgt tcg cat tat ccg aac<br>Met Lys Gln Asn Asn Phe Asn Ala Val Arg Cys Ser His Tyr Pro Asn<br>350                        355                        360 | | 2548 |
| cat ccg ctg tgg tac acg ctg tgc gac cgc tac ggc ctg tat gtg gtg<br>His Pro Leu Trp Tyr Thr Leu Cys Asp Arg Tyr Gly Leu Tyr Val Val<br>365                        370                        375                        380 | | 2596 |
| gat gaa gcc aat att gaa acc cac ggc atg gtg cca atg aat cgt ctg<br>Asp Glu Ala Asn Ile Glu Thr His Gly Met Val Pro Met Asn Arg Leu<br>                      385                        390                        395 | | 2644 |
| acc gat gat ccg cgc tgg cta ccg gcg atg agc gaa cgc gta acg cga<br>Thr Asp Asp Pro Arg Trp Leu Pro Ala Met Ser Glu Arg Val Thr Arg<br>            400                        405                        410 | | 2692 |
| atg gtg cag cgc gat cgt aat cac ccg agt gtg atc atc tgg tcg ctg<br>Met Val Gln Arg Asp Arg Asn His Pro Ser Val Ile Ile Trp Ser Leu<br>                415                        420                        425 | | 2740 |
| ggg aat gaa tca ggc cac ggc gct aat cac gac gcg ctg tat cgc tgg<br>Gly Asn Glu Ser Gly His Gly Ala Asn His Asp Ala Leu Tyr Arg Trp<br>      430                        435                        440 | | 2788 |
| atc aaa tct gtc gat cct tcc cgc ccg gtg cag tat gaa ggc ggc gga<br>Ile Lys Ser Val Asp Pro Ser Arg Pro Val Gln Tyr Glu Gly Gly Gly<br>445                        450                        455                        460 | | 2836 |
| gcc gac acc acg gcc acc gat att att tgc ccg atg tac gcg cgc gtg<br>Ala Asp Thr Thr Ala Thr Asp Ile Ile Cys Pro Met Tyr Ala Arg Val<br>                      465                        470                        475 | | 2884 |
| gat gaa gac cag ccc ttc ccg gct gtg ccg aaa tgg tcc atc aaa aaa<br>Asp Glu Asp Gln Pro Phe Pro Ala Val Pro Lys Trp Ser Ile Lys Lys<br>                480                        485                        490 | | 2932 |
| tgg ctt tcg cta cct gga gag acg cgc ccg ctg atc ctt tgc gaa tac<br>Trp Leu Ser Leu Pro Gly Glu Thr Arg Pro Leu Ile Leu Cys Glu Tyr<br>                      495                        500                        505 | | 2980 |
| gcc cac gcg atg ggt aac agt ctt ggc ggt ttc gct aaa tac tgg cag<br>Ala His Ala Met Gly Asn Ser Leu Gly Gly Phe Ala Lys Tyr Trp Gln<br>            510                        515                        520 | | 3028 |
| gcg ttt cgt cag tat ccc cgt tta cag ggc ggc ttc gtc tgg gac tgg<br>Ala Phe Arg Gln Tyr Pro Arg Leu Gln Gly Gly Phe Val Trp Asp Trp<br>525                        530                        535                        540 | | 3076 |
| gtg gat cag tcg ctg att aaa tat gat gaa aac ggc aac ccg tgg tcg<br>Val Asp Gln Ser Leu Ile Lys Tyr Asp Glu Asn Gly Asn Pro Trp Ser<br>                      545                        550                        555 | | 3124 |
| gct tac ggc ggt gat ttt ggc gat acg ccg aac gat cgc cag ttc tgt<br>Ala Tyr Gly Gly Asp Phe Gly Asp Thr Pro Asn Asp Arg Gln Phe Cys<br>              560                        565                        570 | | 3172 |
| atg aac ggt ctg gtc ttt gcc gac cgc acg ccg cat cca gcg ctg acg<br>Met Asn Gly Leu Val Phe Ala Asp Arg Thr Pro His Pro Ala Leu Thr<br>                      575                        580                        585 | | 3220 |
| gaa gca aaa cac cag cag cag ttt ttc cag ttc cgt tta tcc ggg caa<br>Glu Ala Lys His Gln Gln Gln Phe Phe Gln Phe Arg Leu Ser Gly Gln<br>590                        595                        600 | | 3268 |
| acc atc gaa gtg acc agc gaa tac ctg ttc cgt cat agc gat aac gag<br>Thr Ile Glu Val Thr Ser Glu Tyr Leu Phe Arg His Ser Asp Asn Glu<br>605                        610                        615                        620 | | 3316 |

-continued

```
ctc ctg cac tgg atg gtg gcg ctg gat ggt aag ccg ctg gca agc ggt    3364
Leu Leu His Trp Met Val Ala Leu Asp Gly Lys Pro Leu Ala Ser Gly
            625                 630                 635 gaa gtg cct ctg gat gtc gct cca caa ggt aaa cag ttg att gaa ctg    3412
Glu Val Pro Leu Asp Val Ala Pro Gln Gly Lys Gln Leu Ile Glu Leu
                640                 645                 650 cct gaa cta ccg cag ccg gag agc gcc ggg caa ctc tgg ctc aca gta    3460
Pro Glu Leu Pro Gln Pro Glu Ser Ala Gly Gln Leu Trp Leu Thr Val
                    655                 660                 665 cgc gta gtg caa ccg aac gcg acc gca tgg tca gaa gcc ggg cac atc    3508
Arg Val Val Gln Pro Asn Ala Thr Ala Trp Ser Glu Ala Gly His Ile
            670                 675                 680 agc gcc tgg cag cag tgg cgt ctg gcg gaa aac ctc agt gtg acg ctc    3556
Ser Ala Trp Gln Gln Trp Arg Leu Ala Glu Asn Leu Ser Val Thr Leu
685                 690                 695                 700 ccc gcc gcg tcc cac gcc atc ccg cat ctg acc acc agc gaa atg gat    3604
Pro Ala Ala Ser His Ala Ile Pro His Leu Thr Thr Ser Glu Met Asp
                705                 710                 715 ttt tgc atc gag ctg ggt aat aag cgt tgg caa ttt aac cgc cag tca    3652
Phe Cys Ile Glu Leu Gly Asn Lys Arg Trp Gln Phe Asn Arg Gln Ser
            720                 725                 730 ggc ttt ctt tca cag atg tgg att ggc gat aaa aaa caa ctg ctg acg    3700
Gly Phe Leu Ser Gln Met Trp Ile Gly Asp Lys Lys Gln Leu Leu Thr
                735                 740                 745 ccg ctg cgc gat cag ttc acc cgt gca ccg ctg gat aac gac att ggc    3748
Pro Leu Arg Asp Gln Phe Thr Arg Ala Pro Leu Asp Asn Asp Ile Gly
        750                 755                 760 gta agt gaa gcg acc cgc att gac cct aac gcc tgg gtc gaa cgc tgg    3796
Val Ser Glu Ala Thr Arg Ile Asp Pro Asn Ala Trp Val Glu Arg Trp
765                 770                 775                 780 aag gcg gcg ggc cat tac cag gcc gaa gca gcg ttg ttg cag tgc acg    3844
Lys Ala Ala Gly His Tyr Gln Ala Glu Ala Ala Leu Leu Gln Cys Thr
                785                 790                 795 gca gat aca ctt gct gat gcg gtg ctg att acg acc gct cac gcg tgg    3892
Ala Asp Thr Leu Ala Asp Ala Val Leu Ile Thr Thr Ala His Ala Trp
            800                 805                 810 cag cat cag ggg aaa acc tta ttt atc agc cgg aaa acc tac cgg att    3940
Gln His Gln Gly Lys Thr Leu Phe Ile Ser Arg Lys Thr Tyr Arg Ile
                815                 820                 825 gat ggt agt ggt caa atg gcg att acc gtt gat gtt gaa gtg gcg agc    3988
Asp Gly Ser Gly Gln Met Ala Ile Thr Val Asp Val Glu Val Ala Ser
830                 835                 840 gat aca ccg cat ccg gcg cgg att ggc ctg aac tgc cag ctg gcg cag    4036
Asp Thr Pro His Pro Ala Arg Ile Gly Leu Asn Cys Gln Leu Ala Gln
                845                 850                 855                 860 gta gca gag cgg gta aac tgg ctc gga tta ggg ccg caa gaa aac tat    4084
Val Ala Glu Arg Val Asn Trp Leu Gly Leu Gly Pro Gln Glu Asn Tyr
                    865                 870                 875 ccc gac cgc ctt act gcc gcc tgt ttt gac cgc tgg gat ctg cca ttg    4132
Pro Asp Arg Leu Thr Ala Ala Cys Phe Asp Arg Trp Asp Leu Pro Leu
            880                 885                 890 tca gac atg tat acc ccg tac gtc ttc ccg agc gaa aac ggt ctg cgc    4180
Ser Asp Met Tyr Thr Pro Tyr Val Phe Pro Ser Glu Asn Gly Leu Arg
                895                 900                 905 tgc ggg acg cgc gaa ttg aat tat ggc cca cac cag tgg cgc ggc gac    4228
Cys Gly Thr Arg Glu Leu Asn Tyr Gly Pro His Gln Trp Arg Gly Asp
        910                 915                 920 ttc cag ttc aac atc agc cgc tac agt caa cag caa ctg atg gaa acc    4276
Phe Gln Phe Asn Ile Ser Arg Tyr Ser Gln Gln Gln Leu Met Glu Thr
925                 930                 935                 940
```

```
agc cat cgc cat ctg ctg cac gcg gaa gaa ggc aca tgg ctg aat atc      4324
Ser His Arg His Leu Leu His Ala Glu Glu Gly Thr Trp Leu Asn Ile
            945                 950                 955 gac ggt ttc cat atg ggg att ggt ggc gac gac tcc tgg agc ccg tca      4372
Asp Gly Phe His Met Gly Ile Gly Gly Asp Asp Ser Trp Ser Pro Ser
        960                 965                 970 gta tcg gcg gaa ttc cag ctg agc gcc ggt cgc tac cat tac cag ttg      4420
Val Ser Ala Glu Phe Gln Leu Ser Ala Gly Arg Tyr His Tyr Gln Leu
            975                 980                 985 gtc tgg tgt caa aaa aga tct gac tat aaa gat gag  gac ctc gac cat     4468
Val Trp Cys Gln Lys Arg Ser Asp Tyr Lys Asp Glu  Asp Leu Asp His
        990                 995                 1000 cat  cat cat cat cac cgg  taataatagg tagataagtg actgattaga           4516
His  His His His His Arg
1005                 1010 tgcattgatc cctcgaccaa ttccggttat tttccaccat attgccgtct tttggcaatg    4576
tgagggcccg gaaacctggc cctgtcttct tgacgagcat cctaggggt ctttcccctc     4636 tcgccaaagg aatgcaaggt ctgttgaatg tcgtgaagga agcagttcct ctggaagctt    4696
cttgaagaca acaacgtct gtagcgaccc tttgcaggca gcggaacccc ccacctggcg     4756
acaggtgcct ctgcggccaa agccacgtg tataagatac acctgcaaag gcggcacaac     4816
cccagtgcca cgttgtgagt tggatagttg tggaaagagt caaatggctc tcctcaagcg    4876
tattcaacaa ggggctgaag gatgcccaga aggtacccca ttgtatggga tctgatctgg    4936
ggcctcggtg cacatgcttt acatgtgttt agtcgaggtt aaaaaacgtc taggcccccc    4996
gaaccacggg gacgtggttt tcctttgaaa aacacgatga taataccatg attgaacaag    5056
atggattgca cgcaggttct ccggccgctt gggtggagag gctattcggc tatgactggg    5116
cacaacagac aatcggctgc tctgatgccg ccgtgttccg gctgtcagcg caggggcgcc    5176
cggttctttt tgtcaagacc gacctgtccg gtgccctgaa tgaactgcag gacgaggcag    5236
cgcggctatc gtggctggcc acgacgggcg ttccttgcgc agctgtgctc gacgttgtca    5296
ctgaagcggg aagggactgg ctgctattgg gcgaagtgcc ggggcaggat ctcctgtcat    5356
ctcaccttgc tcctgccgag aaagtatcca tcatggctga tgcaatgcgg cggctgcata    5416
cgcttgatcc ggctacctgc ccattcgacc accaagcgaa acatcgcatc gagcgagcac    5476
gtactcggat ggaagccggt cttgtcgatc aggatgatct ggacgaagag catcaggggc    5536
tcgcgccagc cgaactgttc gccaggctca aggcgcgcat gcccgacggc gaggatctcg    5596
tcgtgaccca tggcgatgcc tgcttgccga atatcatggt ggaaaatggc cgcttttctg    5656
gattcatcga ctgtggccgg ctgggtgtgg cggaccgcta tcaggacata gcgttggcta    5716
cccgtgatat tgctgaagag cttggcggcg aatgggctga ccgcttcctc gtgctttacg    5776
gtatcgccgc tcccgattcg cagcgcatcg ccttctatcg ccttcttgac gagttcttct    5836
gagcgggact ctggggttcg catcgataaa ataaagatt ttatttagtc tccagaaaaa     5896 gggggaatg aaagaccccca cctgtaggtt tggcaagcta gcttaagtaa cgccattttg    5956
caaggcatgg aaaatacat aactgagaat agagaagttc agatcaaggt caggaacaga    6016
tggaacagct gaatatgggc caaacaggat atctgtggta agcagttcct gccccggctc    6076
agggccaaga acagatggaa cagctgaata tgggccaaac aggatatctg tggtaagcag    6136
ttcctgcccc ggctcagggc caagaacaga tggtccccag atgcggtcca gccctcagca    6196
gtttctagag aaccatcaga tgtttccagg gtgccccaag gacctgaaat gaccctgtgc    6256
```

-continued

```
cttatttgaa ctaaccaatc agttcgcttc tcgcttctgt tcgcgcgctt ctgctccccg    6316
agctcaataa aagagcccac aaccccctcac tcggggcgcc agtcctccga ttgactgagt   6376
cgcccgggta cccgtgtatc caataaaccc tcttgcagtt gcatccgact tgtggtctcg   6436
ctgttccttg ggagggtctc ctctgagtga ttgactaccc gtcagcgggg gtctttcatt   6496
catgcagcat gtatcaaaat taatttggtt ttttttctta agtatttaca ttaaatggcc   6556
atagttgcat taatgaatcg gccaacgcgc ggggagaggc ggtttgcgta ttggcgctct   6616
tccgcttcct cgctcactga ctcgctgcgc tcggtcgttc ggctgcggcg agcggtatca   6676
gctcactcaa aggcggtaat acgg                                          6700
```

<210> SEQ ID NO 2
<211> LENGTH: 1010
<212> TYPE: PRT
<213> ORGANISM: Unknown
<220> FEATURE:
<223> OTHER INFORMATION: pICAST ALC.

<400> SEQUENCE: 2

```
Met Gly Val Ile Thr Asp Ser Leu Ala Val Val Ala Arg Thr Asp Arg
  1               5                  10                  15

Pro Ser Gln Gln Leu Arg Ser Leu Asn Gly Glu Trp Arg Phe Ala Trp
             20                  25                  30

Phe Pro Ala Pro Glu Ala Val Pro Glu Ser Trp Leu Glu Cys Asp Leu
         35                  40                  45

Pro Glu Ala Asp Thr Val Val Pro Ser Asn Trp Gln Met His Gly
     50                  55                  60

Tyr Asp Ala Pro Ile Tyr Thr Asn Val Thr Tyr Pro Ile Thr Val Asn
 65                  70                  75                  80

Pro Pro Phe Val Pro Thr Glu Asn Pro Thr Gly Cys Tyr Ser Leu Thr
                 85                  90                  95

Phe Asn Val Asp Glu Ser Trp Leu Gln Glu Gly Gln Thr Arg Ile Ile
            100                 105                 110

Phe Asp Gly Val Asn Ser Ala Phe His Leu Trp Cys Asn Gly Arg Trp
        115                 120                 125

Val Gly Tyr Gly Gln Asp Ser Arg Leu Pro Ser Glu Phe Asp Leu Ser
130                 135                 140

Ala Phe Leu Arg Ala Gly Glu Asn Arg Leu Ala Val Met Val Leu Arg
145                 150                 155                 160

Trp Ser Asp Gly Ser Tyr Leu Glu Asp Gln Asp Met Trp Arg Met Ser
                165                 170                 175

Gly Ile Phe Arg Asp Val Ser Leu Leu His Lys Pro Thr Thr Gln Ile
            180                 185                 190

Ser Asp Phe His Val Ala Thr Arg Phe Asn Asp Asp Phe Ser Arg Ala
        195                 200                 205

Val Leu Glu Ala Glu Val Gln Met Cys Gly Glu Leu Arg Asp Tyr Leu
    210                 215                 220

Arg Val Thr Val Ser Leu Trp Gln Gly Glu Thr Gln Val Ala Ser Gly
225                 230                 235                 240

Thr Ala Pro Phe Gly Gly Glu Ile Ile Asp Glu Arg Gly Gly Tyr Ala
                245                 250                 255

Asp Arg Val Thr Leu Arg Leu Asn Val Glu Asn Pro Lys Leu Trp Ser
            260                 265                 270

Ala Glu Ile Pro Asn Leu Tyr Arg Ala Val Val Glu Leu His Thr Ala
        275                 280                 285
```

-continued

Asp Gly Thr Leu Ile Glu Ala Glu Ala Cys Asp Val Gly Phe Arg Glu
    290                 295                 300

Val Arg Ile Glu Asn Gly Leu Leu Leu Asn Gly Lys Pro Leu Leu
305                 310                 315                 320

Ile Arg Gly Val Asn Arg His Glu His His Pro Leu His Gly Gln Val
                325                 330                 335

Met Asp Glu Gln Thr Met Val Gln Asp Ile Leu Leu Met Lys Gln Asn
            340                 345                 350

Asn Phe Asn Ala Val Arg Cys Ser His Tyr Pro Asn His Pro Leu Trp
        355                 360                 365

Tyr Thr Leu Cys Asp Arg Tyr Gly Leu Tyr Val Val Asp Glu Ala Asn
    370                 375                 380

Ile Glu Thr His Gly Met Val Pro Met Asn Arg Leu Thr Asp Asp Pro
385                 390                 395                 400

Arg Trp Leu Pro Ala Met Ser Glu Arg Val Thr Arg Met Val Gln Arg
                405                 410                 415

Asp Arg Asn His Pro Ser Val Ile Ile Trp Ser Leu Gly Asn Glu Ser
            420                 425                 430

Gly His Gly Ala Asn His Asp Ala Leu Tyr Arg Trp Ile Lys Ser Val
        435                 440                 445

Asp Pro Ser Arg Pro Val Gln Tyr Glu Gly Gly Gly Ala Asp Thr Thr
    450                 455                 460

Ala Thr Asp Ile Ile Cys Pro Met Tyr Ala Arg Val Asp Glu Asp Gln
465                 470                 475                 480

Pro Phe Pro Ala Val Pro Lys Trp Ser Ile Lys Lys Trp Leu Ser Leu
                485                 490                 495

Pro Gly Glu Thr Arg Pro Leu Ile Leu Cys Glu Tyr Ala His Ala Met
            500                 505                 510

Gly Asn Ser Leu Gly Gly Phe Ala Lys Tyr Trp Gln Ala Phe Arg Gln
        515                 520                 525

Tyr Pro Arg Leu Gln Gly Gly Phe Val Trp Asp Trp Val Asp Gln Ser
    530                 535                 540

Leu Ile Lys Tyr Asp Glu Asn Gly Asn Pro Trp Ser Ala Tyr Gly Gly
545                 550                 555                 560

Asp Phe Gly Asp Thr Pro Asn Asp Arg Gln Phe Cys Met Asn Gly Leu
                565                 570                 575

Val Phe Ala Asp Arg Thr Pro His Pro Ala Leu Thr Glu Ala Lys His
            580                 585                 590

Gln Gln Gln Phe Phe Gln Phe Arg Leu Ser Gly Gln Thr Ile Glu Val
        595                 600                 605

Thr Ser Glu Tyr Leu Phe Arg His Ser Asp Asn Glu Leu Leu His Trp
    610                 615                 620

Met Val Ala Leu Asp Gly Lys Pro Leu Ala Ser Gly Glu Val Pro Leu
625                 630                 635                 640

Asp Val Ala Pro Gln Gly Lys Gln Leu Ile Glu Leu Pro Glu Leu Pro
                645                 650                 655

Gln Pro Glu Ser Ala Gly Gln Leu Trp Leu Thr Val Arg Val Val Gln
            660                 665                 670

Pro Asn Ala Thr Ala Trp Ser Glu Ala Gly His Ile Ser Ala Trp Gln
        675                 680                 685

Gln Trp Arg Leu Ala Glu Asn Leu Ser Val Thr Leu Pro Ala Ala Ser
    690                 695                 700

```
His Ala Ile Pro His Leu Thr Thr Ser Glu Met Asp Phe Cys Ile Glu
705                 710                 715                 720

Leu Gly Asn Lys Arg Trp Gln Phe Asn Arg Gln Ser Gly Phe Leu Ser
            725                 730                 735

Gln Met Trp Ile Gly Asp Lys Lys Gln Leu Leu Thr Pro Leu Arg Asp
        740                 745                 750

Gln Phe Thr Arg Ala Pro Leu Asp Asn Asp Ile Gly Val Ser Glu Ala
    755                 760                 765

Thr Arg Ile Asp Pro Asn Ala Trp Val Glu Arg Trp Lys Ala Ala Gly
770                 775                 780

His Tyr Gln Ala Glu Ala Leu Leu Gln Cys Thr Ala Asp Thr Leu
785                 790                 795                 800

Ala Asp Ala Val Leu Ile Thr Thr Ala His Ala Trp Gln His Gln Gly
                805                 810                 815

Lys Thr Leu Phe Ile Ser Arg Lys Thr Tyr Arg Ile Asp Gly Ser Gly
            820                 825                 830

Gln Met Ala Ile Thr Val Asp Val Glu Val Ala Ser Asp Thr Pro His
        835                 840                 845

Pro Ala Arg Ile Gly Leu Asn Cys Gln Leu Ala Gln Val Ala Glu Arg
    850                 855                 860

Val Asn Trp Leu Gly Leu Gly Pro Gln Glu Asn Tyr Pro Asp Arg Leu
865                 870                 875                 880

Thr Ala Ala Cys Phe Asp Arg Trp Asp Leu Pro Leu Ser Asp Met Tyr
                885                 890                 895

Thr Pro Tyr Val Phe Pro Ser Glu Asn Gly Leu Arg Cys Gly Thr Arg
            900                 905                 910

Glu Leu Asn Tyr Gly Pro His Gln Trp Arg Gly Asp Phe Gln Phe Asn
        915                 920                 925

Ile Ser Arg Tyr Ser Gln Gln Gln Leu Met Glu Thr Ser His Arg His
    930                 935                 940

Leu Leu His Ala Glu Glu Gly Thr Trp Leu Asn Ile Asp Gly Phe His
945                 950                 955                 960

Met Gly Ile Gly Gly Asp Asp Ser Trp Ser Pro Ser Val Ser Ala Glu
                965                 970                 975

Phe Gln Leu Ser Ala Gly Arg Tyr His Tyr Gln Leu Val Trp Cys Gln
            980                 985                 990

Lys Arg Ser Asp Tyr Lys Asp Glu  Asp Leu Asp His His  His His His
        995                 1000                1005

His Arg
    1010
```

<210> SEQ ID NO 3
<211> LENGTH: 6700
<212> TYPE: DNA
<213> ORGANISM: Unknown
<220> FEATURE:
<223> OTHER INFORMATION: pICAST ALC.

<400> SEQUENCE: 3

```
gacgtcggac ttatacccgg tttgtcctat agacaccatt cgtcaaggac ggggccgagt    60
cccggttctt gtctaccttg tcgacttata cccgtttgt cctatagaca ccattcgtca   120
aggacgggc cgagtcccgg ttcttgtcta ccagggtct acgccaggtc gggagtcgtc    180
aaagatctct tggtagtcta caaggtccc acggggttcc tggactttac tgggacacgg   240
aataaacttg attggttagt caagcgaaga gcgaagacaa gcgcgcgaag acgaggggct   300
```

```
cgagttattt tctcgggtgt tggggagtga gccccgcggt caggaggcta actgactcag    360
cgggcccatg ggcacatagg ttatttggga gaacgtcaac gtaggctgaa caccagagcg    420
acaaggaacc ctcccagagg agactcacta actgatgggc agtcgccccc agaaagtaaa    480
cccccgagca ggccctagcc ctctggggac gggtccctgg tggctgggtg gtggccctcc    540
gttcgaccgg tcgttgaata gacacagaca ggctaacaga tcacagatac tgactaaaat    600
acgcggacgc agccatgatc aatcgattga tcgagacata gaccgcctgg gcaccacctt    660
gactgctcaa gacttgtggg ccggcgttgg gaccctctgc agggtccctg aaaccccgg    720
caaaaacacc gggctggact ccttccctca gctacacctt aggctggggc agtcctatac    780
accaagacca tcctctgctc ttggattttg tcaaggcgg aggcagactt aaaaacgaaa    840
gccaaacctt ggcttcggcg cgcagaacag acgacgtcgt agcaagacac aacagagaca    900
gactgacaca aagacataaa cagacttta atcccggtct gacaatggtg agggaattca    960
aactggaatc cattgacctt tctacagctc gccgagcgag tgttggtcag ccatctacag   1020
ttcttctctg caacccaatg gaagacgaga cgtcttaccg gttggaaatt gcagcctacc   1080
ggcgctctgc cgtggaaatt ggctctggag tagtgggtcc aattctagtt ccagaaaagt   1140
ggaccgggcg tacctgtggg tctggtccag gggatgtagc actggaccct tcggaaccga   1200
aaactggggg gagggaccca gttcgggaaa catgtgggat tcgaggcgg aggagaagga   1260
ggtaggcggg gcagagaggg ggaacttgga ggagcaagct ggggcggagc taggagggaa   1320
ataggtcggg agtgaggaag agatccgcgg ccggcgagat cgggtaatta tgctgagtga   1380
tatcccgcta agcttagtcc ggaaccgcgc ggcctaggaa ttaattcgcg ttaaccctcc   1440
accgccatcg gagctctacc cgcactaatg cctaagtgac cggcagcacc gggcgtggct   1500
agcgggaagg gttgtcaatg cgtcggactt accgcttacc gcgaaacgga ccaaaggccg   1560
tggtcttcgc cacggccttt cgaccgacct cacgctagaa ggactccggc tatgacagca   1620
gcagggagt ttgaccgtct acgtgccaat gctacgcggg tagatgtggt tgcactggat   1680
agggtaatgc cagttaggcg gcaaacaagg gtgcctctta ggctgcccaa caatgagcga   1740
gtgtaaatta caactacttt cgaccgatgt ccttccggtc tgcgcttaat aaaaactacc   1800
gcaattgagc cgcaaagtag acaccacgtt gcccgcgacc cagccaatgc cggtcctgtc   1860
agcaaacggc agacttaaac tggactcgcg taaaaatgcg cggcctcttt tggcggagcg   1920
ccactaccac gacgcgacct cactgccgtc aatagacctt ctagtcctat acaccgccta   1980
ctcgccgtaa aaggcactgc agagcaacga cgtatttggc tgatgtgttt agtcgctaaa   2040
ggtacaacgg tgagcgaaat tactactaaa gtcggcgcga catgacctcc gacttcaagt   2100
ctacacgccg ctcaacgcac tgatggatgc ccattgtcaa agaaataccg tcccactttg   2160
cgtccagcgc tcgccgtggc gcggaaagcc gccactttaa tagctactcg caccaccaat   2220
acggctagcg cagtgtgatg cagacttgca gcttttgggc tttgacacct cgcggcttta   2280
gggcttagag atagcacgcc accaacttga cgtgtggcgg ctgccgtgcg actaacttcg   2340
tcttcggacg ctacagccaa aggcgctcca cgcctaactt ttaccagacg acgacgactt   2400
gccgttcggc aacgactaag ctccgcaatt ggcagtgctc gtagtaggag acgtaccagt   2460
ccagtaccta ctcgtctgct accacgtcct ataggacgac tacttcgtct tgttgaaatt   2520
gcggcacgcg acaagcgtaa taggcttggt aggcgacacc atgtgcgaca cgctggcgat   2580
gccggacata caccacctac ttcggttata actttgggtg ccgtaccacg gttacttagc   2640
```

```
agactggcta ctaggcgcga ccgatggccg ctactcgctt gcgcattgcg cttaccacgt    2700
cgcgctagca ttagtgggct cacactagta gaccagcgac cccttactta gtccggtgcc    2760
gcgattagtg ctgcgcgaca tagcgaccta gtttagacag ctaggaaggg cgggccacgt    2820
catacttccg ccgcctcggc tgtggtgccg gtggctataa taaacgggct acatgcgcgc    2880
gcacctactt ctggtcggga agggccgaca cggctttacc aggtagtttt ttaccgaaag    2940
cgatggacct ctctgcgcgg gcgactagga aacgcttatg cgggtgcgct acccattgtc    3000
agaaccgcca aagcgattta tgaccgtccg caaagcagtc ataggggcaa atgtcccgcc    3060
gaagcagacc ctgacccacc tagtcagcga ctaatttata ctacttttgc cgttgggcac    3120
cagccgaatg ccgccactaa aaccgctatg cggcttgcta gcggtcaaga catacttgcc    3180
agaccagaaa cggctggcgt gcggcgtagg tcgcgactgc cttcgttttg tggtcgtcgt    3240
caaaaaggtc aagcaaata ggcccgtttg gtagcttcac tggtcgctta tggacaaggc    3300
agtatcgcta ttgctcgagg acgtgaccta ccaccgcgac ctaccattcg gcgaccgttc    3360
gccacttcac ggagacctac agcgaggtgt tccatttgtc aactaacttg acggacttga    3420
tggcgtcggc ctctcgcggc ccgttgagac cgagtgtcat gcgcatcacg ttggcttgcg    3480
ctggcgtacc agtcttcggc ccgtgtagtc gcggaccgtc gtcaccgcag accgcctttt    3540
ggagtcacac tgcgagggc ggcgcagggt gcggtagggc gtagactggt ggtcgcttta    3600
cctaaaaacg tagctcgacc cattattcgc aaccgttaaa ttggcggtca gtccgaaaga    3660
aagtgtctac acctaaccgc tatttttgt tgacgactgc ggcgacgcgc tagtcaagtg    3720
ggcacgtggc gacctattgc tgtaaccgca ttcacttcgc tgggcgtaac tgggattgcg    3780
gacccagctt gcgaccttcc gccgcccggt aatggtccgg cttcgtcgca acaacgtcac    3840
gtgccgtcta tgtgaacgac tacgccacga ctaatgctgg cgagtgcgca ccgtcgtagt    3900
ccccttttgg aataaatagt cggccttttg gatggcctaa ctaccatcac cagtttaccg    3960
ctaatggcaa ctacaacttc accgctcgct atgtggcgta ggccgcgcct aaccggactt    4020
gacggtcgac cgcgtccatc gtctcgccca tttgaccgag cctaatcccg gcgttctttt    4080
gatagggctg gcggaatgac ggcggacaaa actggcgacc ctagacggta acagtctgta    4140 catatgggc atgcagaagg gctcgctttt gccagacgcg acgccctgcg cgcttaactt    4200
aataccgggt gtggtcaccg cgccgctgaa ggtcaagttg tagtcggcga tgtcagttgt    4260
cgttgactac ctttggtcgg tagcggtaga cgacgtgcgc cttcttccgt gtaccgactt    4320
atagctggca aaggtatacc cctaaccacc gctgctgagg acctcgggca gtcatagccg    4380
ccttaaggtc gactcgcggc cagcgatggt aatggtcaac cagaccacag ttttttctag    4440
actgatattt ctactcctgg agctggtagt agtagtagta gtggccatta ttatccatct    4500
attcactgac taatctacgt aactaggag ctggttaagg ccaataaaag gtggtataac    4560
ggcagaaaac cgttacactc ccgggccttt ggaccgggac agaagaactg ctcgtaagga    4620
tccccagaaa ggggagagcg gtttccttac gttccagaca acttacagca cttccttcgt    4680
caaggagacc ttcgaagaac ttctgttttgt tgcagacatc gctgggaaac gtccgtcgcc    4740 ttgggggtg gaccgctgtc cacggagacg ccggttttcg gtgcacatat tctatgtgga    4800
cgtttccgcc gtgttgggt cacggtgcaa cactcaacct atcaacacct ttctcagttt    4860
accgagagga gttcgcataa gttgttcccc gacttcctac gggtcttcca tggggtaaca    4920 tacccctagac tagaccccgg agccacgtgt acgaaatgta cacaaatcag ctccaatttt    4980
ttgcagatcc gggggggcttg gtgcccctgc accaaaagga aacttttttgt gctactatta    5040
```

```
tggtactaac ttgttctacc taacgtgcgt ccaagaggcc ggcgaaccca cctctccgat      5100
aagccgatac tgaccgtgt tgtctgttag ccgacgagac tacggcggca caaggccgac      5160
agtcgcgtcc ccgcgggcca agaaaaacag ttctggctgg acaggccacg ggacttactt      5220
gacgtcctgc tccgtcgcgc cgatagcacc gaccggtgct gcccgcaagg aacgcgtcga      5280
cacgagctgc aacagtgact tcgcccttcc ctgaccgacg ataacccgct tcacggcccc      5340
gtcctagagg acagtagagt ggaacgagga cggctctttc ataggtagta ccgactacgt      5400
tacgccgccg acgtatgcga actaggccga tggacgggta agctggtggt tcgctttgta      5460
gcgtagctcg ctcgtgcatg agcctacctt cggccagaac agctagtcct actagacctg      5520
cttctcgtag tccccgagcg cggtcggctt gacaagcggt ccgagttccg cgcgtacggg      5580
ctgccgctcc tagagcagca ctgggtaccg ctacggacga acggcttata gtaccacctt      5640
ttaccggcga aaagacctaa gtagctgaca ccggccgacc cacaccgcct ggcgatagtc      5700
ctgtatcgca accgatgggc actataacga cttctcgaac cgccgcttac ccgactggcg      5760
aaggagcacg aaatgccata gcggcgaggg ctaagcgtcg cgtagcggaa gatagcggaa      5820
gaactgctca agaagactcg ccctgagacc ccaagcgtag ctatttatt ttctaaaata      5880 aatcagaggt ctttttcccc ccttactttc tggggtggac atccaaaccg ttcgatcgaa      5940
ttcattgcgg taaaacgttc cgtacctttt tatgtattga ctcttatctc ttcaagtcta      6000
gttccagtcc ttgtctacct tgtcgactta tacccggttt gtcctataga caccattcgt      6060
caaggacggg gccgagtccc ggttcttgtc taccttgtcg acttataccc ggtttgtcct      6120
atagacacca ttcgtcaagg acggggccga gtcccggttc ttgtctacca ggggtctacg      6180
ccaggtcggg agtcgtcaaa gatctcttgg tagtctacaa aggtcccacg gggttcctgg      6240
actttactgg gacacggaat aaacttgatt ggttagtcaa gcgaagagcg aagacaagcg      6300
cgcgaagacg aggggctcga gttatttct cgggtgttgg ggagtgagcc ccgcggtcag      6360
gaggctaact gactcagcgg gcccatgggc acataggtta tttgggagaa cgtcaacgta      6420
ggctgaacac cagagcgaca aggaaccctc ccagaggaga ctcactaact gatgggcagt      6480
cgcccccaga aagtaagtac gtcgtacata gttttaatta aaccaaaaaa aagaattcat      6540
aaatgtaatt taccggtatc aacgtaatta cttagccggt tgcgcgcccc tctccgccaa      6600
acgcataacc gcgagaaggc gaaggagcga gtgactgagc gacgcgagcc agcaagccga      6660
cgccgctcgc catagtcgag tgagtttccg ccattatgcc                            6700

<210> SEQ ID NO 4
<211> LENGTH: 8518
<212> TYPE: DNA
<213> ORGANISM: Unknown
<220> FEATURE:
<223> OTHER INFORMATION: pICAST ALN.

<400> SEQUENCE: 4
ctgcagcctg aatatgggcc aaacaggata tctgtggtaa gcagttcctg ccccggctca        60
gggccaagaa cagatggaac agctgaatat gggccaaaca ggatatctgt ggtaagcagt       120
tcctgccccg gctcagggcc aagaacagat ggtccccaga tgcggtccag ccctcagcag       180
tttctagaga accatcagat gtttccaggg tgccccaagg acctgaaatg accctgtgcc       240
ttatttgaac taaccaatca gttcgcttct cgcttctgtt cgcgcgcttc tgctccccga       300
gctcaataaa agagcccaca accgtcact cggggcgcca gtcctccgat tgactgagtc       360
```

-continued

| | |
|---|---|
| gcccgggtac ccgtgtatcc aataaaccct cttgcagttg catccgactt gtggtctcgc | 420 |
| tgttccttgg gagggtctcc tctgagtgat tgactacccg tcagcggggg tctttcattt | 480 |
| gggggctcgt ccgggatcgg gagacccctg cccagggacc accgacccac caccgggagg | 540 |
| caagctggcc agcaacttat ctgtgtctgt ccgattgtct agtgtctatg actgatttta | 600 |
| tgcgcctgcg tcggtactag ttagctaact agctctgtat ctggcggacc cgtggtggaa | 660 |
| ctgacgagtt ctgaacaccc ggccgcaacc ctggagacac tcccagggac tttggggggcc | 720 |
| gtttttgtgg cccgacctga ggaagggagt cgatgtggaa tccgacccccg tcaggatatg | 780 |
| tggttctggt aggagacgag aacctaaaac agttcccgcc tccgtctgaa ttttttgcttt | 840 |
| cggtttggaa ccgaagccgc gcgtcttgtc tgctgcagca tcgttctgtg ttgtctctgt | 900 |
| ctgactgtgt ttctgtattt gtctgaaaat tagggccaga ctgttaccac tcccttaagt | 960 |
| ttgaccttag gtaactggaa agatgtcgag cggctcgctc acaaccagtc ggtagatgtc | 1020 |
| aagaagagac gttgggttac cttctgctct gcagaatggc caacctttaa cgtcggatgg | 1080 |
| ccgcgagacg gcacctttaa ccgagacctc atcacccagg ttaagatcaa ggtcttttca | 1140 |
| cctggcccgc atggacaccc agaccaggtc ccctacatcg tgacctggga agccttggct | 1200 |
| tttgacccccc ctccctgggt caagcccttt gtacacccta agcctccgcc tcctcttcct | 1260 |
| ccatccgccc cgtctctccc ccttgaacct cctcgttcga cccgcctcg atcctcccctt | 1320 |
| tatccagccc tcactccttc tctaggcgcc ggccgctcta gcccattaat acgactcact | 1380 |
| ataggcgat tcgaacacca tgcaccatca tcatcatcac gtcgactata aagatgagga | 1440 |
| cctcgagatg ggcgtgatta cggattcact ggccgtcgtg gcccgcaccg atcgcccttc | 1500 |
| ccaacagtta cgcagcctga atggcgaatg gcgctttgcc tggtttccgg caccagaagc | 1560 |
| ggtgccggaa agctggctgg agtgcgatct tcctgaggcc gatactgtcg tcgtcccctc | 1620 |
| aaactggcag atgcacggtt acgatgcgcc catctacacc aacgtgacct atcccattac | 1680 |
| ggtcaatccg ccgtttgttc ccacggagaa tccgacgggt tgttactcgc tcacatttaa | 1740 |
| tgttgatgaa agctggctac aggaaggcca gacgcgaatt atttttgatg gcgttaactc | 1800 |
| ggcgtttcat ctgtggtgca acgggcgctg ggtcggttac ggccaggaca gtcgtttgcc | 1860 |
| gtctgaattt gacctgagcg catttttacg cgccggagaa aaccgcctcg cggtgatggt | 1920 |
| gctgggctgg agtgacggca gttatctgga agatcaggat atgtggcgga tgagcggcat | 1980 |
| tttccgtgac gtctcgttgc tgcataaacc gactacacaa atcagcgatt tccatgttgc | 2040 |
| cactcgcttt aatgatgatt rcagccgcgc tgtactggag gctgaagttc agatgtgcgg | 2100 |
| cgagttgcgt gactacctac gggtaacagt ttctttatgg cagggtgaaa cgcaggtcgc | 2160 |
| cagcggcacc gcgcctttcg gcggtgaaat tatcgatgag cgtggtggtt atgccgatcg | 2220 |
| cgtcacacta cgtctgaacg tcgaaaaccc gaaactgtgg agcgccgaaa tcccgaatct | 2280 |
| ctatcgtgcg gtggttgaac tgcacaccgc cgacggcacg ctgattgaag cagaagcctg | 2340 |
| cgatgtcggt ttccgcgagg tgcggattga aaatggtctg ctgctgctga acggcaagcc | 2400 |
| gttgctgatt cgaggcgtta accgtcacga gcatcatcct ctgcatggtc aggtcatgga | 2460 |
| tgagcagacg atggtgcagg atatcctgct gatgaagcag aacaacttta cgccgtgcg | 2520 |
| ctgttcgcat tatccgaacc atcgctgtg gtacacgctg tgcgaccgct acggcctgta | 2580 |
| tgtggtggat gaagccaata ttgaaaccca cggcatggtg ccaatgaatc gtctgaccga | 2640 |
| tgatccgcgc tggctaccgg cgatgagcga acgcgtaacg cgaatggtgc agcgcgatcg | 2700 |
| taatcacccg agtgtgatca tctggtcgct ggggaatgaa tcaggccacg gcgctaatca | 2760 |

-continued

```
cgacgcgctg tatcgctgga tcaaatctgt cgatccttcc cgcccggtgc agtatgaagg    2820
cggcggagcc gacaccacgg ccaccgatat tatttgcccg atgtacgcgc gcgtggatga    2880
agaccagccc ttcccggctg tgccgaaatg gtccatcaaa aaatggcttt cgctacctgg    2940
agagacgcgc ccgctgatcc tttgcgaata cgcccacgcg atgggtaaca gtcttggcgg    3000
tttcgctaaa tactggcagg cgtttcgtca gtatccccgt ttacagggcg gcttcgtctg    3060
ggactgggtg gatcagtcgc tgattaaata tgatgaaaac ggcaacccgt ggtcggctta    3120
cggcggtgat tttggcgata cgccgaacga tcgccagttc tgtatgaacg gtctggtctt    3180
tgccgaccgc acgccgcatc agcgctgac ggaagcaaaa caccagcagc agttttttcca    3240 gttccgttta tccgggcaaa ccatcgaagt gaccagcgaa tacctgttcc gtcatagcga    3300
taacgagctc ctgcactgga tggtggcgct ggatggtaag ccgctggcaa gcggtgaagt    3360
gcctctggat gtcgctccac aaggtaaaca gttgattgaa ctgcctgaac taccgcagcc    3420
ggagagcgcc gggcaactct ggctcacagt acgcgtagtg caaccgaacg cgaccgcatg    3480
gtcagaagcc gggcacatca gcgcctggca gcagtggcgt ctggcggaaa acctcagtgt    3540
gacgctcccc gccgcgtccc acgccatccc gcatctgacc accagcgaaa tggattttg    3600 catcgagctg gtaataagc gttggcaatt taaccgccag tcaggctttc tttcacagat    3660
gtggattggc gataaaaaac aactgctgac gccgctgcgc gatcagttca cccgtgcacc    3720
gctggataac gacattggcg taagtgaagc gacccgcatt gaccctaacg cctgggtcga    3780
acgctggaag gcggcgggcc attaccaggc cgaagcagcg ttgttgcagt gcacggcaga    3840
tacacttgct gatgcggtgc tgattacgac cgctcacgcg tggcagcatc aggggaaaac    3900
cttatttatc agccggaaaa cctaccggat tgatggtagt ggtcaaatgg cgattaccgt    3960
tgatgttgaa gtggcgagcg atacaccgca tccggcgcgg attggcctga actgccagct    4020
ggcgcaggta gcagagcggg taaactggct cggattaggg ccgcaagaaa actatcccga    4080
ccgccttact gccgcctgtt ttgaccgctg ggatctgcca ttgtcagaca tgtataccc    4140 gtacgtcttc ccgagcgaaa acggtctgcg ctgcgggacg cgcgaattga attatggccc    4200
acaccagtgg cgcggcgact tccagttcaa catcagccgc tacagtcaac agcaactgat    4260
ggaaaccagc catcgccatc tgctgcacgc ggaagaaggc acatggctga atatcgacgg    4320
tttccatatg gggattggtg gcgacgactc ctggagcccg tcagtatcgg cggaattcca    4380
gctgagcgcc ggtcgctacc attaccagtt ggtctggtgt caaaaaagat ctggaggtgg    4440
tggcagcagg ccttggcgcg ccggatcctt aattaacaat tgaccggtaa taataggtag    4500
ataagtgact gattagatgc attgatccct cgaccaattc cggttatttt ccaccatatt    4560
gccgtctttt ggcaatgtga gggcccggaa acctggccct gtcttcttga cgagcattcc    4620
taggggtctt tcccctctcg ccaaaggaat gcaaggtctg ttgaatgtcg tgaaggaagc    4680
agttcctctg gaagcttctt gaagacaaac aacgtctgta gcgaccctt gcaggcagcg    4740 gaacccccca cctggcgaca ggtgcctctg cggccaaaag ccacgtgtat aagatacacc    4800
tgcaaaggcg gcacaacccc agtgccacgt tgtgagttgg atagttgtgg aaagagtcaa    4860
atggctctcc tcaagcgtat tcaacaaggg gctgaaggat gcccagaagg tacccattg     4920 tatgggatct gatctgggc ctcggtgcac atgctttaca tgtgtttagt cgaggttaaa     4980
aaacgtctag gccccccgaa ccacggggac gtggttttcc tttgaaaaac acgatgataa    5040
taccatgatt gaacaagatg gattgcacgc aggttctccg gccgcttggg tggagaggct    5100
```

-continued

```
attcggctat gactgggcac aacagacaat cggctgctct gatgccgccg tgttccggct      5160
gtcagcgcag gggcgcccgg ttcttttttgt caagaccgac ctgtccggtg ccctgaatga     5220
actgcaggac gaggcagcgc ggctatcgtg gctggccacg acgggcgttc cttgcgcagc      5280
tgtgctcgac gttgtcactg aagcgggaag ggactggctg ctattgggcg aagtgccggg      5340
gcaggatctc ctgtcatctc accttgctcc tgccgagaaa gtatccatca tggctgatgc      5400
aatgcggcgg ctgcatacgc ttgatccggc tacctgccca ttcgaccacc aagcgaaaca      5460
tcgcatcgag cgagcacgta ctcggatgga agccggtctt gtcgatcagg atgatctgga      5520
cgaagagcat caggggctcg cgccagccga actgttcgcc aggctcaagg cgcgcatgcc      5580
cgacggcgag gatctcgtcg tgacccatgg cgatgcctgc ttgccgaata tcatggtgga      5640
aaatggccgc ttttctggat tcatcgactg tggccggctg ggtgtggcgg accgctatca      5700
ggacatagcg ttggctaccc gtgatattgc tgaagagctt ggcggcgaat gggctgaccg      5760
cttcctcgtg ctttacggta tcgccgctcc cgattcgcag cgcatcgcct tctatcgcct      5820
tcttgacgag ttcttctgag cgggactctg gggttcgcat cgataaaata aaagatttta      5880
tttagtctcc agaaaaaggg gggaatgaaa gaccccacct gtaggtttgg caagctagct      5940
taagtaacgc cattttgcaa ggcatggaaa atacataac tgagaataga aagttcaga       6000
tcaaggtcag gaacagatgg aacagctgaa tatgggccaa acaggatatc tgtggtaagc      6060
agttcctgcc ccggctcagg gccaagaaca gatggaacag ctgaatatgg gccaaacagg      6120
atatctgtgg taagcagttc ctgccccggc tcagggccaa gaacagatgg tccccagatg      6180
cggtccagcc ctcagcagtt tctagagaac catcagatgt ttccagggtg ccccaaggac      6240
ctgaaatgac cctgtgcctt atttgaacta accaatcagt tcgcttctcg cttctgttcg      6300
cgcgcttctg ctccccgagc tcaataaaag agcccacaac ccctcactcg gggcgccagt      6360
cctccgattg actgagtcgc ccgggtaccc gtgtatccaa taaaccctct tgcagttgca      6420
tccgacttgt ggtctcgctg ttccttggga gggtctcctc tgagtgattg actacccgtc      6480
agcgggggtc tttcattcat gcagcatgta tcaaaattaa tttggttttt tttcttaagt      6540
atttacatta aatggccata gttgcattaa tgaatcggcc aacgcgcggg gagaggcggt      6600
ttgcgtattg gcgctcttcc gcttcctcgc tcactgactc gctgcgctcg tcgttcggc      6660
tgcggcgagc ggtatcagct cactcaaagg cggtaatacg gttatccaca gaatcagggg      6720
ataacgcagg aaagaacatg tgagcaaaag gccagcaaaa ggccaggaac cgtaaaaagg      6780
ccgcgttgct ggcgtttttc cataggctcc gcccccctga cgagcatcac aaaaatcgac      6840
gctcaagtca gaggtggcga aacccgacag gactataaag ataccaggcg tttccccctg      6900
gaagctccct cgtgcgctct cctgttccga ccctgccgct taccggatac ctgtccgcct      6960
ttctcccttc gggaagcgtg gcgctttctc atagctcacg ctgtaggtat ctcagttcgg      7020
tgtaggtcgt tcgctccaag ctgggctgtg tgcacgaacc cccgttcag cccgaccgct       7080
gcgccttatc cggtaactat cgtcttgagt ccaacccggt aagacacgac ttatcgccac      7140
tggcagcagc cactggtaac aggattagca gagcgaggta tgtaggcggt gctacagagt      7200
tcttgaagtg gtggcctaac tacggctaca ctagaagaac agtatttggt atctgcgctc      7260
tgctgaagcc agttaccttc ggaaaaagag ttggtagctc ttgatccggc aaacaaacca      7320
ccgctggtag cggtggtttt tttgtttgca agcagcagat tacgcgcaga aaaaaggat       7380
ctcaagaaga tcctttgatc ttttctacgg gtctgacgc tcagtggaac gaaaactcac      7440
gttaagggat tttggtcatg agattatcaa aaaggatctt cacctagatc cttttgcggc      7500
```

-continued

| | |
|---|---|
| cgcaaatcaa tctaaagtat atatgagtaa acttggtctg acagttacca atgcttaatc | 7560 |
| agtgaggcac ctatctcagc gatctgtcta tttcgttcat ccatagttgc ctgactcccc | 7620 |
| gtcgtgtaga taactacgat acgggagggc ttaccatctg gccccagtgc tgcaatgata | 7680 |
| ccgcgagacc cacgctcacc ggctccagat ttatcagcaa taaaccagcc agccggaagg | 7740 |
| gccgagcgca gaagtggtcc tgcaactttta tccgcctcca tccagtctat taattgttgc | 7800 |
| cgggaagcta gagtaagtag ttcgccagtt aatagtttgc gcaacgttgt tgccattgct | 7860 |
| acaggcatcg tggtgtcacg ctcgtcgttt ggtatggctt cattcagctc cggttcccaa | 7920 |
| cgatcaaggc gagttacatg atcccccatg ttgtgcaaaa aagcggttag ctccttcggt | 7980 |
| cctccgatcg ttgtcagaag taagttggcc gcagtgttat cactcatggt tatggcagca | 8040 |
| ctgcataatt ctcttactgt catgccatcc gtaagatgct tttctgtgac tggtgagtac | 8100 |
| tcaaccaagt cattctgaga atagtgtatg cggcgaccga gttgctcttg cccggcgtca | 8160 |
| atacgggata ataccgcgcc acatagcaga actttaaaag tgctcatcat tggaaaacgt | 8220 |
| tcttcggggc gaaaactctc aaggatctta ccgctgttga gatccagttc gatgtaaccc | 8280 |
| actcgtgcac ccaactgatc ttcagcatct tttactttca ccagcgtttc tgggtgagca | 8340 |
| aaaacaggaa ggcaaaatgc cgcaaaaaag ggaataaggg cgacacggaa atgttgaata | 8400 |
| ctcatactct tcctttttca atattattga agcatttatc agggttattg tctcatgagc | 8460 |
| ggatacatat ttgaatgtat ttagaaaaat aaacaaatag gggttccgcg cacatttc | 8518 |

<210> SEQ ID NO 5
<211> LENGTH: 8518
<212> TYPE: DNA
<213> ORGANISM: Unknown
<220> FEATURE:
<223> OTHER INFORMATION: pICAST ALN.

<400> SEQUENCE: 5

| | |
|---|---|
| gacgtcggac ttatacccgg tttgtcctat agacaccatt cgtcaaggac ggggccgagt | 60 |
| cccggttctt gtctaccttg tcgacttata cccggtttgt cctatagaca ccattcgtca | 120 |
| aggacggggc cgagtcccgg ttcttgtcta ccaggggtct acgccaggtc gggagtcgtc | 180 |
| aaagatctct tggtagtcta caaaggtccc acggggttcc tggactttac tgggacacgg | 240 |
| aataaacttg attggttagt caagcgaaga gcgaagacaa gcgcgcgaag acgaggggct | 300 |
| cgagttattt tctcgggtgt tggggagtga gccccgcggt caggaggcta actgactcag | 360 |
| cgggcccatg ggcacatagg ttatttggga gaacgtcaac gtaggctgaa caccagagcg | 420 |
| acaaggaacc ctcccagagg agactcacta actgatgggc agtcgccccc agaaagtaaa | 480 |
| cccccgagca ggccctagcc ctctggggac gggtccctgg tggctgggtg gtggccctcc | 540 |
| gttcgaccgg tcgttgaata gacacagaca ggctaacaga tcacagatac tgactaaaat | 600 |
| acgcggacgc agccatgatc aatcgattga tcgagacata gaccgcctgg gcaccacctt | 660 |
| gactgctcaa gacttgtggg ccggcgttgg gaccctctgc agggtccctg aaaccccgg | 720 |
| caaaaacacc gggctggact ccttccctca gctacacctt aggctggggc agtcctatac | 780 |
| accaagacca tcctctgctc ttggattttg tcagggcgg aggcagactt aaaaacgaaa | 840 |
| gccaaacctt ggcttcggcg cgcagaacag acgacgtcgt agcaagacac aacagagaca | 900 |
| gactgacaca aagacataaa cagacttttta atcccggtct gacaatggtg agggaattca | 960 |
| aactggaatc cattgacctt tctacagctc gccgagcgag tgttggtcag ccatctacag | 1020 |

-continued

| | |
|---|---|
| ttcttctctg caacccaatg gaagacgaga cgtcttaccg gttggaaatt gcagcctacc | 1080 |
| ggcgctctgc cgtggaaatt ggctctggag tagtgggtcc aattctagtt ccagaaaagt | 1140 |
| ggaccgggcg tacctgtggg tctggtccag gggatgtagc actggaccct tcggaaccga | 1200 |
| aaactggggg gagggaccca gttcgggaaa catgtgggat tcggaggcgg aggagaagga | 1260 |
| ggtaggcggg gcagagaggg ggaacttgga ggagcaagct ggggcggagc taggagggaa | 1320 |
| ataggtcggg agtgaggaag agatccgcgg ccggcgagat cgggtaatta tgctgagtga | 1380 |
| tatcccgcta agcttgtggt acgtggtagt agtagtagtg cagctgatat ttctactcct | 1440 |
| ggagctctac ccgcactaat gcctaagtga ccggcagcac cgggcgtggc tagcgggaag | 1500 |
| ggttgtcaat gcgtcggact taccgcttac cgcgaaacgg accaaaggcc gtggtcttcg | 1560 |
| ccacggcctt tcgaccgacc tcacgctaga aggactccgg ctatgacagc agcagggag | 1620 |
| tttgaccgtc tacgtgccaa tgctacgcgg gtagatgtgg ttgcactgga tagggtaatg | 1680 |
| ccagttaggc ggcaaacaag ggtgcctctt aggctgccca acaatgagcg agtgtaaatt | 1740 |
| acaactactt tcgaccgatg tccttccggt ctgcgcttaa taaaaactac cgcaattgag | 1800 |
| ccgcaaagta gacaccacgt tgcccgcgac ccagccaatg ccgtcctgt cagcaaacgg | 1860 |
| cagacttaaa ctggactcgc gtaaaaatgc gcggcctctt ttggcggagc gccactacca | 1920 |
| cgacgcgacc tcactgccgt caatagacct tctagtccta tacaccgcct actcgccgta | 1980 |
| aaaggcactg cagagcaacg acgtatttgg ctgatgtgtt tagtcgctaa aggtacaacg | 2040 |
| gtgagcgaaa ttactactaa agtcggcgcg acatgacctc cgacttcaag tctacacgcc | 2100 |
| gctcaacgca ctgatggatg cccattgtca aagaaatacc gtcccacttt gcgtccagcg | 2160 |
| gtcgccgtgg cgcggaaagc cgccactta atagctactc gcaccaccaa tacggctagc | 2220 |
| gcagtgtgat gcagacttgc agcttttggg ctttgacacc tcgcggcttt agggcttaga | 2280 |
| gatagcacgc caccaacttg acgtgtggcg gctgccgtgc gactaacttc gtcttcggac | 2340 |
| gctacagcca aaggcgctcc acgcctaact tttaccagac gacgacgact tgccgttcgg | 2400 |
| caacgactaa gctccgcaat tggcagtgct cgtagtagga gacgtaccag tccagtacct | 2460 |
| actcgtctgc taccacgtcc tataggacga ctacttcgtc ttgttgaaat tgcggcacgc | 2520 |
| gacaagcgta ataggcttgg taggcgacac catgtgcgac acgctggcga tgccggacat | 2580 |
| acaccaccta cttcggttat aactttgggt gccgtaccac ggttacttag cagactggct | 2640 |
| actaggcgcg accgatggcc gctactcgct tgcgcattgc gcttaccacg tcgcgctagc | 2700 |
| attagtgggc tcacactagt agaccagcga ccccttactt agtccggtgc cgcgattagt | 2760 |
| gctgcgcgac atagcgacct agtttagaca gctaggaagg gcgggccacg tcatacttcc | 2820 |
| gccgcctcgg ctgtggtgcc ggtggctata ataaacgggc tacatgcgcg cgcacctact | 2880 |
| tctggtcggg aagggccgac acggctttac caggtagttt tttaccgaaa gcgatggacc | 2940 |
| tctctgcgcg ggcgactagg aaacgcttat gcgggtgcgc tacccattgt cagaaccgcc | 3000 |
| aaagcgattt atgaccgtcc gcaaagcagt catagggca aatgtcccgc cgaagcagac | 3060 |
| cctgacccac ctagtcagcg actaatttat actacttttg ccgttgggca ccagccgaat | 3120 |
| gccgccacta aaaccgctat gcggcttgct agcggtcaag acatacttgc cagaccagaa | 3180 |
| acggctggcg tgcggcgtag gtcgcgactg ccttcgtttt gtggtcgtcg tcaaaaaggt | 3240 |
| caaggcaaat aggcccgttt ggtagcttca ctggtcgctt atggacaagg cagtatcgct | 3300 |
| attgctcgag gacgtgacct accaccgcga cctaccattc ggcgaccgtt cgccacttca | 3360 |
| cggagaccta cagcgaggtg ttccatttgt caactaactt gacggacttg atggcgtcgg | 3420 |

```
cctctcgcgg cccgttgaga ccgagtgtca tgcgcatcac gttggcttgc gctggcgtac    3480
cagtcttcgg cccgtgtagt cgcggaccgt cgtcaccgca gaccgccttt tggagtcaca    3540
ctgcgagggg cggcgcaggg tgcggtaggg cgtagactgg tggtcgcttt acctaaaaac    3600
gtagctcgac ccattattcg caaccgttaa attggcggtc agtccgaaag aaagtgtcta    3660
cacctaaccg ctattttttg ttgacgactg cggcgacgcg ctagtcaagt gggcacgtgg    3720
cgacctattg ctgtaaccgc attcacttcg ctgggcgtaa ctgggattgc ggacccagct    3780
tgcgaccttc cgccgcccgg taatggtccg gcttcgtcgc aacaacgtca cgtgccgtct    3840
atgtgaacga ctacgccacg actaatgctg gcgagtgcgc accgtcgtag tccccttttg    3900
gaataaatag tcggcctttt ggatggccta actaccatca ccagtttacc gctaatggca    3960
actacaactt caccgctcgc tatgtggcgt aggccgcgcc taaccggact tgacggtcga    4020
ccgcgtccat cgtctcgccc atttgaccga gcctaatccc ggcgttcttt tgatagggct    4080
ggcggaatga cggcggacaa aactggcgac cctagacggt aacagtctgt acatatgggg    4140
catgcagaag ggctcgcttt tgccagacgc gacgccctgc gcgcttaact taataccggg    4200
tgtggtcacc gcgccgctga aggtcaagtt gtagtcggcg atgtcagttg tcgttgacta    4260
cctttggtcg gtagcggtag acgacgtgcg ccttcttccg tgtaccgact tatagctgcc    4320
aaaggtatac ccctaaccac cgctgctgag gacctcgggc agtcatagcc gccttaaggt    4380
cgactcgcgg ccagcgatgg taatggtcaa ccagaccaca gttttttcta gacctccacc    4440
accgtcgtcc ggaaccgcgc ggcctaggaa ttaattgtta actggccatt attatccatc    4500
tattcactga ctaatctacg taactaggga gctggttaag gccaataaaa ggtggtataa    4560
cggcagaaaa ccgttacact cccgggcctt tggaccggga cagaagaact gctcgtaagg    4620
atccccagaa aggggagagc ggtttcctta cgttccagac aacttacagc acttccttcg    4680
tcaaggagac cttcgaagaa cttctgtttg ttgcagacat cgctgggaaa cgtccgtcgc    4740 cttgggggt ggaccgctgt ccacggagac gccggttttc ggtgcacata ttctatgtgg    4800
acgtttccgc cgtgttgggg tcacggtgca acactcaacc tatcaacacc tttctcagtt    4860
taccgagagg agttcgcata agttgttccc cgacttccta cgggtcttcc atgggtaac    4920 atccctaga ctagaccccg gagccacgtg tacgaaatgt acacaaatca gctccaattt    4980
tttgcagatc cggggggctt ggtgcccctg caccaaaagg aaacttttttg tgctactatt    5040 atggtactaa cttgttctac ctaacgtgcg tccaagaggc cggcgaaccc acctctccga    5100
taagccgata ctgacccgtg ttgtctgtta gccgacgaga ctacggcggc acaaggccga    5160
cagtcgcgtc cccgcgggcc aagaaaaaca gttctggctg acaggccac gggacttact    5220 tgacgtcctg ctccgtcgcg ccgatagcac cgaccggtgc tgcccgcaag gaacgcgtcg    5280
acacgagctg caacagtgac ttcgcccttc cctgaccgac gataacccgc ttcacggccc    5340
cgtcctagag gacagtagag tggaacgagg acggctcttt cataggtagt accgactacg    5400
ttacgccgcc gacgtatgcg aactaggccg atggacgggt aagctggtgg ttcgctttgt    5460
agcgtagctc gctcgtgcat gagcctacct tcggccagaa cagctagtcc tactagacct    5520
gcttctcgta gtccccgagc gcggtcggct tgacaagcgg tccgagttcc gcgcgtacgg    5580
gctgccgctc ctagagcagc actgggtacc gctacggacg aacggcttat agtaccacct    5640
tttaccggcg aaaagaccta agtagctgac accggccgac ccacaccgcc tggcgatagt    5700
cctgtatcgc aaccgatggg cactataacg acttctcgaa ccgccgctta cccgactggc    5760
```

```
gaaggagcac gaaatgccat agcggcgagg gctaagcgtc gcgtagcgga agatagcgga    5820
agaactgctc aagaagactc gccctgagac cccaagcgta gctattttat tttctaaaat    5880
aaatcagagg tcttttttccc cccttacttt ctggggtgga catccaaacc gttcgatcga   5940
attcattgcg gtaaaacgtt ccgtaccttt ttatgtattg actcttatct cttcaagtct    6000
agttccagtc cttgtctacc ttgtcgactt atacccggtt tgtcctatag acaccattcg    6060
tcaaggacgg ggccgagtcc cggttcttgt ctaccttgtc gacttatacc cggtttgtcc    6120
tatagacacc attcgtcaag gacggggccg agtcccggtt cttgtctacc aggggtctac    6180
gccaggtcgg gagtcgtcaa agatctcttg gtagtctaca aggtccccac ggggttcctg    6240
gactttactg ggacacggaa taaacttgat tggttagtca agcgaagagc gaagacaagc    6300
gcgcgaagac gaggggctcg agttattttc tcgggtgttg gggagtgagc cccgcggtca    6360
ggaggctaac tgactcagcg ggcccatggg cacataggtt atttgggaga acgtcaacgt    6420
aggctgaaca ccagagcgac aaggaaccct cccagaggag actcactaac tgatgggcag    6480
tcgcccccag aaagtaagta cgtcgtacat agttttaatt aaaccaaaaa aaagaattca    6540
taaatgtaat ttaccggtat caacgtaatt acttagccgg ttgcgcgccc ctctccgcca    6600
aacgcataac cgcgagaagg cgaaggagcg agtgactgag cgacgcgagc cagcaagccg    6660
acgccgctcg ccatagtcga gtgagtttcc gccattatgc caataggtgt cttagtcccc    6720
tattgcgtcc tttcttgtac actcgttttc cggtcgtttt ccggtccttg gcatttttcc    6780
ggcgcaacga ccgcaaaaag gtatccgagg cgggggggact gctcgtagtg ttttttagctg   6840 cgagttcagt ctccaccgct ttgggctgtc ctgatatttc tatggtccgc aaaggggggac  6900 cttcgaggga gcacgcgaga ggacaaggct gggacggcga atggcctatg gacaggcgga    6960
aagagggaag cccttcgcac cgcgaaagag tatcgagtgc gacatccata gagtcaagcc    7020
acatccagca agcgaggttc gacccgacac acgtgcttgg ggggcaagtc gggctggcga    7080
cgcggaatag gccattgata gcagaactca ggttgggcca ttctgtgctg aatagcggtg    7140
accgtcgtcg gtgaccattg tcctaatcgt ctcgctccat acatccgcca cgatgtctca    7200
agaacttcac caccggattg atgccgatgt gatcttcttg tcataaacca tagacgcgag    7260
acgacttcgg tcaatggaag cctttttctc aaccatcgag aactaggccg tttgtttggt    7320
ggcgaccatc gccaccaaaa aaacaaacgt tcgtcgtcta atgcgcgtct tttttttccta   7380 gagttcttct aggaaactag aaaagatgcc ccagactgcg agtcaccttg cttttgagtg    7440
caattcccta aaaccagtac tctaatagtt tttcctagaa gtggatctag gaaaacgccg    7500
gcgtttagtt agatttcata tatactcatt tgaaccagac tgtcaatggt tacgaattag    7560
tcactccgtg gatagagtcg ctagacagat aaagcaagta ggtatcaacg gactgagggg    7620
cagcacatct attgatgcta tgccctcccg aatggtagac cggggtcacg acgttactat    7680
ggcgctctgg gtgcgagtgg ccgaggtcta aatagtcgtt atttggtcgg tcggccttcc    7740
cggctcgcgt cttcaccagg acgttgaaat aggcggaggt aggtcagata attaacaacg    7800
gcccttcgat ctcattcatc aagcggtcaa ttatcaaacg cgttgcaaca acggtaacga    7860
tgtccgtagc accacagtgc gagcagcaaa ccataccgaa gtaagtcgag gccaagggtt    7920
gctagttccg ctcaatgtac tagggggtac aacacgtttt ttcgccaatc gaggaagcca    7980
ggaggctagc aacagtcttc attcaaccgg cgtcacaata gtgagtacca ataccgtcgt    8040
gacgtattaa gagaatgaca gtacggtagg cattctacga aaagacactg accactcatg    8100
agttggttca gtaagactct tatcacatac gccgctggct caacgagaac gggccgcagt    8160
```

```
tatgccctat tatggcgcgg tgtatcgtct tgaaattttc acgagtagta acctttttgca    8220 agaagcccccg cttttgagag ttcctagaat ggcgacaact ctaggtcaag ctacattggg   8280
tgagcacgtg ggttgactag aagtcgtaga aaatgaaagt ggtcgcaaag acccactcgt   8340
ttttgtcctt ccgttttacg gcgttttttc ccttattccc gctgtgcctt tacaacttat   8400
gagtatgaga aggaaaaagt tataataact tcgtaaatag tcccaataac agagtactcg   8460
cctatgtata aacttacata aatctttta tttgtttatc cccaaggcgc gtgtaaag     8518
```

<210> SEQ ID NO 6
<211> LENGTH: 8175
<212> TYPE: DNA
<213> ORGANISM: Unknown
<220> FEATURE:
<223> OTHER INFORMATION: pICAST OMC.

<400> SEQUENCE: 6

```
ctgcagcctg aatatgggcc aaacaggata tctgtggtaa gcagttcctg ccccggctca     60
gggccaagaa cagatggaac agctgaatat gggccaaaca ggatatctgt ggtaagcagt   120
tcctgccccg gctcagggcc aagaacagat ggtccccaga tgcggtccag ccctcagcag   180
tttctagaga accatcagat gtttccaggg tgccccaagg acctgaaatg accctgtgcc   240
ttatttgaac taaccaatca gttcgcttct cgcttctgtt cgcgcgcttc tgctccccga   300
gctcaataaa agagcccaca acccctcact cggggcgcca gtcctccgat tgactgagtc   360
gcccgggtac ccgtgtatcc aataaaccct cttgcagttg catccgactt gtggtctcgc   420
tgttccttgg gaggytctcc tctgagtgat tgactacccg tcagcggggg tctttcattt   480
gggggctcgt ccgggatcgg gagacccctg cccaggacc accgacccac caccgggagg   540
caagctggcc agcaacttat ctgtgtctgt ccgattgtct agtgtctatg actgatttta   600
tgcgcctgcg tcggtactag ttagctaact agctctgtat ctggcggacc cgtggtggaa   660
ctgacgagtt ctgaacaccc ggccgcaacc ctgggagacg tcccagggac tttggggggcc   720 gtttttgtgg cccgacctga ggaagggagt cgatgtggaa tccgaccccg tcaggatatg   780
tggttctggt aggagacgag aacctaaaac agttcccgcc tccgtctgaa tttttgctttt   840 cggtttggaa ccgaagccgc gcgtcttgtc tgctgcagca tcgttctgtg ttgtctctgt   900
ctgactgtgt ttctgtattt gtctgaaaat tagggccaga ctgttaccac tcccttaagt   960
ttgaccttag gtaactggaa agatgtcgag cggctcgctc acaaccagtc ggtagatgtc  1020
aagaagagac gttgggttac cttctgctct gcagaatggc caacctttaa cgtcggatgg  1080
ccgcgagacg gcacctttaa ccgagacctc atcacccagg ttaagatcaa ggtcttttca  1140
cctggcccgc atggacaccc agaccaggtc ccctacatcg tgacctggga agccttggct  1200
tttgaccccc ctccctgggt caagcccttt gtacacccta gcctccgcc tcctcttcct  1260 ccatccgccc cgtctctccc ccttgaacct cctcgttcga cccgcctcg atcctccctt  1320 tatccagccc tcactccttc tctaggcgcc ggccgctcta gcccattaat acgactcact  1380 ataggggcgat tcgaatcagg ccttggcgcg ccggatcctt aattaagcgc aattgggagg  1440
tggcggtagc ctcgagatgg gcgtgattac ggattcactg gccgtcgttt tacaacgtcg  1500
tgactgggaa aaccctggcg ttacccaact taatcgcctt gcagcacatc cccctttcgc  1560
cagctggcgt aatagcgaag aggcccgcac cgatcgccct tcccaacagt tacgcagcct  1620
gaatggcgaa tggcgctttg cctggtttcc ggcaccagaa gcggtgccgg aaagctggct  1680
```

```
ggagtgcgat cttcctgagg ccgatactgt cgtcgtcccc tcaaactggc agatgcacgg    1740
ttacgatgcg cccatctaca ccaacgtgac ctatcccatt acggtcaatc cgccgtttgt    1800
tcccacggag aatccgacgg gttgttactc gctcacattt aatgttgatg aaagctggct    1860
acaggaaggc cagacgcgaa ttattttga tggcgttaac tcggcgtttc atctgtggtg      1920
caacgggcgc tgggtcggtt acggccagga cagtcgtttg ccgtctgaat ttgacctgag     1980
cgcattttta cgcgccggag aaaaccgcct cgcggtgatg gtgctgcgct ggagtgacgg    2040
cagttatctg gaagatcagg atatgtggcg gatgagcggc attttccgtg acgtctcgtt    2100
gctgcataaa ccgactacac aaatcagcga tttccatgtt gccactcgct ttaatgatga    2160
tttcagccgc gctgtactgg aggctgaagt tcagatgtgc ggcgagttgc gtgactacct    2220
acgggtaaca gtttctttat ggcagggtga aacgcaggtc gccagcggca ccgcgccttt    2280
cggcggtgaa attatcgatg agcgtggtgg ttatgccgat cgcgtcacac tacgtctgaa    2340
cgtcgaaaac ccgaaactgt ggagcgccga aatcccgaat ctctatcgtg cggtggttga   2400
actgcacacc gccgacggca cgctgattga agcagaagcc tgcgatgtcg gtttccgcga    2460
ggtgcggatt gaaaatggtc tgctgctgct gaacggcaag ccgttgctga ttcgaggcgt    2520
taaccgtcac gagcatcatc ctctgcatgg tcaggtcatg gatgagcaga cgatggtgca    2580
ggatatcctg ctgatgaagc agaacaactt taacgccgtg cgctgttcgc attatccgaa    2640
ccatccgctg tggtacacgc tgtgcgaccg ctacggcctg tatgtggtgg atgaagccaa    2700
tattgaaacc cacggcatgg tgccaatgaa tcgtctgacc gatgatccgc gctggctacc    2760
ggcgatgagc gaacgcgtaa cgcgaatggt gcagcgcgat cgtaatcacc cgagtgtgat    2820
catctggtcg ctggggaatg aatcaggcca cggcgctaat cacgacgcgc tgtatcgctg    2880
gatcaaatct gtcgatcctt cccgcccggt gcagtatgaa ggcggcggag ccgacaccac    2940
ggccaccgat attatttgcc cgatgtacgc gcgcgtggat gaagaccagc ccttcccggc    3000
tgtgccgaaa tggtccatca aaaatggct ttcgctacct ggagagacgc gcccgctgat    3060
cctttgcgaa tacgcccacg cgatgggtaa cagtcttggc ggtttcgcta aatactggca    3120
ggcgtttcgt cagtatcccc gtttacaggg cggcttcgtc tgggactggg tggatcagtc    3180
gctgattaaa tatgatgaaa acggcaaccc gtggtcggct tacggcggtg attttggcga    3240
tacgccgaac gatcgccagt tctgtatgaa cggtctggtc tttgccgacc gcacgccgca    3300
tccagcgctg acggaagcaa aacaccagca gcagttttc cagttccgtt tatccgggca    3360
aaccatcgaa gtgaccagcg aatacctgtt ccgtcatagc gataacgagc tcctgcactg    3420
gatggtggcg ctggatggta agccgctggc aagcggtgaa gtgcctctgg atgtcgctcc    3480
acaaggtaaa cagttgattg aactgcctga actaccgcag ccggagagcg ccgggcaact    3540
ctggctcaca gtacgcgtag tgcaaccgaa cgcgaccgca tggtcagaag ccgggcacat    3600
cagcgcctgg cagcagtggc gtctggcgga aaacctcagt gtgacgctcc ccgccgcgtc    3660
ccacgccatc ccgcatctga ccaccagcga aatggatttt tgcatcgagc tgggtaataa    3720
gcgttggcaa tttaaccgcc agtcaggctt tctttcacag atgtggattg gcgataaaaa    3780
acaactgctg acgccgctgc gcgatcagtt caccgtgtc gatagatctg aacagaaact    3840
catttccgaa gaagacctag tcgaccatca tcatcatcat caccgtgtaat aataggtaga    3900 taagtgactg attagatgca tttcgactag atccctcgac caattccggt tattttccac    3960
catattgccg tcttttggca atgtgagggc ccggaaacct ggccctgtct tcttgacgag    4020
cattcctagg ggtctttccc ctctcgccaa aggaatgcaa ggtctgttga atgtcgtgaa    4080
```

-continued

```
ggaagcagtt cctctggaag cttcttgaag acaaacaacg tctgtagcga ccctttgcag    4140
gcagcggaac cccccacctg gcgacaggtg cctctgcggc aaaagccac gtgtataaga     4200 tacacctgca aaggcggcac aaccccagtg ccacgttgtg agttggatag ttgtggaaag    4260
agtcaaatgg ctctcctcaa gcgtattcaa caaggggctg aaggatgccc agaaggtacc    4320
ccattgtatg ggatctgatc tggggcctcg gtgcacatgc tttacatgtg tttagtcgag    4380
gttaaaaaac gtctaggccc cccgaaccac ggggacgtgg ttttcctttg aaaaacacga    4440
tgataatacc atgaaaaagc ctgaactcac cgcgacgtct gtcgagaagt ttctgatcga    4500
aaagttcgac agcgtctccg acctgatgca gctctcggag ggcgaagaat ctcgtgcttt    4560
cagcttcgat gtaggagggc gtggatatgt cctgcgggta aatagctgcg ccgatggttt    4620
ctacaaagat cgttatgttt atcggcactt tgcatcggcc gcgctcccga ttccggaagt    4680
gcttgacatt ggggaattta gcgagagcct gacctattgc atctcccgcc gtgcacaggg    4740
tgtcacgttg caagacctgc ctgaaaccga actgcccgct gttctgcagc cggtcgcgga    4800
ggccatggat gcgatcgctg cggccgatct tagccgacg agcgggttcg cccattcgg     4860 accgcaagga atcggtcaat acactacatg gcgtgatttc atatgcgcga ttgctgatcc    4920
ccatgtgtat cactggcaaa ctgtgatgga cgacaccgtc agtgcgtccg tcgcgcaggc    4980
tctcgatgag ctgatgcttt gggccgagga ctgccccgaa gtccgcacc tcgtgcacgc     5040 ggatttcggc tccaacaatg tcctgacgga caatggccgc ataacagcgg tcattgactg    5100
gagcgaggcg atgttcgggg attcccaata cgaggtcgcc aacatcttct tctggaggcc    5160
gtggttggct tgtatggagc agcagacgcg ctacttcgag cggaggcatc cggagcttgc    5220
aggatcgccg cggctccggg cgtatatgct ccgcattggt cttgaccaac tctatcagag    5280
cttggttgac ggcaatttcg atgatgcagc ttgggcgcag gtcgatgcg acgcaatcgt     5340 ccgatccgga gccgggactg tcgggcgtac acaaatcgcc cgcagaagcg cggccgtctg    5400
gaccgatggc tgtgtagaag tactcgccga tagtggaaac cgacgcccca gcactcgtcc    5460
gagggcaaag gaatagagta gatgccgacc gggatctatc gataaaataa agatttttat    5520
ttagtctcca gaaaagggg ggaatgaaag accccacctg taggtttggc aagctagctt     5580
aagtaacgcc attttgcaag gcatggaaaa atacataact gagaatagag aagttcagat    5640
caaggtcagg aacagatgga acagctgaat atgggccaaa caggatatct gtggtaagca    5700
gttcctgccc cggctcaggg ccaagaacag atggaacagc tgaatatggg ccaaacagga    5760
tatctgtggt aagcagttcc tgccccggct cagggccaag aacagatggt ccccagatgc    5820
ggtccagccc tcagcagttt ctagagaacc atcagatgtt tccagggtgc cccaaggacc    5880
tgaaatgacc ctgtgcctta tttgaactaa ccaatcagtt cgcttctcgc ttctgttcgc    5940
gcgcttctgc tccccgagct caataaaaga gcccacaacc cctcactcgg gcgccagtc     6000 ctccgattga ctgagtcgcc cgggtacccg tgtatccaat aaaccctctt gcagttgcat    6060
ccgacttgtg gtctcgctgt tccttgggag ggtctcctct gagtgattga ctacccgtca    6120
gcgggggtct ttcattcatg cagcatgtat caaaattaat ttggtttttt tcttaagta     6180 tttacattaa atggccatag ttgcattaat gaatcggcca acgcgcgggg agaggcggtt    6240
tgcgtattgg cgctcttccg cttcctcgct cactgactcg ctgcgctcgg tcgttcggct    6300
gcggcgagcg gtatcagctc actcaaaggc ggtaatacgg ttatccacag aatcagggga    6360
taacgcagga aagaacatgt gagcaaaagg ccagcaaaag gccaggaacc gtaaaaaggc    6420
```

```
cgcgttgctg gcgttttcc ataggctccg cccccctgac gagcatcaca aaaatcgacg    6480
ctcaagtcag aggtggcgaa acccgacagg actataaaga taccaggcgt ttccccctgg    6540
aagctccctc gtgcgctctc ctgttccgac cctgccgctt accggatacc tgtccgcctt    6600
tctcccttcg ggaagcgtgg cgctttctca gctcacgc tgtaggtatc tcagttcggt    6660
gtaggtcgtt cgctccaagc tgggctgtgt gcacgaaccc cccgttcagc ccgaccgctg    6720
cgccttatcc ggtaactatc gtcttgagtc aacccggta agacacgact tatcgccact    6780
ggcagcagcc actggtaaca ggattagcag agcgaggtat gtaggcggtg ctacagagtt    6840
cttgaagtgg tggcctaact acggctacac tagaagaaca gtatttggta tctgcgctct    6900
gctgaagcca gttaccttcg gaaaaagagt tggtagctct tgatccggca acaaaccac    6960 cgctggtagc ggtggttttt ttgtttgcaa gcagcagatt acgcgcagaa aaaaggatc    7020 tcaagaagat cctttgatct tttctacggg gtctgacgct cagtggaacg aaaactcacg    7080
ttaagggatt ttggtcatga gattatcaaa aaggatcttc acctagatcc ttttaaatta    7140
aaaatgaagt ttgcggccgc aaatcaatct aaagtatata tgagtaaact tggtctgaca    7200
gttaccaatg cttaatcagt gaggcaccta tctcagcgat ctgtctattt cgttcatcca    7260
tagttgcctg actccccgtc gtgtagataa ctacgatacg ggagggctta ccatctggcc    7320
ccagtgctgc aatgataccg cgagacccac gctcaccggc tccagatta tcagcaataa    7380 accagccagc cggaagggcc gagcgcagaa gtggtcctgc aactttatcc gcctccatcc    7440
agtctattaa ttgttgccgg gaagctagag taagtagttc gccagttaat agtttgcgca    7500
acgttgttgc cattgctaca ggcatcgtgg tgtcacgctc gtcgtttggt atggcttcat    7560
tcagctccgg ttcccaacga tcaaggcgag ttacatgatc ccccatgttg tgcaaaaaag    7620
cggttagctc cttcggtcct ccgatcgttg tcagaagtaa gttggccgca gtgttatcac    7680
tcatggttat ggcagcactg cataattctc ttactgtcat gccatccgta agatgctttt    7740
ctgtgactgg tgagtactca accaagtcat tctgagaata gtgtatgcgg cgaccgagtt    7800
gctcttgccc ggcgtcaata cgggataata ccgcgccaca tagcagaact ttaaaagtgc    7860
tcatcattgg aaaacgttct tcggggcgaa aactctcaag gatcttaccg ctgttgagat    7920
ccagttcgat gtaacccact cgtgcaccca actgatcttc agcatctttt actttcacca    7980
gcgtttctgg gtgagcaaaa acaggaaggc aaaatgccgc aaaaaaggga ataagggcga    8040
cacggaaatg ttgaatactc atactcttcc ttttcaata ttattgaagc atttatcagg    8100
gttattgtct catgagcgga tacatatttg aatgtattta gaaaataaa caaatagggg    8160 ttccgcgcac atttc    8175
```

<210> SEQ ID NO 7
<211> LENGTH: 8175
<212> TYPE: DNA
<213> ORGANISM: Unknown
<220> FEATURE:
<223> OTHER INFORMATION: pICAST OMC.

<400> SEQUENCE: 7

```
gacgtcggac ttatacccgg tttgtcctat agacaccatt cgtcaaggac ggggccgagt      60
cccggttctt gtctaccttg tcgacttata cccggtttgt cctatagaca ccattcgtca    120
aggacggggc cgagtcccgg ttcttgtcta ccaggggtct acgccaggtc gggagtcgtc    180
aaagatctct tggtagtcta caaggtcccc acggggttcc tggactttac tgggacacgg    240
aataaacttg attggttagt caagcgaaga gcgaagacaa gcgcgcgaag acgaggggct    300
```

-continued

```
cgagttattt tctcgggtgt tggggagtga gccccgcggt caggaggcta actgactcag    360
cgggcccatg ggcacatagg ttatttggga gaacgtcaac gtaggctgaa caccagagcg   420
acaaggaacc ctcccagagg agactcacta actgatgggc agtcgccccc agaaagtaaa   480
cccccgagca ggccctagcc ctctggggac gggtccctgg tggctgggtg gtggccctcc   540
gttcgaccgg tcgttgaata gacacagaca ggctaacaga tcacagatac tgactaaaat   600
acgcggacgc agccatgatc aatcgattga tcgagacata gaccgcctgg gcaccacctt   660
gactgctcaa gacttgtggg ccggcgttgg gaccctctgc agggtccctg aaaccccggg   720
caaaaacacc gggctggact ccttccctca gctacacctt aggctgggc agtcctatac   780 accaagacca tcctctgctc ttggattttg tcaaggcgg aggcagactt aaaaacgaaa    840
gccaaacctt ggcttcggcg cgcagaacag acgacgtcgt agcaagacac aacagagaca   900
gactgacaca aagacataaa cagactttta atcccggtct gacaatggtg agggaattca    960
aactggaatc cattgacctt tctacagctc gccgagcgag tgttggtcag ccatctacag   1020
ttcttctctg caacccaatg gaagacgaga cgtcttaccg gttggaaatt gcagcctacc   1080
ggcgctctgc cgtggaaatt ggctctggag tagtgggtcc aattctagtt ccagaaaagt   1140
ggaccgggcg tacctgtggg tctggtccag gggatgtagc actggaccct tcggaaccga   1200
aaactggggg gagggaccca gttcgggaaa catgtgggat tcgaggcgg aggagaagga    1260 ggtaggcggg gcagagaggg ggaacttgga ggagcaagct ggggcggagc taggagggaa   1320
ataggtcggg agtgaggaag agatccgcgg ccggcgagat cgggtaatta tgctgagtga   1380
tatcccgcta agcttagtcc ggaaccgcgc ggcctaggaa ttaattcgcg ttaaccctcc   1440
accgccatcg gagctctacc cgcactaatg cctaagtgac cggcagcaaa atgttgcagc   1500
actgaccctt tgggaccgc aatgggttga attagcggaa cgtcgtgtag ggggaaagcg    1560
gtcgaccgca ttatcgcttc tccgggcgtg gctagcggga agggttgtca atgcgtcgga   1620
cttaccgctt accgcgaaac ggaccaaagg ccgtggtctt cgccacggcc tttcgaccga   1680
cctcacgcta gaaggactcc ggctatgaca gcagcagggg agtttgaccg tctacgtgcc   1740
aatgctacgc gggtagatgt ggttgcactg gatagggtaa tgccagttag gcggcaaaca   1800
agggtgcctc ttaggctgcc caacaatgag cgagtgtaaa ttacaactac tttcgaccga   1860
tgtccttccg gtctgcgctt aataaaaact accgcaattg agccgcaaag tagacaccac   1920
gttgcccgcg acccagccaa tgccggtcct gtcagcaaac ggcagactta aactggactc   1980
gcgtaaaaat gcgcggcctc ttttggcgga gcgccactac cacgacgcga cctcactgcc   2040
gtcaatagac cttctagtcc tatacaccgc ctactcgccg taaaaggcac tgcagagcaa   2100
cgacgtattt ggctgatgtg tttagtcgct aaaggtacaa cggtgagcga aattactact   2160
aaagtcggcg cgacatgacc tccgacttca agtctacacg ccgctcaacg cactgatgga   2220
tgcccattgt caaagaaata ccgtcccact ttgcgtccag cggtcgccgt ggcgcggaaa   2280
gccgccactt taatagctac tcgcaccacc aatacggcta gcgcagtgtg atgcagactt   2340
gcagcttttg ggctttgaca cctcgcggct ttagggctta gagatagcac gccaccaact   2400
tgacgtgtgg cggctgccgt gcgactaact tcgtcttcgg acgctacagc caaaggcgct   2460
ccacgcctaa cttttaccag acgacgacga cttgccgttc ggcaacgact aagctccgca   2520
attggcagtg ctcgtagtag gagacgtacc agtccagtac ctactcgtct gctaccacgt   2580
cctataggac gactacttcg tcttgttgaa attgcggcac gcgacaagcg taataggctt   2640
```

```
ggtaggcgac accatgtgcg acacgctggc gatgccggac atacaccacc tacttcggtt    2700
ataactttgg gtgccgtacc acggttactt agcagactgg ctactaggcg cgaccgatgg    2760
ccgctactcg cttgcgcatt gcgcttacca cgtcgcgcta gcattagtgg gctcacacta    2820
gtagaccagc gaccccttac ttagtccggt gccgcgatta gtgctgcgcg acatagcgac    2880
ctagtttaga cagctaggaa gggcgggcca cgtcatactt ccgccgcctc ggctgtggtg    2940
ccggtggcta taataaacgg gctacatgcg cgcgcaccta cttctggtcg ggaagggccg    3000
acacggcttt accaggtagt tttttaccga aagcgatgga cctctctgcg cgggcgacta    3060
ggaaacgctt atgcgggtgc gctacccatt gtcagaaccg ccaaagcgat ttatgaccgt    3120
ccgcaaagca gtcataggg caaatgtccc gccgaagcag accctgaccc acctagtcag    3180
cgactaattt atactacttt tgccgttggg caccagccga atgccgccac taaaaccgct    3240
atgcggcttg ctagcggtca agacatactt gccagaccag aaacggctgg cgtgcggcgt    3300
aggtcgcgac tgccttcgtt ttgtggtcgt cgtcaaaaag gtcaaggcaa ataggcccgt    3360
ttggtagctt cactggtcgc ttatggacaa ggcagtatcg ctattgctcg aggacgtgac    3420
ctaccaccgc gacctaccat tcggcgaccg ttcgccactt cacggagacc tacagcgagg    3480
tgttccattt gtcaactaac ttgacggact tgatggcgtc ggcctctcgc ggcccgttga    3540
gaccgagtgt catgcgcatc acgttggctt gcgctggcgt accagtcttc ggcccgtgta    3600
gtcgcggacc gtcgtcaccg cagaccgcct tttggagtca cactgcgagg ggcggcgcag    3660
ggtgcggtag ggcgtagact ggtggtcgct ttacctaaaa acgtagctcg acccattatt    3720
cgcaaccgtt aaattggcgg tcagtccgaa agaaagtgtc tacacctaac cgctattttt    3780
tgttgacgac tgcggcgacg cgctagtcaa gtgggcacag ctatctagac ttgtctttga    3840
gtaaaggctt cttctggatc agctggtagt agtagtagta gtggccatta ttatccatct    3900
attcactgac taatctacgt aaagctgatc tagggagctg gttaaggcca ataaaaggtg    3960
gtataacggc agaaaaccgt tacactcccg ggcctttgga ccgggacaga agaactgctc    4020
gtaaggatcc ccagaaaggg gagagcggtt tccttacgtt ccagacaact tacagcactt    4080
ccttcgtcaa ggagaccttc gaagaacttc tgtttgttgc agacatcgct gggaaacgtc    4140
cgtcgccttg ggggtggac cgctgtccac ggagacgccg gttttcggtg cacatattct    4200
atgtggacgt ttccgccgtg ttgggtcac ggtgcaacac tcaacctatc aacacctttc    4260
tcagtttacc gagaggagtt cgcataagtt gttccccgac ttcctacggg tcttccatgg    4320
ggtaacatac cctagactag accccggagc cacgtgtacg aaatgtacac aaatcagctc    4380
caatttttg cagatccggg gggcttggtg cccctgcacc aaaaggaaac tttttgtgct    4440
actattatgg tacttttcg gacttgagtg gcgctgcaga cagctcttca aagactagct    4500
tttcaagctg tcgcagaggc tggactacgt cgagagcctc ccgcttctta gagcacgaaa    4560
gtcgaagcta catcctcccg cacctataca ggacgcccat ttatcgacgc ggctaccaaa    4620
gatgtttcta gcaatacaaa tagccgtgaa acgtagccgg cgcgagggct aaggccttca    4680
cgaactgtaa cccctaaat cgcrctcgga ctggataacg tagagggcgg cacgtgtccc    4740
acagtgcaac gttctggacg gactttggct tgacgggcga caagacgtcg gccagcgcct    4800
ccggtaccta cgctagcgac gccggctaga atcggtctgc tcgcccaagc cgggtaagcc    4860
tggcgttcct tagccagtta tgtgatgtac cgcactaaag tatacgcgct aacgactagg    4920
ggtacacata gtgaccgttt gacactacct gctgtggcag tcacgcaggc agcgcgtccg    4980
agagctactc gactacgaaa cccggctcct gacggggctt caggccgtgg agcacgtgcg    5040
```

```
cctaaagccg aggttgttac aggactgcct gttaccggcg tattgtcgcc agtaactgac    5100
ctcgctccgc tacaagcccc taagggttat gctccagcgg ttgtagaaga agacctccgg    5160
caccaaccga acatacctcg tcgtctgcgc gatgaagctc gcctccgtag gcctcgaacg    5220
tcctagcggc gccgaggccc gcatatacga ggcgtaacca gaactgcttg agatagtctc    5280
gaaccaactg ccgttaaagc tactacgtcg aacccgcgtc ccagctacgc tgcgttagca    5340
ggctaggcct cggccctgac agcccgcatg tgtttagcgg gcgtcttcgc gccggcagac    5400
ctggctaccg acacatcttc atgagcggct atcacctttg gctgcgggt cgtgagcagg     5460 ctcccgtttc cttatctcat ctacggctgg ccctagatag ctattttatt ttctaaaata    5520
aatcagaggt cttttttcccc ccttactttc tggggtggac atccaaaccg ttcgatcgaa   5580
ttcattgcgg taaaacgttc cgtaccttttt tatgtattga ctcttatctc ttcaagtcta   5640
gttccagtcc ttgtctacct tgtcgactta tacccggttt gtcctataga caccattcgt    5700
caaggacggg gccgagtccc ggttcttgtc taccttgtcg acttatacccc ggtttgtcct   5760 atagacacca ttcgtcaagg acggggccga gtcccggttc ttgtctacca ggggtctacg    5820
ccaggtcggg agtcgtcaaa gatctcttgg tagtctacaa aggtcccacg gggttcctgg    5880
actttactgg gacacggaat aaacttgatt ggttagtcaa gcgaagagcg aagacaagcg    5940
cgcgaagacg aggggctcga gttatttttct cgggtgttgg ggagtgagcc ccgcggtcag   6000
gaggctaact gactcagcgg gcccatgggc acataggtta tttgggagaa cgtcaacgta    6060
ggctgaacac cagagcgaca aggaaccctc ccagaggaga ctcactaact gatgggcagt    6120
cgcccccaga aagtaagtac gtcgtacata gttttaatta aaccaaaaaa aagaattcat    6180
aaatgtaatt taccggtatc aacgtaatta cttagccggt tgcgcgcccc tctccgccaa    6240
acgcataacc gcgagaaggc gaaggagcga gtgactgagc gacgcgagcc agcaagccga    6300
cgccgctcgc catagtcgag tgagtttccg ccattatgcc aataggtgtc ttagtccccct   6360 attgcgtcct ttcttgtaca ctcgtttttcc ggtcgttttc cggtccttgg cattttttccg  6420 gcgcaacgac cgcaaaaagg tatccgaggc ggggggactg ctcgtagtgt ttttagctgc    6480
gagttcagtc tccaccgctt tgggctgtcc tgatatttct atggtccgca aaggggggacc   6540 ttcgagggag cacgcgagag gacaaggctg ggacggcgaa tggcctatgg acaggcggaa    6600
agagggaagc ccttcgcacc gcgaaagagt atcgagtgcg acatccatag agtcaagcca    6660
catccagcaa gcgaggttcg acccgacaca cgtgcttggg gggcaagtcg ggctggcgac    6720
gcggaatagg ccattgatag cagaactcag gttgggccat tctgtgctga atagcggtga    6780
ccgtcgtcgg tgaccattgt cctaatcgtc tcgctccata catccgccac gatgtctcaa    6840
gaacttcacc accggattga tgccgatgtg atcttcttgt cataaaccat agacgcgaga    6900
cgacttcggt caatggaagc cttttttctca accatcgaga actaggccgt ttgtttggtg    6960
gcgaccatcg ccaccaaaaa aacaaacgtt cgtcgtctaa tgcgcgtctt ttttttcctag    7020 agttcttcta ggaaactaga aaagatgccc cagactgcga gtcaccttgc ttttgagtgc    7080
aattccctaa aaccagtact ctaatagttt ttcctagaag tggatctagg aaaatttaat    7140
ttttacttca aacgccggcg tttagttaga tttcatatat actcatttga accagactgt    7200
caatggttac gaattagtca ctccgtggat agagtcgcta gacagataaa gcaagtaggt    7260
atcaacggac tgaggggcag cacatctatt gatgctatgc cctcccgaat ggtagaccgg    7320
ggtcacgacg ttactatggc gctctgggtg cgagtggccg aggtctaaat agtcgttatt    7380
```

-continued

```
tggtcggtcg gccttcccgg ctcgcgtctt caccaggacg ttgaaatagg cggaggtagg     7440
tcagataatt aacaacggcc cttcgatctc attcatcaag cggtcaatta tcaaacgcgt     7500
tgcaacaacg gtaacgatgt ccgtagcacc acagtgcgag cagcaaacca taccgaagta     7560
agtcgaggcc aagggttgct agttccgctc aatgtactag ggggtacaac acgttttttc     7620
gccaatcgag gaagccagga ggctagcaac agtcttcatt caaccggcgt cacaatagtg     7680
agtaccaata ccgtcgtgac gtattaagag aatgacagta cggtaggcat tctacgaaaa     7740
gacactgacc actcatgagt tggttcagta agactcttat cacatacgcc gctggctcaa     7800
cgagaacggg ccgcagttat gccctattat ggcgcggtgt atcgtcttga aattttcacg     7860
agtagtaacc ttttgcaaga agccccgctt ttgagagttc ctagaatggc gacaactcta     7920
ggtcaagcta cattgggtga gcacgtgggt tgactagaaa tcgtagaaaa tgaaagtggt     7980
cgcaaagacc cactcgtttt tgtccttccg ttttacggcg ttttttccct tattcccgct     8040
gtgcctttac aacttatgag tatgagaagg aaaaagttat aataacttcg taaatagtcc     8100
caataacaga gtactcgcct atgtataaac ttacataaat cttttttattt gtttatcccc     8160 aaggcgcgtg taaag                                                     8175
```

<210> SEQ ID NO 8
<211> LENGTH: 8161
<212> TYPE: DNA
<213> ORGANISM: Unknown
<220> FEATURE:
<223> OTHER INFORMATION: pICAST OMN.

<400> SEQUENCE: 8

```
ctgcagcctg aatatgggcc aaacaggata tctgtggtaa gcagttcctg ccccggctca       60
gggccaagaa cagatggaac agctgaatat gggccaaaca ggatatctgt ggtaagcagt      120
tcctgccccg gctcagggcc aagaacagat ggtccccaga tgcggtccag ccctcagcag      180
tttctagaga accatcagat gtttccaggg tgccccaagg acctgaaatg accctgtgcc      240
ttatttgaac taaccaatca gttcgcttct cgcttctgtt cgcgcgcttc tgctccccga      300
gctcaataaa agagcccaca cccctcact cggggcgcca gtcctccgat tgactgagtc      360
gcccgggtac ccgtgtatcc aataaaccct cttgcagttg catccgactt gtggtctcgc      420
tgttccttgg gagggtctcc tctgagtgat tgactacccg tcagcggggg tctttcattt      480
gggggctcgt ccgggatcgg gagacccctg cccaggacc accgaccac caccgggagg      540 caagctggcc agcaacttat ctgtgtctgt ccgattgtct agtgtctatg actgatttta      600
tgcgcctgcg tcggtactag ttagctaact agctctgtat ctggcggacc cgtggtggaa      660
ctgacgagtt ctgaacaccc ggccgcaacc ctggagacyc tccagggac tttgggggcc      720 gttttttgtgg cccgacctga ggaagggagt cgatgtggaa tccgaccccg tcaggatatg      780
tggttctggt aggagacgag aacctaaaac agttcccgcc tccgtctgaa tttttgcttt      840
cggtttggaa ccgaagccgc gcgtcttgtc tgctgcagca tcgttctgtg ttgtctctgt      900
ctgactgtgt ttctgtattt gtctgaaaat tagggccaga ctgttaccac tcccttaagt      960
ttgaccttag gtaactggaa agatgtcgag cggctcgctc acaaccagtc ggtagatgtc     1020
aagaagagac gttgggttac cttctgctct gcagaatggc caacctttaa cgtcggatgg     1080
ccgcgagacg gcacctttaa ccgagacctc atcacccagg ttaagatcaa ggtcttttca     1140
cctgccccgc atggacaccc agaccaggtc cctacatcg tgacctggga agccttggct     1200
tttgaccccc ctccctgggt caagcccttt gtacacccta agcctccgcc tcctcttcct     1260
```

-continued

```
ccatccgccc cgtctctccc ccttgaacct cctcgttcga ccccgcctcg atcctccctt    1320
tatccagccc tcactccttc tctaggcgcc ggccgctcta gcccattaat acgactcact    1380 ataggcgat tcgaacacca tgcaccatca tcatcatcac gtcgacgaac agaaactcat     1440
ttccgaagaa gacctactcg agatgggcgt gattacggat tcactggccg tcgttttaca    1500
acgtcgtgac tgggaaaacc ctggcgttac ccaacttaat cgccttgcag cacatccccc    1560
tttcgccagc tggcgtaata gcgaagaggc ccgcaccgat cgcccttccc aacagttacg    1620
cagcctgaat ggcgaatggc gctttgcctg gtttccggca ccagaagcgg tgccggaaag    1680
ctggctggag tgcgatcttc ctgaggccga tactgtcgtc gtccctcaa actggcagat     1740 gcacggttac gatgcgccca tctacaccaa cgtgacctat cccattacgg tcaatccgcc    1800
gtttgttccc acggagaatc cgacgggttg ttactcgctc acatttaatg ttgatgaaag    1860
ctggctacag gaaggccaga cgcgaattat ttttgatggc gttaactcgg cgtttcatct    1920
gtggtgcaac gggcgctggg tcggttacgg ccaggacagt cgtttgccgt ctgaatttga    1980
cctgagcgca tttttacgcg ccggagaaaa ccgcctcgcg gtgatggtgc tgcgctggag    2040
tgacggcagt tatctggaag atcaggatat gtggcggatg agcggcattt ccgtgacgt     2100 ctcgttgctg cataaaccga ctacacaaat cagcgatttc catgttgcca ctcgctttaa    2160
tgatgatttc agccgcgctg tactggaggc tgaagttcag atgtgcggcg agttgcgtga    2220
ctacctacgg gtaacagttt ctttatggca gggtgaaacg caggtcgcca gcggcaccgc    2280
gcctttcggc ggtgaaatta tcgatgagcg tggtggttat gccgatcgcg tcacactacg    2340
tctgaacgtc gaaaacccga aactgtggag cgccgaaatc ccgaatctct atcgtgcggt    2400
ggttgaactg cacaccgccg acggcacgct gattgaagca gaagcctgcg atgtcggttt    2460
ccgcgaggtg cggattgaaa atggtctgct gctgctgaac ggcaagccgt gctgattcg     2520 aggcgttaac cgtcacgagc atcatcctct gcatggtcag gtcatggatg agcagacgat    2580
ggtgcaggat atcctgctga tgaagcagaa caactttaac gccgtgcgct gttcgcatta    2640
tccgaaccat ccgctgtggt acacgctgtg cgaccgctac ggcctgtatg tggtggatga    2700
agccaatatt gaaacccacg gcatggtgcc aatgaatcgt ctgaccgatg atccgcgctg    2760
gctaccggcg atgagcgaac gcgtaacgcg aatggtgcag cgcgatcgta atcacccgag    2820
tgtgatcatc tggtcgctgg ggaatgaatc aggccacggc gctaatcacg acgcgctgta    2880
tcgctggatc aaatcgtcg atccttcccg cccggtgcag tatgaaggcg gcggagccga    2940
caccacggcc accgatatta tttgcccgat gtacgcgcgc gtggatgaag accagccctt    3000
cccggctgtg ccgaaatggt ccatcaaaaa atggctttcg ctacctggag agacgcgccc    3060
gctgatcctt tgcgaatacg cccacgcgat gggtaacagt cttggcggtt cgctaaata     3120 ctggcaggcg tttcgtcagt atcccgtttt acagggcggc ttcgtctggg actgggtgga    3180
tcagtcgctg attaaatatg atgaaaacgg caacccgtgg tcggcttacg gcggtgattt    3240
tggcgatacg ccgaacgatc gccagttctg tatgaacggt ctggtctttg ccgaccgcac    3300
gccgcatcca gcgctgacgg aagcaaaaca ccagcagcag ttttccagt tccgtttatc     3360 cgggcaaacc atcgaagtga ccagcgaata cctgttccgt catagcgata acgagctcct    3420
gcactggatg gtggcgctgg atggtaagcc gctggcaagc ggtgaagtgc ctctggatgt    3480
cgctccacaa ggtaaacagt tgattgaact gcctgaacta ccgcagcgg agagcgccgg     3540 gcaactctgg ctcacagtac gcgtagtgca accgaacgcg accgcatggt cagaagccgg    3600
```

-continued

```
gcacatcagc gcctggcagc agtggcgtct ggcggaaaac ctcagtgtga cgctccccgc    3660
cgcgtcccac gccatcccgc atctgaccac cagcgaaatg gatttttgca tcgagctggg    3720
taataagcgt tggcaattta accgccagtc aggctttctt tcacagatgt ggattggcga    3780
taaaaaacaa ctgctgacgc cgctgcgcga tcagttcacc cgtgtcgata gatctggagg    3840
tggtggcagc aggccttggc gcgccggatc cttaattaac aattgaccgg taataatagg    3900
tagataagtg actgattaga tgcatttcga ctagatccct cgaccaattc cggttatttt    3960
ccaccatatt gccgtctttt ggcaatgtga gggcccggaa acctggccct gtcttcttga    4020
cgagcattcc taggggtctt tcccctctcg ccaaaggaat gcaaggtctg ttgaatgtcg    4080
tgaaggaagc agttcctctg gaagcttctt gaagacaaac aacgtctgta gcgacccttt    4140
gcaggcagcg gaaccccca cctggcgaca ggtgcctctg cggccaaaag ccacgtgtat    4200
aagatacacc tgcaaaggcg gcacaacccc agtgccacgt tgtgagttgg atagttgtgg    4260
aaagagtcaa atggctctcc tcaagcgtat tcaacaaggg gctgaaggat gcccagaagg    4320
taccccattg tatgggatct gatctggggc ctcggtgcac atgctttaca tgtgtttagt    4380
cgaggttaaa aaacgtctag gcccccccgaa ccacggggac gtggttttcc tttgaaaaac    4440
acgatgataa taccatgaaa aagcctgaac tcaccgcgac gtctgtcgag aagtttctga    4500
tcgaaaagtt cgacagcgtc tccgacctga tgcagctctc ggagggcgaa gaatctcgtg    4560
ctttcagctt cgatgtagga gggcgtggat atgtcctgcg ggtaaatagc tgcgccgatg    4620
gtttctacaa agatcgttat gtttatcggc actttgcatc ggccgcgctc ccgattccgg    4680
aagtgcttga cattggggaa tttagcgaga gcctgaccta ttgcatctcc cgccgtgcac    4740
agggtgtcac gttgcaagac ctgcctgaaa ccgaactgcc cgctgttctg cagccggtcg    4800
cggaggccat ggatgcgatc gctgcggccg atcttagcca gacgagcggg ttcggcccat    4860
tcggaccgca aggaatcggt caatacacta catggcgtga tttcatatgc gcgattgctg    4920
atccccatgt gtatcactgg caaactgtga tggacgacac cgtcagtgcg tccgtcgcgc    4980
aggctctcga tgagctgatg ctttgggccg aggactgccc cgaagtccgg cacctcgtgc    5040
acgcggattt cggctccaac aatgtcctga cggacaatgg ccgcataaca gcggtcattg    5100
actggagcga ggcgatgttc ggggattccc aatacgaggt cgccaacatc ttcttctgga    5160
ggccgtggtt ggcttgtatg gagcagcaga cgcgctactt cgagcggagg catccggagc    5220
ttgcaggatc gccgcggctc cggcgtata tgctccgcat tggtcttgac caactctatc    5280
agagcttggt tgacggcaat ttcgatgatg cagcttgggc gcagggtcga tgcgacgcaa    5340
tcgtccgatc cggagccggg actgtcgggc gtacacaaat cgcccgcaga agcgcggccg    5400
tctggaccga tggctgtgta gaagtactcg ccgatagtgg aaaccgacgc cccagcactc    5460
gtccgagggc aaaggaatag agtagatgcc gaccgggatc tatcgataaa ataaagatt    5520 ttatttagtc tccagaaaaa ggggggaatg aagaccccaa cctgtaggtt tggcaagcta    5580
gcttaagtaa cgccattttg caaggcatgg aaaatacat aactgagaat agagaagttc    5640
agatcaaggt caggaacaga tggaacagct gaatatgggc caaacaggat atctgtggta    5700
agcagttcct gccccggctc agggccaaga acagatggaa cagctgaata tgggccaaac    5760
aggatatctg tggtaagcag ttcctgcccc ggctcagggc caagaacaga tggtcccag    5820 atgcggtcca gccctcagca gtttctagag aaccatcaga tgtttccagg gtgccccaag    5880
gacctgaaat gaccctgtgc cttatttgaa ctaaccaatc agttcgcttc tcgcttctgt    5940
tcgcgcgctt ctgctccccg agctcaataa aagagcccac aaccccctcac tcggggcgcc    6000
```

-continued

```
agtcctccga ttgactgagt cgcccgggta cccgtgtatc caataaaccc tcttgcagtt      6060
gcatccgact tgtggtctcg ctgttccttg ggagggtctc ctctgagtga ttgactaccc      6120
gtcagcgggg gtctttcatt catgcagcat gtatcaaaat taatttggtt ttttttctta      6180
agtatttaca ttaaatggcc atagttgcat taatgaatcg gccaacgcgc ggggagaggc      6240
ggtttgcgta ttggcgctct ccgcttcct cgctcactga ctcgctgcgc tcggtcgttc       6300
ggctgcggcg agcggtatca gctcactcaa aggcggtaat acggttatcc acagaatcag      6360
gggataacgc aggaaagaac atgtgagcaa aaggccagca aaaggccagg aaccgtaaaa      6420
aggccgcgtt gctggcgttt ttccataggc tccgcccccc tgacgagcat cacaaaaatc      6480
gacgctcaag tcagaggtgg cgaaacccga caggactata agataccagg cgtttcccc      6540 ctggaagctc cctcgtgcgc tctcctgttc cgaccctgcc gcttaccgga tacctgtccg      6600
cctttctccc ttcgggaagc gtggcgcttt ctcatagctc acgctgtagg tatctcagtt      6660
cggtgtaggt cgttcgctcc aagctgggct gtgtgcacga accccccgtt cagcccgacc      6720
gctgcgcctt atccggtaac tatcgtcttg agtccaaccc ggtaagacac gacttatcgc      6780
cactggcagc agccactggt aacaggatta gcagagcgag gtatgtaggc ggtgctacag      6840
agttcttgaa gtggtggcct aactacggct acactagaag aacagtattt ggtatctgcg      6900
ctctgctgaa gccagttacc ttcggaaaaa gagttggtag ctcttgatcc ggcaaacaaa      6960
ccaccgctgg tagcggtggt ttttttgttt gcaagcagca gattacgcgc agaaaaaaag      7020
gatctcaaga agatcctttg atcttttcta cggggtctga cgctcagtgg aacgaaaact      7080
cacgttaagg gattttggtc atgagattat caaaaaggat cttcacctag atccttttgc      7140
ggccgcaaat caatctaaag tatatatgag taaacttggt ctgacagtta ccaatgctta      7200
atcagtgagg cacctatctc agcgatctgt ctatttcgtt catccatagt tgcctgactc      7260
cccgtcgtgt agataactac gatacgggag ggcttaccat ctggccccag tgctgcaatg      7320
ataccgcgag acccacgctc accggctcca gatttatcag caataaacca gccagccgga      7380
agggccgagc gcagaagtgg tcctgcaact ttatccgcct ccatccagtc tattaattgt      7440
tgccgggaag ctagagtaag tagttcgcca gttaatagtt tgcgcaacgt tgttgccatt      7500
gctacaggca tcgtggtgtc acgctcgtcg tttggtatgg cttcattcag ctccggttcc      7560
caacgatcaa ggcgagttac atgatccccc atgttgtgca aaaagcggt tagctccttc       7620 ggtcctccga tcgttgtcag aagtaagttg gccgcagtgt tatcactcat ggttatggca      7680
gcactgcata attctcttac tgtcatgcca tccgtaagat gcttttctgt gactggtgag      7740
tactcaacca agtcattctg agaatagtgt atgcggcgac cgagttgctc ttgcccggcg      7800
tcaatacggg ataataccgc gccacatagc agaactttaa aagtgctcat cattggaaaa      7860
cgttcttcgg ggcgaaaact ctcaaggatc ttaccgctgt tgagatccag ttcgatgtaa      7920
cccactcgtg cacccaactg atcttcagca tcttttactt tcaccagcgt ttctgggtga      7980
gcaaaaacag gaaggcaaaa tgccgcaaaa aagggaataa gggcgacacg gaaatgttga     8040
atactcatac tcttcctttt tcaatattat tgaagcattt atcagggtta ttgtctcatg      8100
agcggataca tatttgaatg tatttagaaa aataaacaaa tagggggttcc gcgcacattt     8160 c                                                                      8161
```

<210> SEQ ID NO 9
<211> LENGTH: 8161
<212> TYPE: DNA

-continued

<213> ORGANISM: Unknown
<220> FEATURE:
<223> OTHER INFORMATION: pICAST OMN.

<400> SEQUENCE: 9

```
gacgtcggac ttatacccgg tttgtcctat agacaccatt cgtcaaggac ggggccgagt      60
cccggttctt gtctaccttg tcgacttata cccggtttgt cctatagaca ccattcgtca     120
aggacggggc cgagtcccgg ttcttgtcta ccaggggtct acgccaggtc gggagtcgtc     180
aaagatctct tggtagtcta caaaggtccc acggggttcc tggactttac tgggacacgg     240
aataaacttg attggttagt caagcgaaga gcgaagacaa gcgcgcgaag acgaggggct     300
cgagttattt tctcgggtgt tggggagtga gccccgcggt caggaggcta actgactcag     360
cgggcccatg ggcacatagg ttatttggga gaacgtcaac gtaggctgaa caccagagcg     420
acaaggaacc ctcccagagg agactcacta actgatgggc agtcgccccc agaaagtaaa     480
cccccgagca ggccctagcc ctctggggac gggtccctgg tggctgggtg gtggccctcc     540
gttcgaccgg tcgttgaata gacacagaca ggctaacaga tcacagatac tgactaaaat     600
acgcggacgc agccatgatc aatcgattga tcgagacata accgcctgg gcaccacctt      660
gactgctcaa gacttgtggg ccggcgttgg gaccctctgc agggtccctg aaaccccgg      720
caaaaacacc gggctggact ccttccctca gctacacctt aggctgggc agtcctatac     780
accaagacca tcctctgctc ttggattttg tcaagggcgg aggcagactt aaaaacgaaa     840
gccaaacctt ggcttcggcg cgcagaacag acgacgtcgt agcaagacac aacagagaca     900
gactgacaca aagacataaa cagacttttta atcccggtct gacaatggtg agggaattca     960
aactggaatc cattgacctt tctacagctc gccgagcgag tgttggtcag ccatctacag    1020
ttcttctctg caacccaatg gaagacgaga cgtcttaccg gttggaaatt gcagcctacc    1080
ggcgctctgc cgtggaaatt ggctctggag tagtgggtcc aattctagtt ccagaaaagt    1140
ggaccgggcg tacctgtggg tctggtccag gggatgtagc actggaccct tcggaaccga    1200
aaactggggg gagggaccca gttcgggaaa catgtgggat tcggaggcgg aggagaagga    1260
ggtaggcggg gcagagaggg ggaacttgga ggagcaagct ggggcggagc taggagggaa    1320
ataggtcggg agtgaggaag agatccgcgc ccggcgagat cgggtaatta tgctgagtga    1380
tatcccgcta agcttgtggt acgtggtagt agtagtagtg cagctgcttg tctttgagta    1440
aaggcttctt ctggatgagc tctacccgca ctaatgccta agtgaccggc agcaaaatgt    1500
tgcagcactg accctttttgg gaccgcaatg ggttgaatta gcggaacgtc gtgtaggggg    1560
aaagcggtcg accgcattat cgcttctccg ggcgtggcta gcgggaaggg ttgtcaatgc    1620
gtcggactta ccgcttaccg cgaaacggac caaaggccgt ggtcttcgcc acggcctttc    1680
gaccgacctc acgctagaag gactccggct atgacagcag cagggagtt tgaccgtcta     1740
cgtgccaatg ctacgcgggt agatgtggtt gcactggata gggtaatgcc agttaggcgg    1800
caaacaaggg tgcctcttag gctgcccaac aatgagcgag tgtaaattac aactactttc    1860
gaccgatgtc cttccggtct gcgcttaata aaaactaccg caattgagcc gcaaagtaga    1920
caccacgttg cccgcgaccc agccaatgcc ggtcctgtca gcaaacggca gacttaaact    1980
ggactcgcgt aaaatgcgc ggcctctttt ggcggagcgc cactaccacg acgcgaccctc    2040
actgccgtca atagaccttc tagtcctata caccgcctac tcgccgtaaa aggcactgca    2100
gagcaacgac gtatttggct gatgtgttta gtcgctaaag gtacaacggt gagcgaaatt    2160
actactaaag tcggcgcgac atgaccctccg acttcaagtc tacacgccgc tcaacgcact    2220
```

-continued

```
gatggatgcc cattgtcaaa gaaataccgt cccactttgc gtccagcggt cgccgtggcg    2280
cggaaagccg ccactttaat agctactcgc accaccaata cggctagcgc agtgtgatgc    2340
agacttgcag ctttttgggct ttgacacctc gcggctttag ggcttagaga tagcacgcca    2400
ccaacttgac gtgtggcggc tgccgtgcga ctaacttcgt cttcggacgc tacagccaaa    2460
ggcgctccac gcctaacttt taccagacga cgacgacttg ccgttcggca acgactaagc    2520
tccgcaattg gcagtgctcg tagtaggaga cgtaccagtc cagtacctac tcgtctgcta    2580
ccacgtccta taggacgact acttcgtctt gttgaaattg cggcacgcga caagcgtaat    2640
aggcttggta ggcgacacca tgtgcgacac gctggcgatg ccggacatac accacctact    2700
tcggttataa ctttgggtgc cgtaccacgg ttacttagca gactggctac taggcgcgac    2760
cgatggccgc tactcgcttg cgcattgcgc ttaccacgtc gcgctagcat tagtgggctc    2820
acactagtag accagcgacc ccttacttag tccggtgccg cgattagtgc tgcgcgacat    2880
agcgacctag tttagacagc taggaagggc gggccacgtc atacttccgc cgcctcggct    2940
gtggtgccgg tggctataat aaacgggcta catgcgcgcg cacctacttc tggtcgggaa    3000
gggccgacac ggctttacca ggtagttttt taccgaaagc gatggacctc tctgcgcggg    3060
cgactaggaa acgcttatgc gggtgcgcta cccattgtca gaaccgccaa agcgatttat    3120
gaccgtccgc aaagcagtca tagggcaaa tgtcccgccg aagcagaccc tgacccacct    3180
agtcagcgac taatttatac tacttttgcc gttgggcacc agccgaatgc cgccactaaa    3240
accgctatgc ggcttgctag cggtcaagac atacttgcca gaccagaaac ggctggcgtg    3300
cggcgtaggt cgcgactgcc ttcgttttgt ggtcgtcgtc aaaaggtca aggcaaatag    3360 gcccgttttgg tagcttcact ggtcgcttat ggacaaggca gtatcgctat tgctcgagga    3420
cgtgacctac caccgcgacc taccattcgg cgaccgttcg ccacttcacg gagacctaca    3480
gcgaggtgtt ccatttgtca actaacttga cggacttgat ggcgtcggcc tctcgcggcc    3540
cgttgagacc gagtgtcatg cgcatcacgt tggcttgcgc tggcgtacca gtcttcggcc    3600
cgtgtagtcg cggaccgtcg tcaccgcaga ccgccttttg gagtcacact gcgaggggcg    3660
gcgcagggtg cggtagggcg tagactggtg gtcgctttac ctaaaaacgt agctcgaccc    3720
attattcgca accgttaaat tggcggtcag tccgaaagaa agtgtctaca cctaaccgct    3780
attttttgtt gacgactgcg gcgacgcgct agtcaagtgg gcacagctat ctagacctcc    3840
accaccgtcg tccggaaccg cgcggcctag gaattaattg ttaactggcc attattatcc    3900
atctattcac tgactaatct acgtaaagct gatctaggga gctggttaag gccaataaaa    3960
ggtggtataa cggcagaaaa ccgttacact cccgggcctt tggaccggga cagaagaact    4020
gctcgtaagg atccccagaa aggggagagc ggtttcctta cgttccagac aacttacagc    4080
acttccttcg tcaaggagac cttcgaagaa cttctgtttg ttgcagacat cgctgggaaa    4140
cgtccgtcgc cttggggggt ggaccgctgt ccacggagac gccggttttc ggtgcacata    4200
ttctatgtgg acgtttccgc cgtgttgggg tcacggtgca acactcaacc tatcaacacc    4260
tttctcagtt taccgagagg agttcgcata agttgttccc cgacttccta cgggtcttcc    4320
atggggtaac ataccctaga ctagaccccg gagccacgtg tacgaaatgt acacaaatca    4380
gctccaattt tttgcagatc cggggggctt ggtgcccctg caccaaaagg aaacttttg    4440 tgctactatt atggtacttt ttcggacttg agtggcgctg cagacagctc ttcaaagact    4500
agcttttcaa gctgtcgcag aggctggact acgtcgagag cctcccgctt cttagagcac    4560
```

```
gaaagtcgaa gctacatcct cccgcaccta tacaggacgc ccatttatcg acgcggctac    4620
caaagatgtt tctagcaata caaatagccg tgaaacgtag ccggcgcgag ggctaaggcc    4680
ttcacgaact gtaaccccct aaatcgctct cggactggat aacgtagagg gcggcacgtg    4740
tcccacagtg caacgttctg gacggacttt ggcttgacgg gcgacaagac gtcggccagc    4800
gcctccggta cctacgctag cgacgccggc tagaatcggt ctgctcgccc aagccgggta    4860
agcctggcgt tccttagcca gttatgtgat gtaccgcact aaagtatacg cgctaacgac    4920 tagggtaca catagtgacc gtttgacact acctgctgtg gcagtcacgc aggcagcgcg    4980
tccgagagct actcgactac gaaacccggc tcctgacggg gcttcaggcc gtggagcacg    5040
tgcgcctaaa gccgaggttg ttacaggact gcctgttacc ggcgtattgt cgccagtaac    5100
tgacctcgct ccgctacaag cccctaaggg ttatgctcca gcggttgtag aagaagacct    5160
ccggcaccaa ccgaacatac ctcgtcgtct gcgcgatgaa gctcgcctcc gtaggcctcg    5220
aacgtcctag cggcgccgag gcccgcatat acgaggcgta accagaactg gttgagatag    5280
tctcgaacca actgccgtta aagctactac gtcgaacccg cgtcccagct acgctgcgtt    5340
agcaggctag gcctcggccc tgacagcccg catgtgttta gcgggcgtct tcgcgccggc    5400
agacctggct accgacacat cttcatgagc ggctatcacc tttggctgcg gggtcgtgag    5460
caggctcccg tttccttatc tcatctacgg ctggccctag atagctattt tattttctaa    5520
aataaatcag aggtcttttt ccccccttac tttctggggt ggacatccaa accgttcgat    5580
cgaattcatt gcggtaaaac gttccgtacc tttttatgta ttgactctta tctcttcaag    5640
tctagttcca gtccttgtct accttgtcga cttatacccg gtttgtccta tagacaccat    5700
tcgtcaagga cggggccgag tcccggttct tgtctacctt gtcgacttat acccggtttg    5760
tcctatagac accattcgtc aaggacgggg ccgagtcccg gttcttgtct accagggggc    5820
tacgccaggt cgggagtcgt caaagatctc ttggtagtct acaaaggtcc cacggggttc    5880
ctggacttta ctgggacacg aataaaactt gattggttag tcaagcgaag agcgaagaca    5940
agcgcgcgaa gacgaggggc tcgagttatt ttctcgggtg ttggggagtg agcccgcgg    6000 tcaggaggct aactgactca gcgggcccat gggcacatag gttatttggg agaacgtcaa    6060
cgtaggctga acaccagagc gacaaggaac cctcccagag gagactcact aactgatggg    6120
cagtcgcccc cagaaagtaa gtacgtcgta catagtttta attaaaccaa aaaaaagaat    6180
tcataaatgt aatttaccgg tatcaacgta attacttagc cggttgcgcg cccctctccg    6240
ccaaacgcat aaccgcgaga aggcgaagga gcgagtgact gagcgacgcg agccagcaag    6300
ccgacgccgc tcgccatagt cgagtgagtt ccgccatta tgccaatagg tgtcttagtc    6360
ccctattgcg tccttttcttg tacactcgtt ttccggtcgt tttccggtcc ttggcatttt    6420
tccggcgcaa cgaccgcaaa aaggtatccg aggcgggggg actgctcgta gtgttttag    6480 ctgcgagttc agtctccacc gctttgggct gtcctgatat ttctatggtc cgcaaagggg    6540
gaccttcgag ggagcacgcg agaggacaag gctgggacgg cgaatggcct atggacaggc    6600
ggaaagaggg aagcccttcg caccgcgaaa gagtatcgag tgcgacatcc atagagtcaa    6660
gccacatcca gcaagcgagg ttcgacccga cacacgtgct ggggggcaa gtcgggctgg    6720 cgacgcggaa taggccattg atagcagaac tcaggttggg ccattctgtg ctgaatagcg    6780
gtgaccgtcg tcggtgacca ttgtcctaat cgtctcgctc catacatccg ccacgatgtc    6840
tcaagaactt caccaccgga ttgatgccga tgtgatcttc ttgtcataaa ccatagacgc    6900
gagacgactt cggtcaatgg aagccttttt ctcaaccatc gagaactagg ccgtttgttt    6960
```

-continued

```
ggtggcgacc atcgccacca aaaaaacaaa cgttcgtcgt ctaatgcgcg tcttttttc    7020 ctagagttct tctaggaaac tagaaaagat gccccagact gcgagtcacc ttgcttttga    7080
gtgcaattcc ctaaaaccag tactctaata gttttcccta gaagtggatc taggaaaacg   7140
ccggcgttta gttagatttc atatatactc atttgaacca gactgtcaat ggttacgaat   7200
tagtcactcc gtggatagag tcgctagaca gataaagcaa gtaggtatca acggactgag   7260
gggcagcaca tctattgatg ctatgccctc ccgaatggta gaccggggtc acgacgttac   7320
tatggcgctc tgggtgcgag tggccgaggt ctaaatagtc gttatttggt cggtcggcct   7380
tcccggctcg cgtcttcacc aggacgttga aataggcgga ggtaggtcag ataattaaca   7440 acggccttc gatctcattc atcaagcggt caattatcaa acgcgttgca acaacggtaa    7500
cgatgtccgt agcaccacag tgcgagcagc aaaccatacc gaagtaagtc gaggccaagg   7560
gttgctagtt ccgctcaatg tactaggggg tacaacacgt tttttcgcca atcgaggaag   7620
ccaggaggct agcaacagtc ttcattcaac cggcgtcaca atagtgagta ccaataccgt   7680
cgtgacgtat taagagaatg acagtacggt aggcattcta cgaaaagaca ctgaccactc   7740
atgagttggt tcagtaagac tcttatcaca tacgccgctg gctcaacgag aacgggccgc   7800
agttatgccc tattatggcg cggtgtatcg tcttgaaatt ttcacgagta gtaacctttt   7860
gcaagaagcc ccgcttttga gagttcctag aatggcgaca actctaggtc aagctacatt   7920
gggtgagcac gtgggttgac tagaagtcgt agaaaatgaa agtggtcgca aagacccact   7980 cgttttttgtc cttccgtttt acggcgtttt ttcccttatt cccgctgtgc ctttacaact   8040
tatgagtatg agaaggaaaa agttataata acttcgtaaa tagtcccaat aacagagtac   8100
tcgcctatgt ataaacttac ataaatcttt ttatttgttt atccccaagg cgcgtgtaaa   8160
g                                                                    8161
```

<210> SEQ ID NO 10
<211> LENGTH: 5
<212> TYPE: PRT
<213> ORGANISM: Artificial Sequence
<220> FEATURE:
<223> OTHER INFORMATION: GS Linker

<400> SEQUENCE: 10

Gly Gly Gly Gly Ser
1               5

What is claimed is:

1. A method of assessing the effect of a test condition on G-protein-coupled receptor (GPCR) pathway activity, comprising:
   a) providing a cell that expresses a GPCR as a fusion protein to a first mutant form of a reporter enzyme and an arrestin as a fusion protein to a second mutant form of the reporter enzyme complementary to the first mutant form of the reporter enzyme,
   wherein the arrestin is modified to enhance binding of said arrestin to the GPCR, wherein said enhanced binding between said arrestin and the GPCR increases sensitivity of detection of said effect of the test condition;
   b) exposing the cell to a ligand for said GPCR under the test condition; and
   c) monitoring activation of said GPCR by complementation of the first and second mutant forms of the reporter enzyme;
   wherein increased reporter enzyme activity in the cell compared to that which occurs in the absence of the test condition indicates increased GPCR interaction with the modified arrestin compared to that which occurs in the absence of the test condition, and decreased reporter enzyme activity in the cell compared to that which occurs in the absence of the test condition indicates decreased GPCR interaction with the modified arrestin compared to that which occurs in the absence of the test condition; and
   wherein the GPCR and the first mutant form of reporter enzyme are linked together by a polypeptide linker represented by the formula —(GGGGS)$_n$— (SEQ ID NO:10).

2. The method of claim 1, wherein the modified arrestin exhibits enhanced binding to activated, phosphorylated GPCR.

3. The method of claim 1, wherein the modified arrestin comprises conversion of Arg169 to an amino acid selected from the group consisting of histidine, tyrosine, phenylalanine and threonine.

4. The method of claim 1, wherein the modified arrestin comprises conversion of Val170 to alanine.

5. The method of claim 1, wherein the arrestin is selected from the group consisting of β-arrestin1 and β-arrestin2, and wherein the β-arrestin1 or the β-arrestin2 is truncated for all or part of a carboxyl-terminal half of the β-arrestin1 or the β-arrestin2.

6. The method of claim wherein the 5, wherein the β-arrestin1 or the β-arrestin2 is truncated from amino acid 190 of the β-arrestin1 or the β-arrestin2 to the carboxyl-terminal end of the β-arrestin1 or the β-arrestin2.

7. The method of claim 1, wherein the arrestin is a chimera of β-arrestin1, β-arrestin2 and/or visual arrestin.

8. The method of claim 1, wherein the modified arrestin comprises conversion of Arg170 to an amino acid selected from the group consisting of histidine, tyrosine, phenylalanine and threonine.

9. The method of claim 1, wherein n is 2 or more.

10. The method of claim 1, wherein n is 4.

11. The method of claim 1, wherein the second mutant form of the reporter enzyme is linked to the C-terminal of the arrestin.

12. A method of assessing the effect of a test condition on G-protein-coupled receptor (GPCR) pathway activity, comprising:

a) providing a cell that expresses a GPCR as a fusion protein to a first mutant form of a reporter enzyme and an arrestin as a fusion protein to a second mutant form of the reporter enzyme complementary to the first mutant form of the reporter enzyme, wherein the arrestin is modified by introducing a point mutation in a phosphorylation-recognition domain to remove a requirement for phosphorylation of the GPCR for arrestin binding to permit binding of the arrestin to said GPCR in the cell regardless of whether the GPCR is phosphorylated, b) exposing the cell to a ligand for said GPCR under the test condition; and c) monitoring activation of the GPCR by complementation of the first and second mutant forms of the reporter enzyme;

wherein increased reporter enzyme activity in the cell compared to that which occurs in the absence of the test condition indicates increased GPCR interaction with the modified arrestin compared to that which occurs in the absence of the test condition, and decreased reporter enzyme activity in the cell compared to that which occurs in the absence of the test condition indicates decreased GPCR interaction with the modified arrestin compared to that which occurs in the absence of the test condition; and wherein the GPCR and the first mutant form of reporter enzyme are linked together by a polypeptide linker represented by the formula —(GGGGS)$_n$—(SEQ ID NO:10).

13. The method of claim 12, wherein the arrestin is mutated to increase a property selected from affinity and avidity for activated, non-phosphorylated GPCR.

14. The method of claim 13, wherein the arrestin is β-arrestin2 and wherein the β-arrestin2 is mutated to convert Arg169 to an oppositely charged residue.

15. The method of claim 14, wherein the oppositely charged residue is selected from the group consisting of histidine, tyrosine, phenylalanine and threonine.

16. The method of claim 15, wherein the arrestin is a chimera of β-arrestin1, β-arrestin2 and/or visual arrestin.

17. The method of claim 14, wherein the arrestin is a chimera of β-arrestin1, β-arrestin2 and/or visual arrestin.

18. The method of claim 13, wherein the arrestin is a chimera of β-arrestin1, β-arrestin2 and/or visual arrestin.

19. The method of claim 13, wherein the arrestin is β-arrestin2 and wherein the β-arrestin2 is mutated to convert Arg170 to an oppositely charged residue.

20. The method of claim 12, wherein the arrestin is mutated to increase a property selected from affinity and avidity for activated and phosphorylated GPCR.

21. The method of claim 12, wherein n is 2 or more.

22. The method of claim 12, wherein n is 4.

* * * * *

UNITED STATES PATENT AND TRADEMARK OFFICE
CERTIFICATE OF CORRECTION

PATENT NO. : 6,800,445 B2
DATED : October 5, 2004
INVENTOR(S) : Palmer et al.

It is certified that error appears in the above-identified patent and that said Letters Patent is hereby corrected as shown below:

Column 8,
Line 46, "levels of 3Arr2-..." should be -- levels of $\beta$Arr2-... --.

Column 17,
Line 27, "1$\beta$-arrestin2..." should be -- $\beta$-arrestin2... --.

Signed and Sealed this

Twenty-third Day of May, 2006

JON W. DUDAS
*Director of the United States Patent and Trademark Office*